US011767358B2

(12) United States Patent
Orengo et al.

(10) Patent No.: US 11,767,358 B2
(45) Date of Patent: Sep. 26, 2023

(54) HUMAN ANTIBODIES TO BET V 1 AND METHODS OF USE THEREOF

(71) Applicant: REGENERON PHARMACEUTICALS, INC., Tarrytown, NY (US)

(72) Inventors: Jamie M. Orengo, Cortland Manor, NY (US); Andrew J. Murphy, Croton-on-Hudson, NY (US); Ashok T. Badithe, Basking Ridge, NJ (US); Vishal Kamat, Hopewell Junction, NY (US); Yashu Liu, Burlingame, CA (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 348 days.

(21) Appl. No.: 17/006,599

(22) Filed: Aug. 28, 2020

(65) Prior Publication Data
US 2021/0054056 A1 Feb. 25, 2021

Related U.S. Application Data

(62) Division of application No. 15/994,294, filed on May 31, 2018, now Pat. No. 10,793,624.

(60) Provisional application No. 62/662,165, filed on Apr. 24, 2018, provisional application No. 62/571,696, filed on Oct. 12, 2017, provisional application No. 62/513,872, filed on Jun. 1, 2017.

(51) Int. Cl.
*C07K 16/16* (2006.01)
*A61K 39/395* (2006.01)
*A61P 37/08* (2006.01)
*A61K 39/00* (2006.01)

(52) U.S. Cl.
CPC ............ *C07K 16/16* (2013.01); *A61K 39/395* (2013.01); *A61P 37/08* (2018.01); *A61K 2039/505* (2013.01); *C07K 2317/21* (2013.01); *C07K 2317/33* (2013.01); *C07K 2317/34* (2013.01); *C07K 2317/51* (2013.01); *C07K 2317/515* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| 5,670,626 | A | 9/1997 | Chang |
| 6,596,541 | B2 | 7/2003 | Murphy et al. |
| 6,849,259 | B2 | 2/2005 | Murphy et al. |
| 10,793,624 | B2 * | 10/2020 | Orengo ............... C07K 16/16 |
| 2003/0003133 | A1 | 1/2003 | Schneider |
| 2004/0101920 | A1 | 5/2004 | Radziejewski et al. |
| 2009/0304752 | A1 | 12/2009 | Mistrello et al. |
| 2010/0034812 | A1 | 2/2010 | Majdic et al. |
| 2016/0223563 | A1 | 8/2016 | Yancopoulos et al. |

FOREIGN PATENT DOCUMENTS

| EP | 0 619 323 | 10/1994 |
| WO | WO 1994/010194 | 5/1994 |
| WO | WO 1994/024164 | 10/1994 |
| WO | WO 2005/103081 | 11/2005 |
| WO | WO 2007/134350 | 11/2007 |
| WO | 2018/222854 | 12/2018 |
| WO | 2020/018820 | 1/2020 |

OTHER PUBLICATIONS

Bucher et al (2004) "Effect of Tree Pollen Specific, Subcutaneous Immunotherapy on the Oral Allergy Syndrome to Apple and Hazelnut" Allergy 59(12):1272-1276.
Calderon et al (2014) "A Comparative Analysis of Symptom and Medication Scoring Methods Used in Clinical Trials of Sublingual Immunotherapy for Seasonal Allergic Rhinitis" Clin Exp Allergy 44(10):1228-39.
Carlson and Coop (2019) "Pollen Food Allergy Syndrome (PFAS): A Review of Current Available Literature", Annals of Allergy, Asthma & Immunology, 123:359-365.
Erler et al (2011) "Proteomic Profiling of Birch (*Betula verrucosa*) Pollen Extracts from Different Origins" Proteomics 11(8):1486-1498.
Frew (2010) "Allergen Immunotherapy", Journal of Allergy and Clinical Immunology, 125:S306-313.
Ito et al (2015) "The associations Between Daily Spring Pollen Counts, Over-the-Counter Allergy Medication Sales, and Asthma Syndrome Emergency Department Visits in New York City, 2002-2012", Environmental Health: A Global Access Science Source, 14:71.
Kazane et al (2013) "Self-Assembled Antibody Multimers Through Peptide Nucleic Acid Conjugation", J. Am. Chem. Soc. [Epub: Dec. 4, 2012] 135:340-346.

(Continued)

*Primary Examiner* — Nora M Rooney
(74) *Attorney, Agent, or Firm* — FisherBroyles, LLP; Cara L. Crowley-Weber; Lisa Dornbach Flanagan

(57) ABSTRACT

Provided herein are antibodies that bind Fagales allergens, Fagales related allergens, birch pollen, or Bet v 1, compositions comprising the antibodies, nucleic acids encoding the antibodies, and methods of using the antibodies. According to certain embodiments, the antibodies are fully human monoclonal antibodies that bind to Bet v 1. The antibodies are useful for binding Bet v 1 in vivo, thus preventing binding of the allergen to pre-formed IgE on the surface of mast cells or basophils. In doing so, the antibodies act to prevent the release of histamine and other inflammatory mediators from mast cells and/or basophils, thus ameliorating the untoward response to the Fagales allergens in sensitized individuals.

40 Claims, 11 Drawing Sheets

Specification includes a Sequence Listing.

(56) References Cited

OTHER PUBLICATIONS

Klein et al (2012) "Progress in Overcoming the Chain Association Issue in Bispecific Heterodimeric IgG Antibodies", mAbs 4(6):653-663.
Langer and Wise (eds.) (1984) "Medical Applications of Controlled Release" CRC Pres., Boca Raton, Florida, vol. 2, pp. 115-138.
Mordenti et al (1991) "Interspecies Scaling of Clearance and Volume of Distribution Data for Five Therapeutic Proteins", Pharmaceut. Res. 8(11):1351-1359.
Nolte et al (2016) "Efficacy of House Dust Mite Sublingual Immunotherapy Tablet in North American Adolescents and Adults in a Randomized, Placebo-Controlled Trial", Journal of Allergy and Clinical Immunology, 138:1631-1638.
Pablos et al (2016) "Pollen Allergens for Molecular Diagnosis", Current Allergy and Asthma Reports, 16:31.
Rosario and Bielory (2011) "Epidemiology of Allergic Conjunctivitis" Curr Opin Allergy Clin Immun 11(5):471-476.
Schenk et al (2011) "Proteomic Analysis of the Major Birch Allergen Bet v 1 Predicts Allergenicity for 15 Birch Species", Journal of Proteomics, 74:1290-1300.
Sefton (1987) "Implantable Pumps", CRC Crit. Rev. Biomed. Eng. 14(3):201-240.
Taylor et al (2004) "Birch Pollen Rupture and the Release of Aerosols of Respirable Allergens" Clin Exp Allergy 34(10):1591-1596.
Taylor et al (2007) "Links Between Pollen, Atopy and the Asthma Epidemic", International Archives of Allergy and Immunology, 144:162-170.
Wallace and Dykewicz (2017) "Seasonal Allergic Rhinitis: A Focused Systematic Review and Practice Parameter Update" Curr Opin Allergy Clin Immun 17(4):286-294.
Wallace et al (2008) "The Diagnosis and Management of Rhinitis: An Updated Practice Parameter", Journal of Allergy and Clinical Immunology, 122:S1-84.
Wei (2016) "The Efficacy and Safety of H1-Antihistamine versus Montelukast for Allergic Rhinitis: A Systematic Review and Meta-Analysis" Biomed Phamn 83:989-997.
Pearson (2000) "Flexible Sequence Similarity Searching with the FASTA3 Program Package", Methods in Molecular Biology, 132:185-219.
Atanasio, et al. (2021) "Targeting Immunodominant Bet v 1 Epitopes with Monoclonal Antibodies Prevents the Birch Allergic Response", Journal of Allergy and Clinical Immunology, 12 pages.
Bostrom, et al. (2009) "Improving Antibody Binding Affinity and Specificity for Therapeutic Development", Methods Mol. Biol., 525:353-376.
Gevaert, et al. (2021) "Novel Antibody Cocktail Targeting Bet v 1 Rapidly and Sustainability Treats Birch Allergy Symptoms in a Phase 1 Study", Journal of Allergy and Clinical Immunology, pp. 1-10.
Gonzales, et al. (2005) "Minimizing the Immunogenicity of Antibodies for Clinical Applications", Tumour Biol., 26 (1):31-43.
Orengo, et al. (2018) "Treating Cat Allergy with Monoclonal IgG Antibodies that Bind Allergen and Prevent IgE Engagement", Nature Communications, 9(1):1-15.
PCT International Search Report and Written Opinion received for PCT/US2021/039945, dated Oct. 8, 2021, 15 pages.
Wark and Hudson (2006) "Latest Technologies for the Enhancement of Antibody Affinity", Advanced Drug Delivery Reviews, 58(5-6):657-670.
Al-Lazikani, et al., (1997) "Standard conformations for the canonical structures of immunoglobulins", J. Mol. Biol. 273:927-948.
Altschul, et al. (1990) "Basic Local Alignment Search Tool", J. Mol. Biol. 215: 403-410.
Altschul, et al. (1997) "Gapped BLAST and PSI-BLAST: a new generation of protein database search programs", Nucleic Acids Res. 25(17):3389-3402.

Angal, et al. (1993) "A Single Amino Acid Substitution Abolishes The Heterogeneity of Chimeric Mouse/Human (IgG4) Antibody", Molecular Immunology, 30:105-108.
Antibodies (2014) Harlow and Lane (Cold Spring Harbor Press, Cold Spring Harb., NY) "A Laboratory Manual".
Breiteneder, et al. (1989) "The gene coding for the major birch pollen allergen Betvl, is highly homologous to a pea disease resistance response gene", EMBO J., 8(7):1935-1938.
Buters, et al. (2012) "Release of Bet v 1 from birch pollen from 5 European countries. Results from the HIALINE study", Atomospheric Environment, 55:496-505.
Denepoux, et al. (2000) "Molecular Characterization of Human IgG Monoclonal Antibodies Specific for the Major Birch Pollen Allergen Bet v 1. Anti-allergen IgG Can Enhance the Anaphylactic Reaction", FEBS LETT, 465(1):39-46.
De Pascalis, et al. (2002) "Grafting of "Abbreviated" Complentarity-Determining Regions Containing Specificity-Determining Residues Essential for Ligand Contact to Engineer a Less Immunogenic Humanized Monoclonal Antibody", J. of Immunology, 169:3076-3084.
Ehring (1999) "Hydrogen Exchange/Electrospray Ionization Mass Spectrometry Studies of Structural Features of Protein/Protein Interactions", Analytical Biochemistry, 267(2):252-259.
Engen and Smith (2001) "The Basics of Ion Chromatography", Anal. Chem., 73:256A-265A.
Focke, et al. (2009) "Molecular Composition and Biological Activity of Commercial Birch Pollen Allergen Extracts", European Journal of Clinical Investigation, 39(5):429-436.
Gieras, et al. (2011) "Mapping of Conformational IgE Epitopes with Peptide-Specific Monoclonal Antibodies Reveals Simultaneous Binding of Different IgE Entibodies to a Surface Patch on the Major Birch Pollen Allergen, Bet v 1", J. Immunol., 186(9):5333-5334.
Goel, et al. (2004) "Plasticity within the Antigen-Combining Site May Manifest as Molecular Mimiery in the Humoral Immune Response", J. Immunol., 173(12):7358-7367.
Gonnet, et al. (1992) "Exhaustive Matching of the Entire Protein Sequence Database", Science, 256:1443-1445.
Hauser (2010) "Panallergens and their Impact on the Allergic Patient", Allergy, Asthma & Clinical Immunology, 6:1.
Hauser, et al. (2011) "Bet v 1-like pollen allergens of multiple Fagales species can sensitize atopic individuals", Clin Exp Allergy, 41: 1804-14.
Jakobsen, et al. (2004) "Isolation of High-Affinity Human IgE and IgG Antibodies Recognising Bet v 1 and Humicola Lanuginose Lipase from Combinatorial Phage Libraries", Molecular Immunology, 41(10):941-953.
Jarolim, et al. (1989) "Specificities of IgE and IgG antibodies in patients with birch pollen allergy", Int Arch Allergy Appl Immunol., 88(1-2):180-182.
Kabat and Wu (1991) "Sequences of Proteins of Immunological Interest," National Institutes of Health, Bethesda, Md., 147:1709-1719.
Kahn, et al. (2014) "Adjustable Locks and Flexible Keys: Plasticity of Epitope-Paratope Interaction in Germline Antibodies", J. Immunol., 192:5398-5405.
Kofler, et al. (2012) "Crystallographically Mapped Ligand Binding Differs in High and Low IgE Binding Isoforms of Birch Pollen Allergen Bet v 1", J. Molecular Biology, 422(1):109-23.
Laffer, et al. (1996) "Molecular Characterization of Bip 1, a Monoclonal Antibody that Modulates IgE Binging to Birch Pollen Allergen, Bet v 1", J. Mo. Biol., 157:4953-4962.
Langer (1990) "New Methods of Drug Delivery", Science, 249: 1527-1533.
Lebecque, et al. (1997) "Immunological Characterization of Monoclonal Antibodies that Modulate Human IgE Binding to the Major Birch Pollen Allergen Bet v", Journal of Allergy and Clinical Immuno, 99(3):374-384.
Levin, et al. (2014) "Human IgE Against the Major Allergen Bet v 1—Defining an Epitope with Limited Cross-Reactivity Between Different PR-10 Family Proteins", Clinical & Experimental Allergy: Jounral of the British Society for Allergy and Clinical Immunology, 44(2):288-299.
Liu, et al. (2007) "An essential role for RasGRP1 in mast cellfunction and IgE-mediated allergic response", J Exp Med., 204:93-103.

(56) References Cited

OTHER PUBLICATIONS

Lloyd (1999) The Art, Science and Technology of Pharmaceutical Compounding.
MacCallum, et al. (1996) "Antibody-antigen Interactions: Contact Analysis and Binding Site Topography", J. Mol. Biol., 262:732-745.
Markovic-Housley, et al. (2003) "Crystal Structure of a Hypoallergenic Isoform of the Major Birch Pollen Allergen Bet v 1 and its Likely Biological Functions as a Plant Steroid Carrier", J Mol Biol., 325(1): 123-33.
Martin, et al. (1989) "Modeling antibody hypervariable loops: A combined algorithm", Proc. Natl. Acad. Sci. USA, 86:9268-9272.
Mariuzza, et al. (1987) "The Structural Basis of Antigen-Antibody Recognition", Annu. Rev. Biophyis. Chem., 16:139-159.
Musidlowska-Persson, et al. (2007) "Cloning and Sequencing of the Bet v 1-Homologous Allergen Fra a 1 in Strawberry (*Fragaria ananassa*) Shows the Presence of an Intron and Little Variabilitn in Amino Acid Sequence", Molecular Immunology, 44:1245-1252.
Padlan, et al. (1995) "Identification of specificity-determining residues in antibodies", FASEB J., 9:133-139.
Pearson (1994) "Using the FASTA Program to Search Protein and DNA Sequence Databases", Methods Mol. Biol., 24: 307-331.
Poosarla, et al. (2017) "Computational De Novo Design of Antibodies Bidning to a Peptide With High Affinity", Biotech. Bioeng., 114(6):1331-1342.
Powell, et al. (1998) "Compendium of excipients for parenteral formulations", PDA; J Pharm Sci Technol, 52:238-311.
Reddy, et al. (2000) "Elimination of Fc Receptor-Dependent Effector Functions of a Modified IgG4 Monoclonal Antibody to Human CD4", J. Immunol., 164:1925-1933.
Reineke (2004) "Antibody Epitope Mapping Using Arrays of Synthetic Peptide", Methods Mol Biol, 248:443-63.
Shield, et al. (2002) "Lack of Fucose on HumanIgG1 N-Linked Oligosaccharide Improves Binding to Human FcyRIII and Antibody-dependent Cellular Toxicity", JBC, 277:26733-26740.
Sinha (2013) "Current Overview of Allergens of Plant Pathogenesis Related Protein Families", The Scientific World Journal, 2014:543195:1-19.
Spangfort, et al. (2003) "Dominating IgE-Binding Epitope of Bet v 1, the Major Allergen of Birch Pollen, Characterized by X-ray Crystallography and Site-Directed Mutagenesis", J Immunol. 2003, 171(6): 3084-3090.
Taylor, et al. (1992) "A transgenic mouse that expresses a diversity of human sequence heavy and light chain Immunoglobulins", Nucl. Acids Res., 20:6287-6295.
Tomer (2000) "Characterization of a discontinuous epitope of the human immunodefiency virus (HIV) core protein p24 by eptiope excision and differential chemical modification followed by mass spectrometric peptide mapping analysis", Protein Science, 9:487-496.
Vajdos, et al. (2002) "Comprehensive Functional Maps of the Antigen-bidning Site of an Anti-ErbB2 Antibody Obtained with Shotgun Scanning Mutagenesis", J Mol Biol, 320:415-428.
Visco (1996) "Human IgG Monoclonal Antibodies that Modulate the Binding of Specific IgE to Birch Pollen Bet v 1", The Journal of Immunology, The American Assoc. of Immunologists, 157(2):956-962.
Wangorsch, et al. (2015) "Identification of Sola l 4 as Bet v 1 Homologous Pathogenesis Related-10 Allergen in Tomato Fruits", Molecular Nutr. Food Res., 59:582-592.
Wu, et al. (1987) "Receptor-mediated in Vitro Gene Transformation by a Soluble DNA Carrier System", J. Biol. Chem., 262:4429-4432.
PCT International Search Report and Written Opinion received for PCT/US2018/035366, dated Oct. 22, 2018, 40pages.
Alvares-Cuesta et al. (2006) "Standards for Practical Allergen-Specific Immunotherapy", Allergy, 61(Suppl. 82): 1-20.
Calderon et al. (2007) "Prolonged Preseasonal Treatment Phase with Grazax Sublingual Immunotherapy Increases Clinical Efficacy", Allergy, 62:958-961.
Kunik et al. (2012) "Structural Consensus Among Antibodies Defines the Antigen Binding Site," PLOS Computational Biology, 8(2):e1002388.
Kussie et al. (1994) "A Single Engineered Amino Acid Substitution Changes Antibody Fine Specificity," Journal of Immunology, 152(1):146-152.
Lombardi, et al. (2009) "Administration Regimens for Sublingual immunotherapy to Pollen Allergens: What do we know?", Allergy, 64:849-854.
Morris (1996) "Epitope Mapping of Protein Antiens by Completition ELISA," The Protein Protocols Handbook, Totowa, NJ, Human Press, pp. 595-600.
Panka et al (1988) "Variable Region Framework Differences Result in Decreased or Increased Affinity of Variant Anti-digoxin Antibodies," Proc. Antl, Acad. Sci. USA, 85:3080-3084.
Rudikoff et al. (1982) "Single Amino Acid Substitution Altering Antigen-Binding Specificity," Proc. Natl, Acad. Sci. USA, 79:1979-1983.

\* cited by examiner

Bet v 1 peptides with significant protection upon binding to H4H16992P

| Bet v 1 | 1 minute

Bet v 1 peptides with significant protection upon binding to H4H17082P

| Bet v 1 | 1 minute

Bet v 1 peptides with significant protection upon binding to H4H17O38P2

| Bet v 1 | 1 minute Deuteration | |

Bet v 1 peptides with significant protection upon binding to H4H16987P

| Bet v 1 | 1 minute Deuteration | |

Bet v 1 peptides with significant protection upon binding to 4 antibody combo of H4H16992P, H4H17082

HUMAN ANTIBODIES TO BET V 1 AND METHODS OF USE THEREOF

RELATED APPLICATIONS

This application is a divisional of U.S. patent application Ser. No. 15/994,294, filed May 31, 2018, which claims priority under 35 U.S.C. 119 (e) to U.S. Provisional Patent Application Ser. No. 62/513,872, filed Jun. 1, 2017; U.S. Provisional Application Ser. No. 62/571,696, filed Oct. 12, 2017; and U.S. Provisional Application Ser. No. 62/662,165, filed Apr. 24, 2018, all of which are herein specifically incorporated by reference in their entireties.

FIELD OF THE INVENTION

The present invention is related to human antibodies and antigen-binding fragments of human antibodies that bind to the birch pollen allergen, Bet v 1, therapeutic compositions comprising the antibodies, and methods of using the antibodies.

SEQUENCE LISTING

An official copy of the sequence listing is submitted concurrently with the specification electronically via EFS-Web as an ASCII formatted sequence listing with a file name of 10301US01_SEQ_LIST_ST25, a creation date of May 31, 2018, and a size of about 137 kilobytes. The sequence listing contained in this ASCII formatted document is part of the specification and is herein incorporated by reference in its entirety.

BACKGROUND OF THE INVENTION

Birch is the predominant trigger in 23% of US and 14% of European allergy patients (Datamonitor report on Allergic Rhinitis, July 2010), and the main cause of type 1 allergies in the spring across Europe, North America, Russia, and Australia (Breiteneder et al., *EMBO J.* 1989, 8(7):1935-8). Bet v 1 protein is a major birch allergen identified in pollen from *Betula verrucosa* (European white birch tree, also synonymous with *Betula pendula*), and is responsible for IgE binding in more than 95% of birch pollen allergic patients (Breiteneder, supra). Bet v 1 is a small, 7-stranded anti-parallel β sheet with three α helices and a known crystalline structure (Kofler et al., 2012, 422(1): 109-23; Markovic-Housley et al., J Mol Biol. 2003, 325(1): 123-33; Spangfort et al., J Immunol. 2003, 171(6): 3084-90). WO 94/10194 relates to peptides derived from trees of the Fagales order.

Sixty percent of birch pollen allergic patients react exclusively to Bet v 1 (Jarolim et al., Int Arch Allergy Appl Immunol. 1989, 88(1-2): 180-2). A single birch tree can produce up to five million pollen grains which travel by air up to 100 yards from the tree. Symptoms of birch pollen allergy can range from mild rhinitis and conjunctivitis to life-threatening asthmatic responses.

Immunoglobulin E (IgE) is responsible for type 1 hypersensitivity, which manifests itself in allergic rhinitis, allergic conjunctivitis, hay fever, allergic asthma, bee venom allergy, and food allergies. IgE circulates in the blood and binds to high-affinity FcεR1α receptors for IgE on basophils and mast cells. In most allergic responses, the allergens enter the body through inhalation, ingestion, or through the skin. The allergen then binds to preformed IgE already bound to the high affinity receptor on the surfaces of mast cells and basophils, resulting in cross-linking of several IgE molecules and triggering the release of histamine and other inflammatory mediators causing the various allergic symptoms.

The treatment for allergies includes steroids for suppressing the immune activity and bronchial dilators for relieving asthma symptoms. Desensitization therapy is also used for severely allergic patients. Peptide vaccine combinations have been tested for desensitizing individuals to particular allergens, e.g. Bet v 1 (See U.S. Pat. No. 9,017,689). Antibodies have been proposed as a treatment for allergies, since they may be able to block the entry of allergenic molecules into the mucosal tissues, or may bind the allergen before it has the opportunity to bind to the IgE bound to the high affinity receptor on mast cells or basophils, thus preventing the release of histamine and other inflammatory mediators from these cells.

U.S. Pat. No. 5,670,626 describes the use of monoclonal antibodies for the treatment of IgE-mediated allergic diseases such as allergic rhinitis, allergic asthma, and allergic conjunctivitis by blocking the binding of allergens to the mucosal tissue. U.S. Pat. No. 6,849,259 describes the use of allergen-specific antibodies to inhibit allergic inflammation in an in vivo mouse model of allergy. Milk-based and egg-based antibody systems have been described. For example, US2003/0003133A1 discloses using milk as a carrier for allergens for inducing oral tolerance to birch pollen and other allergens. Compositions and methods for reducing an allergic response in an animal to an allergen in the environment through use of a molecule that inhibits the ability of the allergen to bind to mast cells were described in WO1994/024164A2. Other antibodies to Bet v 1 were mentioned in U.S. 2010/0034812.

The present invention is directed toward overcoming one or more of the problems discussed above.

BRIEF SUMMARY OF THE INVENTION

Provided herein are fully human monoclonal antibodies and antigen-binding fragments thereof that bind birch pollen, e.g. natural Bet v 1, *Betula pendula* birch pollen extract (BPE), *Betula nigra* BPE, or *Betula populifolia* BPE. The antibodies can be useful to bind the Bet v 1 allergen in vivo following exposure of a sensitized patient to the birch allergen, and as such, may act to either promote clearance of natural Bet v 1, *Betula pendula* birch pollen extract (BPE), *Betula nigra* BPE, or *Betula populifolia* BPE or to block the binding of the allergen to pre-formed IgE on the surface of mast cells or basophils. By doing so, the antibodies described herein can prevent the release of histamine or other inflammatory mediators from mast cells or basophils, thereby preventing or diminishing the untoward effects observed in patients sensitized to the birch allergen. In certain embodiments, the antibodies may be capable of reducing, minimizing, or preventing at least one symptom in a patient sensitive to a birch allergen or birch-related allergen, such as sneezing, congestion, nasal blockage, coughing, wheezing, bronchoconstriction, rhinitis, or conjunctivitis. In some embodiments, the antibodies may be capable of preventing even more serious in vivo complications associated with exposure to the birch pollen allergen in sensitized individuals, such as asthmatic responses, anaphylaxis, or even death.

The antibodies provided herein can be full-length, for example, an IgG1 or and IgG4 antibody, or may comprise only an antigen-binding portion, for example, a Fab, F(ab')2, or scFv fragment, and can be modified to affect functionality, e.g., to eliminate residual effector functions (Reddy et al., 2000, *J. Immunol.* 164: 1925-1933).

A first aspect of the invention provides an isolated human monoclonal antibody or antigen-binding fragment thereof that binds natural Bet v 1, *Betula pendula* birch pollen extract (BPE), *Betula nigra* BPE, and/or *Betula populifolia* BPE.

In one embodiment, the isolated human monoclonal antibody or antigen-binding fragment thereof inhibits natural Bet v 1, *Betula pendula* BPE, *Betula nigra* BPE, or *Betula populifolia* BPE binding to allergen specific IgE.

In one embodiment, the isolated human antibody or antigen-binding fragment thereof binds to Bet v 1 with a $K_D$ equal to or less than $10^{-8}$ M. In one embodiment, the human antibody or antigen-binding fragment thereof binds to Bet v 1 with a $K_D$ ranging from about $10^{-8}$ to about $10^{-11}$ M. In one embodiment, the isolated human antibody or antigen-binding fragment thereof binds to Bet v 1 with a $K_D$ equal to or less than 27.9 nM. In one embodiment, the isolated human antibody or antigen-binding fragment thereof binds to Bet v 1 with a $K_D$ equal ranging from about 0.66 nM to about 27.9 nM.

In one embodiment, the isolated human antibody is a fully human monoclonal antibody.

In one embodiment, the isolated human monoclonal antibody or antigen-binding fragment thereof cross-reacts with one or more allergens selected from the group consisting of Aln g1, Cor a1, Car b1, Que a1, Api g2, Api g1, Dau c1, Mal d1, Ost c1, Fag s1, and Cas s1. Such allergens can also be termed PR-10 proteins, or so-called pathogenesis-related (PR) proteins. Additional PR-10 proteins (Bet v 1 family members) also include Act c 8 and Act d 8 (kiwi), Ara h 8 (peanut), Pru ar 1 (apricot), Pru av 1 (cherry), Pru p 1 (peach), Pyr c 1 (pear), Gly m 4 (soybean), Vig r 1 (mung bean), Sola I 4 (tomato), Cuc m 3 (melon), Rub i 1 (raspberry), and Fra a 1 (strawberry). These allergens can also be considered Fagales related allergens.

In one embodiment, the antibody or antigen-binding fragment thereof cross-reacts with one or more allergens selected from the group consisting of Aln g1, Mal d1, Api g1, Car b1, and Cor a1.

In one embodiment, the isolated human antibody or antigen-binding fragment thereof comprises the three heavy chain CDRs (HCDR1, HCDR2 and HCDR3) contained within any one of the heavy chain variable region (HCVR) sequences selected from the group consisting of SEQ ID NOs: 2, 18, 34, 50, 66, 82, 98, 114, 130, 146, 162, 178, 194, 210, 226, 242, 258, 274, 282, and 290; and the three light chain CDRs (LCDR1, LCDR2 and LCDR3) contained within any one of the light chain variable region (LCVR) sequences selected from the group consisting of SEQ ID NOs: 10, 26, 42, 58, 74, 90, 106, 122, 138, 154, 170, 186, 202, 218, 234, 250, 266, and 298. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., (1997), *J. Mol. Biol.* 273:927-948; and Martin et al., (1989), *Proc. Nat.*

*Acad. Sci. USA* 86:9268-9272. Public databases are also available for identifying CDR sequences within an antibody.

In one embodiment, the isolated human antibody or antigen-binding fragment thereof comprises the three heavy chain CDRs (HCDR1, HCDR2 and HCDR3) contained within any one of the heavy chain variable region (HCVR) sequences selected from the group consisting of SEQ ID NOs: 114, 146, 98, and 290; and the three light chain CDRs (LCDR1, LCDR2 and LCDR3) contained within any one of the light chain variable region (LCVR) sequences selected from the group consisting of SEQ ID NOs: 122, 154, 106, and 298.

In one embodiment, the isolated human antibody or antigen-binding fragment thereof comprises a HCVR having an amino acid sequence selected from the group consisting of SEQ ID NOs: 2, 18, 34, 50, 66, 82, 98, 114, 130, 146, 162, 178, 194, 210, 226, 242, 258, 274, 282, and 290.

In one embodiment, the isolated human antibody or antigen-binding fragment thereof comprises a HCVR having an amino acid sequence selected from the group consisting of SEQ ID NOs: 114, 146, 98, and 290.

In one embodiment, the isolated human antibody or antigen-binding fragment thereof comprises a LCVR having an amino acid sequence selected from the group consisting of SEQ ID NOs: 10, 26, 42, 58, 74, 90, 106, 122, 138, 154, 170, 186, 202, 218, 234, 250, 266, and 298.

In one embodiment, the isolated human antibody or antigen-binding fragment thereof comprises a LCVR having an amino acid sequence selected from the group consisting of SEQ ID NOs: 122, 154, 106, and 298.

In one embodiment, the isolated human antibody or antigen-binding fragment thereof comprises: (a) a HCVR having an amino acid sequence selected from the group consisting of SEQ ID NOs: 2, 18, 34, 50, 66, 82, 98, 114, 130, 146, 162, 178, 194, 210, 226, 242, 258, 274, 282, and 290; and (b) a LCVR having an amino acid sequence selected from the group consisting of SEQ ID NO: 10, 26, 42, 58, 74, 90, 106, 122, 138, 154, 170, 186, 202, 218, 234, 250, 266, and 298.

In one embodiment, the isolated human antibody or antigen-binding fragment thereof comprises: (a) a HCVR having an amino acid sequence selected from the group consisting of SEQ ID NOs: 114, 146, 98, and 290; and (b) a LCVR having an amino acid sequence selected from the group consisting of SEQ ID NO: 122, 154, 106, and 298.

In one embodiment, the isolated human antibody or antigen-binding fragment thereof comprises:

(a) a HCDR1 domain having an amino acid sequence selected from the group consisting of SEQ ID NOs: 4, 20, 36, 52, 68, 84, 100, 116, 132, 148, 164, 180, 196, 212, 228, 244, 260, 276, 284, and 292;

(b) a HCDR2 domain having an amino acid sequence selected from the group consisting of SEQ ID NOs: 6, 22, 38, 54, 70, 86, 102, 118, 134, 150, 166, 182, 198, 214, 230, 246, 262, 278, 286, and 294;

(c) a HCDR3 domain having an amino acid sequence selected from the group consisting of SEQ ID NOs: 8, 24, 40, 56, 72, 88, 104, 120, 136, 152, 168, 184, 200, 216, 232, 248, 264, 280, 288, and 296;

(d) a LCDR1 domain having an amino acid sequence selected from the group consisting of SEQ ID NOs: 12, 28, 44, 60, 76, 92, 108, 124, 140, 156, 172, 188, 204, 220, 236, 252, 268, and 300;

(e) a LCDR2 domain having an amino acid sequence selected from the group consisting of SEQ ID NOs: 14, 30, 46, 62, 78, 94, 110, 126, 142, 158, 174, 190, 206, 222, 238, 254, 270, and 302; and (f) a LCDR3 domain having an amino acid sequence selected from the group consisting of SEQ ID NOs: 16, 32, 48, 64, 80, 96, 112, 128, 144, 160, 176, 192, 208, 224, 240, 256, 272, and 304.

In one embodiment, the isolated human antibody or antigen-binding fragment thereof comprises a HCVR/LCVR amino acid sequence pair selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/266, 282/266, and 290/298.

In one embodiment, the isolated human antibody or antigen-binding fragment thereof comprises a HCVR/LCVR amino acid sequence pair selected from the group consisting of SEQ ID NOs: 114/122, 146/154, 98/106, and 290/298.

In one embodiment, the isolated human antibody or antigen-binding fragment thereof which binds to Bet v 1 comprises a HCVR/LCVR amino acid sequence pair selected from the group consisting of SEQ ID NOs: 146/154 and 290/298.

In one embodiment, the isolated human antibody or antigen-binding fragment thereof which binds to Bet v 1 interacts with at least one amino acid sequence selected from the group consisting of amino acid residues ranging from about position 23 to about position 44 of SEQ ID NO: 306; amino acid residues ranging from about position 44 to about 70 of SEQ ID NO: 306; amino acid residues ranging from about 2 to about 19 of SEQ ID NO: 306; amino acid residues ranging from about 57 to about 70 of SEQ ID NO: 306; and amino acid residues ranging from about 81 to about 96 of SEQ ID NO: 306.

In one embodiment, the isolated human antibody or antigen-binding fragment thereof which binds to Bet v 1 interacts with amino acid residues ranging from about position 23 to about position 44 of SEQ ID NO: 306.

In one embodiment, the isolated human antibody or antigen-binding fragment thereof which binds to Bet v 1 interacts with amino acid residues ranging from about position 23 to about position 43 of SEQ ID NO: 306.

In one embodiment, the isolated human antibody or antigen-binding fragment thereof which binds to Bet v 1 interacts with amino acid residues ranging from about position 44 to about position 70 of SEQ ID NO: 306.

In one embodiment, the isolated human antibody or antigen-binding fragment thereof which binds to Bet v 1 interacts with amino acid residues ranging from about position 44 to about position 56 of SEQ ID NO: 306.

In one embodiment, the isolated human antibody or antigen-binding fragment thereof which binds to Bet v 1 interacts with amino acid residues ranging from about position 2 to about position 19 of SEQ ID NO: 306.

In one embodiment, the isolated human antibody or antigen-binding fragment thereof which binds to Bet v 1 interacts with amino acid residues ranging from about position 57 to about position 70 of SEQ ID NO: 306.

In one embodiment, the isolated human antibody or antigen-binding fragment thereof which binds to Bet v 1 interacts with amino acid residues ranging from about position 57 to about position 66 of SEQ ID NO: 306.

In one embodiment, the isolated human antibody or antigen-binding fragment thereof which binds to Bet v 1 interacts with amino acid residues ranging from about position 81 to about position 96 of SEQ ID NO: 306.

In one embodiment, the isolated human antibody or antigen-binding fragment thereof which binds to Bet v 1 interacts with amino acid residues ranging from about position 81 to about position 89 of SEQ ID NO: 306.

In one embodiment, the isolated human antibody or antigen-binding fragment thereof which binds to Bet v 1 interacts with at least one amino acid sequence selected from the group consisting of SEQ ID NO: 307, 308, 309, 310, and 311. The epitopes comprising SEQ ID NOs: 307, 308, 309, 310, or 311 can be extended by 1 to 5 amino acids, or 5 to 10 amino acids, on either the C-terminal end or the N-terminal end. For example, the epitope of SEQ ID NO: 311 when extended by 5 to 10 amino acids encompasses the epitope of SEQ ID NO: 115. In other words, an epitope comprising SEQ ID NO: 311, for example, includes the epitope of SEQ ID NO: 315.

In one embodiment, the isolated human antibody or antigen-binding fragment thereof which binds to Bet v 1 interacts with SEQ ID NO: 307.

In one embodiment, the isolated human antibody or antigen-binding fragment thereof which binds to Bet v 1 interacts with SEQ ID NO: 308.

In one embodiment, the isolated human antibody or antigen-binding fragment thereof which binds to Bet v 1 interacts with SEQ ID NO: 309.

In one embodiment, the isolated human antibody or antigen-binding fragment thereof which binds to Bet v 1 interacts with SEQ ID NO: 310.

In one embodiment, the isolated human antibody or antigen-binding fragment thereof which binds to Bet v 1 interacts with SEQ ID NO: 311.

In one embodiment, the isolated human antibody or antigen-binding fragment thereof which binds to Bet v 1 interacts with SEQ ID NO: 315.

In one embodiment, the isolated human antibody or antigen binding fragment thereof which binds to Bet v 1 interacts with at least one amino acid sequence selected from the group consisting of SEQ ID NOs: 307, 308, 309, 310, 311, and 315 and comprises an HCVR/LCVR sequence pair selected from the group consisting of SEQ ID NOs: 114/122, 146/154, 98/106, and 290/298.

In one embodiment, the isolated human antibody or antigen binding fragment thereof that interacts with SEQ ID NO: 307 comprises the three HCDRs contained in the heavy chain variable region of SEQ ID NO: 146 and the three LCDRs contained in the light chain variable region of SEQ ID NO: 154.

In one embodiment, the isolated human antibody or antigen binding fragment thereof that interacts with SEQ ID NO: 310 comprises the three HCDRs contained in the heavy chain variable region of SEQ ID NO: 290 and the three LCDRs contained in the light chain variable region of SEQ ID NO: 298.

In one embodiment, the human antibody or antigen binding fragment thereof that binds Bet v 1 comprises the HCDR1, HCDR2 and HCDR3 amino acid sequences of SEQ ID NO: 148, 150, and 152, respectively and LCDR1, LCDR2 and LCDR3 amino acid sequences of SEQ ID NO: 156, 158, and 160, respectively.

In one embodiment, the human antibody or antigen binding fragment thereof that binds to Bet v 1 comprises the HCDR1, HCDR2 and HCDR3 amino acid sequences of SEQ ID NO: 292, 294, and 296, respectively and LCDR1, LCDR2 and LCDR3 amino acid sequences of SEQ ID NO: 300, 302, and 304, respectively.

In one embodiment, the human antibody or antigen binding fragment thereof that binds to Bet v 1 comprises the HCDR1, HCDR2 and HCDR3 amino acid sequences of SEQ ID NO: 4, 6, and 8, respectively and LCDR1, LCDR2 and LCDR3 amino acid sequences of SEQ ID NO: 12, 14, and 16, respectively.

In one embodiment, the human antibody or antigen binding fragment thereof that binds to Bet v 1 comprises the HCDR1, HCDR2 and HCDR3 amino acid sequences of SEQ ID NO: 20, 22, and 24, respectively and LCDR1, LCDR2 and LCDR3 amino acid sequences of SEQ ID NO: 28, 30, and 32, respectively.

In one embodiment, the human antibody or antigen binding fragment thereof that binds to Bet v 1 comprises the HCDR1, HCDR2 and HCDR3 amino acid sequences of SEQ ID NO: 36, 38, and 40, respectively and LCDR1, LCDR2 and LCDR3 amino acid sequences of SEQ ID NO: 44, 46, and 48, respectively.

In one embodiment, the human antibody or antigen binding fragment thereof that binds to Bet v 1 comprises the HCDR1, HCDR2 and HCDR3 amino acid sequences of SEQ ID NO: 52, 54, and 56, respectively and LCDR1, LCDR2 and LCDR3 amino acid sequences of SEQ ID NO: 60, 62, and 64, respectively.

In one embodiment, the human antibody or antigen binding fragment thereof that binds to Bet v 1 comprises the HCDR1, HCDR2 and HCDR3 amino acid sequences of SEQ ID NO: 68, 70, and 72, respectively and LCDR1, LCDR2 and LCDR3 amino acid sequences of SEQ ID NO: 76, 78, and 80, respectively.

In one embodiment, the human antibody or antigen binding fragment thereof that binds to Bet v 1 comprises the HCDR1, HCDR2 and HCDR3 amino acid sequences of SEQ ID NO: 84, 86, and 88, respectively and LCDR1, LCDR2 and LCDR3 amino acid sequences of SEQ ID NO: 92, 94, and 96, respectively.

In one embodiment, the human antibody or antigen binding fragment thereof that binds to Bet v 1 comprises the HCDR1, HCDR2 and HCDR3 amino acid sequences of SEQ ID NO: 100, 102, and 104, respectively and LCDR1, LCDR2 and LCDR3 amino acid sequences of SEQ ID NO: 108, 110, and 112, respectively.

In one embodiment, the human antibody or antigen binding fragment thereof that binds to Bet v 1 comprises the HCDR1, HCDR2 and HCDR3 amino acid sequences of SEQ ID NO: 116, 118, and 120, respectively and LCDR1, LCDR2 and LCDR3 amino acid sequences of SEQ ID NO: 124, 126, and 128, respectively.

In one embodiment, the human antibody or antigen binding fragment thereof that binds to Bet v 1 comprises the HCDR1, HCDR2 and HCDR3 amino acid sequences of SEQ ID NO: 132, 134, and 136, respectively and LCDR1, LCDR2 and LCDR3 amino acid sequences of SEQ ID NO: 140, 142, and 144, respectively.

In one embodiment, the human antibody or antigen binding fragment thereof that binds to Bet v 1 comprises the HCDR1, HCDR2 and HCDR3 amino acid sequences of SEQ ID NO: 164, 166, and 168, respectively and LCDR1, LCDR2 and LCDR3 amino acid sequences of SEQ ID NO: 172, 174, and 176, respectively.

In one embodiment, the human antibody or antigen binding fragment thereof that binds to Bet v 1 comprises the HCDR1, HCDR2 and HCDR3 amino acid sequences of SEQ ID NO: 180, 182, and 184, respectively and LCDR1, LCDR2 and LCDR3 amino acid sequences of SEQ ID NO: 188, 190, and 192, respectively.

In one embodiment, the human antibody or antigen binding fragment thereof that binds to Bet v 1 comprises the HCDR1, HCDR2 and HCDR3 amino acid sequences of SEQ ID NO: 196, 198, and 200, respectively and LCDR1, LCDR2 and LCDR3 amino acid sequences of SEQ ID NO: 204, 206, and 208, respectively.

In one embodiment, the human antibody or antigen binding fragment thereof that binds to Bet v 1 comprises the HCDR1, HCDR2 and HCDR3 amino acid sequences of SEQ ID NO: 212, 214, and 216, respectively and LCDR1, LCDR2 and LCDR3 amino acid sequences of SEQ ID NO: 220, 222, and 224, respectively.

In one embodiment, the human antibody or antigen binding fragment thereof that binds to Bet v 1 comprises the HCDR1, HCDR2 and HCDR3 amino acid sequences of SEQ ID NO: 228, 230, and 232, respectively and LCDR1, LCDR2 and LCDR3 amino acid sequences of SEQ ID NO: 236, 238, and 234, respectively.

In one embodiment, the human antibody or antigen binding fragment thereof that binds to Bet v 1 comprises the HCDR1, HCDR2 and HCDR3 amino acid sequences of SEQ ID NO: 244, 246, and 248, respectively and LCDR1, LCDR2 and LCDR3 amino acid sequences of SEQ ID NO: 252, 254, and 256, respectively.

In one embodiment, the human antibody or antigen binding fragment thereof that binds to Bet v 1 comprises the HCDR1, HCDR2 and HCDR3 amino acid sequences of SEQ ID NO: 260, 262, and 264, respectively and LCDR1, LCDR2 and LCDR3 amino acid sequences of SEQ ID NO: 268, 270, and 272, respectively.

In one embodiment, the human antibody or antigen binding fragment thereof that binds to Bet v 1 comprises the HCDR1, HCDR2 and HCDR3 amino acid sequences of SEQ ID NO: 276, 278, and 280, respectively and LCDR1, LCDR2 and LCDR3 amino acid sequences of SEQ ID NO: 268, 270, and 272, respectively.

In one embodiment, the human antibody or antigen binding fragment thereof that binds to Bet v 1 comprises the HCDR1, HCDR2 and HCDR3 amino acid sequences of SEQ ID NO: 284, 286, and 288, respectively and LCDR1, LCDR2 and LCDR3 amino acid sequences of SEQ ID NO: 268, 270, and 272, respectively.

In one embodiment, the invention provides a fully human monoclonal antibody or antigen-binding fragment thereof that binds to natural Bet v 1, *Betula pendula* birch BPE, *Betula nigra* BPE, or *Betula populifolia* BPE, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 282, and 290, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, and 298, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 288, and 296, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, and 304, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 284, and 292, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 286, and 294, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, and 300, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, and 302, or a substantially similar sequence thereof having at least 90%, at least 95%, at least 98% or at least 99% sequence identity; (v) binds to Bet v 1 with a $K_D$ equal to or less than $10^{-8}$ and in a range from about $10^{-8}$ to about $10^{-11}$; (vi) demonstrates efficacy in at least one animal model of anaphylaxis or inflammation; or (vii) competes with a reference antibody for binding to natural Bet v 1, *Betula pendula* birch BPE, *Betula nigra* BPE, or *Betula populifolia* BPE.

In one embodiment, a "reference antibody" may include, for example, antibodies having a combination of heavy chain and light chain amino acid sequence pairs selected from the group consisting of 2/10, 18/26, 34/42, 50/58, 66/74, 82/90, 98/106, 114/122, 130/138, 146/154, 162/170, 178/186, 194/202, 210/218, 226/234, 242/250, 258/266, 274/266, 282/266, and 290/298.

The invention encompasses antibodies having a modified glycosylation pattern. In some applications, modification to remove undesirable glycosylation sites may be useful, or e.g., removal of a fucose moiety to increase antibody dependent cellular cytotoxicity (ADCC) function (see Shield et al., 2002, *JBC* 277: 26733). In other applications, modification of galactosylation can be made in order to modify complement dependent cytotoxicity (CDC).

A second aspect provides an isolated antibody or antigen-binding fragment thereof that competes for specific binding to natural Bet v 1, *Betula pendula* birch BPE, *Betula nigra* BPE, or *Betula populifolia* BPE with an antibody or antigen-binding fragment comprising the complementarity determining regions (CDRs) of a heavy chain variable region (HCVR), wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 282, and 290; and the CDRs of a light chain variable region (LCVR), wherein the LCVR has an amino acid sequence selected from the group consisting of SEQ ID NOs: 10, 26, 42, 58, 74, 90, 106, 122, 138, 154, 170, 186, 202, 218, 234, 250, 266, and 298.

One embodiment provides an isolated antibody or antigen-binding fragment thereof that competes for specific binding to natural Bet v 1, *Betula pendula* birch BPE, *Betula nigra* BPE, or *Betula populifolia* BPE with an antibody or antigen-binding fragment comprising the complementarity determining regions (CDRs) of a heavy chain variable region (HCVR), wherein the HCVR has an amino acid sequence selected from the group consisting of SEQ ID NOs: 114, 146, 98, and 290; and the CDRs of a light chain variable region (LCVR), wherein the LCVR has an amino acid sequence selected from the group consisting of SEQ ID NOs: 122, 154, 106, and 298.

In a related embodiment, the invention provides an isolated antibody or antigen-binding fragment thereof that competes for specific binding to natural Bet v 1, *Betula pendula* birch BPE, *Betula nigra* BPE, or *Betula populifolia* BPE with an antibody or antigen-binding fragment comprising the heavy and light chain CDRs contained within heavy and light chain sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/266, 282/266, and 290/298.

A third aspect provides an isolated antibody or antigen-binding fragment thereof that binds the same epitope on Bet v 1 as an antibody or antigen-binding fragment comprising the complementarity determining regions (CDRs) of a heavy chain variable region (HCVR), wherein the HCVR has an amino acid sequence selected from the group consisting of SEQ ID NOs: 2, 18, 34, 50, 66, 82, 98, 114, 130, 146, 162, 178, 194, 210, 226, 242, 258, 274, 282, and 290; and the CDRs of a light chain variable region (LCVR), wherein the LCVR has an amino acid sequence selected from the group consisting of SEQ ID NOs: 10, 26, 42, 58, 74, 90, 106, 122, 138, 154, 170, 186, 202, 218, 234, 250, 266, and 298.

One embodiment provides an isolated antibody or antigen-binding fragment thereof that binds the same epitope on Bet v 1 as an antibody or antigen-binding fragment comprising the complementarity determining regions (CDRs) of a heavy chain variable region (HCVR), wherein the HCVR has an amino acid sequence selected from the group consisting of SEQ ID NOs: 114, 146, 98, and 290; and the CDRs of a light chain variable region (LCVR), wherein the LCVR has an amino acid sequence selected from the group consisting of SEQ ID NOs: 122, 154, 106, and 298.

In a related embodiment, provided herein is an isolated antibody or antigen-binding fragment thereof that binds the same epitope on Bet v 1 as an antibody or antigen-binding fragment comprising the heavy and light chain CDRs contained within heavy and light chain sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/266, 282/266, and 290/298.

In a fourth aspect, the invention provides nucleic acid molecules encoding Bet v 1 antibodies or fragments thereof. Recombinant expression vectors carrying such nucleic acids, and host cells into which such vectors have been introduced, are also contemplated herein, as are methods of producing the antibodies by culturing the host cells under conditions permitting production of the antibodies, and recovering the antibodies produced.

In one embodiment, provided herein are nucleic acid molecules encoding a human monoclonal antibody or fragment thereof that binds to natural Bet v 1, *Betula pendula* BPE, *Betula nigra* BPE, or *Betula populifolia* BPE.

In one embodiment, provided herein is an antibody or fragment thereof comprising a HCVR encoded by a nucleic acid sequence selected from the group consisting of SEQ ID NO: 1, 17, 33, 49, 65, 81, 97, 113, 129, 145, 161, 177, 193, 209, 225, 241, 257, 273, 281, and 289, or a substantially identical sequence having at least 90%, at least 95%, at least 98%, or at least 99% homology thereof.

In one embodiment, the HCVR is encoded by a nucleic acid sequence selected from the group consisting of SEQ ID NO: 113, 145, 257, and 289.

In one embodiment, the antibody or fragment thereof further comprises a LCVR encoded by a nucleic acid sequence selected from the group consisting of SEQ ID NO:

9, 25, 41, 57, 73, 89, 105, 121, 137, 153, 169, 185, 201, 217, 233, 249, 265, and 297, or a substantially identical sequence having at least 90%, at least 95%, at least 98%, or at least 99% homology thereof.

In one embodiment, the LCVR is encoded by a nucleic acid sequence selected from the group consisting of SEQ ID NO: 121, 153, 265, and 297.

In one embodiment, provided herein is an antibody or antigen-binding fragment of an antibody comprising a HCDR3 domain encoded by a nucleotide sequence selected from the group consisting of SEQ ID NO: 7, 23, 39, 55, 71, 87, 103, 119, 135, 151, 167, 183, 199, 215, 231, 247, 263, 279, 287, and 295, or a substantially similar sequence thereof having at least 90%, at least 95%, at least 98% or at least 99% sequence identity; and a LCDR3 domain encoded by a nucleotide sequence selected from the group consisting of SEQ ID NO: 15, 31, 47, 63, 79, 95, 111, 127, 143, 159, 175, 191, 207, 223, 239, 255, 271, and 303, or a substantially similar sequence thereof having at least 90%, at least 95%, at least 98% or at least 99% sequence identity.

In one embodiment, provided herein is an antibody or fragment thereof further comprising a HCDR1 domain encoded by a nucleotide sequence selected from the group consisting of SEQ ID NO: 3, 19, 35, 51, 67, 83, 99, 115, 131, 147, 163, 179, 195, 211, 227, 243, 259, 275, 283, and 291, or a substantially similar sequence thereof having at least 90%, at least 95%, at least 98% or at least 99% sequence identity; a HCDR2 domain encoded by a nucleotide sequence selected from the group consisting of SEQ ID NO: 5, 21, 37, 53, 69, 85, 101, 117, 133, 149, 165, 181, 197, 213, 229, 245, 261, 277, 285, and 293, or a substantially similar sequence thereof having at least 90%, at least 95%, at least 98% or at least 99% sequence identity; a LCDR1 domain encoded by a nucleotide sequence selected from the group consisting of SEQ ID NO: 11, 27, 43, 59, 75, 91, 107, 123, 139, 155, 171, 187, 203, 219, 235, 251, 267, and 299, or a substantially similar sequence thereof having at least 90%, at least 95%, at least 98% or at least 99% sequence identity; and a LCDR2 domain encoded by a nucleotide sequence selected from the group consisting of SEQ ID NO: 13, 29, 45, 61, 77, 93, 109, 125, 141, 157, 173, 189, 205, 221, 237, 253, 269, and 301, or a substantially similar sequence thereof having at least 90%, at least 95%, at least 98% or at least 99% sequence identity.

A fifth aspect provides a pharmaceutical composition comprising a therapeutically effective amount of one or more isolated human antibodies or antigen-binding fragments thereof that bind natural Bet v 1, *Betula pendula* birch BPE, *Betula nigra* BPE, or *Betula populifolia* BPE, together with one or more pharmaceutically acceptable excipients.

In one embodiment, the pharmaceutical composition comprises a therapeutically effective amount of two or more isolated human antibodies or antigen-binding fragments thereof that bind Bet v 1 together with one or more pharmaceutically acceptable excipients.

In one embodiment, the pharmaceutical composition comprises:
a) a first isolated human monoclonal antibody or antigen-binding fragment thereof that binds Bet v 1, which comprises a HCVR having an amino acid sequence as set forth in SEQ ID NO: 146; and a LCVR having an amino acid sequence as set forth in SEQ ID NO: 154;
b) a second isolated human monoclonal antibody or antigen-binding fragment thereof that binds Bet v 1, which comprises a HCVR having an amino acid sequence selected from the group consisting of SEQ ID NOs: 114, 98, and 290; and a LCVR having an amino acid sequence selected from the group consisting of SEQ ID NOs: 122, 106, and 298; and
c) one or more pharmaceutically acceptable excipients.

In one embodiment, the pharmaceutical composition comprises:
a) a first isolated human monoclonal antibody or antigen-binding fragment thereof that binds Bet v 1, which comprises a HCVR having an amino acid sequence as set forth in SEQ ID NO: 290; and a LCVR having an amino acid sequence as set forth in SEQ ID NO: 298;
b) a second isolated human monoclonal antibody or antigen-binding fragment thereof that binds Bet v 1, which comprises a HCVR having an amino acid sequence selected from the group consisting of SEQ ID NOs: 114, 146, and 98; and a LCVR having an amino acid sequence selected from the group consisting of SEQ ID NOs: 122, 154, and 106; and
c) one or more pharmaceutically acceptable excipients.

In one embodiment, the pharmaceutical composition comprises:
a) a first isolated human monoclonal antibody or antigen-binding fragment thereof that binds Bet v 1, which comprises a HCVR having an amino acid sequence as set forth in SEQ ID NO: 146; and a LCVR having an amino acid sequence as set forth in SEQ ID NO: 154;
b) a second isolated human monoclonal antibody or antigen-binding fragment thereof that binds Bet v 1, which comprises a HCVR having an amino acid sequence as set forth in SEQ ID NOs: 290; and a LCVR having an amino acid sequence as set forth in SEQ ID NOs: 298; and
c) one or more pharmaceutically acceptable excipients.

In one embodiment, the pharmaceutical composition comprises:
a) a first isolated human monoclonal antibody or antigen-binding fragment thereof comprising a HCVR having an amino acid sequence of SEQ ID NO: 146 and a LCVR having an amino acid sequence of SEQ ID NO: 154;
b) a second isolated human monoclonal antibody or antigen-binding fragment thereof comprising a HCVR having an amino acid sequence of SEQ ID NO: 290 and a LCVR having an amino acid sequence of SEQ ID NO: 298;
c) one or more further isolated human monoclonal antibodies or antigen-binding fragments comprising a HCVR having an amino acid sequence selected from the group consisting of SEQ ID NOs: 114 and 98 and a LCVR having an amino acid sequence selected from the group consisting of SEQ ID NOs: 122 and 106; and
d) one or more pharmaceutically acceptable excipients.

In one embodiment, the pharmaceutical composition comprises:
a first isolated human monoclonal antibody or antigen-binding fragment thereof that binds Bet v 1, comprising a HCVR/LCVR amino acid sequence pair consisting of SEQ ID NOs: 146/154;
a second isolated human monoclonal antibody or antigen-binding fragment thereof that binds Bet v 1, comprising a HCVR/LCVR amino acid sequence pair selected from the group consisting of SEQ ID NOs: 114/122, 98/106, and 290/298; and
one or more pharmaceutically acceptable excipients.

In one embodiment, the pharmaceutical composition comprises: a first isolated human monoclonal antibody or antigen-binding fragment thereof that binds to Bet v 1, comprising a HCVR/LCVR amino acid sequence pair consisting of SEQ ID NOs: 146/154;

a second isolated human monoclonal antibody or antigen-binding fragment thereof that binds to Bet v 1, comprising a HCVR/LCVR amino acid sequence pair consisting of SEQ ID NOs: 290/298; and one or more pharmaceutically acceptable excipients.

In one embodiment, the pharmaceutical composition comprises two or more isolated human monoclonal antibodies or antigen-binding fragments thereof that bind to Bet v 1, comprising HCVR/LCVR amino acid sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/266, 282/266, and 290/298; and one or more pharmaceutically acceptable excipients.

In one embodiment, the pharmaceutical composition comprises three or more isolated human monoclonal antibodies or antigen-binding fragments thereof that bind to Bet v 1, comprising HCVR/LCVR amino acid sequence pairs selected from the group consisting of SEQ ID NOs: 2/10, 18/26, 34/42, 50/58, 66/74, 82/90, 98/106, 114/122, 130/138, 146/154, 162/170, 178/186, 194/202, 210/218, 226/234, 242/250, 258/266, 274/266, 282/266, and 290/298; and one or more pharmaceutically acceptable excipients.

In one embodiment, the pharmaceutical composition comprises four isolated human monoclonal antibodies that bind to Bet v 1, or antigen-binding fragments thereof, wherein the human antibodies or antigen-binding fragments thereof comprise the HCVR/LCVR amino acid sequence pairs of SEQ ID NOs: 114/122, 146/154, 98/106, and 290/298; and one or more pharmaceutically acceptable excipients.

In one embodiment, the pharmaceutical composition comprises the antibody designated H4H16992P having the HCVR/LCVR amino acid sequence pair of SEQ ID NOs: 146/154; the antibody designated H4H17082P2 having the HCVR/LCVR amino acid sequence pair of SEQ ID NOs: 290/298; and the antibody designated H4H17038P2 having the HCVR/LCVR amino acid sequence pair of SEQ ID NOs: 98/106.

In one embodiment, the pharmaceutical composition comprises the antibody designated H4H16992P having the HCVR/LCVR amino acid sequence pair of SEQ ID NOs: 146/154; the antibody designated H4H17082P2 having the HCVR/LCVR amino acid sequence pair of SEQ ID NOs: 290/298; the antibody designated H4H17038P2 having the HCVR/LCVR amino acid sequence pair of SEQ ID NOs: 98/106; and the antibody designated H4H16987P having the HCVR/LCVR amino acid sequence pair of SEQ ID NOs: 114/122.

In one embodiment, the pharmaceutical composition comprises a therapeutically effective amount of a first isolated human monoclonal antibody or an antigen-binding fragment thereof that binds to Bet v 1, wherein the first antibody or fragment thereof interacts with amino acid residues ranging from about position 23 to about position 44 of SEQ ID NO: 306, and a second isolated human monoclonal antibody or antigen-binding fragment thereof that binds to Bet v 1, wherein the second antibody or fragment thereof interacts with amino acid residues ranging from about position 44 to about position 70 of SEQ ID NO: 306, together with one or more pharmaceutically acceptable excipients.

In one embodiment, the pharmaceutical composition comprises a therapeutically effective amount of a first isolated human monoclonal antibody or an antigen-binding fragment thereof that binds to Bet v 1, together with one or more pharmaceutically acceptable excipients, wherein the first antibody or fragment thereof interacts with amino acid residues ranging from about position 23 to about position 43 of SEQ ID NO: 306, and a second isolated human monoclonal antibody or antigen-binding fragment thereof that binds to Bet v 1, wherein the second antibody or fragment thereof interacts with amino acid residues ranging from about position 44 to about position 56 of SEQ ID NO: 306.

In one embodiment, the pharmaceutical composition comprises a therapeutically effective amount of a first isolated human monoclonal antibody or an antigen-binding fragment thereof that binds to Bet v 1, together with one or more pharmaceutically acceptable excipients, wherein the first antibody or fragment thereof interacts with the amino acid sequence of SEQ ID NO: 307, and a second isolated human monoclonal antibody or antigen-binding fragment thereof that binds to Bet v 1, wherein the second antibody or fragment thereof interacts with the amino acid sequence of SEQ ID NO: 308, 309, 310, 311 or 315.

In one embodiment, the pharmaceutical composition comprises a therapeutically effective amount of a first isolated human monoclonal antibody or an antigen-binding fragment thereof that binds to Bet v 1, and one or more further isolated human monoclonal antibodies, or antigen-binding fragments thereof that bind to Bet v 1, together with one or more pharmaceutically acceptable excipients, wherein the first antibody or fragment thereof interacts with at least one amino acid sequence selected from group consisting of amino acid residues ranging from about position 23 to about position 43 of SEQ ID NO: 306; amino acid residues ranging from about position 44 to about 56 of SEQ ID NO: 306; amino acid residues ranging from about 2 to about 19 of SEQ ID NO: 306; amino acid residues ranging from about 57 to about 70 of SEQ ID NO: 306; and amino acid residues ranging from about 81 to 89 or about 81 to about 96 of SEQ ID NO: 306.

In one embodiment, the one or more further isolated human monoclonal antibodies or fragments thereof interacts with at least one amino acid sequence selected from the group consisting of amino acid residues ranging from about position 23 to about position 43 of SEQ ID NO: 306; amino acid residues ranging from about position 44 to about 56 of SEQ ID NO: 306; amino acid residues ranging from about 2 to about 19 of SEQ ID NO: 306; amino acid residues ranging from about 57 to about 70 of SEQ ID NO: 306; and amino acid residues ranging from about 81 to 89 or about 81 to about 96 of SEQ ID NO: 306, wherein at least one of the one or more further isolated human monoclonal antibodies interacts with a different amino acid sequence than the first isolated human monoclonal antibody.

In one embodiment, the pharmaceutical composition comprises a therapeutically effective amount of a first isolated human monoclonal antibody or an antigen-binding fragment thereof that binds to Bet v 1, and one or more further isolated human monoclonal antibodies, or antigen-binding fragments thereof that bind to Bet v 1, together with one or more pharmaceutically acceptable excipients, wherein the first antibody or fragment thereof interacts with the amino acid sequence of SEQ ID NO: 307 and wherein the one or more further antibodies or fragments thereof interact with an amino acid sequence selected from the group consisting of SEQ ID NOs: 308, 309, 310, 311, and 315.

In one embodiment, the pharmaceutical composition comprises a therapeutically effective amount of at least two isolated human monoclonal antibodies or antigen-binding fragments thereof that bind to natural Bet v 1 or BPE, together with one or more pharmaceutically acceptable excipients, wherein the at least two antibodies do not compete for binding to natural Bet v 1 or BPE. In some aspects, the antibodies or antigen-binding fragments thereof are the Bet v 1 antibodies H4H16992P and H4H17082P2 comprising the HCVR/LCVR amino acid sequence pairs of SEQ ID NOs: 146/154 and 290/298, respectively.

In one embodiment, the pharmaceutical composition comprises a therapeutically effective amount of at least three isolated human monoclonal antibodies or antigen-binding fragments thereof that bind to natural Bet v 1 or BPE, together with one or more pharmaceutically acceptable excipients, wherein the at least three antibodies do not compete for binding to natural Bet v 1 or BPE. In some aspects, the antibodies or antigen-binding fragments thereof are the Bet v 1 antibodies H4H16992P, H4H17082P2, and H4H17038P2 comprising the HCVR/LCVR amino acid sequence pairs of SEQ ID NOs: 146/154, 290/298, and 98/106, respectively.

In one embodiment, the pharmaceutical composition comprises a therapeutically effective amount of at least four isolated human monoclonal antibodies or antigen-binding fragments thereof that bind to natural Bet v 1 or BPE, together with one or more pharmaceutically acceptable excipients, wherein the at least four antibodies do not compete for binding to natural Bet v 1 or BPE. In some aspects, the antibodies or antigen-binding fragments thereof are the Bet v 1 antibodies H4H16992P, H4H17082P2, H4H17038P2, and H4H16987P comprising the HCVR/LCVR amino acid sequence pairs of SEQ ID NOs: 146/154, 290/298, 98/106, and 114/122, respectively.

In one embodiment, the pharmaceutical composition comprises a therapeutically effective amount of an isolated human monoclonal antibody or antigen-binding fragment thereof that binds to Bet v 1, together with one or more pharmaceutically acceptable excipients, wherein the antibody or antigen-binding fragment thereof cross-reacts with one or more allergens selected from the group consisting of Aln g1, Cor a1, Car b1, Que a1, Api g2, Api g1, Dau c1, Mal d1, Ost c1, Fag s1, and Cas s1. In some embodiments, the antibody or antigen-binding fragment thereof cross-reacts with one or more allergens selected from the group consisting of Aln g1, Mal d1, Api g1, Car b1, and Cor a1.

In one embodiment, the invention features a composition, which is a combination of a therapeutically effective amount of one or more anti-Bet v 1 antibodies or antigen-binding fragments thereof of the invention, and a therapeutically effective amount of a second therapeutic agent, together with one or more pharmaceutically acceptable excipients.

The second therapeutic agent may be a small molecule drug, a protein/polypeptide, an antibody, a nucleic acid molecule, such as an anti-sense molecule, or a siRNA. The second therapeutic agent may be synthetic or naturally derived.

The second therapeutic agent may be any agent that is advantageously combined with an antibody or fragment thereof of the invention, for example, a second antibody other than those described herein that is capable of blocking the binding of Bet v 1 to IgE present on mast cells or basophils. A second therapeutic agent may also be any agent that is used as standard of care in treating an allergic response to any allergen. Such second therapeutic agent may be an antihistamine, epinephrine, a decongestant, a corticosteroid, or a peptide vaccine.

In certain embodiments, the second therapeutic agent may be an agent that helps to counteract or reduce any possible side effect(s) associated with the antibody or antigen-binding fragment of an antibody of the invention, if such side effect(s) should occur.

It will also be appreciated that the antibodies and pharmaceutically acceptable compositions of the present invention can be employed in combination therapies, that is, the antibodies and pharmaceutically acceptable compositions can be administered concurrently with, prior to, or subsequent to, one or more other desired therapeutics or medical procedures, including, for example in combination with an allergen-specific immunotherapy (SIT) regimen where the antibodies are administered before or during SIT. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an antibody may be administered concurrently with another agent used to treat the same disorder), or they may achieve different effects (e.g., control of any adverse effects). As used herein, additional therapeutic agents that are normally administered to treat or prevent a particular disease, or condition, are appropriate for the disease, or condition, being treated.

When multiple therapeutics are co-administered, dosages may be adjusted accordingly, as is recognized in the pertinent art.

A sixth aspect provides a method for treating a patient who demonstrates a sensitivity to, or an allergic reaction against, a Fagales protein, a Fagales related allergen, birch pollen or an extract thereof, or Bet v 1 protein, or for treating at least one symptom or complication associated with a sensitivity to, or allergic reaction against a Fagales protein, a Fagales related allergen, birch pollen or an extract thereof, or Bet v 1 protein, comprising administering an effective amount of one or more isolated human monoclonal antibodies or antigen-binding fragments thereof that bind to natural Bet v 1, *Betula pendula* BPE, *Betula nigra* BPE, or *Betula populifolia* BPE, or a pharmaceutical composition comprising an effective amount of one or more isolated human monoclonal antibodies or fragments thereof that bind to natural Bet v 1, *Betula pendula* BPE, *Betula nigra* BPE, or *Betula populifolia* BPE, to a patient in need thereof, wherein the sensitivity to, or an allergic reaction against, a Fagales protein, a Fagales related allergen, birch pollen or an extract thereof, or Bet v 1 protein is either prevented, or lessened in severity and/or duration, or at least one symptom or complication associated with the sensitivity to, or allergic reaction against, a Fagales protein, a Fagales related allergen, birch pollen or an extract thereof, or Bet v 1 protein is prevented, or ameliorated, or that the frequency and/or duration of, or the severity of the sensitivity to or allergic reaction against, a Fagales protein, a Fagales related-protein, birch pollen or an extract thereof, or Bet v 1 protein is reduced following administration of one or more of the isolated human monoclonal antibodies or fragments thereof that bind to natural Bet v 1, *Betula pendula* BPE, *Betula nigra* BPE, or *Betula populifolia* BPE, or following administration of a composition comprising any one or more of the foregoing antibodies.

In some embodiments, the birch pollen extract is selected from the group consisting of natural Bet v 1, *Betula pendula* BPE, *Betula nigra* BPE, and *Betula populifolia* BPE.

In some embodiments, the treatment results in a reduction in allergic rhinitis, allergic conjunctivitis, allergic asthma, or an anaphylactic response following exposure of the patient to a Fagales protein, a Fagales related allergen, birch pollen or an extract thereof, or Bet v 1 protein.

In some embodiments, the method further comprises administering an effective amount of a second therapeutic agent useful for diminishing an allergic reaction to a Fagales protein, a Fagales related allergen, birch pollen or an extract thereof, or Bet v 1 protein. The second therapeutic agent can be selected from the group consisting of a corticosteroid, a bronchial dilator, an antihistamine, epinephrine, a decongestant, another different antibody to Bet v 1 and a peptide vaccine.

In some embodiments, the method further comprises treating the patient with an allergen-specific immunotherapy (SIT) regimen just after or concurrent with the antibodies or fragments thereof or the pharmaceutical composition comprising the antibodies.

In one embodiment, the invention provides a method for treating a Fagales allergic patient who demonstrates a sensitivity to, or an allergic reaction against, one or more Fagales allergens, or Fagales related allergens, or for treating at least one symptom or complication associated with a sensitivity to, or allergic reaction against one or more Fagales allergens, or Fagales related allergens, comprising administering an effective amount of one or more isolated human monoclonal antibodies or antigen-binding fragments thereof that bind Bet v 1, or a pharmaceutical composition comprising an effective amount of one or more isolated human monoclonal antibodies or fragments thereof that bind to Bet v 1, to a patient in need thereof, wherein the sensitivity to, or an allergic reaction against, a Fagales allergen, or Fagales related allergen, is either prevented, or lessened in severity and/or duration, or at least one symptom or complication associated with the sensitivity to, or allergic reaction against, a Fagales allergen, or Fagales related allergen, is prevented, or ameliorated, or that the frequency and/or duration of, or the severity of the sensitivity to or allergic reaction against, a Fagales allergen, or Fagales related allergen, is reduced following administration of one or more of the isolated human monoclonal antibodies or fragments thereof that bind Bet v 1, or following administration of a composition comprising any one or more of the foregoing antibodies.

In some embodiments, the one or more Fagales allergens is selected from the group consisting of Bet v 1, Aln g1, Cor a1, Car b1, and Que a1.

In one embodiment, the invention provides a pharmaceutical composition comprising one or more of the antibodies described herein that bind natural Bet v 1, *Betula pendula* BPE, *Betula nigra* BPE, and *Betula populifolia* BPE for use in treating a patient who demonstrates a sensitivity to, or an allergic reaction against, a Fagales protein, birch pollen or an extract thereof, or Bet v 1 protein, or for treating at least one symptom or complication associated with a sensitivity to, or allergic reaction against, a Fagales protein, birch pollen or an extract thereof, or Bet v 1 protein, wherein the sensitivity to, or an allergic reaction against, a Fagales protein, birch pollen or an extract thereof, or Bet v 1 protein is either prevented, or lessened in severity and/or duration, or at least one symptom or complication associated with the sensitivity to, or allergic reaction against, a Fagales protein, birch pollen or an extract thereof, or Bet v 1 protein is prevented, or ameliorated, or that the frequency and/or duration of, or the severity of the sensitivity to or allergic reaction against, a Fagales protein, birch pollen or an extract thereof, or Bet v 1 protein is reduced.

In one embodiment, the invention provides for use of a pharmaceutical composition comprising one or more of the antibodies of the invention that binds to Bet v 1 in the manufacture of a medicament for use in treating a patient who demonstrates a sensitivity to, or an allergic reaction against, birch pollen or an extract thereof, or to Bet v 1 protein, or for treating at least one symptom or complication associated with a sensitivity to, or allergic reaction against, birch pollen or an extract thereof, or to Bet v 1 protein, wherein the sensitivity to, or an allergic reaction against, birch pollen or an extract thereof, or to Bet v 1 protein is either prevented, or lessened in severity and/or duration, or at least one symptom or complication associated with the sensitivity to, or allergic reaction against, birch pollen or an extract thereof, or to Bet v 1 protein is prevented, or ameliorated, or that the frequency and/or duration of, or the severity of the sensitivity to or allergic reaction against, birch pollen or an extract thereof, or to Bet v 1 protein is reduced.

In one embodiment, the invention provides use of a pharmaceutical composition as described above, wherein the composition is administered in combination with a second therapeutic agent useful for diminishing an allergic reaction to a Fagales protein, birch pollen or an extract thereof, or Bet v 1 protein. In one embodiment, the invention provides for use of the pharmaceutical composition as described above, wherein the second therapeutic agent is selected from a corticosteroid, a bronchial dilator, an antihistamine, epinephrine, a decongestant, another different antibody to Bet v 1 and a peptide vaccine.

In certain embodiments, the antibodies of the invention that bind to Bet v 1 may be capable of reducing, minimizing, or preventing at least one symptom in a patient sensitive to birch pollen or Bet v 1, such as sneezing, congestion, nasal blockage, coughing, wheezing, bronchoconstriction, rhinitis, or conjunctivitis.

In one embodiment, the antibodies of the invention that bind to Bet v 1, or a composition comprising one or more antibodies of the invention may be used to prevent more serious in vivo complications associated with an allergy to Bet v 1, including asthmatic responses, anaphylactic shock, or even death resulting from anaphylaxis.

In one embodiment, the pharmaceutical composition is administered to the patient in combination with a second therapeutic agent.

In another embodiment, the second therapeutic agent is selected from the group consisting of an antihistamine, epinephrine, a decongestant, a corticosteroid, another different antibody to Bet v 1, a peptide vaccine and any other palliative therapy useful for reducing the severity of the allergic reaction or for ameliorating at least one symptom associated with the allergic reaction.

In yet another embodiment, the pharmaceutical composition is administered concurrently with, prior to, or subsequent to, one or more other desired therapeutics or medical procedures, including, for example, administered prior to or concurrently with an allergen-specific immunotherapy (SIT) regimen. In some aspects, use of a SIT regimen together with the antibodies provided herein provides a synergistic effect.

In one embodiment, a method is provided for enhancing the efficacy and/or safety of an allergen-specific immunotherapy (SIT) regimen, the method comprising administering an effective amount of one or more isolated human monoclonal antibodies or antigen-binding fragments thereof, as provided herein, or a pharmaceutical composition comprising an effective amount of one or more isolated human monoclonal antibodies or fragments thereof, to a patient in need thereof just prior to or concurrent with the SIT regimen, wherein the severity of an allergic reaction to the SIT regimen is mitigated. In some embodiments, the SIT regimen comprises an up-dosing phase followed by a maintenance phase. In some embodiments, the SIT regimen is a rush SIT regimen.

In an additional aspect, a method is provided for preventing or reducing mast cell degranulation associated with Fagales protein, Fagales related allergen, birch pollen or birch pollen extract, or Bet v 1 sensitization, the method comprising administering a pharmaceutical composition described herein to a patient in need thereof.

In some embodiments, the BPE is selected from the group consisting of natural Bet v 1, *Betula pendula* BPE, *Betula nigra* BPE, and *Betula populifolia* BPE.

Other embodiments will become apparent from a review of the ensuing detailed description.

BRIEF DESCRIPTION OF THE FIGURES

FIG. 1 provides H/D exchange/MS epitope mapping for interaction of H4H16992P with Bet v 1.

FIG. 2 provides H/D exchange/MS epitope mapping for interaction of H4H17082P with Bet v 1.

FIG. 3 provides H/D exchange/MS epitope mapping for interaction of H4H17038P2 with Bet v 1.

FIG. 4 provides H/D exchange/MS epitope mapping for interaction of H4H16987P with Bet v 1.

FIG. 5 provides H/D exchange/MS epitope mapping for interaction of H4H16992P, H4H17082P, H4H17038P2 and H4H16987P with Bet v 1.

DESCRIPTION

Figure 6:
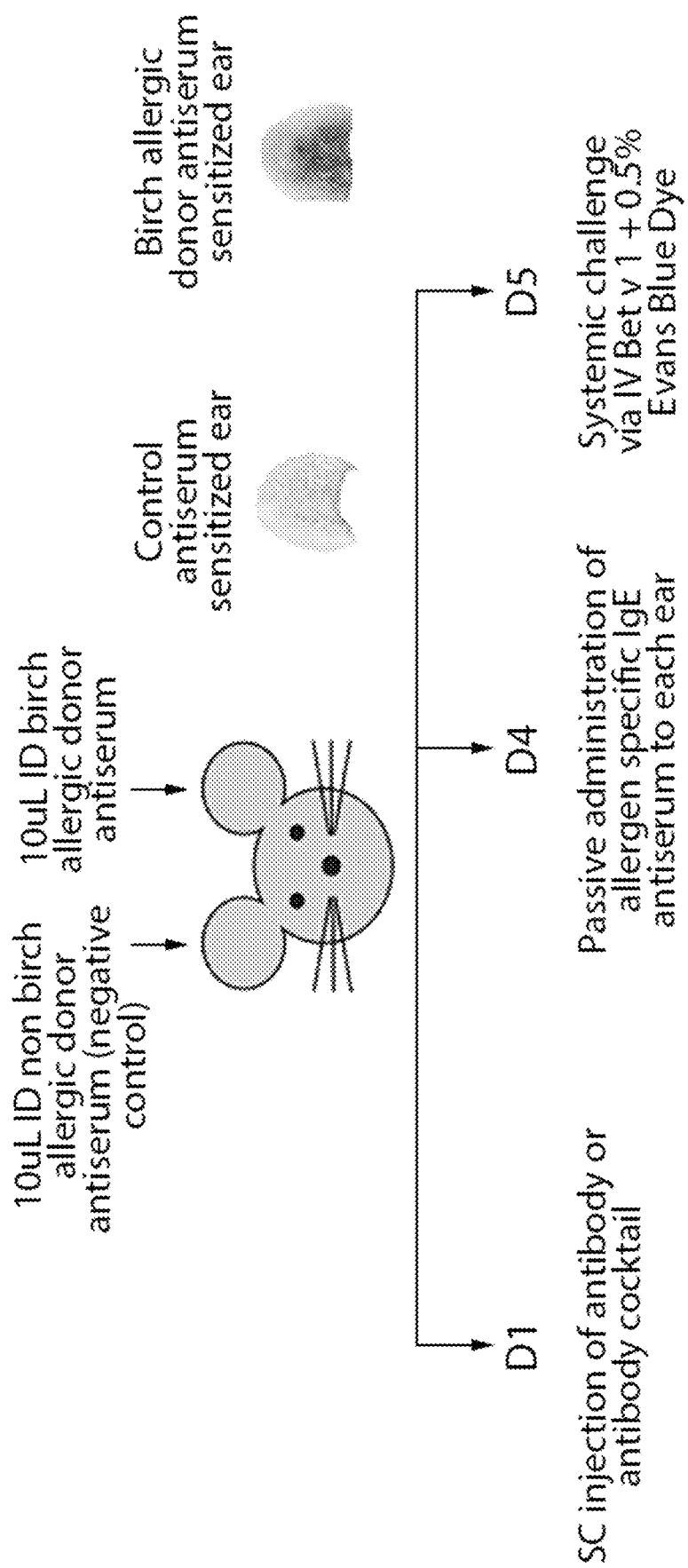
FIG. 6 is a diagram of the protocol used to determine the effectiveness of the antibody combinations in blocking mast cell degranulation induced by Bet v 1 in a humanized mouse PCA model.

Before the present compositions and methods are described, it is to be understood that this invention is not limited to particular compositions and methods, and experimental conditions described, as such methods, compositions, and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, preferred methods and materials are now described.

Definitions

The term "Bet v 1" as used herein, refers to at least one Bet v 1 protein, either in natural/native form, or recombinantly produced. The Bet v 1 protein comprises the amino acid sequence of SEQ ID NO: 306 and the nucleic acid sequence of SEQ ID NO: 305. The natural Bet v 1 protein is approximately 17 kD and exists as a 7 stranded antiparallel β-sheet (β1-β7), two short α-helices (α1 and α2) connecting β1 and β2, a long C-terminal α-helix (α3), and the glycine-rich loop motif between 2 and 3 (Kofler et al. (2012) *J. Mol. Biol.* 422(1): 109-123). A recombinantly produced mutant Bet v 1, SEQ ID NO: 312, comprises G2-N160 of Uniprot P15494 with a S85A substitution and contains a Myc-Myc-hexahistidine tag. The Bet v 1 amino acid sequence from Uniprot: P15494, i.e. SEQ ID NO: 314, can also refer to Bet v 1.

"Bet v 1" is a polypeptide comprising, or alternatively, consisting of, an amino acid sequence of SEQ ID NO: 306 or SEQ ID NO: 314, or a homologous sequence thereof. The phrase "homologous sequence of SEQ ID NO: 306 or SEQ ID NO: 314", as used herein, refers to a polypeptide that has an identity to SEQ ID NO: 306 or SEQ ID NO: 314 which is greater than 70%, preferably greater than 80%, more preferably greater than 90%, and even more preferably greater than 95%.

The term "Bet v 1 fragment" as used herein, refers to a polypeptide comprising or alternatively consisting of, at least one antigenic site of Bet v 1. In one embodiment, the term "Bet v 1 fragment" as used herein, refers to a polypeptide comprising or alternatively consisting of at least two antigenic sites of Bet v 1. In one embodiment, the antigenic sites are covalently linked. In one embodiment, the antigenic sites are linked by at least one peptide bond. In one embodiment, the two antigenic sites are linked by at least one peptide bond and a spacer between the antigenic sites. In one embodiment, the at least two antigenic sites comprise amino acid sequences 23-44 and 44-56 of Uniprot P15494. In one embodiment, the at least two antigenic sites comprise an amino acid sequence within any of SEQ ID NOs: 306, 307, 308, 309, 310, 311, and 315. In one embodiment, any of the Bet v 1 fragments are capable of inducing the production of antibodies in vivo that specifically bind to naturally occurring Bet v 1, or to recombinantly produced Bet v 1.

The term "antibody", as used herein, means any antigen-binding molecule or molecular complex comprising at least one complementarity determining region (CDR) that specifically binds to or interacts with a particular antigen (e.g., Bet v 1). The term "antibody", as used herein, is intended to refer to immunoglobulin molecules comprised of four polypeptide chains, two heavy (H) chains and two light (L) chains inter-connected by disulfide bonds (i.e., "full antibody molecules"), as well as multimers thereof (e.g. IgM) or antigen-binding fragments thereof. Each heavy chain is comprised of a heavy chain variable region ("HCVR" or "$V_H$") and a heavy chain constant region (comprised of domains $C_H1$, $C_H2$ and $C_H3$). Each light chain is comprised of a light chain variable region ("LCVR or "$V_L$") and a light chain constant region ($C_L$). The $V_H$ and $V_L$ regions can be further subdivided into regions of hypervariability, termed complementarity determining regions (CDR), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In certain embodiments of the invention, the FRs of the antibody (or antigen binding fragment thereof) may be identical to the human germline sequences, or may be naturally or artificially modified. An amino acid consensus sequence may be defined based on a side-by-side analysis of two or more CDRs.

Substitution of one or more CDR residues or omission of one or more CDRs is also possible. Antibodies have been described in the scientific literature in which one or two CDRs can be dispensed with for binding. Padlan et al. (1995, *FASEB J.* 9:133-139) analyzed the contact regions between antibodies and their antigens, based on published crystal structures, and concluded that only about one fifth to one third of CDR residues actually contact the antigen. Padlan also found many antibodies in which one or two CDRs had no amino acids in contact with an antigen (see also, Vajdos et al., 2002, *J Mol Biol* 320:415-428).

CDR residues not contacting antigen can be identified based on previous studies (for example residues H60-H65 in CDRH2 are often not required), from regions of Kabat CDRs lying outside Chothia CDRs, by molecular modeling and/or empirically. If a CDR or residue(s) thereof is omitted, it is usually substituted with an amino acid occupying the corresponding position in another human antibody sequence or a consensus of such sequences. Positions for substitution within CDRs and amino acids to substitute can also be selected empirically. Empirical substitutions can be conservative or non-conservative substitutions.

The fully human monoclonal antibodies that specifically bind to Bet v 1, as disclosed herein, may comprise one or more amino acid substitutions, insertions and/or deletions in the framework and/or CDR regions of the heavy and light chain variable domains as compared to the corresponding germline sequences. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived).

Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes fully human monoclonal antibodies comprising variants of any of the HCVR, LCVR, and/or CDR amino acid sequences disclosed herein having one or more conservative substitutions. For example, the present invention includes antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "human antibody", as used herein, is intended to include non-naturally occurring human antibodies. The term includes antibodies that are recombinantly produced in a non-human mammal, or in cells of a non-human mammal. The term is not intended to include antibodies isolated from or generated in a human subject.

The antibodies of the invention may, in some embodiments, be recombinant and/or non-naturally occurring human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al., 1992, *Nucl. Acids Res.* 20:6287-6295) or antibodies prepared, expressed, created or isolated by any other means that involves splicing of human immunoglobulin gene sequences to other DNA sequences. In certain embodiments, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al., 1993, *Molecular Immunology* 30:105) to levels typically observed using a human IgG1 hinge. The instant invention encompasses antibodies having one or more mutations in the hinge, $C_H2$ or $C_H3$ region, which may be desirable, for example, in production, to improve the yield of the desired antibody form.

As used herein, the expression "antigen-binding molecule" means a protein, polypeptide or molecular complex comprising or consisting of at least one complementarity determining region (CDR) that alone, or in combination with one or more additional CDRs and/or framework regions (FRs), specifically binds to a particular antigen. In certain embodiments, an antigen-binding molecule is an antibody or a fragment of an antibody, as those terms are defined elsewhere herein.

The phrase "specifically binds" or "binds specifically to" or the like, means that an antibody or antigen-binding fragment thereof forms a complex with an antigen that is relatively stable under physiologic conditions. Specific binding can be characterized by an equilibrium dissociation constant of at least about $1 \times 10^{-6}$ M or less (e.g., a smaller $K_D$ denotes a tighter binding). Methods for determining whether two molecules specifically bind are well known in the art and include, for example, equilibrium dialysis, surface plasmon resonance, and the like. As described herein, antibodies have been identified by surface plasmon resonance, e.g., BIACORE™, which bind specifically to Bet v 1.

The phrase "high affinity" antibody refers to those monoclonal antibodies having a binding affinity to Bet v 1, expressed as $K_D$, of at least $10^{-8}$ M; preferably $10^{-9}$ M; more preferably $10^{-10}$ M, even more preferably $10^{-11}$ M, even more preferably $10^{-12}$ M, as measured by surface plasmon resonance, e.g., BIACORE™ or solution-affinity ELISA.

By the term "slow off rate", "Koff" or "kd" is meant an antibody that dissociates from Bet v 1, with a rate constant of $1 \times 10^{-3}$ s$^{-1}$ or less, preferably $1 \times 10^{-4}$ s$^{-1}$ or less, as determined by surface plasmon resonance, e.g., BIACORE™.

The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to bind to Bet v 1.

The specific embodiments, antibody or antibody fragments of the invention may be conjugated to a therapeutic moiety ("immunoconjugate"), such as a corticosteroid, a second anti-Bet v 1 antibody, or epinephrine, a vaccine, or any other therapeutic moiety useful for treating an allergic response to Bet v 1.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

According to certain embodiments, an isolated antibody may be substantially free of other antibodies (Abs) having different antigenic specificities (e.g., an isolated antibody that specifically binds Bet v 1, or a fragment thereof, is substantially free of Abs that specifically bind antigens other than Fagales antigens, or in some aspects, other than Bet v 1.

A "blocking antibody" or a "neutralizing antibody", as used herein (or an "antibody that neutralizes Bet v 1 activity"), is intended to refer to an antibody, or an antigen binding portion thereof, whose binding to Bet v 1 results in inhibition of at least one biological activity of Bet v 1. For example, an antibody of the invention may aid in preventing the primary allergic response to Bet v 1. Alternatively, an antibody of the invention may demonstrate the ability to prevent a secondary allergic response to Bet v 1, or at least one symptom of an allergic response to Bet v 1, including sneezing, coughing, an asthmatic condition, or an anaphylactic response caused by Bet v 1. This inhibition of the biological activity of Bet v 1 can be assessed by measuring one or more indicators of Bet v 1 biological activity by one or more of several standard in vitro or in vivo assays (such as a passive cutaneous anaphylaxis assay, as described herein) or other in vivo assays known in the art (for example, other animal models to look at protection from challenge with Bet v 1 following administration of one or more of the antibodies described herein).

The term "surface plasmon resonance", as used herein, refers to an optical phenomenon that allows for the analysis of real-time biomolecular interactions by detection of alterations in protein concentrations within a biosensor matrix, for example using the BIACORE™ system (Pharmacia Biosensor AB, Uppsala, Sweden and Piscataway, N.J.).

The term "$K_D$", as used herein, is intended to refer to the equilibrium dissociation constant of a particular antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. The term "epitope" also refers to a site on an antigen to which B and/or T cells respond. It also refers to a region of an antigen that is bound by an antibody. Epitopes may be either linear or conformational. A linear epitope is one produced by adjacent amino acid residues in a polypeptide chain. A conformational epitope is produced by spatially juxtaposed amino acids from different segments of the linear polypeptide chain. In certain embodiments, epitopes may include determinants that are chemically active surface groupings of molecules such as amino acids, sugar side chains, phosphoryl groups, or sulfonyl groups, and, in certain embodiments, may have specific three-dimensional structural characteristics, and/or specific charge characteristics. Epitopes may also be defined as structural or functional. Functional epitopes are generally a subset of the structural epitopes and have those residues that directly contribute to the affinity of the interaction. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5 or 8-10 amino acids in a unique spatial conformation.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 90%, and more preferably at least about 95%, 96%, 97%, 98% or 99% of the nucleotide bases, as measured by any well-known algorithm of sequence identity, such as FASTA, BLAST or GAP, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 90% sequence identity, even more preferably at least 95%, 98% or 99% sequence identity. Preferably, residue positions, which are not identical, differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent or degree of similarity may be adjusted upwards to correct for the conservative nature of the substitution. Means for making this adjustment are well known to those of skill in the art. (See, e.g., Pearson, 1994, Methods Mol. Biol. 24: 307-331). Examples of groups of amino acids that have side chains with similar chemical properties include 1) aliphatic side chains: glycine, alanine, valine, leucine and isoleucine; 2) aliphatic-hydroxyl side chains: serine and threonine; 3) amide-containing side chains: asparagine and glutamine; 4) aromatic side chains: phenylalanine, tyrosine, and tryptophan; 5) basic side chains: lysine, arginine, and histidine; 6) acidic side chains: aspartate and glutamate, and 7) sulfur-containing side chains: cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992 *Science* 256: 1443-45). A "moderately conservative" replacement is any change having a nonnegative value in the PAM250 log-likelihood matrix.

Sequence similarity for polypeptides is typically measured using sequence analysis software. Protein analysis software matches similar sequences using measures of similarity assigned to various substitutions, deletions and other modifications, including conservative amino acid substitutions. For instance, GCG software contains programs such as GAP and BESTFIT which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA with default or recommended parameters; a program in GCG Version 6.1. FASTA (e.g., FASTA2 and FASTA3) provides alignments and percent sequence identity of the regions of the best overlap between the query and search sequences (Pearson, 2000 supra). Another preferred algorithm when comparing a sequence of the invention to a database containing a large number of sequences from different organisms is the computer program BLAST, especially BLASTP or TBLASTN, using default parameters. (See, e.g., Altschul et al., 1990, *J. Mol. Biol.* 215: 403-410 and 1997 *Nucleic Acids Res.* 25:3389-3402).

By the phrase "therapeutically effective amount" is meant an amount that produces the desired effect for which it is administered. The exact amount will depend on the purpose of the treatment, and will be ascertainable by one skilled in the art using known techniques (see, for example, Lloyd (1999) The Art, Science and Technology of Pharmaceutical Compounding).

The antibodies of the invention may be used to "desensitize" a Fagales allergic individual. The term to "desensitize" is defined herein as to decrease the allergic-reactivity of a Fagales allergic individual to exposure to a Fagales allergen, such as birch pollen, e.g. Bet v 1, Aln g1, Cor a1, Car b1, Que a1, Api g2, Api g1, Dau c1, Mal d1, Ost c1, Fag s, and/or Cas s1 (to a level less than that which the Fagales allergic individual would otherwise experience), or to a Fagales related allergen. The term "desensitize" is further defined herein as to decrease the allergic-reactivity of an individual to PR-10 proteins including Act c 8 and Act d 8 (kiwi), Ara h 8 (peanut), Pru ar 1 (apricot), Pru av 1 (cherry), Pru p 1 (peach), Pyr c 1 (pear), Gly m 4 (soybean), Vig r 1 (mung bean), Sola I 4 (tomato), Cuc m 3 (melon), Rub i 1 (raspberry), and Fra a 1 (strawberry).

General Description

Trees belonging to the order of Fagales are the source of spring allergy symptoms, and the major birch allergen, Bet v 1 is responsible for IgE binding in more than 95% of birch pollen allergic patients (Breiteneder, EMBO J. 1989, 8(7): 1935-8). Birch is the predominant trigger in 23% of US and 14% of European allergy patients. (DataMonitor report on Allergic Rhinitis, July, 2010). The severity of the symptoms in individuals who demonstrate a sensitivity to birch pollen ranges from a relatively mild rhinitis and conjunctivitis to a potentially life-threatening asthmatic condition. It has been shown that greater than 60% of patients who are allergic to birch pollen have IgE antibodies to this Bet v 1 (Jarolim et al., Int Arch Allergy Appl Immunol. 1989, 88(1-2):180-2).

Fagales trees show a distinct geographical distribution where birch and alder are endemic in the northern parts of Europe and North America, while hazel, hornbeam and oak prefer a warmer climate, thus populating rather the southern parts of these continents. Co-populations of all five species are frequently found in temperate climate zones 5. (Spieksma FTM. Regional European pollen calendars. D'Amato G, Spieksma FTM, Bonini S, editors. Allergenic pollen and pollinosis in Europe. Hoboken, N.J.: Wiley-Blackwell; 1991. pp. 49-65) Several Betulaceae trees including alder, hazel and hornbeam have the potential to initiate sensitization to Bet v 1-like allergens in susceptible individuals resulting in the production of highly cross-reactive IgE antibodies. (Hauser, et al., 2011, Clin Exp Allergy. 41: 1804-14)

The Fagales order allergens, or Fagales allergens, as defined herein include birch pollen (Bet v 1), alder pollen (Aln g1 and Aln g4), hazel pollen (Cor a1, Cor a2, Cor a8, Cor a9, Cor a10, Cor a11, Cor a12, Cor a13, and Cor a14), hornbeam pollen (Car b), hop-hornbeam pollen (Ost c1), chestnut pollen (Cas s1, Cas s5, Cas s8, and Cas s9), beech pollen (Fag s1) and white oak pollen (Que a1 and Que a2). Of the non-birch pollens, Aln g1, Cor a1, Car b1, Ost c1, Cas s1, Fag s1, and Que a1 are like or related to Bet v 1, i.e. Fagales related allergens. These allergens are also expressed in nuts of the Fagales trees, and in the fruits of unrelated trees belonging to the order Rosales. Cross-reactivity of these allergens may prompt symptoms of food allergy in pollen allergic patients. Exemplary cross-reactive food allergies include apple, cherry, apricot, pear, medicago, pea, soybean, tomato, celery, carrot, and asparagus. (Allergens and Allergen Immunotherapy: Subcutaneous, Sublingual, and Oral, 5' Edition. Richard F. Lockey, Dennis K. Ledford, editors. CRC Press, Taylor & Francis Group, London, N Y, 2014. pp. 114, 118-119).

As used herein, the phrase "Fagales allergen" includes Fagales related allergens. In some embodiments, the "Fagales related allergen" is defined as a protein having an overall sequence homology with Bet v 1 of at least about 35%, or a sequence homology with epitope 1 of Bet v 1 of at least about 50%, or a sequence homology with epitope 2 of Bet v 1 of at least about 40%, or a sequence homology with epitope 3 of Bet v 1 of at least about 25%, or a sequence homology with epitope 4 of Bet v 1 of at least about 15%. In some embodiments, the "Fagales related allergen" is defined as a protein to which the anti-Bet v 1 antibodies cross-react, including allergens from the Rosales order.

Immunoglobulin E (IgE) is responsible for type 1 hypersensitivity, which manifests itself in allergic rhinitis, allergic conjunctivitis, hay fever, allergic asthma, bee venom allergy, and food allergies. IgE circulates in the blood and binds to high-affinity Fc receptors for IgE on basophils and mast cells. In most allergic responses, the allergens enter the body through inhalation, ingestion, or through the skin. The allergen then binds to preformed IgE already bound to the high affinity receptor on the surfaces of mast cells and basophils, resulting in cross-linking of several IgE molecules and triggering the release of histamine and other inflammatory mediators causing the various allergic symptoms.

The treatment for birch pollen allergies includes desensitization therapy, which involves repeated injections with increasing dosages of either a crude birch pollen extract, or short peptides derived from Bet v 1. Insufficiencies of allergen specific immunotherapy include long treatment duration resulting in patient compliance issues, and frequent allergic reactions (up to 30%) to the injected protein. Desensitization therapy can take several years before the treatment is considered effective. Successful treatment is dependent on composition and quality of extract, and treatment is contraindicated in patients with severe asthma/food allergies due to risk of IgE mediated severe adverse events. Accordingly, there is a need in the field of birch pollen allergy treatment for alternative strategies for treating patients sensitive to Fagales allergens, in particular Bet v 1.

Antibodies have been proposed as a general treatment strategy for allergies, since they may be able to block the entry of allergenic molecules into the mucosal tissues, or may bind the allergen before it has the opportunity to bind to the IgE bound to the high affinity receptor on mast cells or basophils, thus preventing the release of histamine and other inflammatory mediators from these cells. U.S. Pat. No. 5,670,626 describes the use of monoclonal antibodies for the treatment of IgE-mediated allergic diseases such as allergic rhinitis, allergic asthma, and allergic conjunctivitis by blocking the binding of allergens to the mucosal tissue. U.S. Pat. No. 6,849,259 describes the use of allergen-specific antibodies to inhibit allergic inflammation in an in vivo mouse model of allergy. Milk-based and egg-based antibody systems have been described. For example, US20030003133A1 discloses using milk as a carrier for allergens for inducing oral tolerance to birch pollen and other allergens. Compositions and methods for reducing an allergic response in an animal to an allergen in the environment through use of a molecule that inhibits the ability of the allergen to bind to mast cells were described in WO1994/024164A2. Other antibodies to Bet v 1 were mentioned in U.S. 2010/0034812.

The fully human antibodies described herein demonstrate specific binding to Bet v 1 and may be useful for treating patients suffering from birch pollen allergies, in particular, in patients who demonstrate sensitivity to the Bet v 1 allergen. The use of such antibodies may be an effective means of treating patients suffering from allergies to pollen from Fagales trees, or they may be used to prevent a heightened response to Bet v 1 upon secondary exposure, or the accompanying symptoms associated with the allergy, or may be used to lessen the severity and/or the duration of the allergic response associated with a primary exposure to birch pollen allergen or with the recurrence of the symptoms upon secondary exposure. They may be used alone or as adjunct therapy with other therapeutic moieties or modalities known in the art for treating such allergies, such as, but not limited to, treatment with corticosteroids or epinephrine. They may be used in conjunction with a second or third different antibody specific for Bet v 1. They may be used with allergen-specific immunotherapy (SIT). In some embodiments, the combination with SIT results is synergistically effective.

Unlike desensitization therapy, treatment with the antibodies described herein can provide effective relief within about 2 weeks of starting treatment, or within about 10 days or about 8 days of starting treatment. In combination with exposure to Bet v 1 protein or peptides, or one or more additional Fagales allergens, treatment with the fully human antibodies described herein can not only block an allergic reaction, but can more effectively or synergistically desensitize patients suffering from allergies to pollen from Fagales trees.

In certain embodiments, the antibodies of the invention are obtained from mice immunized with a primary immunogen, such as natural Bet v 1, which may be purchased commercially (e.g., from Indoor Biotechnologies, VA, #NA-BV1-1), or may be produced recombinantly. The full-length amino acid sequence of Bet v 1 is shown as SEQ ID NO: 306. The full-length Bet v 1 amino acid sequence may also be found in SEQ ID NO: 314, from Uniprot: P15494.

The immunogen may be a biologically active and/or immunogenic fragment of natural, native, or recombinantly produced Bet v 1, or DNA encoding the active fragment thereof. The fragment may be derived from either the N-terminal or C-terminal of Bet v 1, or from any site within the Bet v 1 amino acid sequence.

Antigen-Binding Fragments of Antibodies

Unless specifically indicated otherwise, the term "antibody," as used herein, shall be understood to encompass antibody molecules comprising two immunoglobulin heavy chains and two immunoglobulin light chains (i.e., "full antibody molecules") as well as antigen-binding fragments thereof. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. The terms "antigen-binding portion" of an antibody, or "antibody fragment", as used herein, refers to one or more fragments of an antibody that retain the ability to specifically bind to Bet v 1. An antibody fragment may include a Fab fragment, a F(ab')$_2$ fragment, a Fv fragment, a dAb fragment, a fragment containing a CDR, or an isolated CDR. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and (optionally) constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR, which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H$1; (ii) $V_H$-$C_H$2; (iii) $V_H$-$C_H$3; (iv) $V_H$-$C_H$1-$C_H$2; (v) $V_H$-$C_H$1-$C_H$2-$C_H$3; (vi) $V_H$-$C_H$2-$C_H$3; (vii) $V_H$-$C_L$; (viii) $V_L$-$C_H$1; (ix) $V_L$-$C_H$2; (x) $V_L$-$C_H$3; (xi) $V_L$-$C_H$1-$C_H$2; (xii) $V_L$-$C_H$1-$C_H$2-$C_H$3; (xiii) $V_L$-$C_H$2-$C_H$3; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids, which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

Preparation of Human Antibodies

Methods for generating human antibodies in transgenic mice are known in the art. Any such known methods can be used in the context of the present invention to make human antibodies that specifically bind to Bet v 1.

Using VELOCIMMUNE™ technology (see, for example, U.S. Pat. No. 6,596,541, Regeneron Pharmaceuticals, VELOCIMMUNE®) or any other known method for generating monoclonal antibodies, high affinity chimeric antibodies to Bet v 1 are initially isolated having a human variable region and a mouse constant region. The VELOCIMMUNE® technology involves generation of a transgenic mouse having a genome comprising human heavy and light chain variable regions operably linked to endogenous mouse constant region loci such that the mouse produces an antibody comprising a human variable region and a mouse constant region in response to antigenic stimulation. The DNA encoding the variable regions of the heavy and light chains of the antibody are isolated and operably linked to DNA encoding the human heavy and light chain constant regions. The DNA is then expressed in a cell capable of expressing the fully human antibody.

Generally, a VELOCIMMUNE® mouse is challenged with the antigen of interest, and lymphatic cells (such as B-cells) are recovered from the mice that express antibodies. The lymphatic cells may be fused with a myeloma cell line to prepare immortal hybridoma cell lines, and such hybridoma cell lines are screened and selected to identify hybridoma cell lines that produce antibodies specific to the antigen of interest. DNA encoding the variable regions of the heavy chain and light chain may be isolated and linked to desirable isotypic constant regions of the heavy chain and light chain. Such an antibody protein may be produced in a cell, such as a CHO cell. Alternatively, DNA encoding the antigen-specific chimeric antibodies or the variable domains of the light and heavy chains may be isolated directly from antigen-specific lymphocytes.

Initially, high affinity chimeric antibodies are isolated having a human variable region and a mouse constant region. As in the experimental section below, the antibodies are characterized and selected for desirable characteristics, including affinity, selectivity, epitope, etc. The mouse constant regions are replaced with a desired human constant region to generate the fully human antibody of the invention, for example wild-type or modified IgG1 or IgG4. While the constant region selected may vary according to specific use, high affinity antigen-binding and target specificity characteristics reside in the variable region.

In general, the antibodies of the instant invention possess very high affinities, typically possessing $K_D$ of from about $10^{-12}$ through about $10^{-9}$ M, when measured by binding to antigen either immobilized on solid phase or in solution phase. The mouse constant regions are replaced with desired human constant regions to generate the fully human antibodies of the invention. While the constant region selected may vary according to specific use, high affinity antigen-binding and target specificity characteristics reside in the variable region.

Bioequivalents

The anti-Bet v 1 antibodies and antibody fragments of the present invention encompass proteins having amino acid sequences that vary from those of the described antibodies, but that retain the ability to bind Bet v 1. Such variant antibodies and antibody fragments comprise one or more additions, deletions, or substitutions of amino acids when compared to parent sequence, but exhibit biological activity that is essentially equivalent to that of the described antibodies. Likewise, the antibody-encoding DNA sequences of the present invention encompass sequences that comprise one or more additions, deletions, or substitutions of nucleotides when compared to the disclosed sequence, but that encode an antibody or antibody fragment that is essentially bioequivalent to an antibody or antibody fragment of the invention.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and/or in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of the antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation. In other contexts, bioequivalent antibodies may include antibody variants comprising amino acid changes, which modify the glycosylation characteristics of the antibodies, e.g., mutations that eliminate or remove glycosylation.

Biological Characteristics of the Antibodies

In general, the antibodies of the present invention may function by binding to Bet v 1, a fragment of Bet v 1, or to Bet v 1 and one or more Fagales allergens or Fagales related allergens.

In certain embodiments, the antibodies of the present invention may bind to an epitope or fragment located within the Bet v 1 protein, for example, an epitope or fragment encompassing amino acid residues ranging from about position 23 to about position 43 of SEQ ID NO: 306; an epitope or fragment encompassing amino acid residues ranging from about position 44 to about 56 of SEQ ID NO: 306; an epitope or fragment encompassing amino acid residues ranging from about 2 to about 19 of SEQ ID NO: 306; an epitope or fragment encompassing amino acid residues ranging from about 57 to about 70 of SEQ ID NO: 306; or an epitope or fragment encompassing amino acid residues ranging from about 81 to about 89 or about 81 to about 96 of SEQ ID NO: 306. In certain embodiments, the antibodies of the present invention may bind to at least one amino acid sequence selected from the group consisting of SEQ ID NOs: 307, 308, 309, 310, 311, and 315, wherein an epitope sequence can be extended by 1 to 5 amino acids, or about 5 to about 10 amino acids on either the C-terminal end or the N-terminal end.

In certain embodiments, the antibodies of the present invention may function by blocking or inhibiting the binding of IgE to mast cells or basophils in a patient sensitive to the Bet v 1 allergen. In certain embodiments, the antibodies provided herein inhibit or block basophil activation by, for example, at least about 70%, when compared to an isotype control antibody. In certain embodiments, the antibodies inhibit or block mast cell degranulation by, for example, at least about 70%, or at least about 75%, or at least about 80%, or at least about 85%, or at least about 90%, or at least about 95%, when compared to an isotype control antibody.

In one embodiment, the invention provides a fully human monoclonal antibody or antigen-binding fragment thereof that binds to Bet v 1, wherein the antibody or fragment thereof exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 282, and 290, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, and 298, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 288, and 296, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, and 304, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 284, and 292, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 286, and 294, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, and 300, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, and 302, or a substantially similar sequence thereof having at least 90%, at least 95%, at least 98% or at least 99% sequence identity; (v) binds to Bet v 1 with a $K_D$ equal to or less than $10^{-8}$ or in a range from about $10^{-8}$ to about $10^{-11}$; (vi) demonstrates efficacy in at least one animal model of anaphylaxis or inflammation; or (vii) competes with a reference antibody for binding to Bet v 1.

In one embodiment, the invention provides for the use of a combination of two or more fully human antibodies of the invention, or fragments thereof, for preparation of a composition, wherein the antibodies bind to Bet v 1, and wherein each antibody or fragment thereof contained within the composition exhibits one or more of the following characteristics: (i) comprises a HCVR having an amino acid sequence selected from the group consisting of SEQ ID NO: 2, 18, 34, 50, 66, 82, 98, 114, 130, 146, 162, 178, 194, 210, 226, 242, 258, 274, 282, and 290, or a substantially similar sequence thereof having at least 90%, at least 95%, at least 98% or at least 99% sequence identity; (ii) comprises a LCVR having an amino acid sequence selected from the group consisting of SEQ ID NO: 10, 26, 42, 58, 74, 90, 106, 122, 138, 154, 170, 186, 202, 218, 234, 250, 266, and 298, or a substantially similar sequence thereof having at least 90%, at least 95%, at least 98% or at least 99% sequence identity; (iii) comprises a HCDR3 domain having an amino acid sequence selected from the group consisting of SEQ ID NO: 8, 24, 40, 56, 72, 88, 104, 120, 136, 152, 168, 184, 200, 216, 232, 248, 264, 280, 288, and 296, or a substantially similar sequence thereof having at least 90%, at least 95%, at least 98% or at least 99% sequence identity; and a LCDR3 domain having an amino acid sequence selected from the group consisting of SEQ ID NO: 16, 32, 48, 64, 80, 96, 112, 128, 144, 160, 176, 192, 208, 224, 240, 256, 272, and 304, or a substantially similar sequence thereof having at least 90%, at least 95%, at least 98% or at least 99% sequence identity; (iv) comprises a HCDR1 domain having an amino acid sequence selected from the group consisting of SEQ ID NO: 4, 20, 36, 52, 68, 84, 100, 116, 132, 148, 164, 180, 196, 212, 228, 244, 260, 276, 284, and 292, or a substantially similar sequence thereof having at least 90%, at least 95%, at least 98% or at least 99% sequence identity; a HCDR2 domain having an amino acid sequence selected from the group consisting of SEQ ID NO: 6, 22, 38, 54, 70, 86, 102, 118, 134, 150, 166, 182, 198, 214, 230, 246, 262, 278, 286, and 294, or a substantially similar sequence thereof having at least 90%, at least 95%, at least 98% or at least 99% sequence identity; a LCDR1 domain having an amino acid sequence selected from the group consisting of SEQ ID NO: 12, 28, 44, 60, 76, 92, 108, 124, 140, 156, 172, 188, 204, 220, 236, 252, 268, and 300, or a substantially similar sequence thereof having at least 90%, at least 95%, at least 98% or at least 99% sequence identity; and a LCDR2 domain having an amino acid sequence selected from the group consisting of SEQ ID NO: 14, 30, 46, 62, 78, 94, 110, 126, 142, 158, 174, 190, 206, 222, 238, 254, 270, and 302, or a substantially similar sequence thereof having at least 90%, at least 95%, at least 98% or at least 99% sequence identity; (v) binds to Bet v 1 with a $K_D$ equal to or less than $10^{-8}$ or in a range from about $10^{-8}$ to about $10^{-11}$; (vi) demonstrates efficacy in at least one animal model of anaphylaxis or inflammation; or (vii) competes with a reference antibody for binding to Bet v 1.

Certain Bet v 1 antibodies of the present invention, when used alone, or in combination, are able to bind to and neutralize at least one biological effect of Bet v 1, as determined by in vitro or in vivo assays. The ability of the antibodies of the invention to bind to and neutralize the activity of Bet v 1 may be measured using any standard method known to those skilled in the art, including binding assays, or neutralization of activity (e.g., protection from anaphylaxis) assays, as described herein.

Non-limiting, exemplary in vitro assays for measuring binding activity are illustrated in Example 3, herein. In Example 3, the binding affinities and kinetic constants of human anti-Bet v 1 antibodies were determined by surface plasmon resonance.

The Bet v 1 proteins or peptides may be modified to include addition or substitution of certain residues for tagging or for purposes of conjugation to carrier molecules, such as, KLH. For example, a cysteine may be added at either the N terminal or C terminal end of a peptide, or a linker sequence may be added to prepare the peptide for conjugation to, for example, KLH for immunization. The antibodies specific for Bet v 1 may contain no additional labels or moieties, or they may contain an N-terminal or C-terminal label or moiety. In one embodiment, the label or moiety is biotin. In a binding assay, the location of a label (if any) may determine the orientation of the peptide relative to the surface upon which the peptide is bound. For example, if a surface is coated with avidin, a peptide containing an N-terminal biotin will be oriented such that the C-terminal portion of the peptide will be distal to the surface.

Epitope Mapping and Related Technologies

The term "epitope," as used herein, refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

Provided herein are anti-Bet v 1 antibodies which interact with one or more amino acids found within the Bet v 1 molecule including, e.g., any fragment of Bet v 1 shown in SEQ ID NO: 306, or within comparable regions of a recombinantly produced Bet v 1 protein. The epitope to which the antibodies bind may consist of a single contiguous sequence of 3 or more (e.g., 3, 4, 5, 6, 7, 8, 9, 10, 11, 12, 13, 14, 15, 16, 17, 18, 19, 20 or more) amino acids located within the Bet v 1 molecule. Exemplary contiguous sequences include amino acid residues ranging from about position 23 to about position 44 of SEQ ID NO: 306; amino acid residues ranging from about position 23 to about position 43 of SEQ ID NO: 306; amino acid residues ranging from about position 23 to about position 38 of SEQ ID NO: 306; amino acid residues ranging from about position 23 to about position 41 of SEQ ID NO: 306; amino acid residues ranging from about position 26 to about position 43 of SEQ ID NO: 306; amino acid residues ranging from about position 29 to about position 43 of SEQ ID NO: 306; amino acid residues ranging from about position 44 to about position 70 of SEQ ID NO: 306; amino acid residues ranging from about position 44 to about position 56 of SEQ ID NO: 306; amino acid residues ranging from about position 45 to about position 56 of SEQ ID NO: 306; amino acid residues ranging from about position 2 to about position 19 of SEQ ID NO: 306; amino acid residues ranging from about position 5 to about position 10 of SEQ ID NO: 306; amino acid residues ranging from about position 5 to about position 19 of SEQ ID NO: 306; amino acid residues ranging from about position 8 to about position 19 of SEQ ID NO: 306; amino acid residues ranging from about position 11 to about position 19 of SEQ ID NO: 306; amino acid residues ranging from about position 57 to about position 70 of SEQ ID NO: 306; amino acid residues ranging from about position 57 to about position 66 of SEQ ID NO: 306; amino acid residues ranging from about position 81 to about position 96 of SEQ ID NO: 306; amino acid residues ranging from about position 84 to about position 96 of SEQ ID NO: 306; amino acid residues ranging from about position 85 to about position 96 of SEQ ID NO: 306; and amino acid residues ranging from about position 81 to about position 89 of SEQ ID NO: 306. Further exemplary contiguous sequences include at least one amino acid sequence selected from the group consisting of SEQ ID NOs: 307, 308, 309, 310, 311, and 315, wherein such sequence can be extended by about 1 to about 5 amino acids, or about 5 to about 10 amino acids, on either the C-terminal end or the N-terminal end. Alternatively, the epitope may consist of a plurality of non-contiguous amino acids (or amino acid sequences) located within the Bet v 1 molecule (e.g. a conformational epitope).

Various techniques known to persons of ordinary skill in the art can be used to determine whether an antibody "interacts with one or more amino acids" within a polypeptide or protein. Exemplary techniques include, for example, routine cross-blocking assays, such as that described in *Antibodies*, Harlow and Lane (Cold Spring Harbor Press, Cold Spring Harb., N.Y.). Other methods include alanine scanning mutational analysis, peptide blot analysis (Reineke (2004) Methods Mol Biol 248:443-63), peptide cleavage analysis crystallographic studies and NMR analysis. In addition, methods such as epitope excision, epitope extraction and chemical modification of antigens can be employed (Tomer (2000) Protein Science 9: 487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water and exchangeable protons within amino acids that are protected by the antibody complex undergo deuterium-to-hydrogen back-exchange at a slower rate than exchangeable protons within amino acids that are not part of the interface. As a result, amino acids that form part of the protein/antibody interface may retain deuterium and therefore exhibit relatively higher mass compared to amino acids not included in the interface. After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) *Analytical Biochemistry* 267(2):252-259; Engen and Smith (2001) *Anal. Chem.* 73:256A-265A. X-ray crystallography of the antigen/antibody complex may also be used for epitope mapping purposes.

Modification-Assisted Profiling (MAP), also known as Antigen Structure-based Antibody Profiling (ASAP) is a method that categorizes large numbers of monoclonal antibodies (monoclonal antibodies) directed against the same antigen according to the similarities of the binding profile of each antibody to chemically or enzymatically modified antigen surfaces (US 2004/0101920). Each category may reflect a unique epitope either distinctly different from or partially overlapping with epitope represented by another category. This technology allows rapid filtering of genetically identical antibodies, such that characterization can be focused on genetically distinct antibodies. When applied to hybridoma screening, MAP may facilitate identification of rare hybridoma clones that produce monoclonal antibodies having the desired characteristics. MAP may be used to sort the antibodies of the invention into groups of antibodies binding different epitopes.

In certain embodiments, the anti-Bet v 1 antibodies or antigen-binding fragments thereof bind an epitope within Bet v 1, in natural or native form, as exemplified in SEQ ID NO: 306 or SEQ ID NO: 314 (Bet v 1 amino acid sequence from Uniprot: P15494), or recombinantly produced, or to a fragment thereof. In certain embodiments, the antibodies of the invention, as shown in Table 1, interact with at least one amino acid sequence selected from the group consisting of amino acid residues ranging from about position 23 to about position 44 of SEQ ID NO: 306; amino acid residues ranging from about position 23 to about position 43 of SEQ ID NO: 306; amino acid residues ranging from about position 23 to about position 38 of SEQ ID NO: 306; amino acid residues ranging from about position 23 to about position 41 of SEQ ID NO: 306; amino acid residues ranging from about position 26 to about position 43 of SEQ ID NO: 306; amino acid residues ranging from about position 29 to about position 43 of SEQ ID NO: 306; amino acid residues ranging from about position 44 to about position 70 of SEQ ID NO: 306; amino acid residues ranging from about position 44 to about position 56 of SEQ ID NO: 306; amino acid residues ranging from about position 45 to about position 56 of SEQ ID NO: 306; amino acid residues ranging from about position 2 to about position 19 of SEQ ID NO: 306; amino acid residues ranging from about position 5 to about position 10 of SEQ ID NO: 306; amino acid residues ranging from about position 5 to about position 19 of SEQ ID NO: 306; amino acid residues ranging from about position 8 to about position 19 of SEQ ID NO: 306; amino acid residues ranging from about position 11 to about position 19 of SEQ ID NO: 306; amino acid residues ranging from about position 57 to about position 70 of SEQ ID NO: 306; amino acid residues ranging from about position 57 to about position 66 of SEQ ID NO: 306; amino acid residues ranging from about position 81 to about position 96 of SEQ ID NO: 306; amino acid residues ranging from about position 84 to about position 96 of SEQ ID NO: 306; amino acid residues ranging from about position 85 to about position 96 of SEQ ID NO: 306; and amino acid residues ranging from about position 81 to about position 89 of SEQ ID NO: 306. These regions are further exemplified in SEQ ID NOs: 307, 308, 309, 310, 311 and 315.

The present invention also includes anti-Bet v 1 antibodies that bind to the same epitope, or a portion of the epitope, as any of the specific exemplary antibodies described herein in Table 1, or an antibody having the CDR sequences of any of the exemplary antibodies described in Table 1. Likewise, the present invention also includes anti-Bet v 1 antibodies that compete for binding to Bet v 1 or a Bet v 1 fragment with any of the specific exemplary antibodies described herein in Table 1, or an antibody having the CDR sequences of any of the exemplary antibodies described in Table 1.

One can easily determine whether an antibody binds to the same epitope as, or competes for binding with, a reference anti-Bet v 1 antibody by using routine methods known in the art. For example, to determine if a test antibody binds to the same epitope as a reference anti-Bet v 1 antibody of the invention, the reference antibody is allowed to bind to a Bet v 1 protein or peptide under saturating conditions. Next, the ability of a test antibody to bind to the Bet v 1 molecule is assessed. If the test antibody is able to bind to Bet v 1 following saturation binding with the reference anti-Bet v 1 antibody, it can be concluded that the test antibody binds to a different epitope than the reference anti-Bet v 1 antibody. On the other hand, if the test antibody is not able to bind to the Bet v 1 molecule following saturation binding with the reference anti-Bet v 1 antibody, then the test antibody may bind to the same epitope as the epitope bound by the reference anti-Bet v 1 antibody of the invention.

To determine if an antibody competes for binding with a reference anti-Bet v 1 antibody, the above-described binding methodology is performed in two orientations: In a first orientation, the reference antibody is allowed to bind to a Bet v 1 molecule under saturating conditions followed by assessment of binding of the test antibody to the Bet v 1 molecule. In a second orientation, the test antibody is allowed to bind to a Bet v 1 molecule under saturating conditions followed by assessment of binding of the reference antibody to the Bet v 1 molecule. If, in both orientations, only the first (saturating) antibody is capable of binding to the Bet v 1 molecule, then it is concluded that the test antibody and the reference antibody compete for binding to Bet v 1. As will be appreciated by a person of ordinary skill in the art, an antibody that competes for binding with a reference antibody may not necessarily bind to the identical epitope as the reference antibody, but may sterically block binding of the reference antibody by binding an overlapping or adjacent epitope.

Two antibodies bind to the same or overlapping epitope if each competitively inhibits (blocks) binding of the other to the antigen. That is, a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990 50:1495-1502). Alternatively, two antibodies have the same epitope if essentially all amino acid mutations in the antigen that reduce or eliminate binding of one antibody reduce or eliminate binding of the other. Two antibodies have overlapping epitopes if some amino acid mutations that reduce or eliminate binding of one antibody reduce or eliminate binding of the other.

Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, surface plasmon resonance, flow cytometry or any other quantitative or qualitative antibody-binding assay available in the art.

Immunoconjugates

The invention encompasses a human anti-Bet v 1 monoclonal antibody conjugated to a therapeutic moiety ("immunoconjugate"), such as an agent that is capable of reducing the severity of an allergic response to the Bet v 1 allergen, or in an environment where Fagales trees are present, or to ameliorate at least one symptom associated with exposure to birch pollen or to the Bet v 1 allergen, including rhinitis, conjunctivitis, or breathing difficulties, or the severity thereof. Such an agent may be a corticosteroid, a second different antibody to Bet v 1, or a vaccine. The type of therapeutic moiety that may be conjugated to the Bet v 1 antibody will take into account the condition to be treated and the desired therapeutic effect to be achieved. Alternatively, if the desired therapeutic effect is to treat the sequelae or symptoms associated with exposure to the Bet v 1 allergen, or any other condition resulting from such exposure, such as, but not limited to, rhinitis or conjunctivitis, it may be advantageous to conjugate an agent appropriate to treat the sequelae or symptoms of the condition, or to alleviate any side effects of the antibodies of the invention. Examples of suitable agents for forming immunoconjugates are known in the art, see for example, WO 05/103081.

Therapeutic Administration and Formulations

The invention provides therapeutic compositions comprising the anti-Bet v 1 antibodies or antigen-binding fragments thereof of the present invention. The administration of therapeutic compositions in accordance with the invention will be administered via a suitable route including, but not limited to, intravenously, subcutaneously, intramuscularly, intranasally, with suitable carriers, excipients, and other agents that are incorporated into formulations to provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody may vary depending upon the age and the size of a patient to be administered, target disease, conditions, route of administration, and the like. When the antibody of the present invention is used for treating the rhinitis or conjunctivitis associated with exposure to pollen from a Fagales tree, or birch pollen, or Bet v 1, in an individual having a sensitivity to Bet v 1, or for preventing an anaphylactic response to the Fagales allergen, or for lessening the severity of the allergic response, it is advantageous to intravenously administer the antibody of the present invention normally at a single dose of about 0.01 to about 30 mg/kg body weight, more preferably about 0.02 to about 7, about 0.03 to about 5, or about 0.05 to about 3 mg/kg body weight. Depending on the severity of the condition, the frequency and the duration of the treatment can be adjusted. In certain embodiments, the antibody or antigen-binding fragment thereof of the invention can be administered as an initial dose of at least about 0.1 mg to about 800 mg, about 1 to about 500 mg, about 5 to about 300 mg, or about 10 to about 200 mg, to about 100 mg, or to about 50 mg. In certain embodiments, the initial dose may be followed by administration of a second or a plurality of subsequent doses of the antibody or antigen-binding fragment thereof in an amount that can be approximately the same or less than that of the initial dose, wherein the subsequent doses are separated by at least 1 day to 3 days; at least one week, at least 2 weeks; at least 3 weeks; at least 4 weeks; at least 5 weeks; at least 6 weeks; at least 7 weeks; at least 8 weeks; at least 9 weeks; at least 10 weeks; at least 12 weeks; or at least 14 weeks.

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, transdermal, intramuscular, intraperitoneal, intravenous, subcutaneous, intranasal, epidural and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

The pharmaceutical composition can be also delivered in a vesicle, in particular a liposome (see, for example, Langer, 1990, Science 249: 1527-1533).

In certain situations, the pharmaceutical composition can be delivered in a controlled release system. In one embodiment, a pump may be used. In another embodiment, polymeric materials can be used. In yet another embodiment, a controlled release system can be placed in proximity of the composition's target, thus requiring only a fraction of the systemic dose.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but certainly are not limited to AUTOPEN™ (Owen Mumford, Inc., Woodstock, UK), DISETRONIC™ pen (Disetronic Medical Systems, Burghdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but certainly are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L.P.) and the HUMIRA™ Pen (Abbott Labs, Abbott Park, Ill.), to name only a few.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

Due to their interaction with Bet v 1, the present antibodies are useful for treating the primary response following exposure of an individual to Fagales allergen, birch pollen, or to an environment containing the Bet v 1 protein, or at least one symptom associated with the allergic response, such as itchy eyes, conjunctivitis, rhinitis, wheezing, breathing difficulties, or for preventing a secondary response to the Bet v 1 allergen, including a more serious anaphylactic response, or for lessening the severity, duration, and/or frequency of symptoms following reexposure to the Fagales allergen. Accordingly, it is envisioned that the antibodies of the present invention may be used prophylactically or therapeutically.

In yet a further embodiment of the invention the present antibodies are used for the preparation of a pharmaceutical composition for treating patients suffering from a sensitivity to birch pollen or an extract thereof and/or the Bet v 1 protein. In yet another embodiment of the invention the present antibodies are used for the preparation of a pharmaceutical composition for reducing the severity of primary exposure to Bet v 1, or for reducing the severity, duration of, and/or number of allergic responses to Bet v 1. In a further embodiment of the invention the present antibodies are used as adjunct therapy with any other agent useful for treating Fagales allergens, including corticosteroids, vaccines, allergen specific immunotherapy (SIT), or any other palliative therapy known to those skilled in the art.

Combination Therapies

Combination therapies may include an anti-Bet v 1 antibody of the invention and any additional therapeutic agent that may be advantageously combined with an antibody of the invention, or with a biologically active fragment of an antibody of the invention.

For example, a second therapeutic agent may be employed to aid in reducing the allergic symptoms following exposure to a Fagales allergen, birch pollen or an extract thereof, or Bet v 1, or exposure to an environment in which Fagales trees are present and blooming, such as a corticosteroid. The antibodies may also be used in conjunction with other therapies, such as a vaccine specific for the Bet v 1 allergen. The additional therapeutically active component(s) may be administered prior to, concurrent with, or after the administration of the anti-Bet v 1 antibody of the present invention. For purposes of the present disclosure, such administration regimens are considered the administration of an anti-Bet v 1 antibody "in combination with" a second therapeutically active component.

Allergen-Specific Immunotherapy (SIT)

As used herein, the expressions "allergen-specific immunotherapy", "specific immunotherapy", "SIT", "SIT regimen", and the like, refer to the repeated administration of an allergen to a patient over time as means for treating or preventing allergies and allergic reactions, or to reduce or eliminate allergic responses. In a typical SIT regimen, small amounts of allergen are initially administered to an allergic patient, followed by administration of increased amounts of allergen. In certain instances, the SIT regimen comprises at least two consecutive phases: (1) an up-dosing phase, and (2) a maintenance phase. In the up-dosing phase, increasing doses of allergen are administered until an effective and safe dose is achieved. The dose that is established at the end of the up-dosing phase is then administered to the patient throughout the course of the maintenance phase. The duration of the up-dosing phase can be several weeks or several months. In certain embodiments, however, the up-dosing phase is of substantially shorter duration (e.g., less than one week, less than 6 days, less than 5 days, less than 4 days, less than 3 days, or less than 2 days). SIT regimens comprising an up-dosing phase of less than 5 days are sometimes referred to as "Rush" immunotherapy or "Rush SIT". The maintenance phase of an SIT regimen can last several weeks, several months, several years, or indefinitely.

Administration Regimens

According to certain embodiments of the present invention, multiple doses of one or more anti-Bet v 1 antibodies (an antibody combination) may be administered to a patient over a defined time course. The methods according to this aspect of the invention comprise sequentially administering to a patient multiple doses of an antibody, antibody combination. As used herein, "sequentially administering" means that each dose of an antibody or antibody combination is administered to the patient at a different point in time, e.g., on different days separated by a predetermined interval (e.g., hours, days, weeks or months). The present invention includes methods, which comprise sequentially administering to the patient a single initial dose of an antibody or antibody combination followed by one or more secondary doses of the antibody, and optionally followed by one or more tertiary doses of the antibody.

The terms "initial dose," "secondary doses," and "tertiary doses," refer to the temporal sequence of administration of an antibody or antibody combination provided herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of an antibody or antibody combination but generally may differ from one another in terms of frequency of administration. In certain embodiments, however, the amount of an antibody or antibody combination, contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In one exemplary embodiment of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of an antibody or antibody combination, which is administered to a patient prior to the administration of the very next dose in the sequence with no intervening doses.

The methods according to this aspect of the invention may comprise administering to a patient any number of secondary and/or tertiary doses of an antibody or antibody combination. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient.

In embodiments involving multiple secondary doses, each secondary dose may be administered at the same frequency as the other secondary doses. For example, each secondary dose may be administered to the patient 1 to 2 weeks after the immediately preceding dose. Similarly, in embodiments involving multiple tertiary doses, each tertiary dose may be administered at the same frequency as the other tertiary doses. For example, each tertiary dose may be administered to the patient 2 to 4 weeks after the immediately preceding dose. Alternatively, the frequency at which the secondary and/or tertiary doses are administered to a patient can vary over the course of the treatment regimen. The frequency of administration may also be adjusted during the course of treatment by a physician depending on the needs of the individual patient following clinical examination.

Diagnostic Uses of the Antibodies

The anti-Bet v 1 antibodies of the present invention may also be used to detect and/or measure Bet v 1 in a sample, e.g., for diagnostic purposes. It is envisioned that confirmation of an allergic response thought to be caused by Bet v 1 may be made by measuring the presence of either Bet v 1 through use of any one or more of the antibodies of the invention. Exemplary diagnostic assays for Bet v 1 may comprise, e.g., contacting a sample, obtained from a patient, with an anti-Bet v 1 antibody of the invention, wherein the anti-Bet v 1 antibody is labeled with a detectable label or reporter molecule or used as a capture ligand to selectively isolate Bet v 1 protein from patient samples. Alternatively, an unlabeled anti-Bet v 1 antibody can be used in diagnostic applications in combination with a secondary antibody which is itself detectably labeled. The detectable label or reporter molecule can be a radioisotope, such as 3H, $^{14}$C, $^{32}$P $^{35}$S, or $^{125}$I; a fluorescent or chemiluminescent moiety such as fluorescein isothiocyanate, or rhodamine; or an enzyme such as alkaline phosphatase, β-galactosidase, horseradish peroxidase, or luciferase. Specific exemplary assays that can be used to detect or measure Bet v 1 in a sample include enzyme-linked immunosorbent assay (ELISA), radioimmunoassay (RIA), and fluorescence-activated cell sorting (FACS).

Samples that can be used in Bet v 1 diagnostic assays according to the present invention include any tissue or fluid sample obtainable from a patient, which contains detectable quantities of Bet v 1 protein, or fragments thereof, under normal or pathological conditions. Generally, levels of Bet v 1 in a particular sample obtained from a healthy/non-allergic patient (e.g., a patient not afflicted with a sensitivity associated with the presence of Bet v 1) will be measured to initially establish a baseline, or standard, level of Bet v 1. This baseline level of Bet v 1 can then be compared against the levels of Bet v 1 measured in samples obtained from individuals suspected of having a sensitivity to Bet v 1 in birch pollen, or symptoms associated with such condition.

While the invention has been particularly shown and described with reference to a number of embodiments, it would be understood by those skilled in the art that changes in the form and details may be made to the various embodiments disclosed herein without departing from the spirit and scope of the invention and that the various embodiments disclosed herein are not intended to act as limitations on the scope of the claims.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1: Generation of Human Antibodies to Bet v 1

An immunogen comprising any one of the following can be used to generate antibodies to Bet v 1. In certain embodiments, the antibodies of the invention are obtained from mice immunized with a primary immunogen, such as full length natural Bet v 1 (nBet v 1), which may be purchased commercially (e.g., from Stallergenes Greer, Lenoir, N.C., #XP527D3A25), or isolated from birch pollen (See, for example, Buters, et al. (2012), Atomospheric Environment 55:496-505), or which may be produced recombinantly (See GenBank accession number P 15494 for the full length amino acid sequence of Bet v 1), or fragments of the Bet v 1 protein, followed by immunization with a secondary immunogen, or with an immunogenically active fragment of the natural protein. Various constructs may be prepared using portions of the Bet v 1 protein known to those skilled in the art. These constructs may be used alone, or in various combinations to elicit antibody responses in vivo. For example, recombinant Bet v 1 constructs, such as those exemplified in SEQ ID NOs: 307, 308, 309, 310, 311, and 315, or fragments thereof, may be used as immunogens.

In certain embodiments, the antibodies of the invention are obtained from mice immunized with a primary immunogen, such as a biologically active and/or immunogenic fragment of natural Bet v 1, or DNA encoding the active fragment thereof. The fragment may be derived from the N-terminal or C-terminal portion of Bet v 1.

In certain embodiments, the recombinant Bet v 1 protein constructs used in the studies described herein may also include a C-terminal tag (myc-myc-hexahistidine tag) as indicated below. In other embodiments, the recombinant Bet v 1 protein construct includes amino acids G2 through N160 of Uniprot P15494. In some embodiments, the construct comprises an S85A substitution. The proteins were expressed in Chinese hamster ovary (CHO) cells. An exogenous signal sequence used to promote expression in CHO cells is not included in the sequence listings.

In certain embodiments, the immunogen may be a Bet v 1 fragment or fusion protein that comprises any one or more of the following: i) amino acid residues 23-43 of Bet v 1 (see Uniprot P15494 and also SEQ ID NO: 307); ii) amino acid residues 44-56 of Bet v 1 (see Uniprot P15494 and also SEQ ID NO: 308); iii) amino acid residues 2-19 of Bet v 1 (see Uniprot P15494 and also SEQ ID NO: 309); iv) amino acid residues 57-70 of Bet v 1 (see Uniprot P15494 and also SEQ ID NO: 310); v) amino acid residues 81-89 of Bet v 1 ((see Uniprot P15494 and also SEQ ID NO: 311) and vi) amino acid residues 81-96 of Bet v 1 ((see Uniprot P15494 and also SEQ ID NO: 315).

In certain embodiments, antibodies that bind specifically to Bet v 1 may be prepared using fragments of the above-noted regions, or peptides that extend beyond the designated regions by about 5 to about 20 amino acid residues from either, or both, the N or C terminal ends of the regions described herein. In certain embodiments, any combination of the above-noted regions or fragments thereof may be used in the preparation of Bet v 1 specific antibodies. In certain embodiments, any one or more of the above-noted regions of Bet v 1, or fragments thereof may be used for preparing monospecific, bispecific, or multispecific antibodies.

The full-length proteins, or fragments thereof, that were used as immunogens, as noted above, were administered directly, with an adjuvant to stimulate the immune response, to a VELOCIMMUNE® mouse comprising DNA encoding human immunoglobulin heavy and kappa light chain variable regions.

Anti-Bet v 1 antibodies were isolated directly from antigen-positive B cells without fusion to myeloma cells, as described in U.S. Pat. No. 7,582,298. Using this method, several fully human anti-Bet v 1 antibodies (i.e., antibodies possessing human variable domains and human constant domains) were obtained; exemplary antibodies generated in this manner were designated as follows: H4H16943P, H4H16946P, H4H16950P, H4H16960P, H4H16967P, H4H16971P, H4H16979P, H4H16987P, H4H16991P, H4H16992P, H4H17001P, H4H17015P, H4H17027P, H4H17028P, H4H17031P, H4H17033P, H4H17038P2, H4H17045P2, H4H17067P2, and H4H17082P2.

The biological properties of the exemplary antibodies generated in accordance with the methods of this Example are described in detail in the Examples set forth below.

Example 2: Heavy and Light Chain Amino Acid Sequences

Table 1a provides the amino acid sequence identifiers of the heavy and light chain variable regions and CDRs of selected anti-Bet v 1 antibodies. Table 1b provides the nucleic acid sequence identifiers of the heavy and light chain variable regions and CDRs of selected anti-Bet v 1 antibodies.

TABLE 1a

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H16943P | 2 | 4 | 6 | 8 | 10 | 12 | 14 | 16 |
| H4H16946P | 18 | 20 | 22 | 24 | 26 | 28 | 30 | 32 |
| H4H16950P | 34 | 36 | 38 | 40 | 42 | 44 | 46 | 48 |
| H4H16960P | 50 | 52 | 54 | 56 | 58 | 60 | 62 | 64 |
| H4H16967P | 66 | 68 | 70 | 72 | 74 | 76 | 78 | 80 |
| H4H16971P | 82 | 84 | 86 | 88 | 90 | 92 | 94 | 96 |
| H4H17038P2 | 98 | 100 | 102 | 104 | 106 | 108 | 110 | 112 |
| H4H16987P | 114 | 116 | 118 | 120 | 122 | 124 | 126 | 128 |
| H4H16991P | 130 | 132 | 134 | 136 | 138 | 140 | 142 | 144 |
| H4H16992P | 146 | 148 | 150 | 152 | 154 | 156 | 158 | 160 |
| H4H17001P | 162 | 164 | 166 | 168 | 170 | 172 | 174 | 176 |
| H4H17015P | 178 | 180 | 182 | 184 | 186 | 188 | 190 | 192 |
| H4H17027P | 194 | 196 | 198 | 200 | 202 | 204 | 206 | 208 |
| H4H17028P | 210 | 212 | 214 | 216 | 218 | 220 | 222 | 224 |
| H4H17031P | 226 | 228 | 230 | 232 | 234 | 236 | 238 | 240 |
| H4H17033P | 242 | 244 | 246 | 248 | 250 | 252 | 254 | 256 |
| H4H16979P | 258 | 260 | 262 | 264 | 266 | 268 | 270 | 272 |
| H4H17045P2 | 274 | 276 | 278 | 280 | 266 | 268 | 270 | 272 |
| H4H17067P2 | 282 | 284 | 286 | 288 | 266 | 268 | 270 | 272 |
| H4H17082P2 | 290 | 292 | 294 | 296 | 298 | 300 | 302 | 304 |

TABLE 1b

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H4H16943P | 1 | 3 | 5 | 7 | 9 | 11 | 13 | 15 |
| H4H16946P | 17 | 19 | 21 | 23 | 25 | 27 | 29 | 31 |
| H4H16950P | 33 | 35 | 37 | 39 | 41 | 43 | 45 | 47 |
| H4H16960P | 49 | 51 | 53 | 55 | 57 | 59 | 61 | 63 |
| H4H16967P | 65 | 67 | 69 | 71 | 73 | 75 | 77 | 79 |
| H4H16971P | 81 | 83 | 85 | 87 | 89 | 91 | 93 | 95 |
| H4H17038P2 | 97 | 99 | 101 | 103 | 105 | 107 | 109 | 111 |
| H4H16987P | 113 | 115 | 117 | 119 | 121 | 123 | 125 | 127 |
| H4H16991P | 129 | 131 | 133 | 135 | 137 | 139 | 141 | 143 |
| H4H16992P | 145 | 147 | 149 | 151 | 153 | 155 | 157 | 159 |
| H4H17001P | 161 | 163 | 165 | 167 | 169 | 171 | 173 | 175 |
| H4H17015P | 177 | 179 | 181 | 183 | 185 | 187 | 189 | 191 |
| H4H17027P | 193 | 195 | 197 | 199 | 201 | 203 | 205 | 207 |
| H4H17028P | 209 | 211 | 213 | 215 | 217 | 219 | 221 | 223 |
| H4H17031P | 225 | 227 | 229 | 231 | 233 | 235 | 237 | 239 |
| H4H17033P | 241 | 243 | 245 | 247 | 249 | 251 | 253 | 255 |
| H4H16979P | 257 | 259 | 261 | 263 | 265 | 267 | 269 | 271 |
| H4H17045P2 | 273 | 275 | 277 | 279 | 265 | 267 | 269 | 271 |
| H4H17067P2 | 281 | 283 | 285 | 287 | 265 | 267 | 269 | 271 |
| H4H17082P2 | 289 | 291 | 293 | 295 | 297 | 299 | 301 | 303 |

Antibodies are typically referred to herein according to the following nomenclature: Fc prefix (e.g. "H4H," "H2M," etc.), followed by a numerical identifier (e.g. "16943," "17001," etc., as shown in Table 1), followed by a "P" or "P2" suffix. The H4H and H2M prefixes on the antibody designations used herein indicate the particular Fc region isotype of the antibody. Thus, according to this nomenclature, an antibody may be referred to herein as, e.g., "H4H16943P", etc., as the "H4H" designates the antibody has a human IgG4 Fc (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a human IgG1 Fc can be converted to an antibody with a human IgG4, etc.), but in any event, the variable domains (including the CDRs)—which are indicated by the numerical identifiers shown in Table 1—will remain the same, and the binding properties to antigen are expected to be identical or substantially similar regardless of the nature of the Fc domain.

Table 1e provides the amino acid sequence identifiers of the full length heavy and light chains of selected anti-Bet v 1 antibodies.

TABLE 1c

Heavy and Light Chain Amino Acid Sequence Identifiers

| Antibody Designation | SEQ ID NOs: | |
|---|---|---|
| | Heavy Chain | Light Chain |
| H4H17038P2 | 316 | 317 |
| H4H16987P | 318 | 319 |
| H4H16992P | 320 | 321 |
| H4H17082P2 | 322 | 323 |

Example 3: Antibody Binding to Bet v 1 as Determined by Surface Plasmon Resonance Equilibrium dissociation constants ($K_D$) for natural Bet v 1 binding to purified anti-Bet v 1 monoclonal antibodies were determined using a real-time surface plasmon resonance biosensor (SPR-Biacore) on a Biacore 4000 instrument. All binding studies were performed in 10 mM HEPES, 150 mM NaCl, 3 mM EDTA, and 0.05% v/v surfactant Tween-20, pH 7.4 (HBS-ET) running buffer at 25° C. and 37° C. The Biacore CM5 sensor surface was first derivatized by amine coupling with a monoclonal mouse anti-human Fc antibody (GE, #BR-1008-39) to subsequently capture anti-Bet v 1 monoclonal antibodies. Different concentrations of natural Bet v 1 (Indoor, Cat #NA-BV1-1) or CHO produced recombinant Bet v 1 containing a S85A mutation with a C-terminal myc-myc hexahistidine tag (mutant Bet v 1-MMH; SEQ ID NO: 312) reagent were first prepared in HBS-ET running buffer (100 nM-1.23 nM; serially diluted by 3-fold) and were injected over anti-human Fc captured anti-Bet v 1 monoclonal antibody surface for 4 minutes at a flow rate of 30 μL/minute, while the dissociation of monoclonal antibody bound Bet v 1 reagent was monitored for 10 minutes in HBS-ET running buffer. Association ($k_a$) and dissociation ($k_d$) rate constants were determined by fitting the real-time binding sensorgrams to a 1:1 binding model with mass transport limitation using Scrubber 2.0c curve-fitting software. Binding dissociation equilibrium constants ($K_D$) and dissociative half-lives (t1/2) were calculated from the kinetic rate constants as:

$$K_D = \frac{kd}{ka}, \text{ and } t^{1/2} = \frac{\ln(2)}{kd}$$

Binding kinetics parameters for natural Bet v 1 and mutant Bet v 1-MMH to different anti-Bet v 1 monoclonal antibodies of the invention at 25° C. and 37° C. are shown in Table 2 through Table 5.

At 25° C., all of the anti-Bet v 1 monoclonal antibodies of the invention bound to natural Bet v 1 with $K_D$ values ranging from 0.66 nM to 13.5 nM, as shown in Table 2. At 37° C., all of the anti-Bet v 1 monoclonal antibodies of the invention bound to natural Bet v 1 with $K_D$ values ranging from 1.59 nM to 27.9 nM, as shown in Table 3. At both 25° C. and 37° C. the isotype control antibody did not demonstrate any measurable binding to natural Bet v 1.

At both 25° C. and 37° C., 3 out of 20 anti-Bet v 1 monoclonal antibodies of the invention did not bind to mutant Bet v 1-MMH. At 25° C., 17 out of 20 anti-Bet v 1 monoclonal antibodies bound to mutant Bet v 1-MMH with $K_D$ values ranging from 348 pM to 43.8 nM, as shown in Table 4. At 37° C., 17 out of 20 anti-Bet v 1 monoclonal antibodies of the invention bound to mutant Bet v 1-MMH with $K_D$ values ranging from 655 pM to 106 nM, as shown in Table 5. At both 25° C. and 37° C. the isotype control antibody did not demonstrate any measurable binding to mutant Bet v 1-MMH.

TABLE 2

Binding kinetics parameters of natural Bet v 1 binding to Bet v 1 monoclonal antibodies at 25° C.

| Antibody | mAb Capture Level (RU) | 100 nM natural Bet v 1 Bound (RU) | $k_a$ (1/Ms) | $k_d$ (1/s) | $K_D$ (M) | t½ (min) |
|---|---|---|---|---|---|---|
| H4H16943P | 346 ± 1.5 | 71 | 1.64E+05 | 2.30E−04 | 1.40E−09 | 50 |
| H4H16946P | 355 ± 1.8 | 74 | 2.05E+05 | 2.01E−04 | 9.82E−10 | 58 |
| H4H16950P | 357 ± 2.3 | 58 | 9.61E+04 | 5.03E−04 | 5.23E−09 | 23 |
| H4H16960P | 342 ± 2.2 | 57 | 4.22E+05 | 6.90E−04 | 1.64E−09 | 17 |
| H4H16967P | 332 ± 0.9 | 27 | 3.76E+04 | 1.49E−04 | 3.98E−09 | 77 |
| H4H16971P | 343 ± 0.5 | 57 | 2.40E+05 | 7.81E−04 | 3.26E−09 | 15 |
| H4H16979P | 295 ± 0.8 | 41 | 2.30E+05 | 2.78E−04 | 1.21E−09 | 42 |
| H4H16987P | 334 ± 0.5 | 61 | 4.10E+05 | 1.14E−03 | 2.77E−09 | 10 |
| H4H16991P | 313 ± 0.4 | 57 | 2.95E+05 | 3.12E−04 | 1.06E−09 | 37 |
| H4H16992P | 351 ± 0.7 | 64 | 3.73E+05 | 2.48E−04 | 6.65E−10 | 47 |
| H4H17001P | 352 ± 0.6 | 71 | 3.29E+05 | 3.29E−04 | 1.00E−09 | 35 |
| H4H17015P | 370 ± 0.7 | 68 | 1.84E+05 | 2.46E−04 | 1.34E−09 | 47 |
| H4H17027P | 340 ± 0.6 | 48 | 6.24E+04 | 2.70E−04 | 4.32E−09 | 43 |
| H4H17028P | 350 ± 0.7 | 63 | 2.81E+05 | 1.07E−03 | 3.79E−09 | 11 |
| H4H17031P | 335 ± 0.7 | 54 | 1.24E+05 | 1.68E−03 | 1.35E−08 | 6.8 |
| H4H17033P | 336 ± 0.4 | 61 | 3.94E+05 | 4.69E−04 | 1.19E−09 | 25 |
| H4H17038P2 | 324 ± 0.9 | 64 | 2.77E+05 | 3.64E−04 | 1.32E−09 | 32 |
| H4H17045P2 | 368 ± 0.9 | 69 | 1.22E+05 | 1.49E−04 | 1.22E−09 | 78 |
| H4H17067P2 | 344 ± 0.5 | 58 | 1.13E+05 | 4.02E−04 | 3.56E−09 | 29 |
| H4H17082P2 | 366 ± 0.6 | 72 | 5.45E+05 | 5.97E−04 | 1.09E−09 | 19 |
| Isotype Control | 345 ± 0.5 | 1 | NB* | NB* | NB* | NB* |

*NB indicates that no binding was observed under the current experimental conditions.

TABLE 3

Binding kinetics parameters of natural Bet v 1 binding to Bet v 1 monoclonal antibodies at 37° C.

| Antibody | mAb Capture Level (RU) | 100 nM natural Bet v 1 Bound (RU) | $k_a$ (1/Ms) | $k_d$ (1/s) | $K_D$ (M) | $t^{1/2}$ (min) |
|---|---|---|---|---|---|---|
| H4H16943P | 451 ± 2.7 | 88 | 2.60E+05 | 1.27E−03 | 4.89E−09 | 9.1 |
| H4H16946P | 469 ± 2.6 | 93 | 2.89E+05 | 6.01E−04 | 2.08E−09 | 19 |
| H4H16950P | 471 ± 2.1 | 76 | 1.41E+05 | 1.21E−03 | 8.57E−09 | 10 |
| H4H16960P | 422 ± 0.9 | 65 | 6.62E+05 | 1.68E−03 | 2.54E−09 | 6.8 |
| H4H16967P | 412 ± 1.9 | 45 | 5.04E+04 | 7.19E−04 | 1.43E−08 | 16 |
| H4H16971P | 433 ± 1.3 | 66 | 3.52E+05 | 2.44E−03 | 6.93E−09 | 4.7 |
| H4H16979P | 352 ± 1.3 | 52 | 3.42E+05 | 6.16E−04 | 1.80E−09 | 19 |
| H4H16987P | 436 ± 1.7 | 74 | 5.20E+05 | 4.77E−03 | 9.16E−09 | 2.4 |
| H4H16991P | 379 ± 1.0 | 66 | 5.00E+05 | 1.08E−03 | 2.16E−09 | 11 |
| H4H16992P | 436 ± 1.1 | 73 | 5.38E+05 | 8.53E−04 | 1.59E−09 | 14 |
| H4H17001P | 457 ± 0.8 | 87 | 4.85E+05 | 1.22E−03 | 2.52E−09 | 9.5 |
| H4H17015P | 464 ± 1.4 | 84 | 2.93E+05 | 7.92E−04 | 2.70E−09 | 15 |
| H4H17027P | 427 ± 0.9 | 67 | 9.81E+04 | 9.30E−04 | 9.48E−09 | 12 |
| H4H17028P | 435 ± 1.3 | 71 | 3.73E+05 | 2.90E−03 | 7.77E−09 | 3.9 |
| H4H17031P | 419 ± 1.8 | 63 | 4.85E+05 | 5.44E−03 | 2.79E−08 | 2.1 |
| H4H17033P | 417 ± 1.4 | 74 | 6.27E+05 | 1.19E−03 | 1.90E−09 | 10 |
| H4H17038P2 | 406 ± 1.4 | 74 | 3.73E+05 | 1.62E−03 | 4.33E−09 | 7.1 |
| H4H17045P2 | 465 ± 1.4 | 90 | 2.37E+05 | 4.41E−04 | 1.86E−09 | 26 |
| H4H17067P2 | 440 ± 1.2 | 80 | 2.68E+05 | 1.47E−03 | 5.48E−09 | 7.9 |
| H4H17082P2 | 453 ± 1.1 | 83 | 7.48E+05 | 1.82E−03 | 2.43E−09 | 6.3 |
| Isotype Control | 426 ± 1 | 1 | NB* | NB* | NB* | NB* |

*NB indicates that no binding was observed under the current experimental conditions.

TABLE 4

Binding kinetics parameters of mutant Bet v 1-MMH binding to Bet v 1 monoclonal antibodies at 25° C.

| Antibody | mAb Capture Level (RU) | 100 nM natural Bet v 1- MMH Bound (RU) | $k_a$ (1/Ms) | $k_d$ (1/s) | $K_D$ (M) | $t^{1/2}$ (min) |
|---|---|---|---|---|---|---|
| H4H16943P | 344 ± 0.8 | 0 | NB* | NB* | NB* | NB* |
| H4H16946P | 354 ± 0.5 | 83 | 4.05E+05 | 1.41E−04 | 3.48E−10 | 82 |
| H4H16950P | 357 ± 0.6 | 70 | 1.51E+05 | 3.35E−04 | 2.21E−09 | 35 |
| H4H16960P | 343 ± 0.8 | 64 | 5.62E+05 | 4.43E−04 | 7.89E−10 | 26 |
| H4H16967P | 331 ± 0.3 | 0 | NB | NB | NB | NB |
| H4H16971P | 343 ± 0.5 | 58 | 4.07E+05 | 3.86E−03 | 9.48E−09 | 3.0 |
| H4H16979P | 293 ± 1.0 | 46 | 2.86E+05 | 2.30E−04 | 8.04E−10 | 50 |
| H4H16987P | 334 ± 0.4 | 46 | 4.90E+05 | 2.15E−02 | 4.38E−08 | 0.5 |
| H4H16991P | 312 ± 0.5 | 61 | 3.90E+05 | 2.87E−04 | 7.35E−10 | 40 |
| H4H16992P | 350 ± 0.4 | 70 | 4.59E+05 | 2.76E−04 | 6.01E−10 | 42 |
| H4H17001P | 351 ± 0.7 | 1 | NB* | NB* | NB* | NB* |
| H4H17015P | 368 ± 0.8 | 76 | 2.72E+05 | 2.81E−04 | 1.03E−09 | 41 |
| H4H17027P | 340 ± 0.4 | 63 | 1.10E+05 | 3.19E−04 | 2.90E−09 | 36 |
| H4H17028P | 349 ± 0.5 | 71 | 8.11E+05 | 6.93E−04 | 8.54E−10 | 17 |
| H4H17031P | 333 ± 0.5 | 63 | 1.87E+05 | 1.05E−03 | 5.61E−09 | 11 |
| H4H17033P | 336 ± 0.5 | 67 | 5.40E+05 | 4.15E−04 | 7.68E−10 | 28 |
| H4H17038P2 | 324 ± 1 | 63 | 6.42E+05 | 6.41E−03 | 9.98E−09 | 1.8 |
| H4H17045P2 | 368 ± 1.1 | 60 | 8.00E+04 | 4.98E−04 | 6.23E−09 | 23 |
| H4H17067P2 | 344 ± 0.3 | 55 | 1.00E+05 | 1.17E−03 | 1.17E−08 | 9.9 |
| H4H17082P2 | 366 ± 0.5 | 78 | 5.30E+05 | 6.12E−04 | 1.16E−09 | 19 |
| Isotype Control | 344 ± 0.8 | 1 | NB* | NB* | NB* | NB* |

*NB indicates that no binding was observed under the current experimental conditions.

TABLE 5

Binding kinetics parameters of mutant Bet v 1-MMH binding to Bet v 1 monoclonal antibodies at 37° C.

| Antibody | mAb Capture Level (RU) | 100 nM natural Bet v 1- MHH Bound (RU) | $k_a$ (1/Ms) | $k_d$ (1/s) | $K_D$ (M) | $t^{1/2}$ (min) |
|---|---|---|---|---|---|---|
| H4H16943P | 441 ± 1.3 | 0 | NB* | NB* | NB* | NB* |
| H4H16946P | 459 ± 1.8 | 97 | 6.03E+05 | 3.95E−04 | 6.55E−10 | 29 |
| H4H16950P | 461 ± 1.2 | 83 | 2.15E+05 | 1.25E−03 | 5.81E−09 | 9.2 |
| H4H16960P | 417 ± 1.4 | 72 | 8.79E+05 | 1.77E−03 | 2.01E−09 | 6.5 |

TABLE 5-continued

Binding kinetics parameters of mutant Bet v 1-MMH
binding to Bet v 1 monoclonal antibodies at 37° C.

| Antibody | mAb Capture Level (RU) | 100 nM natural Bet v 1- MHH Bound (RU) | $k_a$ (1/Ms) | $k_d$ (1/s) | $K_D$ (M) | $t^{1/2}$ (min) |
|---|---|---|---|---|---|---|
| H4H16967P | 405 ± 0.8 | −1 | NB* | NB* | NB* | NB* |
| H4H16971P | 427 ± 1.2 | 60 | 6.48E+05 | 1.20E−02 | 1.86E−08 | 1.0 |
| H4H16979P | 348 ± 0.7 | 56 | 4.62E+05 | 7.30E−04 | 1.58E−09 | 16 |
| H4H16987P | 429 ± 1.1 | 36 | 7.95E+05 | 8.47E−02 | 1.06E−07 | 0.14 |
| H4H16991P | 376 ± 0.7 | 67 | 7.17E+05 | 1.06E−03 | 1.48E−09 | 11 |
| H4H16992P | 432 ± 0.6 | 78 | 7.84E+05 | 8.85E−04 | 1.13E−09 | 13 |
| H4H17001P | 451 ± 0.8 | 2 | NB* | NB* | NB* | NB* |
| H4H17015P | 458 ± 1.1 | 89 | 4.45E+05 | 8.99E−04 | 2.02E−09 | 13 |
| H4H17027P | 421 ± 0.8 | 78 | 1.71E+05 | 1.16E−03 | 6.80E−09 | 9.9 |
| H4H17028P | 430 ± 0.8 | 77 | 1.01E+06 | 2.35E−03 | 2.32E−09 | 4.9 |
| H4H17031P | 413 ± 1.4 | 71 | 2.78E+05 | 4.06E−03 | 1.46E−08 | 2.8 |
| H4H17033P | 414 ± 0.8 | 79 | 8.83E+05 | 1.18E−03 | 1.34E−09 | 9.8 |
| H4H17038P2 | 399 ± 0.9 | 56 | 8.33E+05 | 2.96E−02 | 3.56E−08 | 0.39 |
| H4H17045P2 | 458 ± 1.2 | 84 | 1.62E+05 | 2.32E−03 | 1.43E−08 | 5.0 |
| H4H17067P2 | 435 ± 0.7 | 76 | 2.53E+05 | 4.28E−03 | 1.69E−08 | 2.7 |
| H4H17082P2 | 448 ± 1 | 89 | 8.21E+05 | 1.90E−03 | 2.31E−09 | 6.1 |
| Isotype Control | 421 ± 0.7 | −2 | NB* | NB* | NB* | NB* |

*NB indicates that no binding was observed under the current experimental conditions.

Example 4: Antibody Binding to Related Allergens as Determined by Surface Plasmon Resonance Equilibrium dissociation constants ($K_D$) for different related allergens binding to purified anti-Bet v 1 monoclonal antibodies were determined using a real-time surface plasmon resonance biosensor (SPR-Biacore) on a Biacore 4000 instrument. All binding studies were performed in 10 mM HEPES, 150 mM NaCl, 3 mM EDTA, and 0.05% v/v surfactant Tween-20, pH 7.4 (HBS-ET) running buffer at 25° C. The Biacore CM5 sensor surface was first derivatized by amine coupling with a monoclonal mouse anti-human Fc antibody (GE, #BR-1008-39) to capture the anti-Bet v 1 monoclonal antibodies. Binding studies were performed on the following related allergens: Alder (Aln g 1, MyBiosource, Cat #MBS1041484), Apple (Mal d 1, MyBiosource, Cat #MB S1224919), Carrot (Dau c 1.2, MyBiosource, Cat #MBS1212920), Celery (Api g 1, MyBiosource, Cat #MBS1171376), Celery (Api g 2, MyBiosource, Cat #MBS1047880), European Hornbeam (Car b 1 isoform 1A & 1B, MyBiosource, Cat #MBS1200018), European Hornbeam (Car b 1 isoform 2, MyBiosource, Cat #MBS1043940), Hazel (Cor A 1, MyBiosource, Cat #MBS5304600), and White Oak (Que a 1, MyBiosource, Cat #MBS1258822). Different concentrations of the related allergens were prepared in HBS-ET running buffer (100 nM-6.25 nM; serially diluted by 4-fold) and then were injected over anti-human Fc captured anti-Bet v 1 monoclonal antibody surface for 3 minutes at a flow rate of 30 μL/minute, while the dissociation of monoclonal antibody bound allergens was monitored for 8 minutes in HBS-ET running buffer. Association ($k_a$) and dissociation ($k_d$) rate constants were determined by fitting the real-time binding sensorgrams to a 1:1 binding model with mass transport limitation using Scrubber 2.0 c curve-fitting software. Binding dissociation equilibrium constants ($K_D$) and dissociative half-lives (t1/2) were calculated from the kinetic rate constants as:

$$K_D = \frac{kd}{ka}, \text{ and } t^{1/2} = \frac{\ln(2)}{kd}$$

Binding kinetics parameters for related allergens to different anti-Bet v 1 monoclonal antibodies of the invention at 25° C. are shown in Table 6 through Table 11.

As shown in Table 6 at 25° C., nine of the 20 anti-Bet v 1 antibodies of the invention demonstrated measurable binding to Aln g 1 with $K_D$ values ranging from 1.03 nM to 175 nM. The other 11 antibodies did not demonstrate any measurable binding to Aln g 1 under the tested conditions.

As shown in Table 7 at 25° C., two of the 20 anti-Bet v 1 antibodies of the invention demonstrated measurable binding to Mal d 1 with $K_D$ values of 29.8 nM and 494 nM. The other 18 antibodies did not demonstrate any measurable binding to Mal d 1 under the tested conditions.

As shown in Table 8 at 25° C., one of the anti-Bet v 1 antibodies of the invention demonstrated measurable binding to Api g 1 with a $K_D$ value of 167 nM. The other 19 antibodies did not demonstrate any measurable binding to Api g 1 under the tested conditions.

As shown in Table 9 at 25° C., eight of the 20 of the anti-Bet v 1 antibodies of the invention demonstrated measurable binding to Car b 1 isoform 1A & 1B with $K_D$ values ranging from 1.2 nM to 380 nM. The other 12 antibodies did not demonstrate any measurable binding to Car b 1 isoform 1A & 1B under the tested conditions.

As shown in Table 10 at 25° C., 14 of the 20 of the anti-Bet v 1 antibodies of the invention demonstrated measurable binding to Car b 1 isoform 2 with $K_D$ values ranging from 335 pM to 564 nM. The other 6 antibodies did not demonstrate any measurable binding to Car b 1 isoform 2 under the tested conditions.

As shown in Table 11 at 25° C., one of the anti-Bet v 1 antibodies of the invention demonstrated measurable binding to Cor A 1 with a $K_D$ value of 396 nM. The other 19 antibodies did not demonstrate any measurable binding to Cor A 1 under the tested conditions.

None of the antibodies of the invention demonstrated measurable binding to Dau c 1.2, Api g2, or Que a 1 under the conditions tested (data not shown). The isotype control antibody did not demonstrate any measurable binding to any of the allergens tested.

TABLE 6

Binding kinetics parameters of Alder (Aln g1) binding to Bet v 1 monoclonal antibodies at 25° C.

| Antibody | mAb Capture Level (RU) | 100 nM Analyte Bound (RU) | $k_a$ (1/Ms) | $k_d$ (1/s) | $K_D$ (M) | $t^{1/2}$ (min) |
|---|---|---|---|---|---|---|
| H4H16943P | 675 ± 0.9 | 1 | NB* | NB* | NB* | NB* |
| H4H16946P | 668 ± 1.2 | 2 | NB* | NB* | NB* | NB* |
| H4H16950P | 634 ± 1.7 | 15 | 9.12E+04 | 1.60E-02 | 1.75E-07 | 0.7 |
| H4H16960P | 681 ± 2.1 | 29 | 2.26E+05 | 3.32E-02 | 1.47E-07 | 0.3 |
| H4H16967P | 666 ± 3.1 | 0 | NB* | NB* | NB* | NB* |
| H4H16971P | 668 ± 2.1 | 41 | 9.30E+04 | 1.18E-02 | 1.26E-07 | 1.0 |
| H4H16979P | 545 ± 0.4 | 0 | NB* | NB* | NB* | NB* |
| H4H16987P | 667 ± 1.6 | 139 | 2.21E+05 | 8.70E-04 | 3.94E-09 | 13 |
| H4H16991P | 608 ± 0.4 | 3 | NB* | NB* | NB* | NB* |
| H4H16992P | 653 ± 1.3 | 5 | NB* | NB* | NB* | NB* |
| H4H17001P | 630 ± 1.6 | 49 | 2.64E+05 | 2.78E-02 | 1.05E-07 | 0.4 |
| H4H17015P | 745 ± 3 | 8 | NB* | NB* | NB* | NB* |
| H4H17027P | 772 ± 0.4 | 9 | 9.29E+04 | 6.43E-03 | 6.92E-08 | 1.8 |
| H4H17028P | 708 ± 1.5 | 16 | 5.17E+04 | 1.90E-03 | 3.67E-08 | 6.1 |
| H4H17031P | 727 ± 1.3 | 59 | 5.29E+04 | 2.38E-03 | 4.50E-08 | 4.8 |
| H4H17033P | 649 ± 0.2 | 3 | NB* | NB* | NB* | NB* |
| H4H17038P2 | 660 ± 1.3 | 2 | NB* | NB* | NB* | NB* |
| H4H17045P2 | 746 ± 1.2 | 0 | NB* | NB* | NB* | NB* |
| H4H17067P2 | 617 ± 2.2 | 2 | NB* | NB* | NB* | NB* |
| H4H17082P2 | 662 ± 3.6 | 132 | 3.12E+05 | 3.23E-04 | 1.03E-09 | 36 |
| Isotype Control | 686 ± 1.3 | 0 | NB* | NB* | NB* | NB* |

*NB indicates that no binding was observed under the current experimental conditions.

TABLE 7

Binding kinetics parameters of Apple (Mal d 1) binding to Bet v 1 monoclonal antibodies at 25° C.

| Antibody | mAb Capture Level (RU) | 100 nM Analyte Bound (RU) | $k_a$ (1/Ms) | $k_d$ (1/s) | $K_D$ (M) | $t^{1/2}$ (min) |
|---|---|---|---|---|---|---|
| H4H16943P | 676 ± 0.7 | -1 | NB* | NB* | NB* | NB* |
| H4H16946P | 668 ± 2.2 | 0 | NB* | NB* | NB* | NB* |
| H4H16950P | 635 ± 1.9 | -1 | NB* | NB* | NB* | NB* |
| H4H16960P | 690 ± 8.2 | 1 | NB* | NB* | NB* | NB* |
| H4H16967P | 671 ± 3.2 | -2 | NB* | NB* | NB* | NB* |
| H4H16971P | 667 ± 3.4 | 25 | 1.61E+05 | 7.95E-02 | 4.94E-07 | 0.2 |
| H4H16979P | 545 ± 0.5 | 1 | NB* | NB* | NB* | NB* |
| H4H16987P | 668 ± 0.8 | 2 | NB* | NB* | NB* | NB* |
| H4H16991P | 608 ± 1.4 | 0 | NB* | NB* | NB* | NB* |
| H4H16992P | 652 ± 0.8 | 3 | NB* | NB* | NB* | NB* |
| H4H17001P | 626 ± 0.8 | 0 | NB* | NB* | NB* | NB* |
| H4H17015P | 741 ± 2.6 | 0 | NB* | NB* | NB* | NB* |
| H4H17027P | 767 ± 1.4 | 0 | NB* | NB* | NB* | NB* |
| H4H17028P | 704 ± 2.3 | 1 | NB* | NB* | NB* | NB* |
| H4H17031P | 727 ± 1.6 | 0 | NB* | NB* | NB* | NB* |
| H4H17033P | 650 ± 1.6 | 1 | NB* | NB* | NB* | NB* |
| H4H17038P2 | 658 ± 1.5 | -1 | NB* | NB* | NB* | NB* |
| H4H17045P2 | 747 ± 1.3 | -1 | NB* | NB* | NB* | NB* |
| H4H17067P2 | 616 ± 2 | -1 | NB* | NB* | NB* | NB* |
| H4H17082P2 | 662 ± 1.9 | 112 | 1.25E+06 | 3.74E-02 | 2.98E-08 | 0.3 |
| Isotype Control | 686 ± 1.1 | 0 | NB* | NB* | NB* | NB* |

*NB indicates that no binding was observed under the current experimental conditions.

TABLE 8

Binding kinetics parameters of Celery (Api g 1) binding to Bet v 1 monoclonal antibodies at 25° C.

| Antibody | mAb Capture Level (RU) | 100 nM Analyte Bound (RU) | $k_a$ (1/Ms) | $k_d$ (1/s) | $K_D$ (M) | $t^{1/2}$ (min) |
|---|---|---|---|---|---|---|
| H4H16943P | 674 ± 0.7 | 0 | NB* | NB* | NB* | NB* |
| H4H16946P | 666 ± 0.4 | 1 | NB* | NB* | NB* | NB* |
| H4H16950P | 632 ± 3 | 0 | NB* | NB* | NB* | NB* |
| H4H16960P | 684 ± 3.6 | 0 | NB* | NB* | NB* | NB* |

TABLE 8-continued

Binding kinetics parameters of Celery (Api g 1) binding to Bet v 1 monoclonal antibodies at 25° C.

| Antibody | mAb Capture Level (RU) | 100 nM Analyte Bound (RU) | $k_a$ (1/Ms) | $k_d$ (1/s) | $K_D$ (M) | $t^{1/2}$ (min) |
|---|---|---|---|---|---|---|
| H4H16967P | 668 ± 4.2 | −1 | NB* | NB* | NB* | NB* |
| H4H16971P | 666 ± 0.7 | 0 | NB* | NB* | NB* | NB* |
| H4H16979P | 546 ± 1.1 | 0 | NB* | NB* | NB* | NB* |
| H4H16987P | 668 ± 0.8 | 1 | NB* | NB* | NB* | NB* |
| H4H16991P | 607 ± 1.3 | 0 | NB* | NB* | NB* | NB* |
| H4H16992P | 651 ± 2.9 | 1 | NB* | NB* | NB* | NB* |
| H4H17001P | 625 ± 1.3 | −1 | NB* | NB* | NB* | NB* |
| H4H17015P | 740 ± 1.5 | 0 | NB* | NB* | NB* | NB* |
| H4H17027P | 765 ± 1.1 | 0 | NB* | NB* | NB* | NB* |
| H4H17028P | 705 ± 2.2 | 1 | NB* | NB* | NB* | NB* |
| H4H17031P | 727 ± 1.3 | 0 | NB* | NB* | NB* | NB* |
| H4H17033P | 648 ± 0.3 | 39 | 4.75E+05 | 7.91E−02 | 1.67E−07 | 0.2 |
| H4H17038P2 | 659 ± 0.6 | −1 | NB* | NB* | NB* | NB* |
| H4H17045P2 | 747 ± 0.5 | 0 | NB* | NB* | NB* | NB* |
| H4H17067P2 | 613 ± 0.6 | 0 | NB* | NB* | NB* | NB* |
| H4H17082P2 | 660 ± 3.1 | 0 | NB* | NB* | NB* | NB* |
| Isotype Control | 684 ± 3.1 | −1 | NB* | NB* | NB* | NB* |

*NB indicates that no binding was observed under the current experimental conditions.

TABLE 9

Binding kinetics parameters of European Hornbeam (Car b 1 isoform 1A & 1B) binding to Bet v 1 monoclonal antibodies at 25° C.

| Antibody | mAb Capture Level (RU) | 100 nM Analyte Bound (RU) | $k_a$ (1/Ms) | $k_d$ (1/s) | $K_D$ (M) | $t^{1/2}$ (min) |
|---|---|---|---|---|---|---|
| H4H16943P | 674 ± 1 | 26 | 1.52E+05 | 5.78E−02 | 3.80E−07 | 0.2 |
| H4H16946P | 667 ± 1.6 | 63 | 1.43E+05 | 2.40E−02 | 1.68E−07 | 0.5 |
| H4H16950P | 633 ± 1.6 | −1 | NB* | NB* | NB* | NB* |
| H4H16960P | 687 ± 0.8 | 4 | NB* | NB* | NB* | NB* |
| H4H16967P | 666 ± 3.3 | −1 | NB* | NB* | NB* | NB* |
| H4H16971P | 669 ± 4.6 | 1 | NB* | NB* | NB* | NB* |
| H4H16979P | 545 ± 0.4 | 1 | NB* | NB* | NB* | NB* |
| H4H16987P | 668 ± 0.3 | 0 | NB* | NB* | NB* | NB* |
| H4H16991P | 608 ± 1.8 | 1 | NB* | NB* | NB* | NB* |
| H4H16992P | 653 ± 0.6 | 161 | 2.81E+05 | 3.37E−04 | 1.20E−09 | 34 |
| H4H17001P | 626 ± 1 | 0 | NB* | NB* | NB* | NB* |
| H4H17015P | 742 ± 1.8 | 0 | NB* | NB* | NB* | NB* |
| H4H17027P | 767 ± 0.3 | 41 | 3.14E+04 | 6.73E−03 | 2.14E−07 | 1.7 |
| H4H17028P | 705 ± 0.7 | 159 | 2.10E+05 | 5.11E−04 | 2.43E−09 | 23 |
| H4H17031P | 726 ± 3.2 | 126 | 8.04E+04 | 1.11E−03 | 1.38E−08 | 10 |
| H4H17033P | 650 ± 1.3 | 0 | NB* | NB* | NB* | NB* |
| H4H17038P2 | 659 ± 0.9 | 105 | 1.51E+05 | 6.23E−03 | 4.14E−08 | 1.9 |
| H4H17045P2 | 748 ± 1 | 5 | NB* | NB* | NB* | NB* |
| H4H17067P2 | 616 ± 1 | 0 | NB* | NB* | NB* | NB* |
| H4H17082P2 | 664 ± 1.6 | 69 | 3.90E+05 | 3.53E−02 | 9.05E−08 | 0.3 |
| Isotype Control | 686 ± 0.7 | 0 | NB* | NB* | NB* | NB* |

*NB indicates that no binding was observed under the current experimental conditions.

TABLE 10

Binding kinetics parameters of European Hornbeam (Car b1 isoform 2) binding to Bet v 1 monoclonal antibodies at 25° C.

| Antibody | mAb Capture Level (RU) | 100 nM Analyte Bound (RU) | $k_a$ (1/Ms) | $k_d$ (1/s) | $K_D$ (M) | $t^{1/2}$ (min) |
|---|---|---|---|---|---|---|
| H4H16943P | 675 ± 1.6 | 183 | 1.11E+06 | 3.71E−04 | 3.35E−10 | 31 |
| H4H16946P | 666 ± 0.7 | 63 | 7.69E+04 | 1.38E−02 | 1.79E−07 | 0.8 |
| H4H16950P | 633 ± 3 | 0 | NB* | NB* | NB* | NB* |
| H4H16960P | 682 ± 4.5 | 1 | NB* | NB* | NB* | NB* |
| H4H16967P | 663 ± 5.4 | 0 | NB* | NB* | NB* | NB* |
| H4H16971P | 668 ± 4.1 | 23 | 2.59E+05 | 1.46E−01 | 5.64E−07 | 0 |
| H4H16979P | 547 ± 1.1 | 114 | 9.71E+05 | 2.41E−03 | 2.48E−09 | 4.8 |
| H4H16987P | 667 ± 1.3 | 153 | 1.01E+06 | 5.61E−03 | 5.56E−09 | 2.1 |

TABLE 10-continued

Binding kinetics parameters of European Hornbeam (Car b1 isoform 2) binding to Bet v 1 monoclonal antibodies at 25° C.

| Antibody | mAb Capture Level (RU) | 100 nM Analyte Bound (RU) | $k_a$ (1/Ms) | $k_d$ (1/s) | $K_D$ (M) | $t^{1/2}$ (min) |
| --- | --- | --- | --- | --- | --- | --- |
| H4H16991P | 607 ± 3.4 | 93 | 1.07E+06 | 4.04E−02 | 3.78E−08 | 0.3 |
| H4H16992P | 652 ± 0.6 | 156 | 1.40E+06 | 8.61E−04 | 6.17E−10 | 13 |
| H4H17001P | 625 ± 1.1 | 157 | 2.03E+06 | 3.20E−03 | 1.58E−09 | 3.6 |
| H4H17015P | 741 ± 1.6 | 2 | NB* | NB* | NB* | NB* |
| H4H17027P | 765 ± 1.8 | 42 | 5.84E+04 | 5.77E−03 | 9.89E−08 | 2.0 |
| H4H17028P | 703 ± 4.1 | 95 | 9.71E+04 | 4.37E−03 | 4.50E−08 | 2.6 |
| H4H17031P | 727 ± 1.2 | 160 | 3.95E+05 | 5.17E−03 | 1.31E−08 | 2.2 |
| H4H17033P | 650 ± 1.2 | 111 | 1.34E+06 | 4.47E−02 | 3.34E−08 | 0.3 |
| H4H17038P2 | 660 ± 1.6 | 73 | 1.28E+05 | 6.48E−03 | 5.05E−08 | 1.8 |
| H4H17045P2 | 747 ± 1.2 | 5 | NB* | NB* | NB* | NB* |
| H4H17067P2 | 616 ± 1 | 1 | NB* | NB* | NB* | NB* |
| H4H17082P2 | 661 ± 2 | 166 | 2.18E+06 | 1.24E−03 | 5.67E−10 | 9.3 |
| Isotype Control | 685 ± 1.2 | 0 | NB* | NB* | NB* | NB* |

*NB indicates that no binding was observed under the current experimental conditions.

TABLE 11

Binding kinetics parameters of Hazel (Cor A 1) binding to Bet v 1 monoclonal antibodies at 25° C.

| Antibody | mAb Capture Level (RU) | 100 nM Analyte Bound (RU) | $k_a$ (1/Ms) | $k_d$ (1/s) | $K_D$ (M) | $t^{1/2}$ (min) |
| --- | --- | --- | --- | --- | --- | --- |
| H4H16943P | 673 ± 0.4 | 0 | NB* | NB* | NB* | NB* |
| H4H16946P | 665 ± 0.6 | −1 | NB* | NB* | NB* | NB* |
| H4H16950P | 635 ± 3.3 | 0 | NB* | NB* | NB* | NB* |
| H4H16960P | 687 ± 7 | 0 | NB* | NB* | NB* | NB* |
| H4H16967P | 668 ± 1.7 | 0 | NB* | NB* | NB* | NB* |
| H4H16971P | 666 ± 5.8 | 0 | NB* | NB* | NB* | NB* |
| H4H16979P | 546 ± 1.1 | 0 | NB* | NB* | NB* | NB* |
| H4H16987P | 668 ± 0.7 | 0 | NB* | NB* | NB* | NB* |
| H4H16991P | 607 ± 1.3 | 0 | NB* | NB* | NB* | NB* |
| H4H16992P | 652 ± 1.6 | 0 | NB* | NB* | NB* | NB* |
| H4H17001P | 626 ± 0.4 | 0 | NB* | NB* | NB* | NB* |
| H4H17015P | 740 ± 0.7 | 1 | NB* | NB* | NB* | NB* |
| H4H17027P | 766 ± 2.8 | 0 | NB* | NB* | NB* | NB* |
| H4H17028P | 704 ± 1.3 | 0 | NB* | NB* | NB* | NB* |
| H4H17031P | 727 ± 1.2 | 0 | NB* | NB* | NB* | NB* |
| H4H17033P | 649 ± 1.5 | 0 | NB* | NB* | NB* | NB* |
| H4H17038P2 | 659 ± 0.1 | 0 | NB* | NB* | NB* | NB* |
| H4H17045P2 | 748 ± 0.8 | 0 | NB* | NB* | NB* | NB* |
| H4H17067P2 | 614 ± 0.7 | −1 | NB* | NB* | NB* | NB* |
| H4H17082P2 | 661 ± 0.8 | 20 | 1.06E+05 | 4.18E−02 | 3.96E−07 | 0.3 |
| Isotype Control | 685 ± 0.5 | 1 | NB* | NB* | NB* | NB* |

*NB indicates that no binding was observed under the current experimental conditions.

Example 5: Blocking Bet v 1 Binding to Allergen Specific IgE by Anti-Bet v 1 IgG Antibodies The ability of single anti-Bet v 1 antibodies of the invention or combinations of anti-Bet v 1 antibodies of the invention to block Bet v 1 binding to plate-captured IgE from allergic human donor plasma/sera was determined using an ELISA. Antibodies were tested either alone or in polyclonal mixes. For the assay, microtiter plates were coated overnight at 4° C. with human FcεR1a (the high affinity receptor for IgE) extracellular domain protein that was produced with a C-terminal mouse Fc tag (hFcεR1α-mFc; SEQ ID NO: 313). Plates were then blocked with 0.5% BSA (w/v) for 1 hour at room temperature (RT). Plasma from allergic donors was diluted and total IgE was then captured over the receptor-coated surface. A constant amount of 0.1 nM of biotin labeled natural Bet v 1 (Indoor Biotechnologies, #NA-BV1-1) was pre-mixed with anti-Bet v 1 antibodies, at a single concentration of 1 μg/mL or in serial dilutions starting from either 10 μg/mL or 1 μg/mL of each antibody and incubated for 1 hour at RT to allow Bet v 1-antibody interaction to reach equilibrium. The antibody-Bet v 1 mixture was then added to the IgE-coated plate for 1 hour. Plates were subsequently washed and the amount of natural Bet v 1 bound to plate was detected using streptavidin conjugated to horseradish peroxidase (Thermo Scientific, #N200/QJ223091) at a 1:10,000 dilution and incubated for 1 hour at RT. Plates were then washed with PBS-T in between each step of the ELISA protocol described above. To develop the colorimetric reaction, TMB/$H_2O_2$ substrate (BD Pharmingen Reagent A #51-2602KC+Reagent B, #51-2607KC) was added to the plates and incubated for 20 minutes at RT. The reaction was stopped using 2 N sulfuric acid ($H_2SO_4$; VWR, #BDH3500-1). The absorbance was subsequently measured on a spectrophotometer (Victor, Perkin Elmer) at 450 nm. The percent blocking was calculated using the highest antibody concentration used in each assay as described below.

$$\text{Percent blocking} = \frac{(A_{450} \text{ with no antibody}) - (A_{450} \text{ at highest antibody concentration})}{(A_{450} \text{ with no antibody})} \times 100$$

Twenty anti-Bet v 1 antibodies were tested as single antibodies for their ability to block Bet v 1 binding to plate-captured IgE from allergic human donor plasma using the ELISA described. Individual monoclonal antibodies were able to partially block IgE binding to Bet v 1 by 8.5-64%, which underlines the polyclonality of the IgEs. Seven antibodies showed blocking ranging from 36-64% at the highest antibody concentration tested of 10 µg/mL, as shown in Table 12.

Four anti-Bet v 1 antibodies, H4H17082P2, H4H17038P2, H4H16987P, and H4H16992P were tested in a single point blocking assay. A combination of H4H17082P2 and H4H16992P demonstrated greater than 90% blocking in seven out of ten IgE donors. Three and four monoclonal antibody combinations demonstrated similar results and did not appear to add any additional blocking effect as compared to the two-antibody combination of H4H17082P2 and H4H16992P, as shown in Table 13.

The four monoclonal antibodies, H4H17082P2, H4H17038P2, H4H16987P, and H4H16992P, were subsequently tested as single and 2, 3 and 4 monoclonal antibody combinations in dose response blocking assay with 3 donor IgE samples. The results showed that the anti-Bet v 1 two monoclonal antibody combination of H4H17082P2 and H4H16992P blocked Bet v 1 binding to allergen specific IgE greater than 90% and close to baseline in 3 donors, as shown in Table 14. The tested 3- and 4-antibody combinations showed similar breadth and potency of blocking activity. As positive control, purified mouse anti-Bet v 1 polyclonal IgG demonstrated >90% blocking.

TABLE 12

Anti-Bet v 1 antibodies blocking Bet v 1 binding to allergen specific IgE

| Antibodies | Donor ID: | |
|---|---|---|
| | 23397-PB | 24606-AB |
| | % Blocking of Bet v 1 binding to captured IgE | |
| H4H17082P2 MAB2 | 56.6 | 60.3 |
| H4H16971P | 35.4 | 12.8 |
| H4H17027P | 23.0 | 28.4 |
| H4H17028P | 19.7 | 16.6 |
| H4H16946P | 27.6 | 22.8 |
| H4H17038P2 MAB3 | 49.0 | 55.3 |
| H4H16950P | 32.3 | 20.7 |
| H4H16987P MAB4 | 15.2 | 12.8 |
| H4H17045P2 | 27.4 | 27.2 |
| H4H17067P2 | 25.7 | 22.2 |
| H4H16967P | 21.8 | 23.5 |
| H4H17015P | 41.8 | 63.4 |
| H4H16979P | 33.6 | 12.9 |
| H4H16991P | 30.0 | 32.6 |
| H4H17033P | 51.8 | 49.0 |
| H4H16992 MAB1 | 36.7 | 64.4 |
| H4H16960P | 8.5 | 17.6 |
| H4H17031 | 16.7 | 20.5 |
| H4H17001P | 47.2 | 52.7 |
| H4H16943P | 47.7 | 52.5 |

Allergy donor plasma was diluted 1:50 for these assays.

TABLE 13

Single antibodies and antibody combinations blocking Bet v 1 binding to allergen specific IgE

| Antibodies | Donor ID: | | | | | | | | | |
|---|---|---|---|---|---|---|---|---|---|---|
| | 23658-MD | 23939-MH | 23035-BL | 25414-CW | 25340-RR | 25299-RJ | 25609-MS | 26532-CC | 29718-MW | 22627-MN |
| | Percent Blocking (at 1 µg/mL each antibody) | | | | | | | | | |
| H4H17082P2 MAB2 | 62 | 79 | 52 | 38 | 81 | 66 | 51 | 74 | 49 | 61 |
| H4H17038P2 MAB3 | 24 | 17 | 36 | 23 | 28 | 24 | 17 | 23 | 14 | 23 |
| H4H16987P MAB4 | 27 | 16 | −46 | −4 | 15 | 9 | 16 | 4 | 13 | 12 |
| H4H16992P MAB1 | 44 | 53 | 43 | 53 | 67 | 70 | 89 | 80 | 82 | 62 |
| H4H17082P2 + H4H17038P2 | 70 | 85 | 73 | 57 | 90 | 78 | 65 | 83 | 60 | 79 |
| H4H17082P2 + H4H16987P | 74 | 88 | 21 | 45 | 84 | 69 | 65 | 75 | 61 | 76 |
| H4H17082P2 + H4H16992P | 79 | 93 | 72 | 77 | 91 | 91 | 98 | 94 | 94 | 96 |
| H4H17038P2 + H4H16987P | 47 | 31 | 16 | 28 | 41 | 29 | 33 | 29 | 28 | 47 |
| H4H17038P2 + H4H16992P | 58 | 62 | 51 | 77 | 83 | 75 | 93 | 87 | 87 | 77 |
| H4H16987P + H4H16992P | 61 | 61 | −6 | 63 | 75 | 69 | 94 | 81 | 89 | 64 |
| H4H17082P2 + H4H17038P2 + H4H16987P | 78 | 88 | 39 | 63 | 91 | 79 | 72 | 83 | 68 | 85 |

TABLE 13-continued

Single antibodies and antibody combinations blocking Bet v 1 binding to allergen specific IgE

| Antibodies | Donor ID: | | | | | | | | | |
|---|---|---|---|---|---|---|---|---|---|---|
| | 23658-MD | 23939-MH | 23035-BL | 25414-CW | 25340-RR | 25299-RJ | 25609-MS | 26532-CC | 29718-MW | 22627-MN |
| | Percent Blocking (at 1 µg/mL each antibody) | | | | | | | | | |
| H4H17082P2 + H4H17038P2 + H4H16992P | 83 | 92 | 65 | 91 | 96 | 89 | 98 | 94 | 94 | 90 |
| H4H17082P2 + H4H16987P + H4H16992P | 83 | 91 | 16 | 85 | 91 | 79 | 96 | 90 | 95 | 78 |
| H4H17038P2 + H4H16987P + H4H16992P | 71 | 69 | 3 | 82 | 88 | 71 | 95 | 86 | 93 | 76 |
| H4H17082P2 + H4H17038P2 + H4H16987P + H4H16992P | 86 | 93 | 44 | 89 | 95 | 84 | 98 | 94 | 97 | 87 |
| Biotinylated Bet v 1 (no antibody) at 0.1 nM | 0 | 0 | 0 | 0 | 0 | 0 | 0 | 0 | 0 | 0 |
| Isotype control | −3 | −2 | −5 | −4 | −1 | −4 | −2 | −4 | −2 | −3 |

Allergy donor plasma was normalized to either to 1:20 (6 donors), 1:10 (3 donors) or 1:9 (1 donor) Bet v 1 specific IgE titer and then diluted 1:50 for this assay.

TABLE 14

Antibody combinations blocking Bet v 1 binding to allergen specific IgE

| Antibody | Donor ID: | | |
|---|---|---|---|
| | 23939-MH | 25340-RR | 25609-MS |
| | Percent Blocking (at 1 µg/mL each antibody) | | |
| H4H17082P2 | 82.9 | 82.7 | 56.4 |
| H4H17038P2 | 20.2 | 23.2 | 22.8 |
| H4H16987P | 19.6 | 11.1 | 21.6 |
| H4H16992P | 63.3 | 70.2 | 86.9 |
| H4H17082P2 + H4H16992P | 94.8 | 93.8 | 96.5 |
| H4H17082P2 + H4H17038P2 + H4H16992P | 93.4 | 96.4 | 95.2 |
| H4H17082P2 + H4H16987P + H4H16992P | 91.5 | 93.1 | 94.2 |
| H4H17082P2 + H4H17038P2 + H4H16987P + H4H16992P | 92.6 | 95.4 | 95.7 |
| Isotype control | 16.8 | 10.6 | 8.8 |
| Purified anti-Bet v 1 mouse IgG at 333.3 nM | 92.7 | 93.9 | 94.6 |

Example 6: Epitope Mapping of Anti-Bet v 1 Antibodies Binding to Bet v 1 by Hydrogen Deuterium (H/D) Exchange To determine the amino acid residues of Bet v 1 [(amino acids M1-N160 of Uniprot P15494] with which H4H16992P2, H4H17082P2, H4H17038P2, and H4H16987P interact, a H/D exchange epitope mapping with mass spectrometry study was performed. A general description of the H/D exchange method is set forth in e.g., Ehring (1999) *Analytical Biochemistry* 267(2):252-259; and Engen and Smith (2001) *Anal. Chem.* 73:256A-265A.

The HDX-MS experiments were performed on an integrated Waters HDX/MS platform, consisting of a Leaptec HDX PAL system for the deuterium labeling, a Waters Acquity M-Class (Auxiliary solvent manager) for the sample digestion and loading, a Waters Acquity M-Class (Binary solvent manager) for the analytical column gradient, and Synapt G2-Si mass spectrometer for peptic peptide mass measurement.

The labeling solution was prepared in 10 mM PBS buffer in $D_2O$ at pD 7.0 (equivalent to pH 6.6). For deuterium labeling, 3.8 µL of natural Bet v 1 (Indoor Biotech, Catalog #NA-BV1-1, 28 µmol/L), Bet v 1 premixed with each antibody, or the mixture of all 4 anti-Bet v 1 antibodies in a 1:1 molar ratio was incubated with 56.2 µL $D_2O$ labeling solution for various time-points (e.g., Undeuterated control=0 second, labeled for 1 minute, 5 minutes, 10 minutes and 20 minutes). The deuteration was quenched by transferring 50 µL of the sample to 50 µL of pre-chilled 0.2 M TCEP, 6 M guanidine chloride in 100 mM phosphate buffer, pH 2.5 (quench buffer) and the mixed sample was incubated at 1.0° C. for 2 minutes. The quenched sample was then injected into a Waters HDX Manager for online pepsin/protease XIII digestion. The digested peptides were trapped onto an ACQUITY UPLC BEH C18 1.7-µm, 2.1×5 mm VanGuard pre-column at 0° C. and eluted to an analytical column ACQUITY UPLC BEH C18 1.7-µm, 1.0×50 mm for a 9-minute gradient separation of 5%-40% B (mobile phase A: 0.1% formic acid in water, mobile phase B: 0.1% formic acid in acetonitrile). The mass spectrometer was set at a cone voltage of 37 V, scan time of 0.5 seconds, and mass/charge range of 50-1700 Th.

For the identification of the peptides from Bet v 1, LC-$MS^E$ data from undeuterated sample were processed and searched against the database including Bet v 1 and its randomized sequence via Waters ProteinLynx Global Server (PLGS) software. The identified peptides were imported to DynamX software and filtered by two criteria: 1) minimum products per amino acid: 0.3, and 2) replication file threshold: 3. DynamX software then automatically determined deuterium uptake of each peptide based on retention time and high mass accuracy (<10 ppm) across multiple time points with 3 replicates at each time.

Using the online pepsin/protease XIII column coupled with $MS^E$ data acquisition, a total of 36 peptides from Bet v 1 were reproducibly identified in the absence or presence of the antibody, representing 91.2% sequence coverage. Peptides with significantly reduced deuteration uptake when bound to H4H16992P2, H4H17082P2, H4H17038P2, H4H16987P and 4 antibody combinations are illustrated in FIGS. 1 through 4 and 5, respectively. The recorded peptide mass corresponds to the average value of the centroid $MH^+$ mass from three replicates of Bet v 1 in complex with anti-Bet v 1 antibody or antibodies.

As shown in FIG. 1, the peptides corresponding to amino acids 23-43 (FILDGDNLFPKVAPQAISSVE, SEQ ID NO: 307) had a slower deuteration rate in the presence of H4H16992P.

As shown in FIG. 2, the peptides corresponding to amino acids 44-56 (NIEGNGGPGTIKK, SEQ ID NO: 308) had a slower deuteration rate in the presence of H4H17082P.

As shown in FIG. 3, the peptides corresponding to amino acids 2-19 (GVFNYETETTSVIPAARL, SEQ ID NO: 309) had a slower deuteration rate in the presence of H4H17038P2.

As shown in FIG. 4, the peptides corresponding to amino acids 57-70 (ISFPEGFPFKYVKD, SEQ ID NO: 310) and 81-96 (KYNYSVIEGGPIGDTL, SEQ ID NO: 315) had a slower deuteration rate in the presence of H4H16987P.

As shown in FIG. 5, the peptides corresponding to amino acids 23-43 (FILDGDNLFPKVAPQAISSVE, SEQ ID NO: 307), amino acids 44-56 (NIEGNGGPGTIKK, SEQ ID NO: 308), 2-19 (GVFNYETETTSVIPAARL, SEQ ID NO: 309), amino acids 57-70 (ISFPEGFPFKYVKD, SEQ ID NO: 310) and 81-96 (KYNYSVIEGGPIGDTL, SEQ ID NO: 315) had slower deuteration rates in the presence of the 4 anti-Bet v 1 antibody combination (H4H16992P, H4H17082P, H4H17038P2 and H4H16987P).

In addition, a modest level of protection was observed for peptide 23-43 in the presence of H4H17082P, H4H17038P2 and H4H16987P, identifying that this region could represent a secondary epitope for these monoclonal antibodies.

Example 7: Effect of Anti-Bet v 1 Antibodies in the Passive Cutaneous Anaphylaxis (PCA) In Vivo Model To determine the efficacy of anti-Bet v 1 antibodies of the invention for blocking allergen induced mast cell degranulation the passive cutaneous anaphylaxis (PCA) in vivo model was used. This model involves intradermal injection of an allergen-specific antiserum into a local area on the skin followed by intravenous injection of an antigen along with a dye. The allergic reaction causes capillary dilatation and increased vascular permeability at the site of sensitization, resulting in preferential accumulation of dye at this site. The dye can be extracted from the tissue and quantitated spectrophotometrically. Dye extravasation into tissue sensitized with test antiserum can then be compared to extravasation into tissue sensitized with a non-relevant antiserum.

Antisera were generated for use in the assay by immunizing Balb/c mice with 5 g of natural Bet v 1 protein (Indoor Biotechnologies, #NA-BV1-1) in a solution of 1 mg/mL of alum in 1× phosphate buffered saline (PBS) on day 0. One week later (day 7), sensitized mice were boosted with 5 g natural Bet v 1 protein in a solution of 1 mg/mL alum in 1×PBS. Two weeks after the boost, mice were subjected to an intranasal airway challenge with 0.5 g of natural Bet v 1 protein in 20 µL PBS on days 21, 24 and 28. Mice were then sacrificed on day 31 and serum was collected. The total IgE concentration in the isolated antisera was determined using an OptEIA™ ELISA kit (BD Biosciences, #555248) according to the manufacturer's instructions. The final concentration of Bet v 1 antisera was diluted to 2600 ng/mL of IgE in PBS.

Antisera used as a negative control in the assay was generated by immunizing Balb/c mice with 5 g natural Fel d 1 protein purified from cat hair extract (Indoor Biotechnologies, #LTN-FD1-1) in a solution of 1 mg/mL of alum in PBS on day 0. Mice were boosted with 5 g Fel d 1 protein in a solution of 1 mg/mL alum in PBS on days 14 and 21. One week after the final boost (day 28), mice were sacrificed and serum was collected. The total IgE concentration in the isolated antisera was determined using an OptEIA™ ELISA kit (BD Biosciences, #555248) according to the manufacturer's instructions. The final concentration of antisera was diluted to 2500 ng/mL of IgE in PBS.

For the PCA assays, groups of Balb/c mice (n≥5 per experiment) were first subcutaneously injected with either an isotype control antibody, an anti-Bet v 1 antibody, or a combination of anti-Bet v 1 antibodies at a dose of 1 mg/kg (total antibody dose). Three days after antibody administration, 10 µL of either 1.5 ng Bet v 1 antiserum or 3 ng negative control anti-serum were injected into the right and left ears of mice in each group, respectively. Twenty-four hours after the local administration of allergen-specific antisera, mice were challenged by intravenous injection (100 µL per mouse) of a solution of 1 g/mL of natural Bet v 1 dissolved in PBS containing 0.5% (w/v) Evan's blue dye (Sigma Aldrich, #E2129). One hour after antigen challenge, mice were sacrificed, their ears were excised, placed in 1 mL formamide, and subsequently incubated for 3 days from 50-56° C. to extract the Evan's blue dye. The ear tissue was then removed from the formamide, blotted to remove excess liquid and weighed. Two-hundred microliter aliquots of each formamide extract were transferred to 96 well plates in duplicate and their absorbance was then measured at 620 nm. The optical density measured was converted to Evan's blue dye concentration using a standard curve and represented as ng of Evan's blue dye per mg tissue. Mean values±the standard deviation are shown in Table 15 for each group. Mean difference as compared to isotype control was calculated using Bonferroni's multiple comparisons test in GraphPad Prism.

As shown in Table 15, in the first study, the single anti-Bet v 1 antibody, H4H17082P2, did not demonstrate a significant reduction of dye extravasation compared to isotype control. In contrast in Study 2, the combination of two anti-Bet v 1 antibodies of the invention (H4H16992P and H4H17082P2) and the combination of four anti-Bet v 1 antibodies of the invention (H4H16992P, H4H17082P2, H4H17038P2, and H4H16987P) demonstrated significant reductions of dye extravasation as compared to the isotype control treatment, with reductions of 35.26 and 36.49 ng/mg respectively. Similarly, in Study 3 the combination of two anti-Bet v 1 antibodies of the invention (H4H16992P and H4H17082P2) again demonstrated significant reductions of dye extravasation as compared to the isotype control treatment, with a reduction of 41.09 ng/mg. As was previously demonstrated in Study 1, in Study 3 the single anti-Bet v 1 antibody, H4H17082P2, did not demonstrate a significant reduction of dye extravasation compared to isotype control. However, another single antibody, H4H16992P, demonstrated a significant reduction of dye extravasation compared to isotype control, with a reduction of 25.86 ng/mg. From the studies conducted the single antibody H4H16992P, the two-antibody combination of H4H17082P2+H4H16992P, as well as the four-antibody combination of H4H17082P2+H4H16992P+H4H17038P2+H4H16987P were able to block mast cell degranulation as indicated by a significant reduction of dye extravasation compared to isotype control in the passive cutaneous anaphylaxis in vivo model as determined by two-way ANOVA with Bonferroni's post test. The H4H17082P2 antibody alone was not able to block mast cell degranulation as indicated by an increase in dye extravasation compared to isotype in two of the studies conducted. The number of mice used per group (n) is noted within parentheses in the use in this assay by immunizing Balb/c mice with 5 g of natural Bet v 1 protein (Indoor Biotechnologies, Catalog #NA-BV1-1 Lot 36164) or 5 g of BPE; *pendula* (Stallargenes Greer, Catalog #XP527D3A25 Lot #277329), nigra (Stallargenes Greer Catalog #XP79D3A25 Lot #285077) or *populifolia* (Stallargenes Greer Catalog #XP80D3A2.5 Lot #273622) in a solution of 1 mg/ml of alum in 1× phosphate buffered saline (PBS) on day 0. One week later (day 7), sensitized mice were boosted with 5 g of natural Bet v 1 protein or 5 g of the respective BPE (*pendula*, nigra, or *populifolia*) in a solution of 1 mg/mL alum in 1×PBS. Two weeks after the boost, mice were subjected to an intranasal airway challenge with 0.5 g natural Bet v 1 protein or 0.5 g

TABLE 15

Effect of anti-Bet v 1 antibodies in the passive cutaneous anaphylaxis in vivo model.

| Treatment Group | Negative control allergen (ng Evans Blue/mg tissue ± SD) | Mean Difference Compared to Isotype Control | Bet v 1 (ng Evans Blue/mg tissue ± SD) | Mean Difference Compared to Isotype Control |
|---|---|---|---|---|
| Study 1 | | | | |
| H4H17082P2 (n = 8) | 2.1 ± 0.9 | −0.31 | 46.6 ± 17.3 | 7.5 |
| Study 2 | | | | |
| H4H17082P2 + H4H16992P (n = 10) | 6.3 ± 3.8 | 1.807 | 8.3 ± 7.7 | −35.26 (****) |
| H4H17082P2 + H4H16992P + H4H17038P2 + H4H16987P (n = 10) | 7.6 ± 5.5 | 3.090 | 7.1 ± 4.1 | −36.49 (****) |
| Study 3 | | | | |
| H4H17082P2 (n = 5) | 6.5 ± 1.4 | −0.311 | 89.4 ± 28.3 | 27.37 (*) |
| H4H16992P (n = 5) | 6.4 ± 2.1 | −0.324 | 36.2 ± 14 | −25.86 (*) |
| H4H17082P2 + H4H16992P (n = 5) | 3.6 ± .31 | −3.118 | 21 ± 9.6 | −41.09 (***) |

1 mg/kg total antibody concentration used for all antibody treatment groups
(*) $P < .05$,
(***) $P \leq .001$,
(****) $P \leq .0001$
n = number of mice in each group Example 8: Effect of Anti-Bet v 1 Antibodies Against Three Different Birch Pollen Extracts in the Passive Cutaneous Anaphylaxis (PCA) In Vivo Model Anti-Bet v 1 antibodies provided herein were tested for efficacy in blocking allergen induced mast cell degranulation in the passive cutaneous anaphylaxis (PCA) in vivo model. Allergen-specific antiserum is transdermally injected into a local area on the skin followed by intravenous injection of an antigen along with a dye. The allergic reaction causes capillary dilatation and increased vascular permeability at the site of sensitization, resulting in preferential accumulation of dye at this site. The dye can be extracted from the tissue and quantitated spectrophotometrically. Dye extravasation into tissue sensitized with test antiserum can then be compared to extravasation into tissue sensitized with anonrelevant antiserum.

Antisera to natural Bet v 1, *Betula pendula* (also known as *Betula verrucosa*) birch pollen extract (BPE), *Betula nigra* BPE, and *Betula populifolia* BPE were generated for of the respective birch pollen extract in 20 μL of 1×PBS on days 21, 24 and 28. Mice were then sacrificed on day 31 and serum was collected. The total IgE concentration in the isolated antisera lots was determined using an OptEIA™ ELISA kit (BD Biosciences, #555248) according to the manufacturer's instructions. The final concentration of Bet v 1 antisera was diluted to 2500 ng/mL of IgE in 1×PBS and the final concentration of the birch pollen extract antisera lots were diluted to 3000 ng/mL for *pendula*, 1900 ng/mL for nigra and 3700 ng/mL for *populifolia*.

Antisera used as a negative control in this assay was generated by immunizing Balb/c mice with 5 g natural Fel d 1 protein purified from cat hair extract (Indoor Biotechnologies, Catalog #LTN-FD1-1, Lot #36099) in a solution of 1 mg/mL of alum in 1×PBS. Mice were boosted with 5 g Fel d 1 protein in a solution of 1 mg/mL alum in 1×PBS on days 14 and 21. One week after the final boost (day 28), mice were sacrificed and serum was collected. The total IgE concentration in the isolated antisera was determined using an OptEIA™ ELISA kit (BD Biosciences, #555248) according to the manufacturer's instructions. The final concentration of antisera was diluted to 4800 ng/mL of IgE in PBS.

For the PCA assays, groups of Balb/c mice (n≥4 per experiment, repeated three times) were first subcutaneously injected with either an isotype control antibody or a combination of two anti-Bet v 1 antibodies at a dose of 1 mg/kg (total antibody dose). Three days after antibody administration, 10 µL of either 1 ng Bet v 1 antisera, 25 ng *Betula pendula* antiserum, 25 ng *Betula nigra* antiserum, or 25 ng *Betula populifolia* antiserum was injected into the right ear of mice in assigned groups. Left ears were administered 1 ng or 25 ng Fel d 1 (negative control) to match antiserum concentration of the corresponding right ear. Twenty-four hours after the local administration of allergen-specific antisera, mice were challenged by intravenous injection (100 µL per mouse) with a solution of 1 g/mL natural Bet v 1 (Catalog #NA-BV1-1, Lot 36164) or 1 g/mL of the respective BPE (Stallargenes Greer, Catalog #XP527D3A25 Lot #277329, Catalog #XP79D3A25 Lot #285077, and Catalog #XP80D3A2.5 Lot #273622) dissolved in 1×PBS containing 0.5% (w/v) Evan's blue dye (Sigma Aldrich, #E2129). One hour after antigen challenge, mice were sacrificed, ears were excised, placed in 1 mL formamide and subsequently incubated for 3 days at 50° C. to extract the Evan's blue dye. The ear tissue was then removed from the formamide, blotted to remove excess liquid and weighed. Two-hundred microliter aliquots of each formamide extract were transferred to 96 well plates in duplicate. Absorbance of the resulting supernatants was measured at 620 nm. The optical density measured was converted to Evan's blue dye concentration using a standard curve and is represented as ng of Evan's blue dye per mg ear tissue. Mean values±the standard deviation are shown in Table 1 for each group. Mean difference as compared to isotype control was calculated using Bonferroni's multiple comparisons test in GraphPad Prism.

Table 16 demonstrates efficacy of the combination of two anti-Bet v 1 antibodies, H4H16992P and H4H17082P2, indicated by a significant reduction of dye extravasation when compared to isotype control in all groups tested. As shown, the two anti-Bet v 1 monoclonal antibody combination of H4H17082P2/H4H16992P blocks mast cell degranulation in the passive cutaneous in vivo model against sensitization and subsequent challenge with natural Bet v 1 compared to the isotype control, demonstrating a significant reduction in dye extravasation of 88.34. Similarly, reduction of dye extravasation is also observed in H4H17082P2/H4H16992P treated groups for all three birch pollen extracts as compared to respective isotype control groups with statistically significant reductions of 62.52 for *Betula pendula*, 71.19 for *Betula nigra*, and 91.47 for *Betula populifolia*. The mean difference as compared to isotype control was calculated by two-way ANOVA with Bonferroni's post test. The number of mice used per group (n) is noted within parentheses in the tables.

TABLE 16

Effect of anti-Bet v 1 antibodies in the passive cutaneous anaphylaxis (PCA) in-vivo model

| Sensitization and Treatment | Negative control allergen (ng Evans Blue/mg tissue ± SD) | Mean Difference compared to Isotype control | Bet v 1 or BPE (ng Evans Blue/mg tissue ± SD) | Mean Difference compared to Isotype control |
|---|---|---|---|---|
| 1 ng nBet v 1 H4H17082P2 + H4H16992P (n ≥ 14) | 7.59 + 3.03 | 0.7623 | 9.56 + 3.53 | −88.34 (****) |
| 25 ng *Betula pendula* H4H17082P2 + H4H16992P (n ≥ 14) | 7.76 ± 3.38 | 0.7337 | 15.54 ± 8.21 | −62.52 (****) |
| 25 ng *Betula nigra* H4H17082P2 + H4H16992P (n ≥ 14) | 8.16 ± 4.44 | 1.05 | 23.94 ± 18.32 | −71.19 (****) |
| 25 ng *Betula populifolia* H4H17082P2 + H4H16992P (n ≥ 14) | 7.11 ± 2.37 | 0.5416 | 10.09 ± 5.90 | −91.47 (****) |

1 mg/kg total antibody concentration used for all antibody treatment groups
(*) P ≤ .05,
(***) P ≤ .001,
(***) P ≤ .0001
n = number of mice per group Example 9: Cross-Competition Between Anti-Bet v 1 Monoclonal Antibodies Binding competition within a panel of anti-Bet v 1 monoclonal antibodies was determined using a real time, label-free bio-layer interferometry assay on the Octet HTX biosensor platform (Pall ForteBio Corp.). The entire experiment was performed at 25° C. in 10 mM HEPES, 150 mM NaCl, 3 mM EDTA, and 0.05% v/v Surfactant Tween-20, 1 mg/mL BSA, pH 7.4 (HBS-EBT) buffer with the plate shaking at the speed of 1000 rpm. To assess whether 2 antibodies were able to compete with one another for binding to their respective epitopes on the recombinant mutant Bet v 1 expressed with a C-terminal myc-myc-hexahistidine tag (mutant Bet v 1-MMH; SEQ ID NO: 312), around ~0.21 nm of mutant Bet v 1-MMH was first captured onto anti-Penta-His antibody coated Octet biosensor tips (Fortebio Inc, #18-5122) by submerging the biosensor tips for 90 seconds in wells containing 5 µg/mL solution of mutant Bet v 1-MMH. The antigen captured biosensor tips were then saturated with the first anti-Bet v 1 monoclonal antibody (referred to as mAb-1) by dipping into wells containing 50 μg/mL solution of mAb-1 for 4 minutes. The biosensor tips were then dipped into wells containing 50 μg/mL solution of second anti-Bet v 1 monoclonal antibody (referred to as mAb-2) for 3 minutes. The biosensor tips were washed in HBS-EBT buffer between every step of the experiment. The real-time binding response was monitored during the entire course of the experiment and the binding response at the end of every step was recorded. The response of mAb-2 binding to mutant Bet v 1-MMH pre-complexed with mAb-1 was compared and competitive/non-competitive behavior of different anti-Bet v 1 monoclonal antibodies was determined as shown in Table 17.

Three out of 20 anti-Bet v 1 monoclonal antibodies did not bind to mutant Bet v 1-MMH and cross-competition data was found to be inconclusive.

TABLE 17

Cross-competition between anti-Bet v 1 monoclonal antibodies

| mAb-1 | mAb-2 that competes with mAb-1 |
|---|---|
| H4H17082P2 | H4H16971P |
| H4H16971P | H4H17082P2 |
|  | H4H17027P |
|  | H4H17028P |
|  | H4H16946P |
|  | H4H17038P2 |
| H4H17027P | H4H16971P |
|  | H4H17028P |
|  | H4H16946P |
|  | H4H17038P2 |
|  | H4H16950P |
| H4H17028P | H4H16971P |
|  | H4H17027P |
|  | H4H16946P |
|  | H4H17038P2 |
|  | H4H16950P |
| H4H16946P | H4H16971P |
|  | H4H17027P |
|  | H4H17028P |
|  | H4H17038P2 |
|  | H4H16950P |
| H4H17038P2 | H4H16971P |
|  | H4H17027P |
|  | H4H17028P |
|  | H4H16946P |
|  | H4H16950P |
|  | H4H16979P |
| H4H16950P | H4H17027P |
|  | H4H17028P |
|  | H4H16946P |
|  | H4H17038P2 |
|  | H4H17015P |
| H4H16987P | H4H17045P2 |
|  | H4H17067P2 |
|  | H4H16967P |
| H4H17045P2 | H4H16987P |
|  | H4H17067P2 |
|  | H4H16967P |
|  | H4H17015P |
| H4H17067P2 | H4H16987P |
|  | H4H17045P2 |
|  | H4H16967P |
|  | H4H17015P |
| H4H16967P | H4H16987P |
|  | H4H17045P2 |
|  | H4H17067P2 |
|  | H4H17015P |
|  | H4H16992P |
| H4H17015P | H4H16950P |
|  | H4H17045P2 |
|  | H4H17067P2 |
|  | H4H16967P |
|  | H4H16979P |

TABLE 17-continued

Cross-competition between anti-Bet v 1 monoclonal antibodies

| mAb-1 | mAb-2 that competes with mAb-1 |
|---|---|
|  | H4H16991P |
|  | H4H17033P |
|  | H4H16992P |
| H4H16979P | H4H17038P2 |
|  | H4H17015P |
|  | H4H16991P |
|  | H4H17033P |
|  | H4H16992P |
| H4H16991P | H4H17015P |
|  | H4H16979P |
|  | H4H17033P |
|  | H4H16992P |
| H4H17033P | H4H17015P |
|  | H4H16979P |
|  | H4H16991P |
|  | H4H16992P |
| H4H16992P | H4H16967P |
|  | H4H17015P |
|  | H4H16979P |
|  | H4H16991P |
|  | H4H17033P |
|  | H4H16960P |
|  | H4H17031P |
| H4H16960P | H4H16992P |
|  | H4H17031P |
| H4H17031P | H4H16992P |
|  | H4H16960P |
| H4H16943P | IC* |
| H4H17001P | IC* |

*IC indicates that anti-Bet v 1 monoclonal antibodies did not bind to mutant Bet v 1-MMH and cross-competition data was found to be inconclusive.

Example 10. The Ability of Anti-Bet v 1 Antibody Combinations to Block Mast Cell Degranulation Induced by Bet v 1 in a Humanized Mouse PCA Model To explore the polyclonality of the allergen-specific IgE response across human birch allergic individuals, a humanized FcεR1α mouse model was utilized to facilitate binding of human IgE to FcεR1α on the surface of mouse mast cells. Since human IgE cannot bind mouse FcεR1α, a genetically modified mouse was created where endogenous mouse FcεR1α was replaced by the corresponding human FcεR1α sequence and denoted as FcεR1α$^{hu/hu}$ The FcεR1α$^{hu/hu}$ mice were validated for use in this model by demonstrating surface expression of human FcεR1α and the ability to respond to allergen:IgE activation in the Passive Cutaneous Anaphylaxis (PCA) model in a manner comparable to wild type mice. This PCA model involves intradermal injection of allergic human sera into a local area on the skin followed by intravenous injection of relevant allergen along with a dye. The allergic reaction causes capillary dilatation and increased vascular permeability at the site of sensitization, resulting in preferential accumulation of dye at this site. The dye can be extracted from the tissue and quantitated spectrophotometrically. Dye extravasation into tissue sensitized with test antiserum is compared to extravasation into tissue sensitized with a non-allergic human sera.

Methods

To determine the effect of anti-Bet v 1 antibodies on mast cell degranulation in this model, humanized FcεR1α mice received a subcutaneous injection of isotype control antibody or anti-Bet v 1 antibody combinations on day 1. For each human donor, two independent experiments were performed, n=5 mice per group with data combined. Groups consist of no monoclonal antibody negative control, isotype negative control, REGN5713+REGN5715 dual anti-Bet v 1 antibody treatment group and REGN5713+REGN5714+REGN5715 triple anti-Bet v 1 antibody treatment group. The total or combined antibody concentration was 1 mg/kg or an IgG4 isotype control antibody (anti-IL6Rα as a negative isotype control). Three days later, serum from birch allergic patients or serum from non-birch allergic patients (negative control) was injected intradermally (ID) into the right and left ears, respectively, allowing allergen-specific IgE to bind FcɛRI on mast cells. To ensure that the same amount of allergen specific IgE from each donor was used in the experiment, each antiserum injection was normalized to a Bet v 1-specific IgE ImmunoCAP® of 10 $KU_a/L$.

Twenty-four hours after local administration of allergen-specific antibodies, mice were challenged by IV injection of 1 g Bet v 1 diluted in PBS containing 0.5% Evan's blue dye. One hour after allergen challenge, mice were sacrificed. Evan's blue dye was extracted from ear tissue and quantitated spectrophotometrically using a standard curve. (See FIG. 6 for diagram of protocol used.) The reduction in Evan's blue dye extravasation was calculated on average by subtracting the concentration of Evan's blue dye (normalized by ear tissue weight) for the antibody-treated group's birch allergic serum administered ear, B(mAb,i), from the group treated with isotype control antibody, B(isotype,avg). This number was then divided by the difference between B(isotype,avg) and the dye concentration for antibody-treated group's non-allergic serum administered ear [N(mAb,i)] and multiplied by 100 to give the overall average percent reduction in dye extravasation (% Reduction). The equation is shown below: % Reduction (average)=100*[B(isotype,avg)−B(mAb,i)]/[B(isotype,avg)−N(mAb,i)]

An increase in the percent reduction in dye leakage in the anti-Bet v 1 antibody treated group compared to the negative isotype control group is a measure of effectiveness of the Bet v 1 antibody or antibody combinations in blocking mast cell degranulation.

Results

Figure 7:
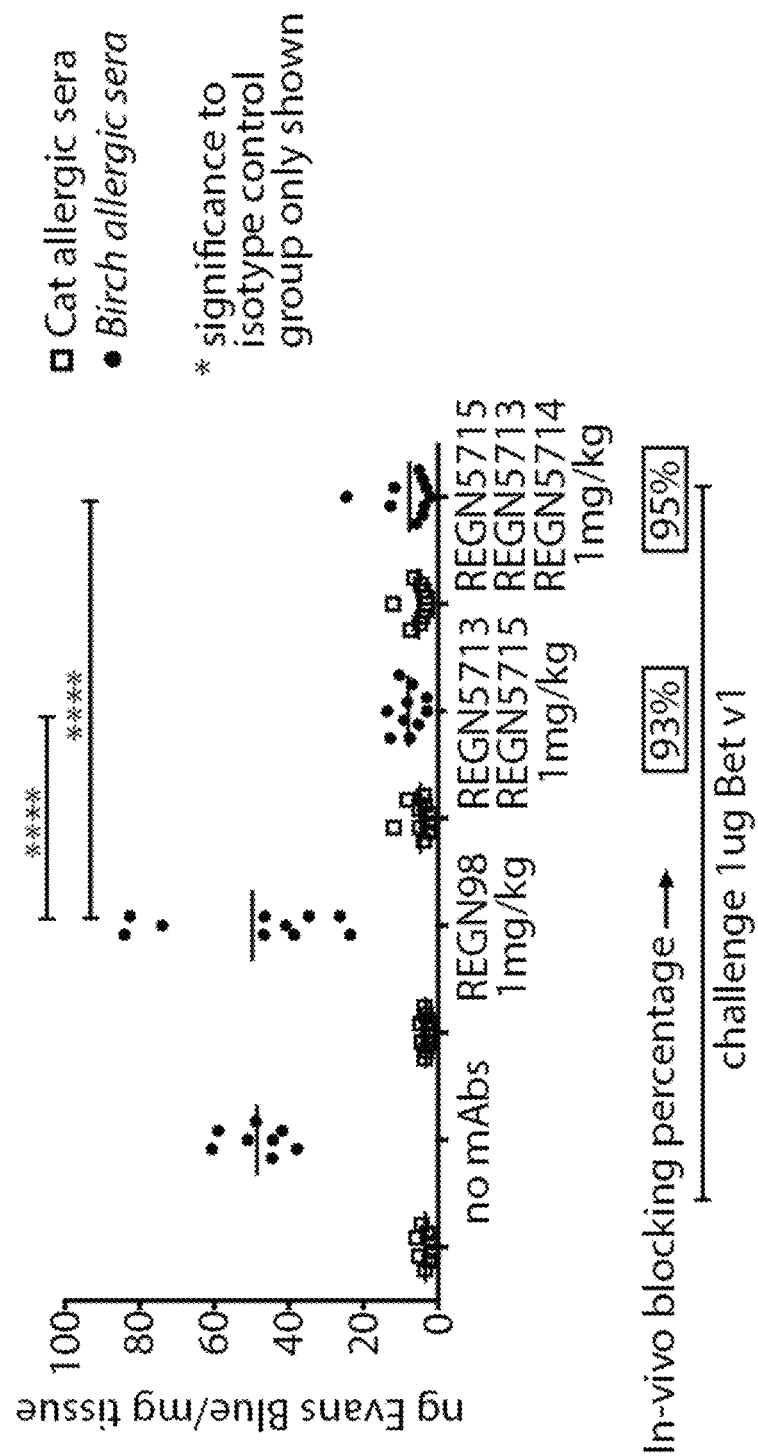
FIG. 7 depicts ability of anti-Bet v 1 antibody combinations to block mast cell degranulation in a humanized mouse PCA model using IgE containing sera obtained from three Bet v 1 sensitive donors.
Figure 7:
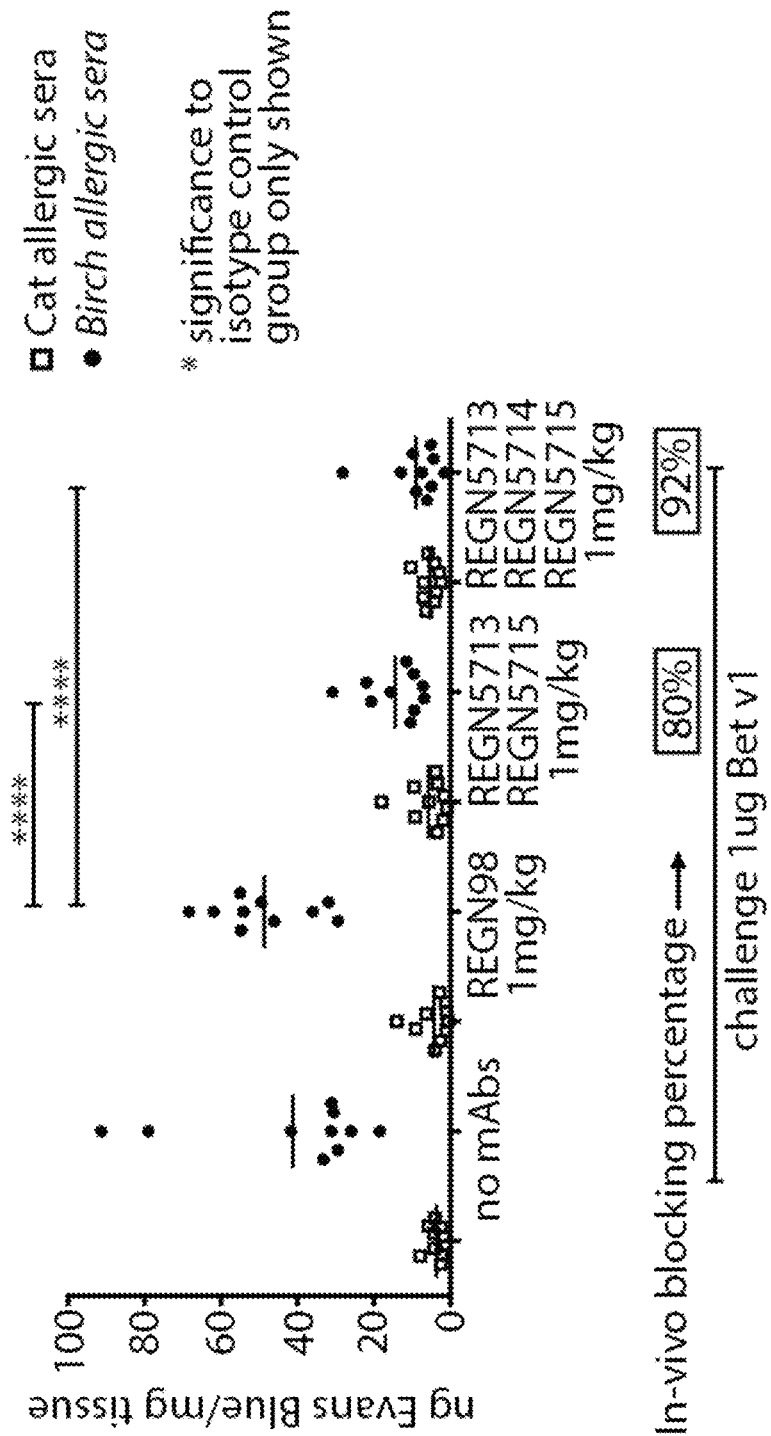
Figure 7:
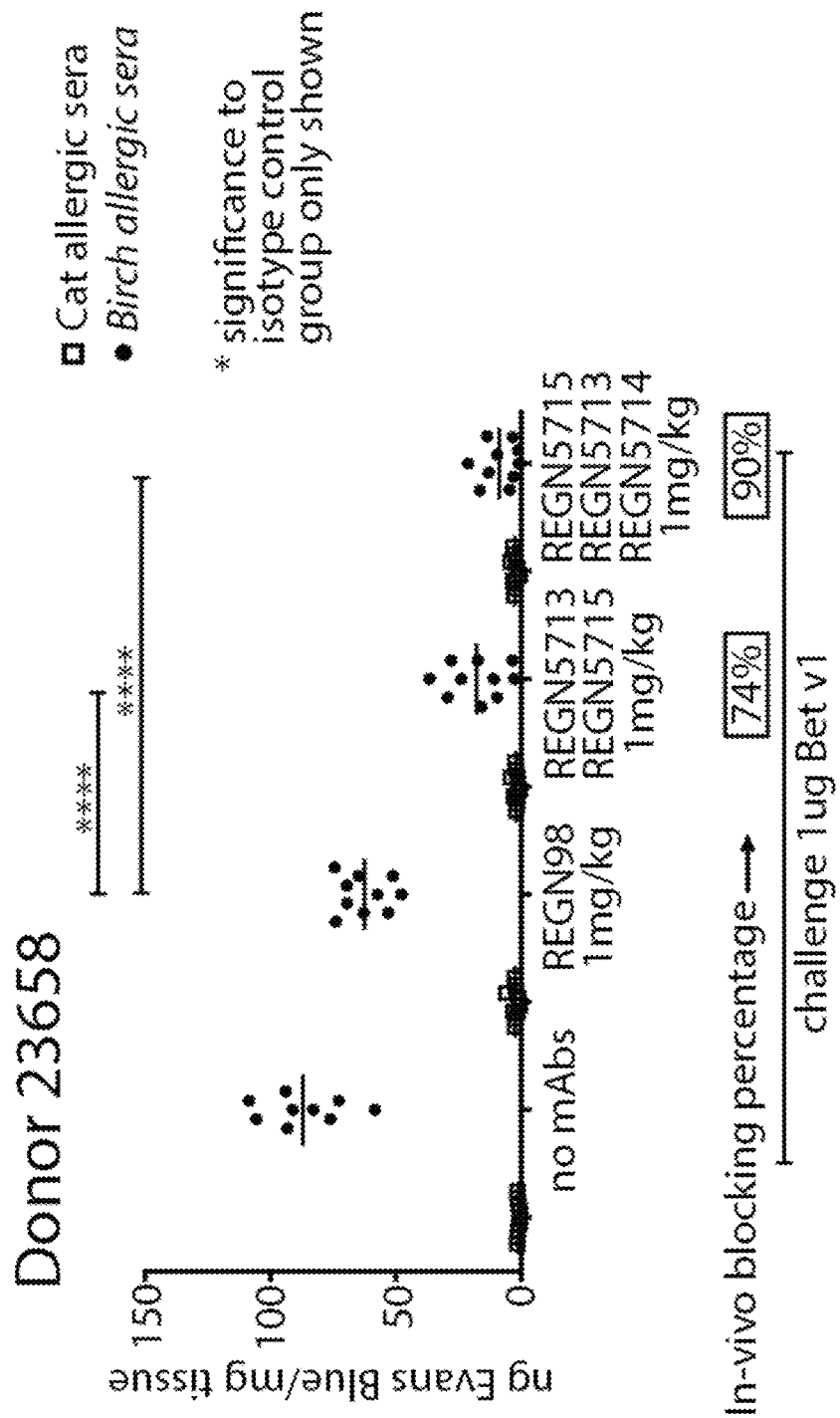

In this model, the combined use of anti-Bet v 1 antibodies designated H4H16992P (also referred to as REGN5713), H4H17038P2 (also referred to as REGN5714) and H4H17082P2 (also referred to as REGN5715) demonstrated maximal blocking of the IgE mediated response when using IgE containing sera from 3/3 birch allergic donors (See FIG. 7). Using sera from birch allergic donor 25609, H4H16992P, H4H17038P2 and H4H17082P2 when combined exhibited 95% blockade of mast cell degranulation compared to isotype control (mean difference −42.04+/−6.9 (p<0.0001)), and the combined use of H4H16992P and H4H17082P2 exhibited 93% blockade of mast cell degranulation compared to isotype control (mean difference −41.74+/−3.7 (p<0.0001)). Using sera from birch allergic donor 23658, H4H16992P, H4H17038P2 and H4H17082P2, when combined exhibited 90% blockade of mast cell degranulation compared to isotype control (mean difference-53.67+/−7.1 (p<0.0001)) and H4H16992P combined with H4H17082P2 exhibited 74% blockade of mast cell degranulation compared to isotype control (mean difference −44.58+/−11.4 (p<0.0001)). Finally, using sera from birch allergic donor 25414, H4H16992P, H4H17038P2 and H4H17082P2, when combined exhibited 92% blockade of mast cell degranulation compared to isotype control (mean difference −39.72+/−7.5 (p<0.0001)) and H4H16992P combined with H4H17082P2 exhibited 80% blockade of mast cell degranulation compared to isotype control (mean difference −34.27+/−7.8 (p<0.0001)).

Example 11. The Ability of Anti-Bet v 1 Antibody Combinations to Block Basophil Activation in the Phospho-Erk Phosphoflow Assay The human IgE response was explored by testing the effect of various combinations of the anti-Bet v 1 antibodies H4H16992P (also referred to as REGN5713), H4H17038P2 (also referred to as REGN5714) and H4H17082P2 (also referred to as REGN5715) on inhibiting basophil activation using samples from 8 birch allergic individuals. More specifically, to assess FcɛR engagement and activation, basophils were tested in a functional phosphoflow based assay that measures phosphorylation of the kinase ERK, a proximal readout of basophil activation and degranulation (Liu, Y. et al. (2007), *J Exp Med* 204, 93-103.

Methods

Blood was drawn from birch allergic patients (n=8) and PBMCs isolated by density centrifugation on a Ficoll layer, washed, resuspended and plated as single points in a 96-well format. In parallel, a 2× stimulation plate was prepared that included a dose response of purified Bet v 1 as well as dose responses of anti-Bet v 1 antibodies and antibody combinations (2.56 pM-200 nM) mixed with a constant dose (final concentration 100 pM) of purified natural Bet v 1. The cells were stimulated and subsequently stained with an antibody cocktail containing pErk-Alexa 488, CD123-BUV395 and HLA-DR-APC antibodies. Following staining, data was acquired using an LSR-Fortessa instrument and analyzed by calculating the MFI of phosphorylated Erk staining within the basophil gate. Percent Max Inhibition was calculated as: 100−((100×Maximum Antibody Response)/Isotype Response). Maximum antibody response was the average Median Fluorescence Intensity (MFI) of phosphorylated Erk in the top three doses of antibody in the dose response curve (plateau of the curve) minus the baseline MFI (average of replicate unstimulated samples), and isotype response is the average of all the MFI values in the dose response of a Regeneron produced isotype control antibody (REGN1945 anti-Fel d 1 $IgG4^P$) minus the baseline MFI.

Results

Figure 8:
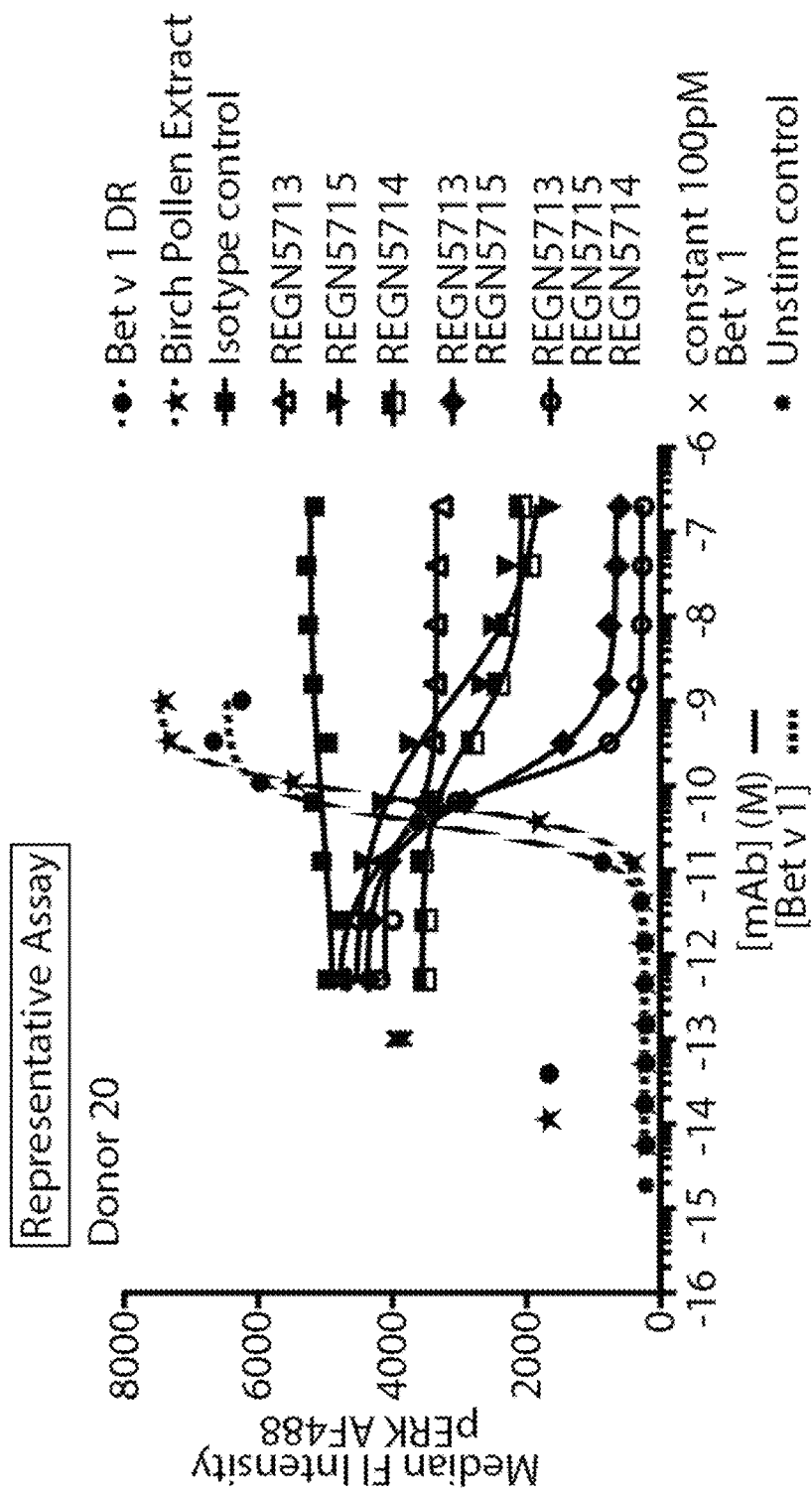
FIG. 8 depicts two graphs, the first providing representative data demonstrating anti-Bet v 1 antibody combinations that block basophil activation in PBMCs obtained from one birch allergic donor. The bar graph provides data depicting percent blocking of basophil activation in PBMCs obtained from multiple donors by the anti-Bet v 1 antibody combinations relative to each antibody alone.
Figure 8:
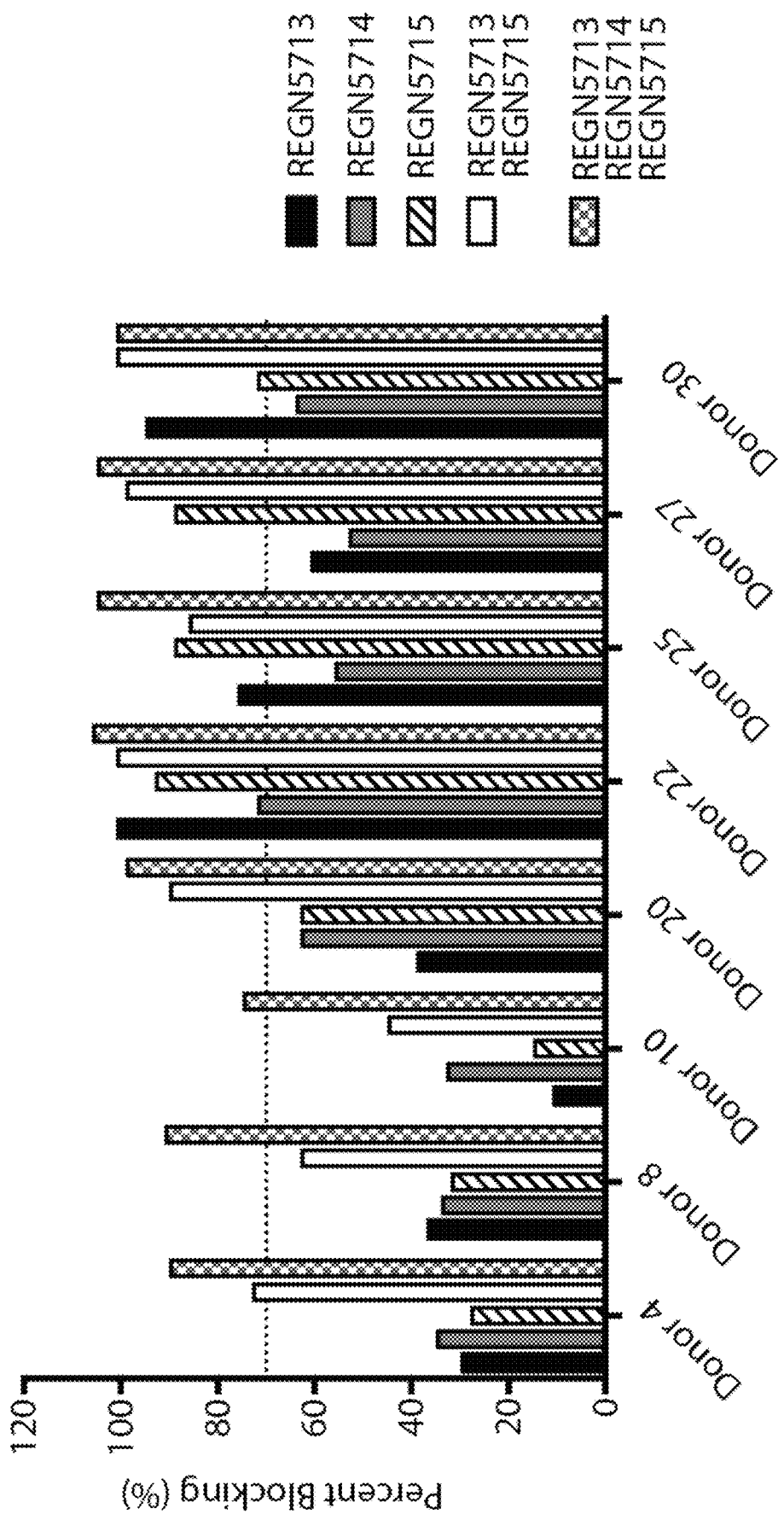

Basophils from all 8-birch pollen-allergic individuals responded to Bet v 1 stimulation with varying intensities. See FIG. 8. H4H16992P, H4H17038P2 and H4H17082P2 inhibited at least 70% of basophil activation in 8/8 donors, while the combination of H4H16992P with H4H17082P2 achieved the same magnitude of inhibition in 6/8 donors. Notably, the individual antibodies when tested separately showed a high degree of variability in the ability to impact allergen binding to IgE. H4H16992P achieved ≥70% blockade in 3/8 donors and H4H17082P2 achieved 70% blockade of basophil activation in 4/8 donors. H4H17038P2 demonstrated 70% blocking in only 1/8 donors tested.

Example 12: Determination of Simultaneous Binding of Three Anti-Bet v 1 Monoclonal Antibodies to Natural Bet v 1

This experiment was performed to ensure that the binding epitopes of three select Bet v 1 monoclonal antibodies were unique and that, irrespective of the order of monoclonal antibody binding, no steric hindrance was exhibited upon simultaneous binding of the three antibodies. Order dependent competition between the three Bet v 1 monoclonal antibodies was also assessed.

Simultaneous binding of three anti-Bet v 1 monoclonal antibodies to the same Bet v 1 was determined using a real time, label-free surface plasmon resonance based Biacore 3000 biosensor platform (GE Healthcare). The entire experiment was performed at 25° C. in running buffer containing 10 mM HEPES, 150 mM NaCl, 3 mM EDTA, and 0.05% v/v Surfactant Tween-20, pH7.4 (HBS-ET). The antibodies were immobilized on different surfaces of CM5 sensor using EDC/NHS chemistry to achieve immobilization levels of 5000-13,000 RU. REGN1945 (Fel d 1 monoclonal antibody) was also immobilized as the negative control. Natural Bet v 1 (nBet v 1), 10 nM or 20 nM, was injected over different Bet v 1 monoclonal antibody immobilized sensor surfaces for 10-12 seconds followed by sequential injection of different Bet v 1 monoclonal antibodies for 6 minutes at 15 L/min.

The binding of different Bet v 1 monoclonal antibodies to nBet v 1 bound to a monoclonal antibody immobilized sensor surface was measured using Scrubber 2.0c. The results are shown in Table 18. A binding signal of less than 1 RU (Resonance Unit) indicates that no binding was observed when the Bet v 1 monoclonal antibody was injected, while a higher binding signal (greater than 2 RU) represents no competition. All three Bet v 1 monoclonal antibodies included in this example were able to simultaneously bind to nBet v 1 and binding response was not affected by the order in which the antibodies were added.

TABLE 18

Anti-Bet v 1 Antibody Simultaneous Binding Competition

| Bet v 1 monoclonal antibody Immobilized on Surface | nBet v 1 Binding (RU) | mAb-1 | mAb-1 Binding (RU) | mAb-2 | mAb-2 Binding (RU) | mAb-3 | mAb-3 Binding (RU) |
|---|---|---|---|---|---|---|---|
| REGN5713 | 10 | REGN5713 | 0 | REGN5714 | 59 | REGN5715 | 44 |
| | 11 | | 0 | REGN5715 | 48 | REGN5714 | 53 |
| | 10 | REGN5714 | 59 | REGN5713 | -3 | REGN5715 | 43 |
| | 10 | | 60 | REGN5715 | 43 | REGN5713 | -6 |
| | 10 | REGN5715 | 46 | REGN5713 | -4 | REGN5714 | 54 |
| | 10 | | 46 | REGN5714 | 54 | REGN5713 | -5 |
| REGN5714 | 14 | REGN5713 | 67 | REGN5714 | -4 | REGN5715 | 40 |
| | 14 | | 63 | REGN5715 | 38 | REGN5714 | -5 |
| | 13 | REGN5714 | 1 | REGN5713 | 48 | REGN5715 | 30 |
| | 13 | | 1 | REGN5715 | 35 | REGN5713 | 42 |
| | 12 | REGN5715 | 42 | REGN5713 | 47 | REGN5714 | -3 |
| | 12 | | 40 | REGN5714 | -2 | REGN5713 | 44 |
| REGN5715 | 14 | REGN5713 | 62 | REGN5714 | 69 | REGN5715 | -5 |
| | 14 | | 60 | REGN5715 | -4 | REGN5714 | 67 |
| | 13 | REGN5714 | 73 | REGN5713 | 56 | REGN5715 | -5 |
| | 13 | | 73 | REGN5715 | -3 | REGN5713 | 54 |
| | 12 | REGN5715 | -1 | REGN5713 | 51 | REGN5714 | 65 |
| | 12 | | 0 | REGN5714 | 69 | REGN5713 | 47 |
| REGN5713 | 10 | REGN5713 | 0 | REGN5714 | 59 | REGN5715 | 44 |
| | 11 | | 0 | REGN5715 | 48 | REGN5714 | 53 |
| | 10 | REGN5714 | 59 | REGN5713 | -3 | REGN5715 | 43 |
| | 10 | | 60 | REGN5715 | 43 | REGN5713 | -6 |
| | 10 | REGN5715 | 46 | REGN5713 | -4 | REGN5714 | 54 |
| | 10 | | 46 | REGN5714 | 54 | REGN5713 | -5 |
| REGN5714 | 14 | REGN5713 | 67 | REGN5714 | -4 | REGN5715 | 40 |
| | 14 | | 63 | REGN5715 | 38 | REGN5714 | -5 |
| | 13 | REGN5714 | 1 | REGN5713 | 48 | REGN5715 | 30 |
| | 13 | | 1 | REGN5715 | 35 | REGN5713 | 42 |
| | 12 | REGN5715 | 42 | REGN5713 | 47 | REGN5714 | -3 |
| | 12 | | 40 | REGN5714 | -2 | REGN5713 | 44 |
| REGN5715 | 14 | REGN5713 | 62 | REGN5714 | 69 | REGN5715 | -5 |
| | 14 | | 60 | REGN5715 | -4 | REGN5714 | 67 |
| | 13 | REGN5714 | 73 | REGN5713 | 56 | REGN5715 | -5 |
| | 13 | | 73 | REGN5715 | -3 | REGN5713 | 54 |
| | 12 | REGN5715 | -1 | REGN5713 | 51 | REGN5714 | 65 |
| | 12 | | 0 | REGN5714 | 69 | REGN5713 | 47 |

Data represents average of at least 3 independent injections of Bet v 1 monoclonal antibodies over the complex of nBet v 1 and immobilized Bet v 1 monoclonal antibody Summary Regardless of the order of antibody binding to Bet v 1, there was no competition impeding the simultaneous binding of all three antibodies, suggesting that REGN5713, REGN5714, and REGN5715 bind to non-overlapping, distinct epitopes.

---

What is claimed is:

1. A method of preventing or reducing mast cell degranulation or blocking basophil activation associated with natural Bet v 1, *Betula pendula* birch pollen extract (BPE), *Betula nigra* BPE, or *Betula populifolia* BPE sensitization, the method comprising administering to a patient in need thereof one or more human monoclonal antibodies or antigen-binding fragments thereof that bind to natural Bet v 1 or BPE, or a pharmaceutical composition comprising one or more antibodies or antigen-binding fragments thereof, wherein the one or more antibodies or antigen-binding fragments thereof comprises:

(a) a heavy chain complementarity determining region (HCDR)1 comprising the amino acid sequence of SEQ ID NO: 148; an HCDR2 comprising the amino acid sequence of SEQ ID NO: 150; an HCDR3 comprising the amino acid sequence of SEQ ID NO: 152; a light chain complementarity determining region (LCDR)1 comprising the amino acid sequence of SEQ ID NO: 156; an LCDR2 comprising the amino acid sequence of SEQ ID NO: 158; and an LCDR3 comprising the amino acid sequence of SEQ ID NO: 160; or (b) an HCDR1 comprising the amino acid sequence of SEQ ID NO: 292; an HCDR2 comprising the amino acid sequence of SEQ ID NO: 294; an HCDR3 comprising the amino acid sequence of SEQ ID NO: 296; an LCDR1 comprising the amino acid sequence of SEQ ID NO: 300; an LCDR2 comprising the amino acid sequence of SEQ ID NO: 302; and an LCDR3 comprising the amino acid sequence of SEQ ID NO: 304; or (c) an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; or (d) an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128; or (e) an HCDR1 comprising the amino acid sequence of SEQ ID NO: 4; an HCDR2 comprising the amino acid sequence of SEQ ID NO: 6; an HCDR3 comprising the amino acid sequence of SEQ ID NO: 8; an LCDR1 comprising the amino acid sequence of SEQ ID NO: 12: an LCDR2 comprising the amino acid sequence of SEQ ID NO: 14; and an LCDR3 comprising the amino acid sequence of SEQ ID NO: 16; or (f) an HCDR1 comprising the amino acid sequence of SEQ ID NO: 20; an HCDR2 comprising the amino acid sequence of SEQ ID NO: 22; an HCDR3 comprising the amino acid sequence of SEQ ID NO: 24; an LCDR1 comprising the amino acid sequence of SEQ ID NO: 28; an LCDR2 comprising the amino acid sequence of SEQ ID NO: 30; and an LCDR3 comprising the amino acid sequence of SEQ ID NO: 32; or (g) an HCDR1 comprising the amino acid sequence of SEQ ID NO: 36; an HCDR2 comprising the amino acid sequence of SEQ ID NO: 38; an HCDR3 comprising the amino acid sequence of SEQ ID NO: 40; an LCDR1 comprising the amino acid sequence of SEQ ID NO: 44; an LCDR2 comprising the amino acid sequence of SEQ ID NO: 46; and an LCDR3 comprising the amino acid sequence of SEQ ID NO: 48; or (h) an HCDR1 comprising the amino acid sequence of SEQ ID NO: 52; an HCDR2 comprising the amino acid sequence of SEQ ID NO: 54; an HCDR3 comprising the amino acid sequence of SEQ ID NO: 56; an LCDR1 comprising the amino acid sequence of SEQ ID NO: 60; an LCDR2 comprising the amino acid sequence of SEQ ID NO: 62; and an LCDR3 comprising the amino acid sequence of SEQ ID NO: 64; or (i) an HCDR1 comprising the amino acid sequence of SEQ ID NO: 68; an HCDR2 comprising the amino acid sequence of SEQ ID NO: 70; an HCDR3 comprising the amino acid sequence of SEQ ID NO: 72; an LCDR1 comprising the amino acid sequence of SEQ ID NO: 76; an LCDR2 comprising the amino acid sequence of SEQ ID NO: 78; and an LCDR3 comprising the amino acid sequence of SEQ ID NO: 80; or (j) an HCDR1 comprising the amino acid sequence of SEQ ID NO: 84; an HCDR2 comprising the amino acid sequence of SEQ ID NO: 86; an HCDR3 comprising the amino acid sequence of SEQ ID NO: 88; an LCDR1 comprising the amino acid sequence of SEQ ID NO: 92; an LCDR2 comprising the amino acid sequence of SEQ ID NO: 94; and an LCDR3 comprising the amino acid sequence of SEQ ID NO: 96; or (k) an HCDR1 comprising the amino acid sequence of SEQ ID NO: 132; an HCDR2 comprising the amino acid sequence of SEQ ID NO: 134; an HCDR3 comprising the amino acid sequence of SEQ ID NO: 136; an LCDR1 comprising the amino acid sequence of SEQ ID NO: 140; an LCDR2 comprising the amino acid sequence of SEQ ID NO: 142; and an LCDR3 comprising the amino acid sequence of SEQ ID NO: 144; or (l) an HCDR1 comprising the amino acid sequence of SEQ ID NO: 164; an HCDR2 comprising the amino acid sequence of SEQ ID NO: 166; an HCDR3 comprising the amino acid sequence of SEQ ID NO: 168; an LCDR1 comprising the amino acid sequence of SEQ ID NO: 172; an LCDR2 comprising the amino acid sequence of SEQ ID NO: 174; and an LCDR3 comprising the amino acid sequence of SEQ ID NO: 176; or (m) an HCDR1 comprising the amino acid sequence of SEQ ID NO: 180; an HCDR2 comprising the amino acid sequence of SEQ ID NO: 182; an HCDR3 comprising the amino acid sequence of SEQ ID NO: 184; an LCDR1 comprising the amino acid sequence of SEQ ID NO: 188; an LCDR2 comprising the amino acid sequence of SEQ ID NO: 190; and an LCDR3 comprising the amino acid sequence of SEQ ID NO: 192; or (n) an HCDR1 comprising the amino acid sequence of SEQ ID NO: 196; an HCDR2 comprising the amino acid sequence of SEQ ID NO: 198; an HCDR3 comprising the amino acid sequence of SEQ ID NO: 200; an LCDR1 comprising the amino acid sequence of SEQ ID NO: 204; an LCDR2 comprising the amino acid sequence of SEQ ID NO: 206; and an LCDR3 comprising the amino acid sequence of SEQ ID NO: 208; or (o) an HCDR1 comprising the amino acid sequence of SEQ ID NO: 212; an HCDR2 comprising the amino acid sequence of SEQ ID NO: 214; an HCDR3 comprising the amino acid sequence of SEQ ID NO: 216; an LCDR1 comprising the amino acid sequence of SEQ ID NO: 220; an LCDR2 comprising the amino acid sequence of SEQ ID NO: 222; and an LCDR3 comprising the amino acid sequence of SEQ ID NO: 224; or (p) an HCDR1 comprising the amino acid sequence of SEQ ID NO: 228; an HCDR2 comprising the amino acid sequence of SEQ ID NO: 230; an HCDR3 comprising the amino acid sequence of SEQ ID NO: 232; an LCDR1 comprising the amino acid sequence of SEQ ID NO: 236; an LCDR2 comprising the amino acid sequence of SEQ ID NO: 238; and an LCDR3 comprising the amino acid sequence of SEQ ID NO: 240; or (q) an HCDR1 comprising the amino acid sequence of SEQ ID NO: 244; an HCDR2 comprising the amino acid sequence of SEQ ID NO: 246; an HCDR3 comprising the amino acid sequence of SEQ ID NO: 248; an LCDR1 comprising the amino acid sequence of SEQ ID NO: 252; an LCDR2 comprising the amino acid sequence of SEQ ID NO: 254; and an LCDR3 comprising the amino acid sequence of SEQ ID NO: 256; or (r) an HCDR1 comprising the amino acid sequence of SEQ ID NO: 260; an HCDR2 comprising the amino acid sequence of SEQ ID NO: 262; an HCDR3 comprising the amino acid sequence of SEQ ID NO: 264; an LCDR1 comprising the amino acid sequence of SEQ ID NO: 268; an LCDR2 comprising the amino acid sequence of SEQ ID NO: 270; and an LCDR3 comprising the amino acid sequence of SEQ ID NO: 272; or (s) an HCDR1 comprising the amino acid sequence of SEQ ID NO: 276; an HCDR2 comprising the amino acid sequence of SEQ ID NO: 278; an HCDR3 comprising the amino acid sequence of SEQ ID NO: 280; an LCDR1 comprising the amino acid sequence of SEQ ID NO: 268; an LCDR2 comprising the amino acid sequence of SEQ ID NO: 270; and an LCDR3 comprising the amino acid sequence of SEQ ID NO: 272; or (t) an HCDR1 comprising the amino acid sequence of SEQ ID NO: 284; an HCDR2 comprising the amino acid sequence of SEQ ID NO: 286; an HCDR3 comprising the amino acid sequence of SEQ ID NO: 288; an LCDR1 comprising the amino acid sequence of SEQ ID NO: 268; an LCDR2 comprising the amino acid sequence of SEQ ID NO: 270; and an LCDR3 comprising the amino acid sequence of SEQ ID NO: 272.

2. A method for treating at least one symptom or complication associated with a sensitivity to, or allergic reaction against a Fagales protein, a Fagales related allergen, birch pollen or an extract thereof, or Bet v 1 protein, comprising administering to a patient in need thereof one or more human monoclonal antibodies or antigen-binding fragments thereof that bind to natural Bet v 1 or BPE, or a pharmaceutical composition comprising one or more antibodies or antigen-binding fragments thereof, wherein the one or more antibodies or antigen-binding fragments thereof comprises:

(a) a heavy chain complementarity determining region (HCDR)1 comprising the amino acid sequence of SEQ ID NO: 148; an HCDR2 comprising the amino acid sequence of SEQ ID NO: 150; an HCDR3 comprising the amino acid sequence of SEQ ID NO: 152; a light chain complementarity determining region (LCDR)1 comprising the amino acid sequence of SEQ ID NO: 156; an LCDR2 comprising the amino acid sequence of SEQ ID NO: 158; and an LCDR3 comprising the amino acid sequence of SEQ ID NO: 160; or (b) an HCDR1 comprising the amino acid sequence of SEQ ID NO: 292; an HCDR2 comprising the amino acid sequence of SEQ ID NO: 294; an HCDR3 comprising the amino acid sequence of SEQ ID NO: 296; an LCDR1 comprising the amino acid sequence of SEQ ID NO: 300; an LCDR2 comprising the amino acid sequence of SEQ ID NO: 302; and an LCDR3 comprising the amino acid sequence of SEQ ID NO: 304; or (c) an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; or (d) an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128; or (e) an HCDR1 comprising the amino acid sequence of SEQ ID NO: 4; an HCDR2 comprising the amino acid sequence of SEQ ID NO: 6; an HCDR3 comprising the amino acid sequence of SEQ ID NO: 8; an LCDR1 comprising the amino acid sequence of SEQ ID NO: 12; an LCDR2 comprising the amino acid sequence of SEQ ID NO: 14; and an LCDR3 comprising the amino acid sequence of SEQ ID NO: 16; or (f) an HCDR1 comprising the amino acid sequence of SEQ ID NO: 20; an HCDR2 comprising the amino acid sequence of SEQ ID NO: 22; an HCDR3 comprising the amino acid sequence of SEQ ID NO: 24; an LCDR1 comprising the amino acid sequence of SEQ ID NO: 28; an LCDR2 comprising the amino acid sequence of SEQ ID NO: 30; and an LCDR3 comprising the amino acid sequence of SEQ ID NO: 32; or (g) an HCDR1 comprising the amino acid sequence of SEQ ID NO: 36; an HCDR2 comprising the amino acid sequence of SEQ ID NO: 38; an HCDR3 comprising the amino acid sequence of SEQ ID NO: 40; an LCDR1 comprising the amino acid sequence of SEQ ID NO: 44; an LCDR2 comprising the amino acid sequence of SEQ ID NO: 46; and an LCDR3 comprising the amino acid sequence of SEQ ID NO: 48; or (h) an HCDR1 comprising the amino acid sequence of SEQ ID NO: 52; an HCDR2 comprising the amino acid sequence of SEQ ID NO: 54; an HCDR3 comprising the amino acid sequence of SEQ ID NO: 56; an LCDR1 comprising the amino acid sequence of SEQ ID NO: 60; an LCDR2 comprising the amino acid sequence of SEQ ID NO: 62; and an LCDR3 comprising the amino acid sequence of SEQ ID NO: 64; or (i) an HCDR1 comprising the amino acid sequence of SEQ ID NO: 68; an HCDR2 comprising the amino acid sequence of SEQ ID NO: 70; an HCDR3 comprising the amino acid sequence of SEQ ID NO: 72; an LCDR1 comprising the amino acid sequence of SEQ ID NO: 76; an LCDR2 comprising the amino acid sequence of SEQ ID NO: 78; and an LCDR3 comprising the amino acid sequence of SEQ ID NO: 80; or (j) an HCDR1 comprising the amino acid sequence of SEQ ID NO: 84; an HCDR2 comprising the amino acid sequence of SEQ ID NO: 86; an HCDR3 comprising the amino acid sequence of SEQ ID NO: 88; an LCDR1 comprising the amino acid sequence of SEQ ID NO: 92; an LCDR2 comprising the amino acid sequence of SEQ ID NO: 94; and an LCDR3 comprising the amino acid sequence of SEQ ID NO: 96; or (k) an HCDR1 comprising the amino acid sequence of SEQ ID NO: 132; an HCDR2 comprising the amino acid sequence of SEQ ID NO: 134; an HCDR3 comprising the amino acid sequence of SEQ ID NO: 136; an LCDR1 comprising the amino acid sequence of SEQ ID NO: 140; an LCDR2 comprising the amino acid sequence of SEQ ID NO: 142; and an LCDR3 comprising the amino acid sequence of SEQ ID NO: 144; or (l) an HCDR1 comprising the amino acid sequence of SEQ ID NO: 164; an HCDR2 comprising the amino acid sequence of SEQ ID NO: 166; an HCDR3 comprising the amino acid sequence of SEQ ID NO: 168; an LCDR1 comprising the amino acid sequence of SEQ ID NO: 172; an LCDR2 comprising the amino acid sequence of SEQ ID NO: 174; and an LCDR3 comprising the amino acid sequence of SEQ ID NO: 176; or (m) an HCDR1 comprising the amino acid sequence of SEQ ID NO: 180; an HCDR2 comprising the amino acid sequence of SEQ ID NO: 182; an HCDR3 comprising the amino acid sequence of SEQ ID NO: 184; an LCDR1 comprising the amino acid sequence of SEQ ID NO: 188; an LCDR2 comprising the amino acid sequence of SEQ ID NO: 190; and an LCDR3 comprising the amino acid sequence of SEQ ID NO: 192; or (n) an HCDR1 comprising the amino acid sequence of SEQ ID NO: 196; an HCDR2 comprising the amino acid sequence of SEQ ID NO: 198; an HCDR3 comprising the amino acid sequence of SEQ ID NO: 200; an LCDR1 comprising the amino acid sequence of SEQ ID NO: 204; an LCDR2 comprising the amino acid sequence of SEQ ID NO: 206; and an LCDR3 comprising the amino acid sequence of SEQ ID NO: 208; or (o) an HCDR1 comprising the amino acid sequence of SEQ ID NO: 212; an HCDR2 comprising the amino acid sequence of SEQ ID NO: 214; an HCDR3 comprising the amino acid sequence of SEQ ID NO: 216; an LCDR1 comprising the amino acid sequence of SEQ ID NO: 220; an LCDR2 comprising the amino acid sequence of SEQ ID NO: 222; and an LCDR3 comprising the amino acid sequence of SEQ ID NO: 224; or (p) an HCDR1 comprising the amino acid sequence of SEQ ID NO: 228; an HCDR2 comprising the amino acid sequence of SEQ ID NO: 230; an HCDR3 comprising the amino acid sequence of SEQ ID NO: 232; an LCDR1 comprising the amino acid sequence of SEQ ID NO: 236; an LCDR2 comprising the amino acid sequence of SEQ ID NO: 238; and an LCDR3 comprising the amino acid sequence of SEQ ID NO: 240; or (q) an HCDR1 comprising the amino acid sequence of SEQ ID NO: 244; an HCDR2 comprising the amino acid sequence of SEQ ID NO: 246; an HCDR3 comprising the amino acid sequence of SEQ ID NO: 248; an LCDR1 comprising the amino acid sequence of SEQ ID NO: 252; an LCDR2 comprising the amino acid sequence of SEQ ID NO: 254; and an LCDR3 comprising the amino acid sequence of SEQ ID NO: 256; or (r) an HCDR1 comprising the amino acid sequence of SEQ ID NO: 260; an HCDR2 comprising the amino acid sequence of SEQ ID NO: 262; an HCDR3 comprising the amino acid sequence of SEQ ID NO: 264; an LCDR1 comprising the amino acid sequence of SEQ ID NO: 268; an LCDR2 comprising the amino acid sequence of SEQ ID NO: 270; and an LCDR3 comprising the amino acid sequence of SEQ ID NO: 272; or (s) an HCDR1 comprising the amino acid sequence of SEQ ID NO: 276; an HCDR2 comprising the amino acid sequence of SEQ ID NO: 278; an HCDR3 comprising the amino acid sequence of SEQ ID NO: 280; an LCDR1 comprising the amino acid sequence of SEQ ID NO: 268; an LCDR2 comprising the amino acid sequence of SEQ ID NO: 270; and an LCDR3 comprising the amino acid sequence of SEQ ID NO: 272; or (t) an HCDR1 comprising the amino acid sequence of SEQ ID NO: 284; an HCDR2 comprising the amino acid sequence of SEQ ID NO: 286; an HCDR3 comprising the amino acid sequence of SEQ ID NO: 288; an LCDR1 comprising the amino acid sequence of SEQ ID NO: 268; an LCDR2 comprising the amino acid sequence of SEQ ID NO: 270; and an LCDR3 comprising the amino acid sequence of SEQ ID NO: 272.

3. The method of claim 2, further comprising administering an effective amount of a second therapeutic agent, wherein the second therapeutic agent is a corticosteroid, a bronchial dilator, an antihistamine, epinephrine, or a decongestant.

4. The method of claim 2, further comprising treating the patient with an allergen-specific immunotherapy (SIT) regimen.

5. The method of claim 2, wherein the treatment results in a reduction in allergic rhinitis, allergic conjunctivitis, allergic asthma, or an anaphylactic response following exposure of the patient to a Fagales protein, birch pollen or an extract thereof, or Bet v 1 protein.

6. A method for enhancing the efficacy and/or safety of an allergen-specific immunotherapy (SIT) regimen, the method comprising administering to a patient in need thereof one or more human monoclonal antibodies or antigen-binding fragments thereof that bind to natural Bet v 1 or BPE, or a pharmaceutical composition comprising one or more antibodies or antigen-binding fragments thereof, in combination with the SIT regimen, wherein the one or more antibodies or antigen-binding fragments thereof comprises:

(a) a heavy chain complementarity determining region (HCDR)1 comprising the amino acid sequence of SEQ ID NO: 148; an HCDR2 comprising the amino acid sequence of SEQ ID NO: 150; an HCDR3 comprising the amino acid sequence of SEQ ID NO: 152; a light chain complementarity determining region (LCDR)1 comprising the amino acid sequence of SEQ ID NO: 156; an LCDR2 comprising the amino acid sequence of SEQ ID NO: 158; and an LCDR3 comprising the amino acid sequence of SEQ ID NO: 160; or (b) an HCDR1 comprising the amino acid sequence of SEQ ID NO: 292; an HCDR2 comprising the amino acid sequence of SEQ ID NO: 294; an HCDR3 comprising the amino acid sequence of SEQ ID NO: 296; an LCDR1 comprising the amino acid sequence of SEQ ID NO: 300; an LCDR2 comprising the amino acid sequence of SEQ ID NO: 302; and an LCDR3 comprising the amino acid sequence of SEQ ID NO: 304; or (c) an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; or (d) an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128; or (e) an HCDR1 comprising the amino acid sequence of SEQ ID NO: 4; an HCDR2 comprising the amino acid sequence of SEQ ID NO: 6; an HCDR3 comprising the amino acid sequence of SEQ ID NO: 8; an LCDR1 comprising the amino acid sequence of SEQ ID NO: 12: an LCDR2 comprising the amino acid sequence of SEQ ID NO: 14; and an LCDR3 comprising the amino acid sequence of SEQ ID NO: 16; or (f) an HCDR1 comprising the amino acid sequence of SEQ ID NO: 20; an HCDR2 comprising the amino acid sequence of SEQ ID NO: 22; an HCDR3 comprising the amino acid sequence of SEQ ID NO: 24; an LCDR1 comprising the amino acid sequence of SEQ ID NO: 28; an LCDR2 comprising the amino acid sequence of SEQ ID NO: 30; and an LCDR3 comprising the amino acid sequence of SEQ ID NO: 32; or (g) an HCDR1 comprising the amino acid sequence of SEQ ID NO: 36; an HCDR2 comprising the amino acid sequence of SEQ ID NO: 38; an HCDR3 comprising the amino acid sequence of SEQ ID NO: 40; an LCDR1 comprising the amino acid sequence of SEQ ID NO: 44; an LCDR2 comprising the amino acid sequence of SEQ ID NO: 46; and an LCDR3 comprising the amino acid sequence of SEQ ID NO: 48; or (h) an HCDR1 comprising the amino acid sequence of SEQ ID NO: 52; an HCDR2 comprising the amino acid sequence of SEQ ID NO: 54; an HCDR3 comprising the amino acid sequence of SEQ ID NO: 56; an LCDR1 comprising the amino acid sequence of SEQ ID NO: 60; an LCDR2 comprising the amino acid sequence of SEQ ID NO: 62; and an LCDR3 comprising the amino acid sequence of SEQ ID NO: 64; or (i) an HCDR1 comprising the amino acid sequence of SEQ ID NO: 68; an HCDR2 comprising the amino acid sequence of SEQ ID NO: 70; an HCDR3 comprising the amino acid sequence of SEQ ID NO: 72; an LCDR1 comprising the amino acid sequence of SEQ ID NO: 76; an LCDR2 comprising the amino acid sequence of SEQ ID NO: 78; and an LCDR3 comprising the amino acid sequence of SEQ ID NO: 80; or (j) an HCDR1 comprising the amino acid sequence of SEQ ID NO: 84; an HCDR2 comprising the amino acid sequence of SEQ ID NO: 86; an HCDR3 comprising the amino acid sequence of SEQ ID NO: 88; an LCDR1 comprising the amino acid sequence of SEQ ID NO: 92; an LCDR2 comprising the amino acid sequence of SEQ ID NO: 94; and an LCDR3 comprising the amino acid sequence of SEQ ID NO: 96; or
(k) an HCDR1 comprising the amino acid sequence of SEQ ID NO: 132; an HCDR2 comprising the amino acid sequence of SEQ ID NO: 134; an HCDR3 comprising the amino acid sequence of SEQ ID NO: 136; an LCDR1 comprising the amino acid sequence of SEQ ID NO: 140; an LCDR2 comprising the amino acid sequence of SEQ ID NO: 142; and an LCDR3 comprising the amino acid sequence of SEQ ID NO: 144; or
(l) an HCDR1 comprising the amino acid sequence of SEQ ID NO: 164; an HCDR2 comprising the amino acid sequence of SEQ ID NO: 166; an HCDR3 comprising the amino acid sequence of SEQ ID NO: 168; an LCDR1 comprising the amino acid sequence of SEQ ID NO: 172; an LCDR2 comprising the amino acid sequence of SEQ ID NO: 174; and an LCDR3 comprising the amino acid sequence of SEQ ID NO: 176; or
(m) an HCDR1 comprising the amino acid sequence of SEQ ID NO: 180; an HCDR2 comprising the amino acid sequence of SEQ ID NO: 182; an HCDR3 comprising the amino acid sequence of SEQ ID NO: 184; an LCDR1 comprising the amino acid sequence of SEQ ID NO: 188; an LCDR2 comprising the amino acid sequence of SEQ ID NO: 190; and an LCDR3 comprising the amino acid sequence of SEQ ID NO: 192; or
(n) an HCDR1 comprising the amino acid sequence of SEQ ID NO: 196; an HCDR2 comprising the amino acid sequence of SEQ ID NO: 198; an HCDR3 comprising the amino acid sequence of SEQ ID NO: 200; an LCDR1 comprising the amino acid sequence of SEQ ID NO: 204; an LCDR2 comprising the amino acid sequence of SEQ ID NO: 206; and an LCDR3 comprising the amino acid sequence of SEQ ID NO: 208; or
(o) an HCDR1 comprising the amino acid sequence of SEQ ID NO: 212; an HCDR2 comprising the amino acid sequence of SEQ ID NO: 214; an HCDR3 comprising the amino acid sequence of SEQ ID NO: 216; an LCDR1 comprising the amino acid sequence of SEQ ID NO: 220; an LCDR2 comprising the amino acid sequence of SEQ ID NO: 222; and an LCDR3 comprising the amino acid sequence of SEQ ID NO: 224; or
(p) an HCDR1 comprising the amino acid sequence of SEQ ID NO: 228; an HCDR2 comprising the amino acid sequence of SEQ ID NO: 230; an HCDR3 comprising the amino acid sequence of SEQ ID NO: 232; an LCDR1 comprising the amino acid sequence of SEQ ID NO: 236; an LCDR2 comprising the amino acid sequence of SEQ ID NO: 238; and an LCDR3 comprising the amino acid sequence of SEQ ID NO: 240; or
(q) an HCDR1 comprising the amino acid sequence of SEQ ID NO: 244; an HCDR2 comprising the amino acid sequence of SEQ ID NO: 246; an HCDR3 comprising the amino acid sequence of SEQ ID NO: 248; an LCDR1 comprising the amino acid sequence of SEQ ID NO: 252; an LCDR2 comprising the amino acid sequence of SEQ ID NO: 254; and an LCDR3 comprising the amino acid sequence of SEQ ID NO: 256; or
(r) an HCDR1 comprising the amino acid sequence of SEQ ID NO: 260; an HCDR2 comprising the amino acid sequence of SEQ ID NO: 262; an HCDR3 comprising the amino acid sequence of SEQ ID NO: 264; an LCDR1 comprising the amino acid sequence of SEQ ID NO: 268; an LCDR2 comprising the amino acid sequence of SEQ ID NO: 270; and an LCDR3 comprising the amino acid sequence of SEQ ID NO: 272; or
(s) an HCDR1 comprising the amino acid sequence of SEQ ID NO: 276; an HCDR2 comprising the amino acid sequence of SEQ ID NO: 278; an HCDR3 comprising the amino acid sequence of SEQ ID NO: 280; an LCDR1 comprising the amino acid sequence of SEQ ID NO: 268; an LCDR2 comprising the amino acid sequence of SEQ ID NO: 270; and an LCDR3 comprising the amino acid sequence of SEQ ID NO: 272; or
(t) an HCDR1 comprising the amino acid sequence of SEQ ID NO: 284; an HCDR2 comprising the amino acid sequence of SEQ ID NO: 286; an HCDR3 comprising the amino acid sequence of SEQ ID NO: 288; an LCDR1 comprising the amino acid sequence of SEQ ID NO: 268; an LCDR2 comprising the amino acid sequence of SEQ ID NO: 270; and an LCDR3 comprising the amino acid sequence of SEQ ID NO: 272.

7. The method of claim 6, wherein the SIT regimen is a rush SIT regimen.

8. The method of claim 1, wherein the one or more antibodies and antigen-binding fragments thereof comprises:
a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304; or
an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; or
an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; or
an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

9. The method of claim 2, wherein the one or more antibodies and antigen-binding fragments thereof comprises:
- a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304; or
- an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; or
- an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; or
- an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

10. The method of claim 6, wherein the one or more antibodies and antigen-binding fragments thereof comprises:
- a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304; or
- an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; or
- an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; or
- an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

11. The method of claim 1, wherein the one or more antibodies and antigen-binding fragments thereof comprises:
- a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304; and
- an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160.

12. The method of claim 2, wherein the one or more antibodies and antigen-binding fragments thereof comprises:
- a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304; and
- an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160.

13. The method of claim 6, wherein the one or more antibodies and antigen-binding fragments thereof comprises:
- a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304; and an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160.

14. The method of claim 1, wherein the one or more antibodies and antigen-binding fragments thereof comprises:
a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304; and
an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112.

15. The method of claim 2, wherein the one or more antibodies and antigen-binding fragments thereof comprises:
a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304; and
an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112.

16. The method of claim 6, wherein the one or more antibodies and antigen-binding fragments thereof comprises:
a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304; and
an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112.

17. The method of claim 1, wherein the one or more antibodies and antigen-binding fragments thereof comprises:
a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304; and
an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

18. The method of claim 2, wherein the one or more antibodies and antigen-binding fragments thereof comprises:
a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304; and
an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

19. The method of claim 6, wherein the one or more antibodies and antigen-binding fragments thereof comprises:
a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304; and
an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

20. The method of claim 1, wherein the one or more antibodies and antigen-binding fragments thereof comprises:
an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; and
an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112.

21. The method of claim 2, wherein the one or more antibodies and antigen-binding fragments thereof comprises:
an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; and
an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112.

22. The method of claim 6, wherein the one or more antibodies and antigen-binding fragments thereof comprises:
an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; and
an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112.

23. The method of claim 1, wherein the one or more antibodies and antigen-binding fragments thereof comprises:
an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; and
an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

24. The method of claim 2, wherein the one or more antibodies and antigen-binding fragments thereof comprises:
an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; and
an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

25. The method of claim 6, wherein the one or more antibodies and antigen-binding fragments thereof comprises:
an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; and
an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

26. The method of claim 1, wherein the one or more antibodies and antigen-binding fragments thereof comprises:
an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; and
an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

27. The method of claim 2, wherein the one or more antibodies and antigen-binding fragments thereof comprises:
   an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; and
   an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

28. The method of claim 6, wherein the one or more antibodies and antigen-binding fragments thereof comprises:
   an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 12; and
   an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

29. The method of claim 1, wherein the one or more antibodies and antigen-binding fragments thereof comprises:
   a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304;
   an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; and
   an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112.

30. The method of claim 2, wherein the one or more antibodies and antigen-binding fragments thereof comprises:
   a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304;
   an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; and
   an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112.

31. The method of claim 6, wherein the one or more antibodies and antigen-binding fragments thereof comprises:
   a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304;
   an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; and
   an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112.

32. The method of claim 1, wherein the one or more antibodies and antigen-binding fragments thereof comprises:
- a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304;
- an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; and
- an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

33. The method of claim 2, wherein the one or more antibodies and antigen-binding fragments thereof comprises:
- a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304;
- an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; and
- an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

34. The method of claim 6, wherein the one or more antibodies and antigen-binding fragments thereof comprises:
- a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304;
- an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160; and
- an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

35. The method of claim 1, wherein the one or more antibodies and antigen-binding fragments thereof comprises:
- an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160;
- an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; and
- an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

36. The method of claim 2, wherein the one or more antibodies and antigen-binding fragments thereof comprises:
- an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160;

an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; and an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

37. The method of claim 6, wherein the one or more antibodies and antigen-binding fragments thereof comprises:

an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160;

an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; and an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

38. The method of claim 1, wherein the one or more antibodies and antigen-binding fragments thereof comprises:

a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304;

an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160;

an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; and an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

39. The method of claim 2, wherein the one or more antibodies and antigen-binding fragments thereof comprises:

a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304;

an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160;

an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; and an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

40. The method of claim 6, wherein the one or more antibodies and antigen-binding fragments thereof comprises:

a heavy chain complementarity determining region (HCDR)1 comprising the amino acid sequence of SEQ ID NO: 292; an HCDR2 comprising the amino acid sequence of SEQ ID NO: 294; an HCDR3 comprising the amino acid sequence of SEQ ID NO: 296; a light chain complementarity determining region (LCDR)1 comprising the amino acid sequence of SEQ ID NO: 300; an LCDR2 comprising the amino acid sequence of SEQ ID NO: 302; and an LCDR3 comprising the amino acid sequence of SEQ ID NO: 304;

an HCDR1 comprising the amino acid sequence of SEQ ID NO: 148; an HCDR2 comprising the amino acid sequence of SEQ ID NO: 150; an HCDR3 comprising the amino acid sequence of SEQ ID NO: 152; an LCDR1 comprising the amino acid sequence of SEQ ID NO: 156; an LCDR2 comprising the amino acid sequence of SEQ ID NO: 158; and an LCDR3 comprising the amino acid sequence of SEQ ID NO: 160;

an HCDR1 comprising the amino acid sequence of SEQ ID NO: 100; an HCDR2 comprising the amino acid sequence of SEQ ID NO: 102; an HCDR3 comprising the amino acid sequence of SEQ ID NO: 104; an LCDR1 comprising the amino acid sequence of SEQ ID NO: 108; an LCDR2 comprising the amino acid sequence of SEQ ID NO: 110; and an LCDR3 comprising the amino acid sequence of SEQ ID NO: 112; and an HCDR1 comprising the amino acid sequence of SEQ ID NO: 116; an HCDR2 comprising the amino acid sequence of SEQ ID NO: 118; an HCDR3 comprising the amino acid sequence of SEQ ID NO: 120; an LCDR1 comprising the amino acid sequence of SEQ ID NO: 124; an LCDR2 comprising the amino acid sequence of SEQ ID NO: 126; and an LCDR3 comprising the amino acid sequence of SEQ ID NO: 128.

* * * * *

SEQUENCE LISTING

<160> NUMBER OF SEQ ID NOS: 323

<210> SEQ ID NO 1
<211> LENGTH: 375
<212> TYPE: DNA
<213> ORGANISM: Artificial Sequence
<220> FEATURE:
<223> OTHER INFORMATION: synthetic

<400> SEQUENCE: 1

```
gaggtgcagc tggtggagtc tgggggaggc ttggtccagc ctgggggggtc cctgagactc      60
tcctgtacag cctctggatt catgtctagt atgtattgga tgagctgggt ccgccaggct     120
ccagggaagg ggctggagtg ggtgtccaac ataaagcaag atggaactga aaaaactat      180
gtggagtctg tgaagggccg attcaccatc tccagagaca acgccaagaa ctcactgtat     240
ctgcaaataa acagcctgag aggcgaggac acggctgtgt attactgtgc gagagatctg     300
tatagcagtt cgtccggcta ctattactac ggtttggacg tctggggcca agggaccacg     360
gtcaccgtct cctca                                                      375
```

<210> SEQ ID NO 2
<211> LENGTH: 125
<212> TYPE: PRT
<213> ORGANISM: Artificial Sequence
<220> FEATURE:
<223> OTHER INFORMATION: synthetic

<400> SEQUENCE: 2

```
Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Met Ser Ser Met Tyr
            20                  25                  30

Trp Met Ser Trp Val Arg Gln Ala Pro Gly Lys Gly Leu Glu Trp Val
        35                  40                  45

Ser Asn Ile Lys Gln Asp Gly Thr Glu Lys Asn Tyr Val Glu Ser Val
    50                  55                  60

Lys Gly Arg Phe Thr Ile Ser Arg Asp Asn Ala Lys Asn Ser Leu Tyr
65                  70                  75                  80

Leu Gln Ile Asn Ser Leu Arg Gly Glu Asp Thr Ala Val Tyr Tyr Cys
                85                  90                  95

Ala Arg Asp Leu Tyr Ser Ser Ser Gly Tyr Tyr Tyr Gly Leu
            100                 105                 110

Asp Val Trp Gly Gln Gly Thr Thr Val Thr Val Ser Ser
        115                 120                 125
```

<210> SEQ ID NO 3
<211> LENGTH: 24
<212> TYPE: DNA
<213> ORGANISM: Artificial Sequence
<220> FEATURE:
<223> OTHER INFORMATION: synthetic

<400> SEQUENCE: 3
ggattcatgt ctagtatgta ttgg                                    24

<210> SEQ ID NO 4
<211> LENGTH: 8
<212> TYPE: PRT
<213> ORGANISM: Artificial Sequence
<220> FEATURE:
<223> OTHER INFORMATION: synthetic

<400> SEQUENCE: 4

Gly Phe Met Ser Ser Met Tyr Trp
1               5

<210> SEQ ID NO 5
<211> LENGTH: 24
<212> TYPE: DNA
<213> ORGANISM: Artificial Sequence
<220> FEATURE:
<223> OTHER INFORMATION: synthetic

<400> SEQUENCE: 5
ataaagcaag atggaactga gaaa                                    24

<210> SEQ ID NO 6
<211> LENGTH: 8
<212> TYPE: PRT
<213> ORGANISM: Artificial Sequence
<220> FEATURE:
<223> OTHER INFORMATION: synthetic

<400> SEQUENCE: 6

Ile Lys Gln Asp Gly Thr Glu Lys
1               5

<210> SEQ ID NO 7
<211> LENGTH: 54
<212> TYPE: DNA
<213> ORGANISM: Artificial Sequence
<220> FEATURE:
<223> OTHER INFORMATION: synthetic

<400> SEQUENCE: 7
gcgagagatc tgtatagcag ttcgtccggc tactattact acggtttgga cgtc      54

<210> SEQ ID NO 8
<211> LENGTH: 18
<212> TYPE: PRT
<213> ORGANISM: Artificial Sequence
<220> FEATURE:
<223> OTHER INFORMATION: synthetic

<400> SEQUENCE: 8

Ala Arg Asp Leu Tyr Ser Ser Ser Ser Gly Tyr Tyr Tyr Tyr Gly Leu
1               5                   10                  15

Asp Val

<210> SEQ ID NO 9
<211> LENGTH: 336
<212> TYPE: DNA
<213> ORGANISM: Artificial Sequence
<220> FEATURE:
<223> OTHER INFORMATION: synthetic

<400> SEQUENCE: 9

```
gatattgtga tgactcagtc tccactctcc ctgcccgtca cccctggaga gccggcctcc    60
atctcctgca ggtctagtca gagcctcctg catagtaata aatacaatta tttggattgg   120
tacctgcaga agccagggca gtctccacag ctcctgatct atttgagttc taatcgggcc   180 tccgggggtcc ctgacaggtt cagtggcagt ggctcaggca cagaatttac actgaaaatc   240
agcagagtgg aggctgagga tgttggtatt tattactgca tgcaagctct acacactccg   300
ctcactttcg gcggagggac caaggtggag atcaaa                              336
```

<210> SEQ ID NO 10
<211> LENGTH: 112
<212> TYPE: PRT
<213> ORGANISM: Artificial Sequence
<220> FEATURE:
<223> OTHER INFORMATION: synthetic

<400> SEQUENCE: 10

```
Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Lys Tyr Asn Tyr Leu Asp Trp Tyr Leu Gln Lys Pro Gly Gln Ser
        35                  40                  45

Pro Gln Leu Leu Ile Tyr Leu Ser Ser Asn Arg Ala Ser Gly Val Pro
    50                  55                  60

Asp Arg Phe Ser Gly Ser Gly Ser Gly Thr Glu Phe Thr Leu Lys Ile
65                  70                  75                  80

Ser Arg Val Glu Ala Glu Asp Val Gly Ile Tyr Tyr Cys Met Gln Ala
                85                  90                  95

Leu His Thr Pro Leu Thr Phe Gly Gly Gly Thr Lys Val Glu Ile Lys
            100                 105                 110
```

<210> SEQ ID NO 11
<211> LENGTH: 33
<212> TYPE: DNA
<213> ORGANISM: Artificial Sequence
<220> FEATURE:
<223> OTHER INFORMATION: synthetic

<400> SEQUENCE: 11

```
cagagcctcc tgcatagtaa taaatacaat tat                                  33
```

<210> SEQ ID NO 12
<211> LENGTH: 11
<212> TYPE: PRT
<213> ORGANISM: Artificial Sequence
<220> FEATURE:
<223> OTHER INFORMATION: synthetic

<400> SEQUENCE: 12

```
Gln Ser Leu Leu His Ser Asn Lys Tyr Asn Tyr
1               5                   10
```

<210> SEQ ID NO 13
<211> LENGTH: 9
<212> TYPE: DNA
<213> ORGANISM: Artificial Sequence
<220> FEATURE:
<223> OTHER INFORMATION: synthetic

<400> SEQUENCE: 13

```
ttgagttct                                                                9
```

<210> SEQ ID NO 14
<211> LENGTH: 3
<212> TYPE: PRT
<213> ORGANISM: Artificial Sequence
<220> FEATURE:
<223> OTHER INFORMATION: synthetic

<400> SEQUENCE: 14

Leu Ser Ser
1

<210> SEQ ID NO 15
<211> LENGTH: 27
<212> TYPE: DNA
<213> ORGANISM: Artificial Sequence
<220> FEATURE:
<223> OTHER INFORMATION: synthetic

<400> SEQUENCE: 15

```
atgcaagctc tacacactcc gctcact                                           27
```

<210> SEQ ID NO 16
<211> LENGTH: 9
<212> TYPE: PRT
<213> ORGANISM: Artificial Sequence
<220> FEATURE:
<223> OTHER INFORMATION: synthetic

<400> SEQUENCE: 16

Met Gln Ala Leu His Thr Pro Leu Thr
1               5

<210> SEQ ID NO 17
<211> LENGTH: 357
<212> TYPE: DNA
<213> ORGANISM: Artificial Sequence
<220> FEATURE:
<223> OTHER INFORMATION: synthetic

<400> SEQUENCE: 17

```
gaggtgcagc tggtggagtc tgggggaggc ttggttcagc ctggagggtc cctgagactc       60
tcctgtgtag cctctggatt caccttcagt aattatgaca tgaactgggt ccgccaggct      120
ccaggggagg ggctggaatg gatttcatac attagttata gtgatcataa catatactat      180
atagactctg tgaagggccg attcaccatc tccagagaca cgccaagaa ctcactgtat       240 ctgcaaatga acagcctgag agccgaggac acggctattt attactgtgc gagagaggcc     300
ctagcatcat cttcctttga ctactggggc cagggaaccc tggtcaccgt ctcctca        357
```

<210> SEQ ID NO 18
<211> LENGTH: 119
<212> TYPE: PRT
<213> ORGANISM: Artificial Sequence
<220> FEATURE:
<223> OTHER INFORMATION: synthetic

<400> SEQUENCE: 18

Glu Val Gln Leu Val Glu Ser Gly Gly Gly Leu Val Gln Pro Gly Gly
1               5                   10                  15

Ser Leu Arg Leu Ser Cys Val Ala Ser Gly Phe Thr Phe Ser Asn Tyr
            20                  25                  30

Asp Met Asn Trp Val Arg Gln Ala Pro Gly Glu Gly Leu Glu Trp Ile

```
                35                  40                  45
Ser Tyr Ile Ser Tyr Ser Asp His Asn Ile Tyr Tyr Ile Asp Ser Val
     50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Ile Tyr Tyr Cys
                 85                  90                  95

Ala Arg Glu Ala Leu Ala Ser Ser Phe Asp Tyr Trp Gly Gln Gly
            100                 105                 110

Thr Leu Val Thr Val Ser Ser
        115
```

<210> SEQ ID NO 19
<211> LENGTH: 24
<212> TYPE: DNA
<213> ORGANISM: Artificial Sequence
<220> FEATURE:
<223> OTHER INFORMATION: synthetic

<400> SEQUENCE: 19
ggattcacct tcagtaatta tgac        24

<210> SEQ ID NO 20
<211> LENGTH: 8
<212> TYPE: PRT
<213> ORGANISM: Artificial Sequence
<220> FEATURE:
<223> OTHER INFORMATION: synthetic

<400> SEQUENCE: 20

```
Gly Phe Thr Phe Ser Asn Tyr Asp
 1               5
```

<210> SEQ ID NO 21
<211> LENGTH: 24
<212> TYPE: DNA
<213> ORGANISM: Artificial Sequence
<220> FEATURE:
<223> OTHER INFORMATION: synthetic

<400> SEQUENCE: 21
attagttata gtgatcataa cata        24

<210> SEQ ID NO 22
<211> LENGTH: 8
<212> TYPE: PRT
<213> ORGANISM: Artificial Sequence
<220> FEATURE:
<223> OTHER INFORMATION: synthetic

<400> SEQUENCE: 22

```
Ile Ser Tyr Ser Asp His Asn Ile
 1               5
```

<210> SEQ ID NO 23
<211> LENGTH: 36
<212> TYPE: DNA
<213> ORGANISM: Artificial Sequence
<220> FEATURE:
<223> OTHER INFORMATION: synthetic

<400> SEQUENCE: 23
gcgagagagg ccctagcatc atcttccttt gactac        36

<210> SEQ ID NO 24
<211> LENGTH: 12
<212> TYPE: PRT
<213> ORGANISM: Artificial Sequence
<220> FEATURE:
<223> OTHER INFORMATION: synthetic

<400> SEQUENCE: 24

Ala Arg Glu Ala Leu Ala Ser Ser Ser Phe Asp Tyr
1               5                   10

<210> SEQ ID NO 25
<211> LENGTH: 321
<212> TYPE: DNA
<213> ORGANISM: Artificial Sequence
<220> FEATURE:
<223> OTHER INFORMATION: synthetic

<400> SEQUENCE: 25
gaaatagtga tgacgcagtc tccagccacc ctgtctgtgt ctccagggga aagagtcacc     60
ctctcctgca gggccagtca gagtgttagt ggcaacttag cctggtacca gcagaaacct   120
ggccaggctc ccaggctcct catctatagt gcatccaccg gggccactgg tgtcccagcc   180
aggttcagtg gcagtgggtc tgggacagag ttcactctca ccatcagcag cctgcagtct   240
gaagattttg cactttatta ctgtcagcag tataataaat ggcctcggac gatcggccaa   300
gggaccaagg tggaaatcaa a                                              321

<210> SEQ ID NO 26
<211> LENGTH: 107
<212> TYPE: PRT
<213> ORGANISM: Artificial Sequence
<220> FEATURE:
<223> OTHER INFORMATION: synthetic

<400> SEQUENCE: 26

Glu Ile Val Met Thr Gln Ser Pro Ala Thr Leu Ser Val Ser Pro Gly
1               5                   10                  15

Glu Arg Val Thr Leu Ser Cys Arg Ala Ser Gln Ser Val Ser Gly Asn
            20                  25                  30

Leu Ala Trp Tyr Gln Gln Lys Pro Gly Gln Ala Pro Arg Leu Leu Ile
        35                  40                  45

Tyr Ser Ala Ser Thr Gly Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Leu Tyr Tyr Cys Gln Gln Tyr Asn Lys Trp Pro Arg
                85                  90                  95

Thr Ile Gly Gln Gly Thr Lys Val Glu Ile Lys
            100                 105

<210> SEQ ID NO 27
<211> LENGTH: 18
<212> TYPE: DNA
<213> ORGANISM: Artificial Sequence
<220> FEATURE:
<223> OTHER INFORMATION: synthetic

<400> SEQUENCE: 27
cagagtgtta gtggcaac                                                   18

```
<210> SEQ ID NO 28
<211> LENGTH: 6
<212> TYPE: PRT
<213> ORGANISM: Artificial Sequence
<220> FEATURE:
<223> OTHER INFORMATION: synthetic

<400> SEQUENCE: 28

Gln Ser Val Ser Gly Asn
1               5

<210> SEQ ID NO 29
<211> LENGTH: 9
<212> TYPE: DNA
<213> ORGANISM: Artificial Sequence
<220> FEATURE:
<223> OTHER INFORMATION: synthetic

<400> SEQUENCE: 29 agtgcatcc                                                                 9

<210> SEQ ID NO 30
<211> LENGTH: 3
<212> TYPE: PRT
<213> ORGANISM: Artificial Sequence
<220> FEATURE:
<223> OTHER INFORMATION: synthetic

<400> SEQUENCE: 30

Ser Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: synthetic

<400> SEQUENCE: 31
cagcagtata ataaatggcc tcggacg                                            27

<210> SEQ ID NO 32
<211> LENGTH: 9
<212> TYPE: PRT
<213> ORGANISM: Artificial Sequence
<220> FEATURE:
<223> OTHER INFORMATION: synthetic

<400> SEQUENCE: 32

Gln Gln Tyr Asn Lys Trp Pro Arg Thr
1               5

<210> SEQ ID NO 33
<211> LENGTH: 354
<212> TYPE: DNA
<213> ORGANISM: Artificial Sequence
<220> FEATURE:
<223> OTHER INFORMATION: synthetic

<400> SEQUENCE: 33
caggttcagc tggtgcagtc tggagctgag gtgaagaagc ctggggcctc agtgaaggtc        60
tcctgcaaga cttctggtta cacctttacc aactatggta tcacctgggt gcgacaggcc       120
cctggacaag gacttgagtg gatgggatgg atcagcgctt acaatggtaa cacaaactat       180
gcacagaatg tccagggcag agtcactatg accacggaca catccacgag cacagcctac       240
```

-continued

```
atggaggtga ggagcctgag atctgacgac acggccgtgt attactgtgc gagaagaagc    300
agcatgttac acttccagca ctggggccag ggcaccctgg tcactgtctc ctca          354
```

<210> SEQ ID NO 34
<211> LENGTH: 118
<212> TYPE: PRT
<213> ORGANISM: Artificial Sequence
<220> FEATURE:
<223> OTHER INFORMATION: synthetic

<400> SEQUENCE: 34

```
Gln Val Gln Leu Val Gln Ser Gly Ala Glu Val Lys Lys Pro Gly Ala
1               5                   10                  15

Ser Val Lys Val Ser Cys Lys Thr Ser Gly Tyr Thr Phe Thr Asn Tyr
            20                  25                  30

Gly Ile Thr Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Asn Val
    50                  55                  60

Gln Gly Arg Val Thr Met Thr Thr Asp Thr Ser Thr Ser Thr Ala Tyr
65                  70                  75                  80

Met Glu Val Arg Ser Leu Arg Ser Asp Asp Thr Ala Val Tyr Tyr Cys
                85                  90                  95

Ala Arg Arg Ser Ser Met Leu His Phe Gln His Trp Gly Gln Gly Thr
            100                 105                 110

Leu Val Thr Val Ser Ser
        115
```

<210> SEQ ID NO 35
<211> LENGTH: 24
<212> TYPE: DNA
<213> ORGANISM: Artificial Sequence
<220> FEATURE:
<223> OTHER INFORMATION: synthetic

<400> SEQUENCE: 35

```
ggttacacct ttaccaacta tggt                                            24
```

<210> SEQ ID NO 36
<211> LENGTH: 8
<212> TYPE: PRT
<213> ORGANISM: Artificial Sequence
<220> FEATURE:
<223> OTHER INFORMATION: synthetic

<400> SEQUENCE: 36

```
Gly Tyr Thr Phe Thr Asn Tyr Gly
1               5
```

<210> SEQ ID NO 37
<211> LENGTH: 24
<212> TYPE: DNA
<213> ORGANISM: Artificial Sequence
<220> FEATURE:
<223> OTHER INFORMATION: synthetic

<400> SEQUENCE: 37

```
atcagcgctt acaatggtaa caca                                            24
```

<210> SEQ ID NO 38
<211> LENGTH: 8

```
<212> TYPE: PRT
<213> ORGANISM: Artificial Sequence
<220> FEATURE:
<223> OTHER INFORMATION: synthetic

<400> SEQUENCE: 38

Ile Ser Ala Tyr Asn Gly Asn Thr
1               5

<210> SEQ ID NO 39
<211> LENGTH: 33
<212> TYPE: DNA
<213> ORGANISM: Artificial Sequence
<220> FEATURE:
<223> OTHER INFORMATION: synthetic

<400> SEQUENCE: 39
gcgagaagaa gcagcatgtt acacttccag cac                                    33

<210> SEQ ID NO 40
<211> LENGTH: 11
<212> TYPE: PRT
<213> ORGANISM: Artificial Sequence
<220> FEATURE:
<223> OTHER INFORMATION: synthetic

<400> SEQUENCE: 40

Ala Arg Arg Ser Ser Met Leu His Phe Gln His
1               5                   10

<210> SEQ ID NO 41
<211> LENGTH: 339
<212> TYPE: DNA
<213> ORGANISM: Artificial Sequence
<220> FEATURE:
<223> OTHER INFORMATION: synthetic

<400> SEQUENCE: 41
gacatcgtga tgacccagtc tccagactcc ctggctgtgt ctctgggcga gagggccacc        60
atcaactgca gtccagcca gcatgtttta tacgactcca gtaatgagaa ctacttagct       120
tggttccagc agaagccagg acagcctcct aaacttctca tttactgggc atctacccgg       180
gaatccgggg tccctgaccg attcagtggc agcgggtctg ggacagattt cactctcacc       240
atcagcagtc tgcaggctga agatgtggcg gtttattact gtcagcaata ttctagtgct       300
ccgtacactt ttggccaggg gaccaagctg gagatcaaa                              339

<210> SEQ ID NO 42
<211> LENGTH: 113
<212> TYPE: PRT
<213> ORGANISM: Artificial Sequence
<220> FEATURE:
<223> OTHER INFORMATION: synthetic

<400> SEQUENCE: 42

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln His Val Leu Tyr Asp
            20                  25                  30

Ser Ser Asn Glu Asn Tyr Leu Ala Trp Phe Gln Gln Lys Pro Gly Gln
        35                  40                  45

Pro Pro Lys Leu Leu Ile Tyr Trp Ala Ser Thr Arg Glu Ser Gly Val
    50                  55                  60
```

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Ser Ser Ala Pro Tyr Thr Phe Gly Gln Gly Thr Lys Leu Glu Ile
            100                 105                 110

Lys

<210> SEQ ID NO 43
<211> LENGTH: 36
<212> TYPE: DNA
<213> ORGANISM: Artificial Sequence
<220> FEATURE:
<223> OTHER INFORMATION: synthetic

<400> SEQUENCE: 43
cagcatgttt tatacgactc cagtaatgag aactac                                    36

<210> SEQ ID NO 44
<211> LENGTH: 12
<212> TYPE: PRT
<213> ORGANISM: Artificial Sequence
<220> FEATURE:
<223> OTHER INFORMATION: synthetic

<400> SEQUENCE: 44

Gln His Val Leu Tyr Asp Ser Ser Asn Glu Asn Tyr
1               5                   10

<210> SEQ ID NO 45
<211> LENGTH: 9
<212> TYPE: DNA
<213> ORGANISM: Artificial Sequence
<220> FEATURE:
<223> OTHER INFORMATION: synthetic

<400> SEQUENCE: 45 tgggcatct                                                                   9

<210> SEQ ID NO 46
<211> LENGTH: 3
<212> TYPE: PRT
<213> ORGANISM: Artificial Sequence
<220> FEATURE:
<223> OTHER INFORMATION: synthetic

<400> SEQUENCE: 46

Trp Ala Ser
1

<210> SEQ ID NO 47
<211> LENGTH: 27
<212> TYPE: DNA
<213> ORGANISM: Artificial Sequence
<220> FEATURE:
<223> OTHER INFORMATION: synthetic

<400> SEQUENCE: 47
cagcaatatt ctagtgctcc gtacact                                              27

<210> SEQ ID NO 48
<211> LENGTH: 9
<212> TYPE: PRT
<213> ORGANISM: Artificial Sequence
<220> FEATURE:

<223> OTHER INFORMATION: synthetic

<400> SEQUENCE: 48

Gln Gln Tyr Ser Ser Ala Pro Tyr Thr
1               5

<210> SEQ ID NO 49
<211> LENGTH: 354
<212> TYPE: DNA
<213> ORGANISM: Artificial Sequence
<220> FEATURE:
<223> OTHER INFORMATION: synthetic

<400> SEQUENCE: 49
cagctgcagc tgcaggagtc gggcccaggg ctggtgaggc cttcggagac cctgtccctc    60
acctgcactg tctctggtgg ctccatcagc agtagtaatt actggtgggg ctggatccgc   120
cagcccccag ggaaggggct ggagtggatt ggtagtatct attatagcgg gatcacctac   180
tacaacccgt ccctcaagag tcgagtcacc atatccgcgg acacgtctaa ggaccagttc   240
tccctgaagc tgaggtctgt gaccgccgcg gacacggctg tgtattactg tgcgaaattg   300
gagtggctgc gcttggactt ctggggccag ggaaccacgg tcaccgtctc ctca         354

<210> SEQ ID NO 50
<211> LENGTH: 118
<212> TYPE: PRT
<213> ORGANISM: Artificial Sequence
<220> FEATURE:
<223> OTHER INFORMATION: synthetic

<400> SEQUENCE: 50

Gln Leu Gln Leu Gln Glu Ser Gly Pro Gly Leu Val Arg Pro Ser Glu
1               5                   10                  15

Thr Leu Ser Leu Thr Cys Thr Val Ser Gly Gly Ser Ile Ser Ser Ser
            20                  25                  30

Asn Tyr Trp Trp Gly Trp Ile Arg Gln Pro Pro Gly Lys Gly Leu Glu
        35                  40                  45

Trp Ile Gly Ser Ile Tyr Tyr Ser Gly Ile Thr Tyr Tyr Asn Pro Ser
    50                  55                  60

Leu Lys Ser Arg Val Thr Ile Ser Ala Asp Thr Ser Lys Asp Gln Phe
65                  70                  75                  80

Ser Leu Lys Leu Arg Ser Val Thr Ala Ala Asp Thr Ala Val Tyr Tyr
                85                  90                  95

Cys Ala Lys Leu Glu Trp Leu Arg Leu Asp Phe Trp Gly Gln Gly Thr
            100                 105                 110

Thr Val Thr Val Ser Ser
        115

<210> SEQ ID NO 51
<211> LENGTH: 30
<212> TYPE: DNA
<213> ORGANISM: Artificial Sequence
<220> FEATURE:
<223> OTHER INFORMATION: synthetic

<400> SEQUENCE: 51
ggtggctcca tcagcagtag taattactgg                                      30

<210> SEQ ID NO 52
<211> LENGTH: 10
<212> TYPE: PRT

<210> SEQ ID NO 52
<211> LENGTH: 10
<212> TYPE: PRT
<213> ORGANISM: Artificial Sequence
<220> FEATURE:
<223> OTHER INFORMATION: synthetic

<400> SEQUENCE: 52

Gly Gly Ser Ile Ser Ser Ser Asn Tyr Trp
1               5                   10

<210> SEQ ID NO 53
<211> LENGTH: 21
<212> TYPE: DNA
<213> ORGANISM: Artificial Sequence
<220> FEATURE:
<223> OTHER INFORMATION: synthetic

<400> SEQUENCE: 53
atctattata gcgggatcac c                                          21

<210> SEQ ID NO 54
<211> LENGTH: 7
<212> TYPE: PRT
<213> ORGANISM: Artificial Sequence
<220> FEATURE:
<223> OTHER INFORMATION: synthetic

<400> SEQUENCE: 54

Ile Tyr Tyr Ser Gly Ile Thr
1               5

<210> SEQ ID NO 55
<211> LENGTH: 30
<212> TYPE: DNA
<213> ORGANISM: Artificial Sequence
<220> FEATURE:
<223> OTHER INFORMATION: synthetic

<400> SEQUENCE: 55
gcgaaattgg agtggctgcg cttggacttc                                 30

<210> SEQ ID NO 56
<211> LENGTH: 10
<212> TYPE: PRT
<213> ORGANISM: Artificial Sequence
<220> FEATURE:
<223> OTHER INFORMATION: synthetic

<400> SEQUENCE: 56

Ala Lys Leu Glu Trp Leu Arg Leu Asp Phe
1               5                   10

<210> SEQ ID NO 57
<211> LENGTH: 321
<212> TYPE: DNA
<213> ORGANISM: Artificial Sequence
<220> FEATURE:
<223> OTHER INFORMATION: synthetic

<400> SEQUENCE: 57
gacatccaga tgacccagtc tccatcttcc gtgtctgcat ctgtaggaga cagagtcacc     60
atcacttgtc gggcgagtca gggtattagt agctggttag tctggtatca gcagaaacca    120
gggaaagtcc ccaagctcct gatctatgct gcatccagtt tacaaagtgg ggtcccatta    180
aggttcagcg gcagtggatc tgggacagat ttcactctca ccatcagcag cctgcagcct    240
gaagattttg caacttacta ttgtcaacag gctaaaagtt tccctctcac cttcggccaa    300
gggacacgac tggagattaa a                                           321

<210> SEQ ID NO 58
<211> LENGTH: 107
<212> TYPE: PRT
<213> ORGANISM: Artificial Sequence
<220> FEATURE:
<223> OTHER INFORMATION: synthetic

<400> SEQUENCE: 58

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Val Trp Tyr Gln Gln Lys Pro Gly Lys Val Pro Lys Leu Leu Ile
        35                  40                  45

Tyr Ala Ala Ser Ser Leu Gln Ser Gly Val Pro Leu Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ala Lys Ser Phe Pro Leu
                85                  90                  95

Thr Phe Gly Gln Gly Thr Arg Leu Glu Ile Lys
            100                 105

<210> SEQ ID NO 59
<211> LENGTH: 18
<212> TYPE: DNA
<213> ORGANISM: Artificial Sequence
<220> FEATURE:
<223> OTHER INFORMATION: synthetic

<400> SEQUENCE: 59
cagggtatta gtagctgg                                               18

<210> SEQ ID NO 60
<211> LENGTH: 6
<212> TYPE: PRT
<213> ORGANISM: Artificial Sequence
<220> FEATURE:
<223> OTHER INFORMATION: synthetic

<400> SEQUENCE: 60

Gln Gly Ile Ser Ser Trp
1               5

<210> SEQ ID NO 61
<211> LENGTH: 9
<212> TYPE: DNA
<213> ORGANISM: Artificial Sequence
<220> FEATURE:
<223> OTHER INFORMATION: synthetic

<400> SEQUENCE: 61 gctgcatcc                                                         9

<210> SEQ ID NO 62
<211> LENGTH: 3
<212> TYPE: PRT
<213> ORGANISM: Artificial Sequence
<220> FEATURE:
<223> OTHER INFORMATION: synthetic

<400> SEQUENCE: 62

Ala Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: synthetic

<400> SEQUENCE: 63
caacaggcta aaagtttccc tctcacc                                         27

<210> SEQ ID NO 64
<211> LENGTH: 9
<212> TYPE: PRT
<213> ORGANISM: Artificial Sequence
<220> FEATURE:
<223> OTHER INFORMATION: synthetic

<400> SEQUENCE: 64

Gln Gln Ala Lys Ser Phe Pro Leu Thr
1               5

<210> SEQ ID NO 65
<211> LENGTH: 369
<212> TYPE: DNA
<213> ORGANISM: Artificial Sequence
<220> FEATURE:
<223> OTHER INFORMATION: synthetic

<400> SEQUENCE: 65
caggtgcagc tggtggagtc tgggggaggc gtggtccagc ctggggaggtc cctgagactc     60 tcctgtgcag cgtctggatt caccttcagt agctatggca tgcactggtt ccgccaggct    120
ccaggcaagg ggctggagtg ggtgggagtt atatggtctg atggaagtga taaaagtat     180 gcagactccg tgaagggccg attcaccatc tccagagaca attccaagaa cacgctgtat    240
cttcttatga acagcctgag agacgatgac acggctgtgt atcactgtgc gagagagggg    300
gggttccttt atagcagctc gtcccacttt gactactggg gccagggaac cctggtcacc    360
gtctcctca                                                            369

<210> SEQ ID NO 66
<211> LENGTH: 123
<212> TYPE: PRT
<213> ORGANISM: Artificial Sequence
<220> FEATURE:
<223> OTHER INFORMATION: synthetic

<400> SEQUENCE: 66

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Gly Met His Trp Phe Arg Gln Ala Pro Gly Lys Gly Leu Glu Trp Val
        35                  40                  45

Gly Val Ile Trp Ser Asp Gly Ser Asp Lys Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Leu Met Asn Ser Leu Arg Asp Asp Asp Thr Ala Val Tyr His Cys 85                  90                  95
Ala Arg Glu Gly Gly Phe Leu Tyr Ser Ser Ser His Phe Asp Tyr
            100                 105                 110

Trp Gly Gln Gly Thr Leu Val Thr Val Ser Ser
        115                 120

<210> SEQ ID NO 67
<211> LENGTH: 24
<212> TYPE: DNA
<213> ORGANISM: Artificial Sequence
<220> FEATURE:
<223> OTHER INFORMATION: synthetic

<400> SEQUENCE: 67
ggattcacct tcagtagcta tggc                                        24

<210> SEQ ID NO 68
<211> LENGTH: 8
<212> TYPE: PRT
<213> ORGANISM: Artificial Sequence
<220> FEATURE:
<223> OTHER INFORMATION: synthetic

<400> SEQUENCE: 68

Gly Phe Thr Phe Ser Ser Tyr Gly
1               5

<210> SEQ ID NO 69
<211> LENGTH: 24
<212> TYPE: DNA
<213> ORGANISM: Artificial Sequence
<220> FEATURE:
<223> OTHER INFORMATION: synthetic

<400> SEQUENCE: 69
atatggtctg atggaagtga taaa                                        24

<210> SEQ ID NO 70
<211> LENGTH: 8
<212> TYPE: PRT
<213> ORGANISM: Artificial Sequence
<220> FEATURE:
<223> OTHER INFORMATION: synthetic

<400> SEQUENCE: 70

Ile Trp Ser Asp Gly Ser Asp Lys
1               5

<210> SEQ ID NO 71
<211> LENGTH: 48
<212> TYPE: DNA
<213> ORGANISM: Artificial Sequence
<220> FEATURE:
<223> OTHER INFORMATION: synthetic

<400> SEQUENCE: 71
gcgagagagg gggggttcct ttatagcagc tcgtcccact ttgactac              48

<210> SEQ ID NO 72
<211> LENGTH: 16
<212> TYPE: PRT
<213> ORGANISM: Artificial Sequence
<220> FEATURE:
<223> OTHER INFORMATION: synthetic

<400> SEQUENCE: 72

Ala Arg Glu Gly Gly Phe Leu Tyr Ser Ser Ser His Phe Asp Tyr
1               5                   10                  15

<210> SEQ ID NO 73
<211> LENGTH: 321
<212> TYPE: DNA
<213> ORGANISM: Artificial Sequence
<220> FEATURE:
<223> OTHER INFORMATION: synthetic

<400> SEQUENCE: 73
gccatccaga tgacccagtc tccatcctcc ctgtctgcat ctgtaggaga cagagtcacc      60
atcacttgcc ggacaagtca gggcattaga aatgatttag gctggtatca gcagaaacca     120
gggaaagccc ctaaactcct gatctttgct gcatccagtt tacaaagtgg ggtcccatca     180
aggttcagcg gcagtggatc tggcacagat ttcactctca ccatcagcag cctgcagcct     240
gaagattttg caatttatta ctgtctacaa gattacaagt acccattcac tttcggcgga     300
gggaccaagg tggagatcaa a                                               321

<210> SEQ ID NO 74
<211> LENGTH: 107
<212> TYPE: PRT
<213> ORGANISM: Artificial Sequence
<220> FEATURE:
<223> OTHER INFORMATION: synthetic

<400> SEQUENCE: 74

Ala Ile Gln Met Thr Gln Ser Pro Ser Ser Leu Ser Ala Ser Val Gly
1               5                   10                  15

Asp Arg Val Thr Ile Thr Cys Arg Thr Ser Gln Gly Ile Arg Asn Asp
                20                  25                  30

Leu Gly Trp Tyr Gln Gln Lys Pro Gly Lys Ala Pro Lys Leu Leu Ile
            35                  40                  45

Phe Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Ile Tyr Tyr Cys Leu Gln Asp Tyr Lys Tyr Pro Phe
                85                  90                  95

Thr Phe Gly Gly Gly Thr Lys Val Glu Ile Lys
            100                 105

<210> SEQ ID NO 75
<211> LENGTH: 18
<212> TYPE: DNA
<213> ORGANISM: Artificial Sequence
<220> FEATURE:
<223> OTHER INFORMATION: synthetic

<400> SEQUENCE: 75
cagggcatta gaaatgat                                                    18

<210> SEQ ID NO 76
<211> LENGTH: 6
<212> TYPE: PRT
<213> ORGANISM: Artificial Sequence
<220> FEATURE:
<223> OTHER INFORMATION: synthetic

<400> SEQUENCE: 76

Gln Gly Ile Arg Asn Asp
1               5

<210> SEQ ID NO 77
<211> LENGTH: 9
<212> TYPE: DNA
<213> ORGANISM: Artificial Sequence
<220> FEATURE:
<223> OTHER INFORMATION: synthetic

<400> SEQUENCE: 77 gctgcatcc                                                              9

<210> SEQ ID NO 78
<211> LENGTH: 3
<212> TYPE: PRT
<213> ORGANISM: Artificial Sequence
<220> FEATURE:
<223> OTHER INFORMATION: synthetic

<400> SEQUENCE: 78

Ala Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: synthetic

<400> SEQUENCE: 79
ctacaagatt acaagtaccc attcact                                         27

<210> SEQ ID NO 80
<211> LENGTH: 9
<212> TYPE: PRT
<213> ORGANISM: Artificial Sequence
<220> FEATURE:
<223> OTHER INFORMATION: synthetic

<400> SEQUENCE: 80

Leu Gln Asp Tyr Lys Tyr Pro Phe Thr
1               5

<210> SEQ ID NO 81
<211> LENGTH: 363
<212> TYPE: DNA
<213> ORGANISM: Artificial Sequence
<220> FEATURE:
<223> OTHER INFORMATION: synthetic

<400> SEQUENCE: 81
caggtgcagc tggtggagtc tgggggaggc gtggtccagc ctggggaggtc cctgagactc     60 tcctgtgcag cctctgggtt caccttcagt cctatggcc tgcactgggt ccgccaggct     120
ccaggcaagg ggctggagtg ggtggcagtt atatcagatg atggaagtta taaattctat     180
gcagactcca tgaagggccg attcaccatc tctagagaca attccaagaa cacgctgtat     240
ctgcaaatga acagcctgag agctgaggac acggctgtgt attactgtgc gaaagatcgg     300
ggtcgcagtg gctggtacta ctttgactac tggggccagg gaaccctggt cactgtctcc     360
tca                                                                  363

<210> SEQ ID NO 82

```
<211> LENGTH: 121
<212> TYPE: PRT
<213> ORGANISM: Artificial Sequence
<220> FEATURE:
<223> OTHER INFORMATION: synthetic

<400> SEQUENCE: 82

Gln Val Gln Leu Val Glu Ser Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Leu His Trp Val Arg Gln Ala Pro Gly Lys Gly Leu Glu Trp Val
            35                  40                  45

Ala Val Ile Ser Asp Asp Gly Ser Tyr Lys Phe Tyr Ala Asp Ser Met
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Arg Gly Arg Ser Gly Trp Tyr Tyr Phe Asp Tyr Trp Gly
            100                 105                 110

Gln Gly Thr Leu Val Thr Val Ser Ser
        115                 120

<210> SEQ ID NO 83
<211> LENGTH: 24
<212> TYPE: DNA
<213> ORGANISM: Artificial Sequence
<220> FEATURE:
<223> OTHER INFORMATION: synthetic

<400> SEQUENCE: 83
gggttcacct tcagttccta tggc                                          24

<210> SEQ ID NO 84
<211> LENGTH: 8
<212> TYPE: PRT
<213> ORGANISM: Artificial Sequence
<220> FEATURE:
<223> OTHER INFORMATION: synthetic

<400> SEQUENCE: 84

Gly Phe Thr Phe Ser Ser Tyr Gly
1               5

<210> SEQ ID NO 85
<211> LENGTH: 24
<212> TYPE: DNA
<213> ORGANISM: Artificial Sequence
<220> FEATURE:
<223> OTHER INFORMATION: synthetic

<400> SEQUENCE: 85
atatcagatg atggaagtta taaa                                          24

<210> SEQ ID NO 86
<211> LENGTH: 8
<212> TYPE: PRT
<213> ORGANISM: Artificial Sequence
<220> FEATURE:
<223> OTHER INFORMATION: synthetic

<400> SEQUENCE: 86
```

```
Ile Ser Asp Asp Gly Ser Tyr Lys
1               5
```

<210> SEQ ID NO 87
<211> LENGTH: 42
<212> TYPE: DNA
<213> ORGANISM: Artificial Sequence
<220> FEATURE:
<223> OTHER INFORMATION: synthetic

<400> SEQUENCE: 87

```
gcgaaagatc ggggtcgcag tggctggtac tactttgact ac                42
```

<210> SEQ ID NO 88
<211> LENGTH: 14
<212> TYPE: PRT
<213> ORGANISM: Artificial Sequence
<220> FEATURE:
<223> OTHER INFORMATION: synthetic

<400> SEQUENCE: 88

```
Ala Lys Asp Arg Gly Arg Ser Gly Trp Tyr Tyr Phe Asp Tyr
1               5                   10
```

<210> SEQ ID NO 89
<211> LENGTH: 321
<212> TYPE: DNA
<213> ORGANISM: Artificial Sequence
<220> FEATURE:
<223> OTHER INFORMATION: synthetic

<400> SEQUENCE: 89

```
gacatccaga tgacccagtc tccttccacc ctgtctgcat ctgtagggga cagagtcacc    60
atcacttgcc gggccagtca gagtattagt agctggttgg cctggtatca gcagaaacca   120
gggaaagccc ctaagctcct gatctataag gcgtctagtt tagaaagtgg ggtcccatca   180
aggttcagcg gcagtggatc tgggacagaa ttcactctca ccatcagcag cctgcagcct   240
gatgattttg caacttatta ctgccaacag tatgatagtt attctcggac gttcggccaa   300
gggaccaagg tggaaatcaa a                                             321
```

<210> SEQ ID NO 90
<211> LENGTH: 107
<212> TYPE: PRT
<213> ORGANISM: Artificial Sequence
<220> FEATURE:
<223> OTHER INFORMATION: synthetic

<400> SEQUENCE: 90

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Lys Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asp Ser Tyr Ser Arg
                85                  90                  95

Thr Phe Gly Gln Gly Thr Lys Val Glu Ile Lys
```

-continued

<210> SEQ ID NO 91
<211> LENGTH: 18
<212> TYPE: DNA
<213> ORGANISM: Artificial Sequence
<220> FEATURE:
<223> OTHER INFORMATION: synthetic

<400> SEQUENCE: 91
cagagtatta gtagctgg                                              18

<210> SEQ ID NO 92
<211> LENGTH: 6
<212> TYPE: PRT
<213> ORGANISM: Artificial Sequence
<220> FEATURE:
<223> OTHER INFORMATION: synthetic

<400> SEQUENCE: 92

Gln Ser Ile Ser Ser Trp
1               5

<210> SEQ ID NO 93
<211> LENGTH: 9
<212> TYPE: DNA
<213> ORGANISM: Artificial Sequence
<220> FEATURE:
<223> OTHER INFORMATION: synthetic

<400> SEQUENCE: 93 aaggcgtct                                                         9

<210> SEQ ID NO 94
<211> LENGTH: 3
<212> TYPE: PRT
<213> ORGANISM: Artificial Sequence
<220> FEATURE:
<223> OTHER INFORMATION: synthetic

<400> SEQUENCE: 94

Lys Ala Ser
1

<210> SEQ ID NO 95
<211> LENGTH: 27
<212> TYPE: DNA
<213> ORGANISM: Artificial Sequence
<220> FEATURE:
<223> OTHER INFORMATION: synthetic

<400> SEQUENCE: 95
caacagtatg atagttattc tcggacg                                    27

<210> SEQ ID NO 96
<211> LENGTH: 9
<212> TYPE: PRT
<213> ORGANISM: Artificial Sequence
<220> FEATURE:
<223> OTHER INFORMATION: synthetic

<400> SEQUENCE: 96

Gln Gln Tyr Asp Ser Tyr Ser Arg Thr
1               5

<210> SEQ ID NO 97

<211> LENGTH: 357
<212> TYPE: DNA
<213> ORGANISM: Artificial Sequence
<220> FEATURE:
<223> OTHER INFORMATION: synthetic

<400> SEQUENCE: 97

```
gaggtgcagc tggtggagtc tgggggagac ttggtacagc ctggagggtc cctgagactc      60
tcctgtgcag cctctggatt caccttcagt agttatgaaa tgaactgggt ccgccaggct     120
ccagggaagg gtctggagtg ggtttcattc attagtgata gtagtagtaa catatactac     180
gcagactctg tgaagggccg attcaccatc tccagagaca atgccaagaa gtcactgtat     240
cttcaaatga ccagcctgag ggccgaggac acggctgttt attactgtgc gagagaagcc     300
attggcagca cctcctttga caactggggc cagggaaccc tggtcaccgt ctcctca       357
```

<210> SEQ ID NO 98
<211> LENGTH: 119
<212> TYPE: PRT
<213> ORGANISM: Artificial Sequence
<220> FEATURE:
<223> OTHER INFORMATION: synthetic

<400> SEQUENCE: 98

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Phe Ile Ser Asp Ser Ser Ser Asn Ile Tyr Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Thr Ser Leu Arg Ala Glu Asp Thr Ala Val Tyr Tyr Cys
                85                  90                  95

Ala Arg Glu Ala Ile Gly Ser Thr Ser Phe Asp Asn Trp Gly Gln Gly
            100                 105                 110

Thr Leu Val Thr Val Ser Ser
        115
```

<210> SEQ ID NO 99
<211> LENGTH: 24
<212> TYPE: DNA
<213> ORGANISM: Artificial Sequence
<220> FEATURE:
<223> OTHER INFORMATION: synthetic

<400> SEQUENCE: 99

```
ggattcacct tcagtagtta tgaa                                            24
```

<210> SEQ ID NO 100
<211> LENGTH: 8
<212> TYPE: PRT
<213> ORGANISM: Artificial Sequence
<220> FEATURE:
<223> OTHER INFORMATION: synthetic

<400> SEQUENCE: 100

```
Gly Phe Thr Phe Ser Ser Tyr Glu
1               5
```

<210> SEQ ID NO 101
<211> LENGTH: 24
<212> TYPE: DNA
<213> ORGANISM: Artificial Sequence
<220> FEATURE:
<223> OTHER INFORMATION: synthetic

<400> SEQUENCE: 101
attagtgata gtagtagtaa cata                                              24

<210> SEQ ID NO 102
<211> LENGTH: 8
<212> TYPE: PRT
<213> ORGANISM: Artificial Sequence
<220> FEATURE:
<223> OTHER INFORMATION: synthetic

<400> SEQUENCE: 102

Ile Ser Asp Ser Ser Ser Asn Ile
1               5

<210> SEQ ID NO 103
<211> LENGTH: 36
<212> TYPE: DNA
<213> ORGANISM: Artificial Sequence
<220> FEATURE:
<223> OTHER INFORMATION: synthetic

<400> SEQUENCE: 103
gcgagagaag ccattggcag cacctccttt gacaac                                 36

<210> SEQ ID NO 104
<211> LENGTH: 12
<212> TYPE: PRT
<213> ORGANISM: Artificial Sequence
<220> FEATURE:
<223> OTHER INFORMATION: synthetic

<400> SEQUENCE: 104

Ala Arg Glu Ala Ile Gly Ser Thr Ser Phe Asp Asn
1               5                   10

<210> SEQ ID NO 105
<211> LENGTH: 321
<212> TYPE: DNA
<213> ORGANISM: Artificial Sequence
<220> FEATURE:
<223> OTHER INFORMATION: synthetic

<400> SEQUENCE: 105
gaaatagtga tgacgcagtc tccagccacc ctgtctgtgt ctccagggga aagagccacc       60
ctctcctgca gggccagtca gagtgttagc agcagtttag cctggtacca gcagaaacct     120
ggccaggctc ccaggcgcct catctatagt gcatccacca gggccactgg tatcccagcc     180
aggttcagtg gcagtgggtc tgggacagag ttcactctca ccatcagcag cctgcagtct     240
gaagattttg caattttatta ctgtcatcaa tataataact ggcctctcac tttcggcgga    300
gggaccaagg tggagatcaa a                                              321

<210> SEQ ID NO 106
<211> LENGTH: 107
<212> TYPE: PRT
<213> ORGANISM: Artificial Sequence
<220> FEATURE:
<223> OTHER INFORMATION: synthetic

<400> SEQUENCE: 106

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Ser
            20                  25                  30

Leu Ala Trp Tyr Gln Gln Lys Pro Gly Gln Ala Pro Arg Arg Leu Ile
        35                  40                  45

Tyr Ser Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys His Gln Tyr Asn Asn Trp Pro Leu
                85                  90                  95

Thr Phe Gly Gly Gly Thr Lys Val Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: synthetic

<400> SEQUENCE: 107
cagagtgtta gcagcagt                                                 18

<210> SEQ ID NO 108
<211> LENGTH: 6
<212> TYPE: PRT
<213> ORGANISM: Artificial Sequence
<220> FEATURE:
<223> OTHER INFORMATION: synthetic

<400> SEQUENCE: 108

Gln Ser Val Ser Ser Ser
1               5

<210> SEQ ID NO 109
<211> LENGTH: 9
<212> TYPE: DNA
<213> ORGANISM: Artificial Sequence
<220> FEATURE:
<223> OTHER INFORMATION: synthetic

<400> SEQUENCE: 109 agtgcatcc                                                            9

<210> SEQ ID NO 110
<211> LENGTH: 3
<212> TYPE: PRT
<213> ORGANISM: Artificial Sequence
<220> FEATURE:
<223> OTHER INFORMATION: synthetic

<400> SEQUENCE: 110

Ser Ala Ser
1

<210> SEQ ID NO 111
<211> LENGTH: 27
<212> TYPE: DNA
<213> ORGANISM: Artificial Sequence
<220> FEATURE:
<223> OTHER INFORMATION: synthetic

<400> SEQUENCE: 111
catcaatata ataactggcc tctcact                                              27

<210> SEQ ID NO 112
<211> LENGTH: 9
<212> TYPE: PRT
<213> ORGANISM: Artificial Sequence
<220> FEATURE:
<223> OTHER INFORMATION: synthetic

<400> SEQUENCE: 112

His Gln Tyr Asn Asn Trp Pro Leu Thr
1               5

<210> SEQ ID NO 113
<211> LENGTH: 357
<212> TYPE: DNA
<213> ORGANISM: Artificial Sequence
<220> FEATURE:
<223> OTHER INFORMATION: synthetic

<400> SEQUENCE: 113
gaggtgcagc tggtggagtc tggaggaggc ttggtccagc ctggggggtc cctgagactc          60
tcctgtgcag cctctgggtt caccgtcagt agcaactcca tgagctgggt ccgccaggct         120
ccaggggagg ggctggagtg ggtctcagtt attttagcg gtggtatcac atactactca          180
gactccgtga agggccgatt caccatctcc agacacaatt ccaagaacac gctgtatctt         240
caaatgaaca gcctgagaac tgaggacacg gccgtatatt actgtgcgcg tcattctaac         300
tggaactttg atgcttttga tatctggggc caagggacaa tggtcaccgt ctcttca           357

<210> SEQ ID NO 114
<211> LENGTH: 119
<212> TYPE: PRT
<213> ORGANISM: Artificial Sequence
<220> FEATURE:
<223> OTHER INFORMATION: synthetic

<400> SEQUENCE: 114

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Ser Ser Asn
            20                  25                  30

Ser Met Ser Trp Val Arg Gln Ala Pro Gly Glu Gly Leu Glu Trp Val
        35                  40                  45

Ser Val Ile Phe Ser Gly Gly Ile Thr Tyr Tyr Ser Asp Ser Val Lys
    50                  55                  60

Gly Arg Phe Thr Ile Ser Arg His Asn Ser Lys Asn Thr Leu Tyr Leu
65                  70                  75                  80

Gln Met Asn Ser Leu Arg Thr Glu Asp Thr Ala Val Tyr Tyr Cys Ala
                85                  90                  95

Arg His Ser Asn Trp Asn Phe Asp Ala Phe Asp Ile Trp Gly Gln Gly
            100                 105                 110

Thr Met Val Thr Val Ser Ser
        115

<210> SEQ ID NO 115
<211> LENGTH: 24

<210> SEQ ID NO 115
<211> LENGTH: 24
<212> TYPE: DNA
<213> ORGANISM: Artificial Sequence
<220> FEATURE:
<223> OTHER INFORMATION: synthetic

<400> SEQUENCE: 115
gggttcaccg tcagtagcaa ctcc                                              24

<210> SEQ ID NO 116
<211> LENGTH: 8
<212> TYPE: PRT
<213> ORGANISM: Artificial Sequence
<220> FEATURE:
<223> OTHER INFORMATION: synthetic

<400> SEQUENCE: 116

Gly Phe Thr Val Ser Ser Asn Ser
1               5

<210> SEQ ID NO 117
<211> LENGTH: 21
<212> TYPE: DNA
<213> ORGANISM: Artificial Sequence
<220> FEATURE:
<223> OTHER INFORMATION: synthetic

<400> SEQUENCE: 117
atttttagcg gtggtatcac a                                                 21

<210> SEQ ID NO 118
<211> LENGTH: 7
<212> TYPE: PRT
<213> ORGANISM: Artificial Sequence
<220> FEATURE:
<223> OTHER INFORMATION: synthetic

<400> SEQUENCE: 118

Ile Phe Ser Gly Gly Ile Thr
1               5

<210> SEQ ID NO 119
<211> LENGTH: 39
<212> TYPE: DNA
<213> ORGANISM: Artificial Sequence
<220> FEATURE:
<223> OTHER INFORMATION: synthetic

<400> SEQUENCE: 119
gcgcgtcatt ctaactggaa ctttgatgct tttgatatc                              39

<210> SEQ ID NO 120
<211> LENGTH: 13
<212> TYPE: PRT
<213> ORGANISM: Artificial Sequence
<220> FEATURE:
<223> OTHER INFORMATION: synthetic

<400> SEQUENCE: 120

Ala Arg His Ser Asn Trp Asn Phe Asp Ala Phe Asp Ile
1               5                   10

<210> SEQ ID NO 121
<211> LENGTH: 321
<212> TYPE: DNA
<213> ORGANISM: Artificial Sequence
<220> FEATURE:
<223> OTHER INFORMATION: synthetic

<400> SEQUENCE: 121

```
gacatccaga tgacccagtc tccatcctcc ctgtctgcat ctgtaggaga cagagtcacc    60
atcacttgcc gggcaagtca gagctttgac acctatttaa attggtatca gcagaaacca   120
gggaaagccc ctaacctcct gatctatgct acatccagtt tgcaaagtgg ggtcccatca   180
aggttcagtg gcagtggatc tgggacagat ttcactctca ccatcagcag tctgcaacct   240
gaagattttg gaacttacta ttgtcaacag agttacagta tcccgtacac ttttggccag   300
gggaccaagc tggagatcaa a                                             321
```

<210> SEQ ID NO 122
<211> LENGTH: 107
<212> TYPE: PRT
<213> ORGANISM: Artificial Sequence
<220> FEATURE:
<223> OTHER INFORMATION: synthetic

<400> SEQUENCE: 122

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Phe Asp Thr Tyr
            20                  25                  30

Leu Asn Trp Tyr Gln Gln Lys Pro Gly Lys Ala Pro Asn Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Gln Gln Ser Tyr Ser Ile Pro Tyr
                85                  90                  95

Thr Phe Gly Gln Gly Thr Lys Leu Glu Ile Lys
            100                 105
```

<210> SEQ ID NO 123
<211> LENGTH: 18
<212> TYPE: DNA
<213> ORGANISM: Artificial Sequence
<220> FEATURE:
<223> OTHER INFORMATION: synthetic

<400> SEQUENCE: 123

```
cagagctttg acacctat                                                  18
```

<210> SEQ ID NO 124
<211> LENGTH: 6
<212> TYPE: PRT
<213> ORGANISM: Artificial Sequence
<220> FEATURE:
<223> OTHER INFORMATION: synthetic

<400> SEQUENCE: 124

```
Gln Ser Phe Asp Thr Tyr
1               5
```

<210> SEQ ID NO 125
<211> LENGTH: 9
<212> TYPE: DNA
<213> ORGANISM: Artificial Sequence
<220> FEATURE:
<223> OTHER INFORMATION: synthetic

```
<400> SEQUENCE: 125 gctacatcc                                                                  9

<210> SEQ ID NO 126
<211> LENGTH: 3
<212> TYPE: PRT
<213> ORGANISM: Artificial Sequence
<220> FEATURE:
<223> OTHER INFORMATION: synthetic

<400> SEQUENCE: 126

Ala Thr Ser
1

<210> SEQ ID NO 127
<211> LENGTH: 27
<212> TYPE: DNA
<213> ORGANISM: Artificial Sequence
<220> FEATURE:
<223> OTHER INFORMATION: synthetic

<400> SEQUENCE: 127
caacagagtt acagtatccc gtacact                                             27

<210> SEQ ID NO 128
<211> LENGTH: 9
<212> TYPE: PRT
<213> ORGANISM: Artificial Sequence
<220> FEATURE:
<223> OTHER INFORMATION: synthetic

<400> SEQUENCE: 128

Gln Gln Ser Tyr Ser Ile Pro Tyr Thr
1               5

<210> SEQ ID NO 129
<211> LENGTH: 354
<212> TYPE: DNA
<213> ORGANISM: Artificial Sequence
<220> FEATURE:
<223> OTHER INFORMATION: synthetic

<400> SEQUENCE: 129
caggtgcagc tggtacagtc tggggctgag gtgaggaagc ctggggcctc agtgaaggtc         60
tcctgcaagg cttctggata caccttcacc ggctactatc tacactgggt gcgacaggcc        120
cctggacaag gcttgagtg gatgggattg atcaaccta atactggtgg cacaaacttt         180
gcacagaaat ttcagggcag ggtcaccatg accagggact cgtcaatcag cgcagcctac        240
atggaactga gcaggctgag atctgacgac acggccgtgt attactgtgc gagacaacac        300
tggaaccgtt attttgacaa ctgggggccag ggaaccctgg tcaccgtctc ctca              354

<210> SEQ ID NO 130
<211> LENGTH: 118
<212> TYPE: PRT
<213> ORGANISM: Artificial Sequence
<220> FEATURE:
<223> OTHER INFORMATION: synthetic

<400> SEQUENCE: 130

Gln Val Gln Leu Val Gln Ser Gly Ala Glu Val Arg Lys Pro Gly Ala
1               5                   10                  15

Ser Val Lys Val Ser Cys Lys Ala Ser Gly Tyr Thr Phe Thr Gly Tyr
            20                  25                  30
```

Tyr Leu His Trp Val Arg Gln Ala Pro Gly Gln Gly Leu Glu Trp Met
            35                  40                  45

Gly Leu Ile Asn Pro Asn Thr Gly Gly Thr Asn Phe Ala Gln Lys Phe
 50                  55                  60

Gln Gly Arg Val Thr Met Thr Arg Asp Ser Ser Ile Ser Ala Ala Tyr
 65                  70                  75                  80

Met Glu Leu Ser Arg Leu Arg Ser Asp Thr Ala Val Tyr Tyr Cys
                85                  90                  95

Ala Arg Gln His Trp Asn Arg Tyr Phe Asp Asn Trp Gly Gln Gly Thr
            100                 105                 110

Leu Val Thr Val Ser Ser
        115

<210> SEQ ID NO 131
<211> LENGTH: 24
<212> TYPE: DNA
<213> ORGANISM: Artificial Sequence
<220> FEATURE:
<223> OTHER INFORMATION: synthetic

<400> SEQUENCE: 131
ggatacacct tcaccggcta ctat                                        24

<210> SEQ ID NO 132
<211> LENGTH: 8
<212> TYPE: PRT
<213> ORGANISM: Artificial Sequence
<220> FEATURE:
<223> OTHER INFORMATION: synthetic

<400> SEQUENCE: 132

Gly Tyr Thr Phe Thr Gly Tyr Tyr
 1               5

<210> SEQ ID NO 133
<211> LENGTH: 24
<212> TYPE: DNA
<213> ORGANISM: Artificial Sequence
<220> FEATURE:
<223> OTHER INFORMATION: synthetic

<400> SEQUENCE: 133 atcaaccctaatactggtgg caca                                         24

<210> SEQ ID NO 134
<211> LENGTH: 8
<212> TYPE: PRT
<213> ORGANISM: Artificial Sequence
<220> FEATURE:
<223> OTHER INFORMATION: synthetic

<400> SEQUENCE: 134

Ile Asn Pro Asn Thr Gly Gly Thr
 1               5

<210> SEQ ID NO 135
<211> LENGTH: 33
<212> TYPE: DNA
<213> ORGANISM: Artificial Sequence
<220> FEATURE:
<223> OTHER INFORMATION: synthetic

<400> SEQUENCE: 135
gcgagacaac actggaaccg ttattttgac aac        33

<210> SEQ ID NO 136
<211> LENGTH: 11
<212> TYPE: PRT
<213> ORGANISM: Artificial Sequence
<220> FEATURE:
<223> OTHER INFORMATION: synthetic

<400> SEQUENCE: 136

Ala Arg Gln His Trp Asn Arg Tyr Phe Asp Asn
1               5                   10

<210> SEQ ID NO 137
<211> LENGTH: 321
<212> TYPE: DNA
<213> ORGANISM: Artificial Sequence
<220> FEATURE:
<223> OTHER INFORMATION: synthetic

<400> SEQUENCE: 137
gacatccaga tgacccagtc tccttccacc ctgtctgcct ctgttggaga cagagtcacc        60
atcacttgcc gggccagtca gagtgttggt aactggttgg cctggtatca gcagaaacca       120
gggaaagccc ctaaactcct gatccaagag gcgtccagta tagaaagtgg ggtcccatca       180
aggttcagcg gcagtggatc tgggacagaa ttcactctta tcgtcagcag cctgcagcct       240
gatgattttg caacttatta ctgccaacag tataatagtt attcgtggac gttcggccac       300
gggaccaagg tggaaatcaa a                                                 321

<210> SEQ ID NO 138
<211> LENGTH: 107
<212> TYPE: PRT
<213> ORGANISM: Artificial Sequence
<220> FEATURE:
<223> OTHER INFORMATION: synthetic

<400> SEQUENCE: 138

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Val Gly Asn Trp
            20                  25                  30

Leu Ala Trp Tyr Gln Gln Lys Pro Gly Lys Ala Pro Lys Leu Leu Ile
        35                  40                  45

Gln Glu Ala Ser Ser Ile Glu Ser Gly Val Pro Ser Arg Phe Ser Gly
    50                  55                  60

Ser Gly Ser Gly Thr Glu Phe Thr Leu Ile Val Ser Ser Leu Gln Pro
65                  70                  75                  80

Asp Asp Phe Ala Thr Tyr Tyr Cys Gln Gln Tyr Asn Ser Tyr Ser Trp
                85                  90                  95

Thr Phe Gly His Gly Thr Lys Val Glu Ile Lys
            100                 105

<210> SEQ ID NO 139
<211> LENGTH: 18
<212> TYPE: DNA
<213> ORGANISM: Artificial Sequence
<220> FEATURE:
<223> OTHER INFORMATION: synthetic

<400> SEQUENCE: 139
cagagtgttg gtaactgg        18

<210> SEQ ID NO 140
<211> LENGTH: 6
<212> TYPE: PRT
<213> ORGANISM: Artificial Sequence
<220> FEATURE:
<223> OTHER INFORMATION: synthetic

<400> SEQUENCE: 140

Gln Ser Val Gly Asn Trp
1               5

<210> SEQ ID NO 141
<211> LENGTH: 9
<212> TYPE: DNA
<213> ORGANISM: Artificial Sequence
<220> FEATURE:
<223> OTHER INFORMATION: synthetic

<400> SEQUENCE: 141 gaggcgtcc                                                                  9

<210> SEQ ID NO 142
<211> LENGTH: 3
<212> TYPE: PRT
<213> ORGANISM: Artificial Sequence
<220> FEATURE:
<223> OTHER INFORMATION: synthetic

<400> SEQUENCE: 142

Glu Ala Ser
1

<210> SEQ ID NO 143
<211> LENGTH: 27
<212> TYPE: DNA
<213> ORGANISM: Artificial Sequence
<220> FEATURE:
<223> OTHER INFORMATION: synthetic

<400> SEQUENCE: 143
caacagtata atagttattc gtggacg                                             27

<210> SEQ ID NO 144
<211> LENGTH: 9
<212> TYPE: PRT
<213> ORGANISM: Artificial Sequence
<220> FEATURE:
<223> OTHER INFORMATION: synthetic

<400> SEQUENCE: 144

Gln Gln Tyr Asn Ser Tyr Ser Trp Thr
1               5

<210> SEQ ID NO 145
<211> LENGTH: 348
<212> TYPE: DNA
<213> ORGANISM: Artificial Sequence
<220> FEATURE:
<223> OTHER INFORMATION: synthetic

<400> SEQUENCE: 145
caggtgcagc tgcaggagtc gggcccagga ctggtgaagc cttcggagac cctgtccctc        60
acctgctctg tctctggtgg ctccatcact aattacttct ggacctggat ccggcagtcc       120
ccagggaagg gactggaatg gattgggtat atctattaca gtgggggcac caactataac       180

```
ccctccctca agagtcgagt caccatatca atagacacgt ccaagaacca attctccctg    240
aatatgaatt ctgtgaccgc tgcggacacg gccgtctatt actgtgcggg gagctactac    300
tacggtgtgg acgtctgggg ccaagggacc acggtcaccg tctcctca                 348
```

<210> SEQ ID NO 146
<211> LENGTH: 116
<212> TYPE: PRT
<213> ORGANISM: Artificial Sequence
<220> FEATURE:
<223> OTHER INFORMATION: synthetic

<400> SEQUENCE: 146

```
Gln Val Gln Leu Gln Glu Ser Gly Pro Gly Leu Val Lys Pro Ser Glu
1               5                   10                  15

Thr Leu Ser Leu Thr Cys Ser Val Ser Gly Ser Ile Thr Asn Tyr
            20                  25                  30

Phe Trp Thr Trp Ile Arg Gln Ser Pro Gly Lys Gly Leu Glu Trp Ile
        35                  40                  45

Gly Tyr Ile Tyr Tyr Ser Gly Gly Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Asn Met Asn Ser Val Thr Ala Ala Asp Thr Ala Val Tyr Tyr Cys Ala
                85                  90                  95

Gly Ser Tyr Tyr Tyr Gly Val Asp Val Trp Gly Gln Gly Thr Thr Val
            100                 105                 110

Thr Val Ser Ser
        115
```

<210> SEQ ID NO 147
<211> LENGTH: 24
<212> TYPE: DNA
<213> ORGANISM: Artificial Sequence
<220> FEATURE:
<223> OTHER INFORMATION: synthetic

<400> SEQUENCE: 147

```
ggtggctcca tcactaatta cttc                                            24
```

<210> SEQ ID NO 148
<211> LENGTH: 8
<212> TYPE: PRT
<213> ORGANISM: Artificial Sequence
<220> FEATURE:
<223> OTHER INFORMATION: synthetic

<400> SEQUENCE: 148

```
Gly Gly Ser Ile Thr Asn Tyr Phe
1               5
```

<210> SEQ ID NO 149
<211> LENGTH: 21
<212> TYPE: DNA
<213> ORGANISM: Artificial Sequence
<220> FEATURE:
<223> OTHER INFORMATION: synthetic

<400> SEQUENCE: 149

```
atctattaca gtgggggcac c                                               21
```

<210> SEQ ID NO 150
<211> LENGTH: 7
<212> TYPE: PRT
<213> ORGANISM: Artificial Sequence
<220> FEATURE:
<223> OTHER INFORMATION: synthetic

<400> SEQUENCE: 150

Ile Tyr Tyr Ser Gly Gly Thr
1               5

<210> SEQ ID NO 151
<211> LENGTH: 30
<212> TYPE: DNA
<213> ORGANISM: Artificial Sequence
<220> FEATURE:
<223> OTHER INFORMATION: synthetic

<400> SEQUENCE: 151
gcggggagct actactacgg tgtggacgtc                                    30

<210> SEQ ID NO 152
<211> LENGTH: 10
<212> TYPE: PRT
<213> ORGANISM: Artificial Sequence
<220> FEATURE:
<223> OTHER INFORMATION: synthetic

<400> SEQUENCE: 152

Ala Gly Ser Tyr Tyr Tyr Gly Val Asp Val
1               5                   10

<210> SEQ ID NO 153
<211> LENGTH: 321
<212> TYPE: DNA
<213> ORGANISM: Artificial Sequence
<220> FEATURE:
<223> OTHER INFORMATION: synthetic

<400> SEQUENCE: 153
gaaattgtgt tgacacagtc tccagccacc ctgtctttgt ctccagggga aagagccacc    60
ctctcctgca gggccagtca gagtattaaa agcttcttag cctggtaccg acagaaacct   120
ggccaggctc ccagactcct catctatgat gcatccaaca ggccactgg catcccagcc    180 aggttcagtg gcagtgggtc tgggacagac ttcactctca ccatcaacag cctagagtct   240
gaagattttg cagtttattt ctgtcagcag cgtaacaact ggccattcac tttcggccct   300
gggaccaaag tggatatcaa a                                            321

<210> SEQ ID NO 154
<211> LENGTH: 107
<212> TYPE: PRT
<213> ORGANISM: Artificial Sequence
<220> FEATURE:
<223> OTHER INFORMATION: synthetic

<400> SEQUENCE: 154

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Lys Ser Phe
            20                  25                  30

Leu Ala Trp Tyr Arg Gln Lys Pro Gly Gln Ala Pro Arg Leu Leu Ile
        35                  40                  45

Tyr Asp Ala Ser Asn Arg Pro Thr Gly Ile Pro Ala Arg Phe Ser Gly

```
                50                  55                  60
Ser Gly Ser Gly Thr Asp Phe Thr Leu Thr Ile Asn Ser Leu Glu Ser
 65                  70                  75                  80

Glu Asp Phe Ala Val Tyr Phe Cys Gln Gln Arg Asn Asn Trp Pro Phe
                 85                  90                  95

Thr Phe Gly Pro Gly Thr Lys Val Asp Ile Lys
            100                 105
```

<210> SEQ ID NO 155
<211> LENGTH: 18
<212> TYPE: DNA
<213> ORGANISM: Artificial Sequence
<220> FEATURE:
<223> OTHER INFORMATION: synthetic

<400> SEQUENCE: 155
cagagtatta aaagcttc                                              18

<210> SEQ ID NO 156
<211> LENGTH: 6
<212> TYPE: PRT
<213> ORGANISM: Artificial Sequence
<220> FEATURE:
<223> OTHER INFORMATION: synthetic

<400> SEQUENCE: 156

```
Gln Ser Ile Lys Ser Phe
 1               5
```

<210> SEQ ID NO 157
<211> LENGTH: 9
<212> TYPE: DNA
<213> ORGANISM: Artificial Sequence
<220> FEATURE:
<223> OTHER INFORMATION: synthetic

<400> SEQUENCE: 157 gatgcatcc                                                         9

<210> SEQ ID NO 158
<211> LENGTH: 3
<212> TYPE: PRT
<213> ORGANISM: Artificial Sequence
<220> FEATURE:
<223> OTHER INFORMATION: synthetic

<400> SEQUENCE: 158

```
Asp Ala Ser
 1
```

<210> SEQ ID NO 159
<211> LENGTH: 27
<212> TYPE: DNA
<213> ORGANISM: Artificial Sequence
<220> FEATURE:
<223> OTHER INFORMATION: synthetic

<400> SEQUENCE: 159
cagcagcgta acaactggcc attcact                                    27

<210> SEQ ID NO 160
<211> LENGTH: 9
<212> TYPE: PRT
<213> ORGANISM: Artificial Sequence
<220> FEATURE:

<223> OTHER INFORMATION: synthetic

<400> SEQUENCE: 160

Gln Gln Arg Asn Asn Trp Pro Phe Thr
1               5

<210> SEQ ID NO 161
<211> LENGTH: 375
<212> TYPE: DNA
<213> ORGANISM: Artificial Sequence
<220> FEATURE:
<223> OTHER INFORMATION: synthetic

<400> SEQUENCE: 161

```
caggtgcagc tggtggagtc tgggggaggc ttggtcaagc ctggagggtc cctgagactc    60
tcctgtgcag cctctggatt caccttcagt gactactaca tgaactggat ccgccaggct   120
ccaggaaagg ggctagagtg gatttcactc attagtagta gtggtagtgc catatattac   180
tcagactctg tgaagggccg attcaccata tccagggaca atgccaggaa atcactgtat   240
ctgcaagtga acagcctgag agccgaggac acggccgtat attactgtgc gagagatcgg   300
ggggagtggg ccctcggagc ctactactac ggtttggacg tctggggcca agggaccacg   360
gtcaccgtct cctca                                                   375
```

<210> SEQ ID NO 162
<211> LENGTH: 125
<212> TYPE: PRT
<213> ORGANISM: Artificial Sequence
<220> FEATURE:
<223> OTHER INFORMATION: synthetic

<400> SEQUENCE: 162

Gln Val Gln Leu Val Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Asn Trp Ile Arg Gln Ala Pro Gly Lys Gly Leu Glu Trp Ile
        35                  40                  45

Ser Leu Ile Ser Ser Ser Gly Ser Ala Ile Tyr Tyr Ser Asp Ser Val
    50                  55                  60

Lys Gly Arg Phe Thr Ile Ser Arg Asp Asn Ala Arg Lys Ser Leu Tyr
65                  70                  75                  80

Leu Gln Val Asn Ser Leu Arg Ala Glu Asp Thr Ala Val Tyr Tyr Cys
                85                  90                  95

Ala Arg Asp Arg Gly Glu Trp Ala Leu Gly Ala Tyr Tyr Tyr Gly Leu
            100                 105                 110

Asp Val Trp Gly Gln Gly Thr Thr Val Thr Val Ser Ser
        115                 120                 125

<210> SEQ ID NO 163
<211> LENGTH: 24
<212> TYPE: DNA
<213> ORGANISM: Artificial Sequence
<220> FEATURE:
<223> OTHER INFORMATION: synthetic

<400> SEQUENCE: 163

```
ggattcacct tcagtgacta ctac                                          24
```

<210> SEQ ID NO 164

<210> SEQ ID NO 164
<211> LENGTH: 8
<212> TYPE: PRT
<213> ORGANISM: Artificial Sequence
<220> FEATURE:
<223> OTHER INFORMATION: synthetic

<400> SEQUENCE: 164

Gly Phe Thr Phe Ser Asp Tyr Tyr
1               5

<210> SEQ ID NO 165
<211> LENGTH: 24
<212> TYPE: DNA
<213> ORGANISM: Artificial Sequence
<220> FEATURE:
<223> OTHER INFORMATION: synthetic

<400> SEQUENCE: 165
attagtagta gtggtagtgc cata                                          24

<210> SEQ ID NO 166
<211> LENGTH: 8
<212> TYPE: PRT
<213> ORGANISM: Artificial Sequence
<220> FEATURE:
<223> OTHER INFORMATION: synthetic

<400> SEQUENCE: 166

Ile Ser Ser Ser Gly Ser Ala Ile
1               5

<210> SEQ ID NO 167
<211> LENGTH: 54
<212> TYPE: DNA
<213> ORGANISM: Artificial Sequence
<220> FEATURE:
<223> OTHER INFORMATION: synthetic

<400> SEQUENCE: 167
gcgagagatc gggggagtg ggccctcgga gcctactact acggtttgga cgtc          54

<210> SEQ ID NO 168
<211> LENGTH: 18
<212> TYPE: PRT
<213> ORGANISM: Artificial Sequence
<220> FEATURE:
<223> OTHER INFORMATION: synthetic

<400> SEQUENCE: 168

Ala Arg Asp Arg Gly Glu Trp Ala Leu Gly Ala Tyr Tyr Tyr Gly Leu
1               5                   10                  15

Asp Val

<210> SEQ ID NO 169
<211> LENGTH: 336
<212> TYPE: DNA
<213> ORGANISM: Artificial Sequence
<220> FEATURE:
<223> OTHER INFORMATION: synthetic

<400> SEQUENCE: 169
gatattgtga tgactcagtc tccactctcc ctgcccgtca cccctggaga gccggcctcc    60
atctcctgca ggtctagtca gagcctccta catagtgatg gatacaacta tttggattgg   120
tacctgcaga agtcagggca gtctccacag ctcctgatct atttgggttc aatcgggcc    180

```
tccggggtcc ctgacaggtt cagtggcagt ggatcaggca cagatttttac actgaaaatc    240 agcagaatgg aggctgagga tgttggggtt tattactgca tgcaagctct acaaactccg    300 tacactttg gccaggggac caagctggag atcaaa                                336
```

```
<210> SEQ ID NO 170
<211> LENGTH: 112
<212> TYPE: PRT
<213> ORGANISM: Artificial Sequence
<220> FEATURE:
<223> OTHER INFORMATION: synthetic

<400> SEQUENCE: 170

Asp Ile Val Met Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asp Gly Tyr Asn Tyr Leu Asp Trp Tyr Leu Gln Lys Ser Gly Gln Ser
        35                  40                  45

Pro Gln Leu Leu Ile Tyr Leu Gly Ser Asn Arg Ala Ser Gly Val Pro
    50                  55                  60

Asp Arg Phe Ser Gly Ser Gly Ser Gly Thr Asp Phe Thr Leu Lys Ile
65                  70                  75                  80

Ser Arg Met Glu Ala Glu Asp Val Gly Val Tyr Tyr Cys Met Gln Ala
                85                  90                  95

Leu Gln Thr Pro Tyr Thr Phe Gly Gln Gly Thr Lys Leu Glu Ile Lys
            100                 105                 110
```

```
<210> SEQ ID NO 171
<211> LENGTH: 33
<212> TYPE: DNA
<213> ORGANISM: Artificial Sequence
<220> FEATURE:
<223> OTHER INFORMATION: synthetic

<400> SEQUENCE: 171
cagagcctcc tacatagtga tggatacaac tat                                  33
```

```
<210> SEQ ID NO 172
<211> LENGTH: 11
<212> TYPE: PRT
<213> ORGANISM: Artificial Sequence
<220> FEATURE:
<223> OTHER INFORMATION: synthetic

<400> SEQUENCE: 172

Gln Ser Leu Leu His Ser Asp Gly Tyr Asn Tyr
1               5                   10
```

```
<210> SEQ ID NO 173
<211> LENGTH: 9
<212> TYPE: DNA
<213> ORGANISM: Artificial Sequence
<220> FEATURE:
<223> OTHER INFORMATION: synthetic

<400> SEQUENCE: 173 ttgggttct                                                              9
```

```
<210> SEQ ID NO 174
<211> LENGTH: 3
<212> TYPE: PRT
<213> ORGANISM: Artificial Sequence
```

<220> FEATURE:
<223> OTHER INFORMATION: synthetic

<400> SEQUENCE: 174

Leu Gly Ser
1

<210> SEQ ID NO 175
<211> LENGTH: 27
<212> TYPE: DNA
<213> ORGANISM: Artificial Sequence
<220> FEATURE:
<223> OTHER INFORMATION: synthetic

<400> SEQUENCE: 175
atgcaagctc tacaaactcc gtacact                                         27

<210> SEQ ID NO 176
<211> LENGTH: 9
<212> TYPE: PRT
<213> ORGANISM: Artificial Sequence
<220> FEATURE:
<223> OTHER INFORMATION: synthetic

<400> SEQUENCE: 176

Met Gln Ala Leu Gln Thr Pro Tyr Thr
1               5

<210> SEQ ID NO 177
<211> LENGTH: 375
<212> TYPE: DNA
<213> ORGANISM: Artificial Sequence
<220> FEATURE:
<223> OTHER INFORMATION: synthetic

<400> SEQUENCE: 177
caggtgcagc tgcaggagtc gggcccagga ctggtgaagc cttcacagac cctgtccctc      60
acctgcactg tctctggtgg ctccatcagc agtgctgatc actactggag ctggatccgc     120
cagcagccag ggaagggcct ggaatggatt gggtacattt cttatagagg acaacctac     180 tacaacccga ccctcgagag tcgtgttagc atttcagtag acacgtttaa gaatcaattc     240
tccctgatgt tgcactccgt gactgtcgcg gacacggccg tgtattattg tgcgaaagta     300
ctccaagggc tcgtcagatt cagggactac ggtttcgacg tctggggcca agggaccacg     360
gtcaccgtct cctca                                                      375

<210> SEQ ID NO 178
<211> LENGTH: 125
<212> TYPE: PRT
<213> ORGANISM: Artificial Sequence
<220> FEATURE:
<223> OTHER INFORMATION: synthetic

<400> SEQUENCE: 178

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Ala
            20                  25                  30

Asp His Tyr Trp Ser Trp Ile Arg Gln Gln Pro Gly Lys Gly Leu Glu
        35                  40                  45

Trp Ile Gly Tyr Ile Ser Tyr Arg Gly Thr Thr Tyr Tyr Asn Pro Thr
    50                  55                  60

```
Leu Glu Ser Arg Val Ser Ile Ser Val Asp Thr Phe Lys Asn Gln Phe
 65                  70                  75                  80

Ser Leu Met Leu His Ser Val Thr Val Ala Asp Thr Ala Val Tyr Tyr
                 85                  90                  95

Cys Ala Lys Val Leu Gln Gly Leu Val Arg Phe Arg Asp Tyr Gly Phe
            100                 105                 110

Asp Val Trp Gly Gln Gly Thr Thr Val Thr Val Ser Ser
        115                 120                 125

<210> SEQ ID NO 179
<211> LENGTH: 30
<212> TYPE: DNA
<213> ORGANISM: Artificial Sequence
<220> FEATURE:
<223> OTHER INFORMATION: synthetic

<400> SEQUENCE: 179
ggtggctcca tcagcagtgc tgatcactac                                        30

<210> SEQ ID NO 180
<211> LENGTH: 10
<212> TYPE: PRT
<213> ORGANISM: Artificial Sequence
<220> FEATURE:
<223> OTHER INFORMATION: synthetic

<400> SEQUENCE: 180

Gly Gly Ser Ile Ser Ser Ala Asp His Tyr
 1               5                   10

<210> SEQ ID NO 181
<211> LENGTH: 21
<212> TYPE: DNA
<213> ORGANISM: Artificial Sequence
<220> FEATURE:
<223> OTHER INFORMATION: synthetic

<400> SEQUENCE: 181
atttcttata gagggacaac c                                                 21

<210> SEQ ID NO 182
<211> LENGTH: 7
<212> TYPE: PRT
<213> ORGANISM: Artificial Sequence
<220> FEATURE:
<223> OTHER INFORMATION: synthetic

<400> SEQUENCE: 182

Ile Ser Tyr Arg Gly Thr Thr
 1               5

<210> SEQ ID NO 183
<211> LENGTH: 51
<212> TYPE: DNA
<213> ORGANISM: Artificial Sequence
<220> FEATURE:
<223> OTHER INFORMATION: synthetic

<400> SEQUENCE: 183
gcgaaagtac tccaagggct cgtcagattc agggactacg gtttcgacgt c                51

<210> SEQ ID NO 184
<211> LENGTH: 17
<212> TYPE: PRT
<213> ORGANISM: Artificial Sequence
```

<220> FEATURE:
<223> OTHER INFORMATION: synthetic

<400> SEQUENCE: 184

Ala Lys Val Leu Gln Gly Leu Val Arg Phe Arg Asp Tyr Gly Phe Asp
1               5                   10                  15

Val

<210> SEQ ID NO 185
<211> LENGTH: 321
<212> TYPE: DNA
<213> ORGANISM: Artificial Sequence
<220> FEATURE:
<223> OTHER INFORMATION: synthetic

<400> SEQUENCE: 185

```
gacatccagt tgacccagtc tccacccttc ctgtctgcat ctgtaggaga cagagtcacc      60
atcacttgct gggccagtca ggacattagc agttatttag cctggtatca gcaaaatccc     120
gggaaatccc ctaaactcct gatctatgat gcttttactt tacacactgg ggtcccatca     180
aggtttagcg gcagtggatc tgggacagaa ttcactctca caatcagcag cctgcagcct     240
gaggattttg caacttttta ctgtcaacac ctttatagtt ttccattcac tttcggccct     300
gggaccaaag tggatatcaa a                                                321
```

<210> SEQ ID NO 186
<211> LENGTH: 107
<212> TYPE: PRT
<213> ORGANISM: Artificial Sequence
<220> FEATURE:
<223> OTHER INFORMATION: synthetic

<400> SEQUENCE: 186

Asp Ile Gln Leu Thr Gln Ser Pro Pro Phe Leu Ser Ala Ser Val Gly
1               5                   10                  15

Asp Arg Val Thr Ile Thr Cys Trp Ala Ser Gln Asp Ile Ser Ser Tyr
            20                  25                  30

Leu Ala Trp Tyr Gln Gln Asn Pro Gly Lys Ser Pro Lys Leu Leu Ile
        35                  40                  45

Tyr Asp Ala Phe Thr Leu His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Phe Tyr Cys Gln His Leu Tyr Ser Phe Pro Phe
                85                  90                  95

Thr Phe Gly Pro Gly Thr Lys Val Asp Ile Lys
            100                 105

<210> SEQ ID NO 187
<211> LENGTH: 18
<212> TYPE: DNA
<213> ORGANISM: Artificial Sequence
<220> FEATURE:
<223> OTHER INFORMATION: synthetic

<400> SEQUENCE: 187

```
caggacatta gcagttat                                                    18
```

<210> SEQ ID NO 188
<211> LENGTH: 6
<212> TYPE: PRT

```
<213> ORGANISM: Artificial Sequence
<220> FEATURE:
<223> OTHER INFORMATION: synthetic

<400> SEQUENCE: 188

Gln Asp Ile Ser Ser Tyr
1               5

<210> SEQ ID NO 189
<211> LENGTH: 9
<212> TYPE: DNA
<213> ORGANISM: Artificial Sequence
<220> FEATURE:
<223> OTHER INFORMATION: synthetic

<400> SEQUENCE: 189 gatgctttt                                                              9

<210> SEQ ID NO 190
<211> LENGTH: 3
<212> TYPE: PRT
<213> ORGANISM: Artificial Sequence
<220> FEATURE:
<223> OTHER INFORMATION: synthetic

<400> SEQUENCE: 190

Asp Ala Phe
1

<210> SEQ ID NO 191
<211> LENGTH: 27
<212> TYPE: DNA
<213> ORGANISM: Artificial Sequence
<220> FEATURE:
<223> OTHER INFORMATION: synthetic

<400> SEQUENCE: 191
caacaccttt atagttttcc attcact                                         27

<210> SEQ ID NO 192
<211> LENGTH: 9
<212> TYPE: PRT
<213> ORGANISM: Artificial Sequence
<220> FEATURE:
<223> OTHER INFORMATION: synthetic

<400> SEQUENCE: 192

Gln His Leu Tyr Ser Phe Pro Phe Thr
1               5

<210> SEQ ID NO 193
<211> LENGTH: 357
<212> TYPE: DNA
<213> ORGANISM: Artificial Sequence
<220> FEATURE:
<223> OTHER INFORMATION: synthetic

<400> SEQUENCE: 193
gaagtgcagc tggtggagtc tgggggaggc ttggtacagc ctggcgggtc cctgagactc     60
tcctgtgcag cctctggatt cacctttagg aattatgcca tgcactgggt ccgacaagct    120
ccaggggagg gcctggagtg ggtcgcagcc atttatcgga atagtgattc catagactat    180
gcggactctg tgaagggccg attcaccatt tccagagaca cgccaagaa ctccctatat     240 ctgcaaatga acagtctgaa aactgaggac acggcgttgt attactgtgc aaaagatgag    300
```

```
ggattttttgg agtactttga ctcctggggc agggaaccc tggtcaccgt ctcctca      357
```

<210> SEQ ID NO 194
<211> LENGTH: 119
<212> TYPE: PRT
<213> ORGANISM: Artificial Sequence
<220> FEATURE:
<223> OTHER INFORMATION: synthetic

<400> SEQUENCE: 194

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Arg Asn Tyr
            20                  25                  30

Ala Met His Trp Val Arg Gln Ala Pro Gly Glu Gly Leu Glu Trp Val
        35                  40                  45

Ala Ala Ile Tyr Arg Asn Ser Asp Ser Ile Asp Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Lys Thr Glu Asp Thr Ala Leu Tyr Tyr Cys
                85                  90                  95

Ala Lys Asp Glu Gly Phe Leu Glu Tyr Phe Asp Ser Trp Gly Gln Gly
            100                 105                 110

Thr Leu Val Thr Val Ser Ser
        115
```

<210> SEQ ID NO 195
<211> LENGTH: 24
<212> TYPE: DNA
<213> ORGANISM: Artificial Sequence
<220> FEATURE:
<223> OTHER INFORMATION: synthetic

<400> SEQUENCE: 195

```
ggattcacct ttaggaatta tgcc                                           24
```

<210> SEQ ID NO 196
<211> LENGTH: 8
<212> TYPE: PRT
<213> ORGANISM: Artificial Sequence
<220> FEATURE:
<223> OTHER INFORMATION: synthetic

<400> SEQUENCE: 196

```
Gly Phe Thr Phe Arg Asn Tyr Ala
1               5
```

<210> SEQ ID NO 197
<211> LENGTH: 24
<212> TYPE: DNA
<213> ORGANISM: Artificial Sequence
<220> FEATURE:
<223> OTHER INFORMATION: synthetic

<400> SEQUENCE: 197

```
atttatcgga atagtgattc cata                                           24
```

<210> SEQ ID NO 198
<211> LENGTH: 8
<212> TYPE: PRT
<213> ORGANISM: Artificial Sequence
<220> FEATURE:

<223> OTHER INFORMATION: synthetic

<400> SEQUENCE: 198

Ile Tyr Arg Asn Ser Asp Ser Ile
1               5

<210> SEQ ID NO 199
<211> LENGTH: 36
<212> TYPE: DNA
<213> ORGANISM: Artificial Sequence
<220> FEATURE:
<223> OTHER INFORMATION: synthetic

<400> SEQUENCE: 199
gcaaaagatg agggattttt ggagtactttt gactcc                                    36

<210> SEQ ID NO 200
<211> LENGTH: 12
<212> TYPE: PRT
<213> ORGANISM: Artificial Sequence
<220> FEATURE:
<223> OTHER INFORMATION: synthetic

<400> SEQUENCE: 200

Ala Lys Asp Glu Gly Phe Leu Glu Tyr Phe Asp Ser
1               5                   10

<210> SEQ ID NO 201
<211> LENGTH: 324
<212> TYPE: DNA
<213> ORGANISM: Artificial Sequence
<220> FEATURE:
<223> OTHER INFORMATION: synthetic

<400> SEQUENCE: 201
gaaattgtgt tgacgcagtc tccaggcacc ctgtctttgt ctccagggga aagagcctcc           60
ctctcctgca gggccagtca gagtgttagc agcagcttct tagcctggta ccagcagaaa          120
cctggccagg ctcccaggct cctcatctac ggtgtatcca gcaggttcat tggcatccca          180
gacaggttca gtggcggtgg gtctgggaca gacttcactc tcaccatcac cagactggag          240
cctgaagatt ttgcagtgta ttactgtcag cagtatggta ggtcaccgtg gacgttcggc          300
caagggacca aggtggaaat caaa                                                 324

<210> SEQ ID NO 202
<211> LENGTH: 108
<212> TYPE: PRT
<213> ORGANISM: Artificial Sequence
<220> FEATURE:
<223> OTHER INFORMATION: synthetic

<400> SEQUENCE: 202

Glu Ile Val Leu Thr Gln Ser Pro Gly Thr Leu Ser Leu Ser Pro Gly
1               5                   10                  15

Glu Arg Ala Ser Leu Ser Cys Arg Ala Ser Gln Ser Val Ser Ser
            20                  25                  30

Phe Leu Ala Trp Tyr Gln Gln Lys Pro Gly Gln Ala Pro Arg Leu Leu
        35                  40                  45

Ile Tyr Gly Val Ser Ser Arg Phe Ile Gly Ile Pro Asp Arg Phe Ser
    50                  55                  60

Gly Gly Gly Ser Gly Thr Asp Phe Thr Leu Thr Ile Thr Arg Leu Glu
65                  70                  75                  80

```
Pro Glu Asp Phe Ala Val Tyr Tyr Cys Gln Gln Tyr Gly Arg Ser Pro
            85                  90                  95

Trp Thr Phe Gly Gln Gly Thr Lys Val Glu Ile Lys
            100                 105
```

<210> SEQ ID NO 203
<211> LENGTH: 21
<212> TYPE: DNA
<213> ORGANISM: Artificial Sequence
<220> FEATURE:
<223> OTHER INFORMATION: synthetic

<400> SEQUENCE: 203
cagagtgtta gcagcagctt c                                           21

<210> SEQ ID NO 204
<211> LENGTH: 7
<212> TYPE: PRT
<213> ORGANISM: Artificial Sequence
<220> FEATURE:
<223> OTHER INFORMATION: synthetic

<400> SEQUENCE: 204

```
Gln Ser Val Ser Ser Ser Phe
1               5
```

<210> SEQ ID NO 205
<211> LENGTH: 9
<212> TYPE: DNA
<213> ORGANISM: Artificial Sequence
<220> FEATURE:
<223> OTHER INFORMATION: synthetic

<400> SEQUENCE: 205 ggtgtatcc                                                          9

<210> SEQ ID NO 206
<211> LENGTH: 3
<212> TYPE: PRT
<213> ORGANISM: Artificial Sequence
<220> FEATURE:
<223> OTHER INFORMATION: synthetic

<400> SEQUENCE: 206

```
Gly Val Ser
1
```

<210> SEQ ID NO 207
<211> LENGTH: 27
<212> TYPE: DNA
<213> ORGANISM: Artificial Sequence
<220> FEATURE:
<223> OTHER INFORMATION: synthetic

<400> SEQUENCE: 207
cagcagtatg gtaggtcacc gtggacg                                     27

<210> SEQ ID NO 208
<211> LENGTH: 9
<212> TYPE: PRT
<213> ORGANISM: Artificial Sequence
<220> FEATURE:
<223> OTHER INFORMATION: synthetic

<400> SEQUENCE: 208

Gln Gln Tyr Gly Arg Ser Pro Trp Thr

<210> SEQ ID NO 209
<211> LENGTH: 366
<212> TYPE: DNA
<213> ORGANISM: Artificial Sequence
<220> FEATURE:
<223> OTHER INFORMATION: synthetic

<400> SEQUENCE: 209

```
caggtgcagc tggtggagtc tgggggaggc gtggtccagc ctgggaggtc cctgcgactc    60
tcctgtgcag cctctggatt caccttcagt agatatgcca tacattgggt ccgccaggct   120
ccaggcaagg gactggaatg ggtggcagtt atatcatatg atggagatga taaatactat   180
ggagactccg tgaagggccg attcaccatt tccagagaca attccaagac catggtgtat   240
ctgcacatga acagcctgag aactgaggac acggctgtgt attattgtgc gaaagatgga   300
tatagtctct acgggaagga ctactttgac tattggggcc agggaaccct ggtcaccgtc   360
tcctca                                                              366
```

<210> SEQ ID NO 210
<211> LENGTH: 122
<212> TYPE: PRT
<213> ORGANISM: Artificial Sequence
<220> FEATURE:
<223> OTHER INFORMATION: synthetic

<400> SEQUENCE: 210

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
            20                  25                  30

Ala Ile His Trp Val Arg Gln Ala Pro Gly Lys Gly Leu Glu Trp Val
        35                  40                  45

Ala Val Ile Ser Tyr Asp Gly Asp Asp Lys Tyr Tyr Gly Asp Ser Val
    50                  55                  60

Lys Gly Arg Phe Thr Ile Ser Arg Asp Asn Ser Lys Thr Met Val Tyr
65                  70                  75                  80

Leu His Met Asn Ser Leu Arg Thr Glu Asp Thr Ala Val Tyr Tyr Cys
                85                  90                  95

Ala Lys Asp Gly Tyr Ser Leu Tyr Gly Lys Asp Tyr Phe Asp Tyr Trp
            100                 105                 110

Gly Gln Gly Thr Leu Val Thr Val Ser Ser
        115                 120

<210> SEQ ID NO 211
<211> LENGTH: 24
<212> TYPE: DNA
<213> ORGANISM: Artificial Sequence
<220> FEATURE:
<223> OTHER INFORMATION: synthetic

<400> SEQUENCE: 211

```
ggattcacct tcagtagata tgcc                                           24
```

<210> SEQ ID NO 212
<211> LENGTH: 8
<212> TYPE: PRT
<213> ORGANISM: Artificial Sequence
<220> FEATURE:
<223> OTHER INFORMATION: synthetic

<400> SEQUENCE: 212

Gly Phe Thr Phe Ser Arg Tyr Ala
1               5

<210> SEQ ID NO 213
<211> LENGTH: 24
<212> TYPE: DNA
<213> ORGANISM: Artificial Sequence
<220> FEATURE:
<223> OTHER INFORMATION: synthetic

<400> SEQUENCE: 213
atatcatatg atggagatga taaa                                          24

<210> SEQ ID NO 214
<211> LENGTH: 8
<212> TYPE: PRT
<213> ORGANISM: Artificial Sequence
<220> FEATURE:
<223> OTHER INFORMATION: synthetic

<400> SEQUENCE: 214

Ile Ser Tyr Asp Gly Asp Asp Lys
1               5

<210> SEQ ID NO 215
<211> LENGTH: 45
<212> TYPE: DNA
<213> ORGANISM: Artificial Sequence
<220> FEATURE:
<223> OTHER INFORMATION: synthetic

<400> SEQUENCE: 215
gcgaaagatg gatatagtct ctacgggaag gactactttg actat                   45

<210> SEQ ID NO 216
<211> LENGTH: 15
<212> TYPE: PRT
<213> ORGANISM: Artificial Sequence
<220> FEATURE:
<223> OTHER INFORMATION: synthetic

<400> SEQUENCE: 216

Ala Lys Asp Gly Tyr Ser Leu Tyr Gly Lys Asp Tyr Phe Asp Tyr
1               5                   10                  15

<210> SEQ ID NO 217
<211> LENGTH: 324
<212> TYPE: DNA
<213> ORGANISM: Artificial Sequence
<220> FEATURE:
<223> OTHER INFORMATION: synthetic

<400> SEQUENCE: 217
gaaattgtgt tgacacagtc tccaggcacc ctgcctttgt ctccagggga aagagccacc    60
ctctcctgca gggccagtca gagtattacc aacagctact tagcctggta ccagcagaaa   120
cctgaccagg ctcccagact cctcatctat ggtgcgtcca gcagggccac tggcatccca   180
gacaggttca gtggcagtga gtctgggaca gactttactc tcaccatcag cagactggag   240
cctgaagatt ttgcagtgta ttactgtcag cagtatgtta ggtcaccgtg acgttcggc    300 caagggacca aggtggaaat caaa                                         324

```
<210> SEQ ID NO 218
<211> LENGTH: 108
<212> TYPE: PRT
<213> ORGANISM: Artificial Sequence
<220> FEATURE:
<223> OTHER INFORMATION: synthetic

<400> SEQUENCE: 218

Glu Ile Val Leu Thr Gln Ser Pro Gly Thr Leu Pro Leu Ser Pro Gly
1               5                   10                  15

Glu Arg Ala Thr Leu Ser Cys Arg Ala Ser Gln Ser Ile Thr Asn Ser
            20                  25                  30

Tyr Leu Ala Trp Tyr Gln Gln Lys Pro Asp Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Glu Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Val Arg Ser Pro
                85                  90                  95

Trp Thr Phe Gly Gln Gly Thr Lys Val Glu Ile Lys
            100                 105

<210> SEQ ID NO 219
<211> LENGTH: 21
<212> TYPE: DNA
<213> ORGANISM: Artificial Sequence
<220> FEATURE:
<223> OTHER INFORMATION: synthetic

<400> SEQUENCE: 219
cagagtatta ccaacagcta c                                            21

<210> SEQ ID NO 220
<211> LENGTH: 7
<212> TYPE: PRT
<213> ORGANISM: Artificial Sequence
<220> FEATURE:
<223> OTHER INFORMATION: synthetic

<400> SEQUENCE: 220

Gln Ser Ile Thr Asn Ser Tyr
1               5

<210> SEQ ID NO 221
<211> LENGTH: 9
<212> TYPE: DNA
<213> ORGANISM: Artificial Sequence
<220> FEATURE:
<223> OTHER INFORMATION: synthetic

<400> SEQUENCE: 221 ggtgcgtcc                                                           9

<210> SEQ ID NO 222
<211> LENGTH: 3
<212> TYPE: PRT
<213> ORGANISM: Artificial Sequence
<220> FEATURE:
<223> OTHER INFORMATION: synthetic

<400> SEQUENCE: 222

Gly Ala Ser
1
```

<210> SEQ ID NO 223
<211> LENGTH: 27
<212> TYPE: DNA
<213> ORGANISM: Artificial Sequence
<220> FEATURE:
<223> OTHER INFORMATION: synthetic

<400> SEQUENCE: 223
cagcagtatg ttaggtcacc gtggacg                                27

<210> SEQ ID NO 224
<211> LENGTH: 9
<212> TYPE: PRT
<213> ORGANISM: Artificial Sequence
<220> FEATURE:
<223> OTHER INFORMATION: synthetic

<400> SEQUENCE: 224

Gln Gln Tyr Val Arg Ser Pro Trp Thr
1               5

<210> SEQ ID NO 225
<211> LENGTH: 363
<212> TYPE: DNA
<213> ORGANISM: Artificial Sequence
<220> FEATURE:
<223> OTHER INFORMATION: synthetic

<400> SEQUENCE: 225
caggtgcagc tacagcagtg gggcgcagga ctgttgaagc cctcggagac cctgtccctc      60
acctgcgttg tctatggtga gtctttcggt aattaccatt ggaattggat ccgccagtcc     120
ccagggaagc ggctggagtg gattggggaa atcaatcaaa atggacacac caattacaac     180
ccgtccctca gagtcgagt caccatatca gtggacacgt ccaagatcca atttccctg      240 agactgaact ctgtgaccgc cgcggacacg gctgtgtatt tctgtgcgag aggccataac     300
tacgtaaatt cctacttcgg tttggacgtc tggggccaag ggaccacggt caccgtctcc     360
tca                                                                  363

<210> SEQ ID NO 226
<211> LENGTH: 121
<212> TYPE: PRT
<213> ORGANISM: Artificial Sequence
<220> FEATURE:
<223> OTHER INFORMATION: synthetic

<400> SEQUENCE: 226

Gln Val Gln Leu Gln Gln Trp Gly Ala Gly Leu Leu Lys Pro Ser Glu
1               5                   10                  15

Thr Leu Ser Leu Thr Cys Val Val Tyr Gly Glu Ser Phe Gly Asn Tyr
            20                  25                  30

His Trp Asn Trp Ile Arg Gln Ser Pro Gly Lys Arg Leu Glu Trp Ile
        35                  40                  45

Gly Glu Ile Asn Gln Asn Gly His Thr Asn Tyr Asn Pro Ser Leu Lys
    50                  55                  60

Ser Arg Val Thr Ile Ser Val Asp Thr Ser Lys Ile Gln Phe Ser Leu
65                  70                  75                  80

Arg Leu Asn Ser Val Thr Ala Ala Asp Thr Ala Val Tyr Phe Cys Ala
                85                  90                  95

Arg Gly His Asn Tyr Val Asn Ser Tyr Phe Gly Leu Asp Val Trp Gly 100                 105                 110
Gln Gly Thr Thr Val Thr Val Ser Ser
            115                 120

<210> SEQ ID NO 227
<211> LENGTH: 24
<212> TYPE: DNA
<213> ORGANISM: Artificial Sequence
<220> FEATURE:
<223> OTHER INFORMATION: synthetic

<400> SEQUENCE: 227
ggtgagtctt tcggtaatta ccat                                          24

<210> SEQ ID NO 228
<211> LENGTH: 8
<212> TYPE: PRT
<213> ORGANISM: Artificial Sequence
<220> FEATURE:
<223> OTHER INFORMATION: synthetic

<400> SEQUENCE: 228

Gly Glu Ser Phe Gly Asn Tyr His
1               5

<210> SEQ ID NO 229
<211> LENGTH: 21
<212> TYPE: DNA
<213> ORGANISM: Artificial Sequence
<220> FEATURE:
<223> OTHER INFORMATION: synthetic

<400> SEQUENCE: 229
atcaatcaaa atggacacac c                                             21

<210> SEQ ID NO 230
<211> LENGTH: 7
<212> TYPE: PRT
<213> ORGANISM: Artificial Sequence
<220> FEATURE:
<223> OTHER INFORMATION: synthetic

<400> SEQUENCE: 230

Ile Asn Gln Asn Gly His Thr
1               5

<210> SEQ ID NO 231
<211> LENGTH: 45
<212> TYPE: DNA
<213> ORGANISM: Artificial Sequence
<220> FEATURE:
<223> OTHER INFORMATION: synthetic

<400> SEQUENCE: 231
gcgagaggcc ataactacgt aaattcctac ttcggtttgg acgtc                   45

<210> SEQ ID NO 232
<211> LENGTH: 15
<212> TYPE: PRT
<213> ORGANISM: Artificial Sequence
<220> FEATURE:
<223> OTHER INFORMATION: synthetic

<400> SEQUENCE: 232

Ala Arg Gly His Asn Tyr Val Asn Ser Tyr Phe Gly Leu Asp Val
1               5                   10                  15

<210> SEQ ID NO 233
<211> LENGTH: 321
<212> TYPE: DNA
<213> ORGANISM: Artificial Sequence
<220> FEATURE:
<223> OTHER INFORMATION: synthetic

<400> SEQUENCE: 233

```
gaaattgtga tgacgcagtc tccagccacc ctgtctgtgt ctccagggga aagagccacc    60
ctctcctgca ggaccagtca gagtgtaagc atcagcttag cctggtacca gcggaaacct   120
ggccaggctc ccaggctcct catctttggt tcatccacca gggccactgg tgtcccagcc   180
aggttcagtg gcagtgggtc tgggacagag ttcactctca ccatcagcag cctgcagtct   240
gaagattttg cagtttatta ctgtcagcag tataataact ggccgtacac ttttggccag   300
gggaccaagc tggagatcaa a                                             321
```

<210> SEQ ID NO 234
<211> LENGTH: 107
<212> TYPE: PRT
<213> ORGANISM: Artificial Sequence
<220> FEATURE:
<223> OTHER INFORMATION: synthetic

<400> SEQUENCE: 234

```
Glu Ile Val Met Thr Gln Ser Pro Ala Thr Leu Ser Val Ser Pro Gly
1               5                   10                  15

Glu Arg Ala Thr Leu Ser Cys Arg Thr Ser Gln Ser Val Ser Ile Ser
            20                  25                  30

Leu Ala Trp Tyr Gln Arg Lys Pro Gly Gln Ala Pro Arg Leu Leu Ile
        35                  40                  45

Phe Gly Ser Ser Thr Arg Ala Thr Gly Val Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Tyr
                85                  90                  95

Thr Phe Gly Gln Gly Thr Lys Leu Glu Ile Lys
            100                 105
```

<210> SEQ ID NO 235
<211> LENGTH: 18
<212> TYPE: DNA
<213> ORGANISM: Artificial Sequence
<220> FEATURE:
<223> OTHER INFORMATION: synthetic

<400> SEQUENCE: 235

```
cagagtgtaa gcatcagc                                                  18
```

<210> SEQ ID NO 236
<211> LENGTH: 6
<212> TYPE: PRT
<213> ORGANISM: Artificial Sequence
<220> FEATURE:
<223> OTHER INFORMATION: synthetic

<400> SEQUENCE: 236

```
Gln Ser Val Ser Ile Ser
1               5
```

```
<210> SEQ ID NO 237
<211> LENGTH: 9
<212> TYPE: DNA
<213> ORGANISM: Artificial Sequence
<220> FEATURE:
<223> OTHER INFORMATION: synthetic

<400> SEQUENCE: 237 ggttcatcc                                                                     9

<210> SEQ ID NO 238
<211> LENGTH: 3
<212> TYPE: PRT
<213> ORGANISM: Artificial Sequence
<220> FEATURE:
<223> OTHER INFORMATION: synthetic

<400> SEQUENCE: 238

Gly Ser Ser
1

<210> SEQ ID NO 239
<211> LENGTH: 27
<212> TYPE: DNA
<213> ORGANISM: Artificial Sequence
<220> FEATURE:
<223> OTHER INFORMATION: synthetic

<400> SEQUENCE: 239
cagcagtata ataactggcc gtacact                                                 27

<210> SEQ ID NO 240
<211> LENGTH: 9
<212> TYPE: PRT
<213> ORGANISM: Artificial Sequence
<220> FEATURE:
<223> OTHER INFORMATION: synthetic

<400> SEQUENCE: 240

Gln Gln Tyr Asn Asn Trp Pro Tyr Thr
1               5

<210> SEQ ID NO 241
<211> LENGTH: 360
<212> TYPE: DNA
<213> ORGANISM: Artificial Sequence
<220> FEATURE:
<223> OTHER INFORMATION: synthetic

<400> SEQUENCE: 241
caggtgcagc tggtgcagtc tggggctgag gtgaagaagc ctggggcctc agtgaaggtc             60
tcctgcaagg cttctggata caccttcgcc gcccactata tgcactgggt gcgacaggcc            120
cctggacaag gcttgagtg gatgggatgg atcaacactt acactggtgg cacaaactat            180
gggcagaagt tcagggcag ggtcaccatg accagggaca cgtccatcac cacagcctac            240
atggagctga gcaggctgag atctgacgac acggccgttt attactgtgc gcgagatcgg            300
cggaactgga acttcgtctt tgaatattgg ggccagggaa ccctggtcac cgtctcctca            360

<210> SEQ ID NO 242
<211> LENGTH: 120
<212> TYPE: PRT
<213> ORGANISM: Artificial Sequence
<220> FEATURE:
<223> OTHER INFORMATION: synthetic
```

<400> SEQUENCE: 242

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ala Ala His
            20                  25                  30

Tyr Met His Trp Val Arg Gln Ala Pro Gly Gln Gly Leu Glu Trp Met
        35                  40                  45

Gly Trp Ile Asn Thr Tyr Thr Gly Gly Thr Asn Tyr Gly Gln Lys Phe
    50                  55                  60

Gln Gly Arg Val Thr Met Thr Arg Asp Thr Ser Ile Thr Thr Ala Tyr
65                  70                  75                  80

Met Glu Leu Ser Arg Leu Arg Ser Asp Asp Thr Ala Val Tyr Tyr Cys
                85                  90                  95

Ala Arg Asp Arg Arg Asn Trp Asn Phe Val Phe Glu Tyr Trp Gly Gln
            100                 105                 110

Gly Thr Leu Val Thr Val Ser Ser
        115                 120

<210> SEQ ID NO 243
<211> LENGTH: 24
<212> TYPE: DNA
<213> ORGANISM: Artificial Sequence
<220> FEATURE:
<223> OTHER INFORMATION: synthetic

<400> SEQUENCE: 243
ggatacacct tcgccgccca ctat                                    24

<210> SEQ ID NO 244
<211> LENGTH: 8
<212> TYPE: PRT
<213> ORGANISM: Artificial Sequence
<220> FEATURE:
<223> OTHER INFORMATION: synthetic

<400> SEQUENCE: 244

Gly Tyr Thr Phe Ala Ala His Tyr
1               5

<210> SEQ ID NO 245
<211> LENGTH: 24
<212> TYPE: DNA
<213> ORGANISM: Artificial Sequence
<220> FEATURE:
<223> OTHER INFORMATION: synthetic

<400> SEQUENCE: 245
atcaacactt acactggtgg caca                                    24

<210> SEQ ID NO 246
<211> LENGTH: 8
<212> TYPE: PRT
<213> ORGANISM: Artificial Sequence
<220> FEATURE:
<223> OTHER INFORMATION: synthetic

<400> SEQUENCE: 246

Ile Asn Thr Tyr Thr Gly Gly Thr
1               5

<210> SEQ ID NO 247

<210> SEQ ID NO 247
<211> LENGTH: 39
<212> TYPE: DNA
<213> ORGANISM: Artificial Sequence
<220> FEATURE:
<223> OTHER INFORMATION: synthetic

<400> SEQUENCE: 247
gcgcgagatc ggcggaactg gaacttcgtc tttgaatat                    39

<210> SEQ ID NO 248
<211> LENGTH: 13
<212> TYPE: PRT
<213> ORGANISM: Artificial Sequence
<220> FEATURE:
<223> OTHER INFORMATION: synthetic

<400> SEQUENCE: 248

Ala Arg Asp Arg Arg Asn Trp Asn Phe Val Phe Glu Tyr
1               5                   10

<210> SEQ ID NO 249
<211> LENGTH: 321
<212> TYPE: DNA
<213> ORGANISM: Artificial Sequence
<220> FEATURE:
<223> OTHER INFORMATION: synthetic

<400> SEQUENCE: 249
gacatccaga tgacccagtc tccatcctcc ctgtctgcat ctgtaggaga cagagtcacc    60
atcagttgcc gggcaagtca gaacattaag aactatttaa attggtatca gcagaaacca   120
gggaaagccc ctaaactcct gatctatgaa gcatctaatt tgcaaagtgg ggccccatca   180
aggttcagtg gcagtggatc tgggacagat ttcactctca ccatcagcag tctggaacct   240
gaagattttg caacttacta ctgtcaacag agttttagta ttccgtggac gttcggccaa   300
gggaccaagg tggaaatcaa a                                            321

<210> SEQ ID NO 250
<211> LENGTH: 107
<212> TYPE: PRT
<213> ORGANISM: Artificial Sequence
<220> FEATURE:
<223> OTHER INFORMATION: synthetic

<400> SEQUENCE: 250

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asn Ile Lys Asn Tyr
            20                  25                  30

Leu Asn Trp Tyr Gln Gln Lys Pro Gly Lys Ala Pro Lys Leu Leu Ile
        35                  40                  45

Tyr Glu Ala Ser Asn Leu Gln Ser Gly Ala Pro Ser Arg Phe Ser Gly
    50                  55                  60

Ser Gly Ser Gly Thr Asp Phe Thr Leu Thr Ile Ser Ser Leu Glu Pro
65                  70                  75                  80

Glu Asp Phe Ala Thr Tyr Tyr Cys Gln Gln Ser Phe Ser Ile Pro Trp
                85                  90                  95

Thr Phe Gly Gln Gly Thr Lys Val Glu Ile Lys
            100                 105

<210> SEQ ID NO 251
<211> LENGTH: 18

```
<212> TYPE: DNA
<213> ORGANISM: Artificial Sequence
<220> FEATURE:
<223> OTHER INFORMATION: synthetic

<400> SEQUENCE: 251
cagaacatta agaactat                                                 18

<210> SEQ ID NO 252
<211> LENGTH: 6
<212> TYPE: PRT
<213> ORGANISM: Artificial Sequence
<220> FEATURE:
<223> OTHER INFORMATION: synthetic

<400> SEQUENCE: 252

Gln Asn Ile Lys Asn Tyr
1               5

<210> SEQ ID NO 253
<211> LENGTH: 9
<212> TYPE: DNA
<213> ORGANISM: Artificial Sequence
<220> FEATURE:
<223> OTHER INFORMATION: synthetic

<400> SEQUENCE: 253 gaagcatct                                                            9

<210> SEQ ID NO 254
<211> LENGTH: 3
<212> TYPE: PRT
<213> ORGANISM: Artificial Sequence
<220> FEATURE:
<223> OTHER INFORMATION: synthetic

<400> SEQUENCE: 254

Glu Ala Ser
1

<210> SEQ ID NO 255
<211> LENGTH: 27
<212> TYPE: DNA
<213> ORGANISM: Artificial Sequence
<220> FEATURE:
<223> OTHER INFORMATION: synthetic

<400> SEQUENCE: 255
caacagagtt ttagtattcc gtggacg                                       27

<210> SEQ ID NO 256
<211> LENGTH: 9
<212> TYPE: PRT
<213> ORGANISM: Artificial Sequence
<220> FEATURE:
<223> OTHER INFORMATION: synthetic

<400> SEQUENCE: 256

Gln Gln Ser Phe Ser Ile Pro Trp Thr
1               5

<210> SEQ ID NO 257
<211> LENGTH: 366
<212> TYPE: DNA
<213> ORGANISM: Artificial Sequence
<220> FEATURE:
<223> OTHER INFORMATION: synthetic
```

<400> SEQUENCE: 257

```
caggtgcagc tggtgcagtc tggggctgaa gtgaagaagc ctggggcctc agtgaaggtc      60
tcctgcaagg cttctggata caccttcatc gcctactatt tacactgggt gcgacaggcc     120
cctggacaag gcttgagtg gatgggattg ctcaacccctt atactggtgg ctcatactat     180
acacagaagt ttcagggcag ggtcaccatg accagggaca cgtccatcga cacagcctac     240
atggaactga acagtctgag atctgacgac acggccatct attactgtgc gagagataag     300
aggagctact acatccctta tgcttttgaa atctggggcc aagggacaat ggtcaccgtc     360
tcttca                                                                366
```

<210> SEQ ID NO 258
<211> LENGTH: 122
<212> TYPE: PRT
<213> ORGANISM: Artificial Sequence
<220> FEATURE:
<223> OTHER INFORMATION: synthetic

<400> SEQUENCE: 258

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Ile Ala Tyr
            20                  25                  30
Tyr Leu His Trp Val Arg Gln Ala Pro Gly Gln Gly Leu Glu Trp Met
        35                  40                  45
Gly Leu Leu Asn Pro Tyr Thr Gly Gly Ser Tyr Tyr Thr Gln Lys Phe
    50                  55                  60
Gln Gly Arg Val Thr Met Thr Arg Asp Thr Ser Ile Asp Thr Ala Tyr
65                  70                  75                  80
Met Glu Leu Asn Ser Leu Arg Ser Asp Asp Thr Ala Ile Tyr Tyr Cys
                85                  90                  95
Ala Arg Asp Lys Arg Ser Tyr Tyr Ile Pro Tyr Ala Phe Glu Ile Trp
            100                 105                 110
Gly Gln Gly Thr Met Val Thr Val Ser Ser
        115                 120
```

<210> SEQ ID NO 259
<211> LENGTH: 24
<212> TYPE: DNA
<213> ORGANISM: Artificial Sequence
<220> FEATURE:
<223> OTHER INFORMATION: synthetic

<400> SEQUENCE: 259

```
ggatacacct tcatcgccta ctat                                             24
```

<210> SEQ ID NO 260
<211> LENGTH: 8
<212> TYPE: PRT
<213> ORGANISM: Artificial Sequence
<220> FEATURE:
<223> OTHER INFORMATION: synthetic

<400> SEQUENCE: 260

```
Gly Tyr Thr Phe Ile Ala Tyr Tyr
1               5
```

<210> SEQ ID NO 261
<211> LENGTH: 24

<210> SEQ ID NO 261
<211> LENGTH: 24
<212> TYPE: DNA
<213> ORGANISM: Artificial Sequence
<220> FEATURE:
<223> OTHER INFORMATION: synthetic

<400> SEQUENCE: 261 ctcaacccttt atactggtgg ctca                          24

<210> SEQ ID NO 262
<211> LENGTH: 8
<212> TYPE: PRT
<213> ORGANISM: Artificial Sequence
<220> FEATURE:
<223> OTHER INFORMATION: synthetic

<400> SEQUENCE: 262

Leu Asn Pro Tyr Thr Gly Gly Ser
1               5

<210> SEQ ID NO 263
<211> LENGTH: 45
<212> TYPE: DNA
<213> ORGANISM: Artificial Sequence
<220> FEATURE:
<223> OTHER INFORMATION: synthetic

<400> SEQUENCE: 263
gcgagagata agaggagcta ctacatccct tatgcttttg aaatc        45

<210> SEQ ID NO 264
<211> LENGTH: 15
<212> TYPE: PRT
<213> ORGANISM: Artificial Sequence
<220> FEATURE:
<223> OTHER INFORMATION: synthetic

<400> SEQUENCE: 264

Ala Arg Asp Lys Arg Ser Tyr Tyr Ile Pro Tyr Ala Phe Glu Ile
1               5                   10                  15

<210> SEQ ID NO 265
<211> LENGTH: 324
<212> TYPE: DNA
<213> ORGANISM: Artificial Sequence
<220> FEATURE:
<223> OTHER INFORMATION: synthetic

<400> SEQUENCE: 265
gacatccaga tgacccagtc tccatcctcc ctgtctgcat ctgtaggaga cagagtcacc    60
atcacttgcc gggcaagtca gagcattagc agctatttaa attggtatca gcagaaacca   120
gggaaagccc ctaagctcct gatctatgct gcatccagtt tgcaaagtgg ggtcccgtca   180
aggttcagtg gcagtggatc tgggacagat ttcactctca ccatcagcag tctgcaacct   240
gaagattttg caacttacta ctgtcaacag agttacagta cccctccgat caccttcggc   300
caagggacac gactggagat taaa                                         324

<210> SEQ ID NO 266
<211> LENGTH: 108
<212> TYPE: PRT
<213> ORGANISM: Artificial Sequence
<220> FEATURE:
<223> OTHER INFORMATION: synthetic

<400> SEQUENCE: 266

-continued

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Ile Thr Phe Gly Gln Gly Thr Arg Leu Glu Ile Lys
            100                 105
```

```
<210> SEQ ID NO 267
<211> LENGTH: 18
<212> TYPE: DNA
<213> ORGANISM: Artificial Sequence
<220> FEATURE:
<223> OTHER INFORMATION: synthetic

<400> SEQUENCE: 267
cagagcatta gcagctat                                                    18
```

```
<210> SEQ ID NO 268
<211> LENGTH: 6
<212> TYPE: PRT
<213> ORGANISM: Artificial Sequence
<220> FEATURE:
<223> OTHER INFORMATION: synthetic

<400> SEQUENCE: 268

Gln Ser Ile Ser Ser Tyr
1               5
```

```
<210> SEQ ID NO 269
<211> LENGTH: 9
<212> TYPE: DNA
<213> ORGANISM: Artificial Sequence
<220> FEATURE:
<223> OTHER INFORMATION: synthetic

<400> SEQUENCE: 269 gctgcatcc                                                               9
```

```
<210> SEQ ID NO 270
<211> LENGTH: 3
<212> TYPE: PRT
<213> ORGANISM: Artificial Sequence
<220> FEATURE:
<223> OTHER INFORMATION: synthetic

<400> SEQUENCE: 270

Ala Ala Ser
1
```

```
<210> SEQ ID NO 271
<211> LENGTH: 30
<212> TYPE: DNA
<213> ORGANISM: Artificial Sequence
<220> FEATURE:
<223> OTHER INFORMATION: synthetic
```

-continued

<400> SEQUENCE: 271
caacagagtt acagtacccc tccgatcacc        30

<210> SEQ ID NO 272
<211> LENGTH: 10
<212> TYPE: PRT
<213> ORGANISM: Artificial Sequence
<220> FEATURE:
<223> OTHER INFORMATION: synthetic

<400> SEQUENCE: 272

Gln Gln Ser Tyr Ser Thr Pro Pro Ile Thr
1               5                   10

<210> SEQ ID NO 273
<211> LENGTH: 369
<212> TYPE: DNA
<213> ORGANISM: Artificial Sequence
<220> FEATURE:
<223> OTHER INFORMATION: synthetic

<400> SEQUENCE: 273
gaggtgcagc tggtggagtc tgggggaggc ttggttcagc ctggggtgtc cctgagactc        60
tcctgtgtag cctctggatt cacctttagc aattatgaca taacctggat ccgccagatt       120
ccagggaagg ggctggagtg ggtctcaaga atcagtggta gtggtggaag tacatatttc       180
gcagactccg tgaagggtcg gttcatcatc tccagagaca attccaaaaa tacggtgtat       240
atgcaaatga acagtttgag agccgaagac tcggccgtat attactgtgc gagaagagat       300
tccgtcttat ttagtatgaa cagttggctc gaccectggg gccagggaac cctggtcacc       360
gtctcctca                                                               369

<210> SEQ ID NO 274
<211> LENGTH: 123
<212> TYPE: PRT
<213> ORGANISM: Artificial Sequence
<220> FEATURE:
<223> OTHER INFORMATION: synthetic

<400> SEQUENCE: 274

Glu Val Gln Leu Val Glu Ser Gly Gly Gly Leu Val Gln Pro Gly Val
1               5                   10                  15

Ser Leu Arg Leu Ser Cys Val Ala Ser Gly Phe Thr Phe Ser Asn Tyr
            20                  25                  30

Asp Ile Thr Trp Ile Arg Gln Ile Pro Gly Lys Gly Leu Glu Trp Val
        35                  40                  45

Ser Arg Ile Ser Gly Ser Gly Gly Ser Thr Tyr Phe Ala Asp Ser Val
    50                  55                  60

Lys Gly Arg Phe Ile Ile Ser Arg Asp Asn Ser Lys Asn Thr Val Tyr
65                  70                  75                  80

Met Gln Met Asn Ser Leu Arg Ala Glu Asp Ser Ala Val Tyr Tyr Cys
                85                  90                  95

Ala Arg Arg Asp Ser Val Leu Phe Ser Met Asn Ser Trp Leu Asp Pro
            100                 105                 110

Trp Gly Gln Gly Thr Leu Val Thr Val Ser Ser
        115                 120

<210> SEQ ID NO 275
<211> LENGTH: 24
<212> TYPE: DNA

```
<213> ORGANISM: Artificial Sequence
<220> FEATURE:
<223> OTHER INFORMATION: synthetic

<400> SEQUENCE: 275
ggattcacct ttagcaatta tgac                                              24

<210> SEQ ID NO 276
<211> LENGTH: 8
<212> TYPE: PRT
<213> ORGANISM: Artificial Sequence
<220> FEATURE:
<223> OTHER INFORMATION: synthetic

<400> SEQUENCE: 276

Gly Phe Thr Phe Ser Asn Tyr Asp
1               5

<210> SEQ ID NO 277
<211> LENGTH: 24
<212> TYPE: DNA
<213> ORGANISM: Artificial Sequence
<220> FEATURE:
<223> OTHER INFORMATION: synthetic

<400> SEQUENCE: 277
atcagtggta gtggtggaag taca                                              24

<210> SEQ ID NO 278
<211> LENGTH: 8
<212> TYPE: PRT
<213> ORGANISM: Artificial Sequence
<220> FEATURE:
<223> OTHER INFORMATION: synthetic

<400> SEQUENCE: 278

Ile Ser Gly Ser Gly Gly Ser Thr
1               5

<210> SEQ ID NO 279
<211> LENGTH: 48
<212> TYPE: DNA
<213> ORGANISM: Artificial Sequence
<220> FEATURE:
<223> OTHER INFORMATION: synthetic

<400> SEQUENCE: 279
gcgagaagag attccgtctt atttagtatg aacagttggc tcgacccc                    48

<210> SEQ ID NO 280
<211> LENGTH: 16
<212> TYPE: PRT
<213> ORGANISM: Artificial Sequence
<220> FEATURE:
<223> OTHER INFORMATION: synthetic

<400> SEQUENCE: 280

Ala Arg Arg Asp Ser Val Leu Phe Ser Met Asn Ser Trp Leu Asp Pro
1               5                   10                  15

<210> SEQ ID NO 281
<211> LENGTH: 369
<212> TYPE: DNA
<213> ORGANISM: Artificial Sequence
<220> FEATURE:
<223> OTHER INFORMATION: synthetic
```

<400> SEQUENCE: 281

```
gaggtgcagc tggtgcagtc tggagcagag gtgaaaaagc ccggggagtc tctgaagatc      60
tcctgttcgg gatctggata caggtttacc aactactgga tcgcctgggt gcgccagatg     120
cccgggaaag gcctggagtg gatgggtctc attcatcctg atgactctga tattagatac     180
agcccgtcct tccaaggcca ggtcaccttt tcagtcgaca agtccatcaa caccgcctac     240
ctgcagtgga gcagcctgaa ggcctcggac accgccatgt attactgtac gcgacaagac     300
ggaatactat ggtctcataa tgcctggttc gacccctggg gccagggaac cctggtcacc     360
gtctcctca                                                             369
```

<210> SEQ ID NO 282
<211> LENGTH: 123
<212> TYPE: PRT
<213> ORGANISM: Artificial Sequence
<220> FEATURE:
<223> OTHER INFORMATION: synthetic

<400> SEQUENCE: 282

```
Glu Val Gln Leu Val Gln Ser Gly Ala Glu Val Lys Lys Pro Gly Glu
1               5                   10                  15

Ser Leu Lys Ile Ser Cys Ser Gly Ser Gly Tyr Arg Phe Thr Asn Tyr
            20                  25                  30

Trp Ile Ala Trp Val Arg Gln Met Pro Gly Lys Gly Leu Glu Trp Met
        35                  40                  45

Gly Leu Ile His Pro Asp Asp Ser Asp Ile Arg Tyr Ser Pro Ser Phe
    50                  55                  60

Gln Gly Gln Val Thr Phe Ser Val Asp Lys Ser Ile Asn Thr Ala Tyr
65                  70                  75                  80

Leu Gln Trp Ser Ser Leu Lys Ala Ser Asp Thr Ala Met Tyr Tyr Cys
                85                  90                  95

Thr Arg Gln Asp Gly Ile Leu Trp Ser His Asn Ala Trp Phe Asp Pro
            100                 105                 110

Trp Gly Gln Gly Thr Leu Val Thr Val Ser Ser
        115                 120
```

<210> SEQ ID NO 283
<211> LENGTH: 24
<212> TYPE: DNA
<213> ORGANISM: Artificial Sequence
<220> FEATURE:
<223> OTHER INFORMATION: synthetic

<400> SEQUENCE: 283

```
ggatacaggt ttaccaacta ctgg                                             24
```

<210> SEQ ID NO 284
<211> LENGTH: 8
<212> TYPE: PRT
<213> ORGANISM: Artificial Sequence
<220> FEATURE:
<223> OTHER INFORMATION: synthetic

<400> SEQUENCE: 284

```
Gly Tyr Arg Phe Thr Asn Tyr Trp
1               5
```

<210> SEQ ID NO 285
<211> LENGTH: 24
<212> TYPE: DNA

```
<213> ORGANISM: Artificial Sequence
<220> FEATURE:
<223> OTHER INFORMATION: synthetic

<400> SEQUENCE: 285
attcatcctg atgactctga tatt                                          24

<210> SEQ ID NO 286
<211> LENGTH: 8
<212> TYPE: PRT
<213> ORGANISM: Artificial Sequence
<220> FEATURE:
<223> OTHER INFORMATION: synthetic

<400> SEQUENCE: 286

Ile His Pro Asp Asp Ser Asp Ile
1               5

<210> SEQ ID NO 287
<211> LENGTH: 48
<212> TYPE: DNA
<213> ORGANISM: Artificial Sequence
<220> FEATURE:
<223> OTHER INFORMATION: synthetic

<400> SEQUENCE: 287
acgcgacaag acggaatact atggtctcat aatgcctggt tcgacccc               48

<210> SEQ ID NO 288
<211> LENGTH: 16
<212> TYPE: PRT
<213> ORGANISM: Artificial Sequence
<220> FEATURE:
<223> OTHER INFORMATION: synthetic

<400> SEQUENCE: 288

Thr Arg Gln Asp Gly Ile Leu Trp Ser His Asn Ala Trp Phe Asp Pro
1               5                   10                  15

<210> SEQ ID NO 289
<211> LENGTH: 360
<212> TYPE: DNA
<213> ORGANISM: Artificial Sequence
<220> FEATURE:
<223> OTHER INFORMATION: synthetic

<400> SEQUENCE: 289
caggtgcagc tggtgcagtc tggggctgag gtgaagaagc ctggggcctc agtgaaggtc   60
tcctgcaagg cctctggata caccttcatt agttacaata tcttctgggt gcgacaggcc  120
actggtcagg gccttgattg gatgggatgg atgaacccct tcagaaataa cgcaggttat  180
gcacagaagt ttcagggcag agtcaccgtg acctgggaca cctccatcag cacagcctac  240
atggaactgt ccagcctgag ctctgaggac acggccatat attactgtgc gagagaacat  300
ggcagtagct ggggcttctt tgactactgg ggccagggaa ccctggtcac cgtctcctca  360

<210> SEQ ID NO 290
<211> LENGTH: 120
<212> TYPE: PRT
<213> ORGANISM: Artificial Sequence
<220> FEATURE:
<223> OTHER INFORMATION: synthetic

<400> SEQUENCE: 290

Gln Val Gln Leu Val Gln Ser Gly Ala Glu Val Lys Lys Pro Gly Ala
```

```
  1               5                  10                 15
Ser Val Lys Val Ser Cys Lys Ala Ser Gly Tyr Thr Phe Ile Ser Tyr
                20                  25                 30

Asn Ile Phe Trp Val Arg Gln Ala Thr Gly Gln Gly Leu Asp Trp Met
            35                  40                  45

Gly Trp Met Asn Pro Phe Arg Asn Asn Ala Gly Tyr Ala Gln Lys Phe
        50                  55                  60

Gln Gly Arg Val Thr Val Thr Trp Asp Thr Ser Ile Ser Thr Ala Tyr
 65                 70                  75                  80

Met Glu Leu Ser Ser Leu Ser Ser Glu Asp Thr Ala Ile Tyr Tyr Cys
                85                  90                  95

Ala Arg Glu His Gly Ser Ser Trp Gly Phe Phe Asp Tyr Trp Gly Gln
                100                 105                110

Gly Thr Leu Val Thr Val Ser Ser
        115                 120
```

<210> SEQ ID NO 291
<211> LENGTH: 24
<212> TYPE: DNA
<213> ORGANISM: Artificial Sequence
<220> FEATURE:
<223> OTHER INFORMATION: synthetic

<400> SEQUENCE: 291
ggatacacct tcattagtta caat                                          24

<210> SEQ ID NO 292
<211> LENGTH: 8
<212> TYPE: PRT
<213> ORGANISM: Artificial Sequence
<220> FEATURE:
<223> OTHER INFORMATION: synthetic

<400> SEQUENCE: 292

```
Gly Tyr Thr Phe Ile Ser Tyr Asn
 1               5
```

<210> SEQ ID NO 293
<211> LENGTH: 24
<212> TYPE: DNA
<213> ORGANISM: Artificial Sequence
<220> FEATURE:
<223> OTHER INFORMATION: synthetic

<400> SEQUENCE: 293
atgaacccct tcagaaataa cgca                                          24

<210> SEQ ID NO 294
<211> LENGTH: 8
<212> TYPE: PRT
<213> ORGANISM: Artificial Sequence
<220> FEATURE:
<223> OTHER INFORMATION: synthetic

<400> SEQUENCE: 294

```
Met Asn Pro Phe Arg Asn Asn Ala
 1               5
```

<210> SEQ ID NO 295
<211> LENGTH: 39
<212> TYPE: DNA
<213> ORGANISM: Artificial Sequence
<220> FEATURE:

<223> OTHER INFORMATION: synthetic

<400> SEQUENCE: 295
gcgagagaac atggcagtag ctggggcttc tttgactac                                39

<210> SEQ ID NO 296
<211> LENGTH: 13
<212> TYPE: PRT
<213> ORGANISM: Artificial Sequence
<220> FEATURE:
<223> OTHER INFORMATION: synthetic

<400> SEQUENCE: 296

Ala Arg Glu His Gly Ser Ser Trp Gly Phe Phe Asp Tyr
1               5                   10

<210> SEQ ID NO 297
<211> LENGTH: 324
<212> TYPE: DNA
<213> ORGANISM: Artificial Sequence
<220> FEATURE:
<223> OTHER INFORMATION: synthetic

<400> SEQUENCE: 297
gaaattgtgt tgacgcagtc tccaggcacc ctgtctttgt ctccagggga aagagccacc        60
ctctcctgca gggccagtca gagtgttagc agcagctact tagcctggta ccagcagaaa       120
cctggccagg ctcccaggct cctcatctat ggtgcatcca gcagggccac tggcatccca       180
gacaggttca gtggcagtgg gtctgggaca gacttcactc tcaccatcag cagactggag       240
cctgaagatt ttgcagtgta ttactgtcag cagtatggta gctcaccttg gacgttcggc       300
caagggacca aggtggaaat caaa                                              324

<210> SEQ ID NO 298
<211> LENGTH: 108
<212> TYPE: PRT
<213> ORGANISM: Artificial Sequence
<220> FEATURE:
<223> OTHER INFORMATION: synthetic

<400> SEQUENCE: 298

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105

<210> SEQ ID NO 299
<211> LENGTH: 21
<212> TYPE: DNA
<213> ORGANISM: Artificial Sequence
<220> FEATURE:
<223> OTHER INFORMATION: synthetic

<400> SEQUENCE: 299
cagagtgtta gcagcagcta c                                          21

<210> SEQ ID NO 300
<211> LENGTH: 7
<212> TYPE: PRT
<213> ORGANISM: Artificial Sequence
<220> FEATURE:
<223> OTHER INFORMATION: synthetic

<400> SEQUENCE: 300

Gln Ser Val Ser Ser Ser Tyr
1               5

<210> SEQ ID NO 301
<211> LENGTH: 9
<212> TYPE: DNA
<213> ORGANISM: Artificial Sequence
<220> FEATURE:
<223> OTHER INFORMATION: synthetic

<400> SEQUENCE: 301 ggtgcatcc                                                         9

<210> SEQ ID NO 302
<211> LENGTH: 3
<212> TYPE: PRT
<213> ORGANISM: Artificial Sequence
<220> FEATURE:
<223> OTHER INFORMATION: synthetic

<400> SEQUENCE: 302

Gly Ala Ser
1

<210> SEQ ID NO 303
<211> LENGTH: 27
<212> TYPE: DNA
<213> ORGANISM: Artificial Sequence
<220> FEATURE:
<223> OTHER INFORMATION: synthetic

<400> SEQUENCE: 303
cagcagtatg gtagctcacc ttggacg                                    27

<210> SEQ ID NO 304
<211> LENGTH: 9
<212> TYPE: PRT
<213> ORGANISM: Artificial Sequence
<220> FEATURE:
<223> OTHER INFORMATION: synthetic

<400> SEQUENCE: 304

Gln Gln Tyr Gly Ser Ser Pro Trp Thr
1               5

<210> SEQ ID NO 305
<211> LENGTH: 483
<212> TYPE: DNA
<213> ORGANISM: Artificial Sequence
<220> FEATURE:
<223> OTHER INFORMATION: Bet v1

<400> SEQUENCE: 305
atgggtgtgt taattatga gactgagacc acctctgtta tcccagcagc tcgactgttc   60

```
aaggccttta tccttgatgg cgataacctc tttccaaagg ttgcacccca agccattagc    120
agtgttgaaa acattgaagg aaatggaggg cctggaacca ttaagaagat cagctttccc    180
gaaggcctcc ctttcaagta cgtgaaggac agagttgatg aggtggacca cacaaacttc    240
aaatacaatt acagcgtgat cgagggcggt cccataggcg acacattgga gaagatctcc    300
aacgagataa agatagtggc aacccctgat ggaggatcca tcttgaagat cagcaacaag    360
taccacacca aggtgaccta tgaggtgaag gcagagcagg ttaaggcaag taaagaaatg    420
ggcgagacac ttttgagggc cgttgagagc tacctcttgg cacactccga tgcctacaac    480
taa                                                                  483
```

```
<210> SEQ ID NO 306
<211> LENGTH: 160
<212> TYPE: PRT
<213> ORGANISM: Artificial Sequence
<220> FEATURE:
<223> OTHER INFORMATION: Bet v1 (M1-N160 of accession number CAB02159)

<400> SEQUENCE: 306
```

```
Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Leu Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Ile Gly Asp Thr Leu
                85                  90                  95

Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160
```

```
<210> SEQ ID NO 307
<211> LENGTH: 21
<212> TYPE: PRT
<213> ORGANISM: Artificial Sequence
<220> FEATURE:
<223> OTHER INFORMATION: AA 23-43 of Bet v1

<400> SEQUENCE: 307
```

```
Phe Ile Leu Asp Gly Asp Asn Leu Phe Pro Lys Val Ala Pro Gln Ala
1               5                   10                  15

Ile Ser Ser Val Glu
            20
```

```
<210> SEQ ID NO 308
<211> LENGTH: 13
<212> TYPE: PRT
<213> ORGANISM: Artificial Sequence
<220> FEATURE:
```

```
<223> OTHER INFORMATION: AA 44-56 of Bet v1

<400> SEQUENCE: 308

Asn Ile Glu Gly Asn Gly Gly Pro Gly Thr Ile Lys Lys
1               5                   10

<210> SEQ ID NO 309
<211> LENGTH: 18
<212> TYPE: PRT
<213> ORGANISM: Artificial Sequence
<220> FEATURE:
<223> OTHER INFORMATION: AA 2-19 of Bet v1

<400> SEQUENCE: 309

Gly Val Phe Asn Tyr Glu Thr Glu Thr Thr Ser Val Ile Pro Ala Ala
1               5                   10                  15

Arg Leu

<210> SEQ ID NO 310
<211> LENGTH: 14
<212> TYPE: PRT
<213> ORGANISM: Artificial Sequence
<220> FEATURE:
<223> OTHER INFORMATION: AA 57-70 of Bet v1

<400> SEQUENCE: 310

Ile Ser Phe Pro Glu Gly Leu Pro Phe Lys Tyr Val Lys Asp
1               5                   10

<210> SEQ ID NO 311
<211> LENGTH: 9
<212> TYPE: PRT
<213> ORGANISM: Artificial Sequence
<220> FEATURE:
<223> OTHER INFORMATION: AA 81-89 of Bet v1

<400> SEQUENCE: 311

Lys Tyr Asn Tyr Ser Val Ile Glu Gly
1               5

<210> SEQ ID NO 312
<211> LENGTH: 187
<212> TYPE: PRT
<213> ORGANISM: Artificial Sequence
<220> FEATURE:
<223> OTHER INFORMATION: Mutant Bet v 1-MMH w S85A (1-159: Bet v1
      (G2-N160 of accession number CAB02159) with Myc-Myc hexahistidine
      tag

<400> SEQUENCE: 312

Gly Val Phe Asn Tyr Glu Thr Glu Thr Thr Ser Val Ile Pro Ala Ala
1               5                   10                  15

Arg Leu Phe Lys Ala Phe Ile Leu Asp Gly Asp Asn Leu Phe Pro Lys
                20                  25                  30

Val Ala Pro Gln Ala Ile Ser Ser Val Glu Asn Ile Glu Gly Asn Gly
            35                  40                  45

Gly Pro Gly Thr Ile Lys Lys Ile Ser Phe Pro Glu Gly Leu Pro Phe
        50                  55                  60

Lys Tyr Val Lys Asp Arg Val Asp Glu Val Asp His Thr Asn Phe Lys
65                  70                  75                  80

Tyr Asn Tyr Ala Val Ile Glu Gly Gly Pro Ile Gly Asp Thr Leu Glu
                85                  90                  95

Lys Ile Ser Asn Glu Ile Lys Ile Val Ala Thr Pro Asp Gly Gly Ser
```

```
              100                 105                 110
Ile Leu Lys Ile Ser Asn Lys Tyr His Thr Lys Gly Asp His Glu Val
            115                 120                 125

Lys Ala Glu Gln Val Lys Ala Ser Lys Glu Met Gly Glu Thr Leu Leu
        130                 135                 140

Arg Ala Val Glu Ser Tyr Leu Leu Ala His Ser Asp Ala Tyr Asn Glu
145                 150                 155                 160

Gln Lys Leu Ile Ser Glu Glu Asp Leu Gly Gly Glu Gln Lys Leu Ile
                165                 170                 175

Ser Glu Glu Asp Leu His His His His His His
                180                 185

<210> SEQ ID NO 313
<211> LENGTH: 413
<212> TYPE: PRT
<213> ORGANISM: Artificial Sequence
<220> FEATURE:
<223> OTHER INFORMATION: hFceR1alpha-mFc

<400> SEQUENCE: 313

Val Pro Gln Lys Pro Lys Val Ser Leu Asn Pro Pro Trp Asn Arg Ile
1               5                   10                  15

Phe Lys Gly Glu Asn Val Thr Leu Thr Cys Asn Gly Asn Asn Phe Phe
            20                  25                  30

Glu Val Ser Ser Thr Lys Trp Phe His Asn Gly Ser Leu Ser Glu Glu
        35                  40                  45

Thr Asn Ser Ser Leu Asn Ile Val Asn Ala Lys Phe Glu Asp Ser Gly
50                  55                  60

Glu Tyr Lys Cys Gln His Gln Gln Val Asn Glu Ser Glu Pro Val Tyr
65                  70                  75                  80

Leu Glu Val Phe Ser Asp Trp Leu Leu Leu Gln Ala Ser Ala Glu Val
                85                  90                  95

Val Met Glu Gly Gln Pro Leu Phe Leu Arg Cys His Gly Trp Arg Asn
            100                 105                 110

Trp Asp Val Tyr Lys Val Ile Tyr Tyr Lys Asp Gly Glu Ala Leu Lys
        115                 120                 125

Tyr Trp Tyr Glu Asn His Asn Ile Ser Ile Thr Asn Ala Thr Val Glu
130                 135                 140

Asp Ser Gly Thr Tyr Tyr Cys Thr Gly Lys Val Trp Gln Leu Asp Tyr
145                 150                 155                 160

Glu Ser Glu Pro Leu Asn Ile Thr Val Ile Lys Ala Pro Arg Glu Lys
                165                 170                 175

Tyr Trp Leu Gln Glu Pro Arg Gly Pro Thr Ile Lys Pro Cys Pro Pro
            180                 185                 190

Cys Lys Cys Pro Ala Pro Asn Leu Leu Gly Gly Pro Ser Val Phe Ile
        195                 200                 205

Phe Pro Pro Lys Ile Lys Asp Val Leu Met Ile Ser Leu Ser Pro Ile
210                 215                 220

Val Thr Cys Val Val Val Asp Val Ser Glu Asp Asp Pro Asp Val Gln
225                 230                 235                 240

Ile Ser Trp Phe Val Asn Asn Val Glu Val His Thr Ala Gln Thr Gln
                245                 250                 255

Thr His Arg Glu Asp Tyr Asn Ser Thr Leu Arg Val Val Ser Ala Leu
            260                 265                 270

Pro Ile Gln His Gln Asp Trp Met Ser Gly Lys Glu Phe Lys Cys Lys
```

```
                  275                 280                 285
Val Asn Asn Lys Asp Leu Pro Ala Pro Ile Glu Arg Thr Ile Ser Lys
            290                 295                 300

Pro Lys Gly Ser Val Arg Ala Pro Gln Val Tyr Val Leu Pro Pro Pro
305                 310                 315                 320

Glu Glu Glu Met Thr Lys Lys Gln Val Thr Leu Thr Cys Met Val Thr
                325                 330                 335

Asp Phe Met Pro Glu Asp Ile Tyr Val Glu Trp Thr Asn Asn Gly Lys
            340                 345                 350

Thr Glu Leu Asn Tyr Lys Asn Thr Glu Pro Val Leu Asp Ser Asp Gly
                355                 360                 365

Ser Tyr Phe Met Tyr Ser Lys Leu Arg Val Glu Lys Lys Asn Trp Val
            370                 375                 380

Glu Arg Asn Ser Tyr Ser Cys Ser Val Val His Glu Gly Leu His Asn
385                 390                 395                 400

His His Thr Thr Lys Ser Phe Ser Arg Thr Pro Gly Lys
                405                 410

<210> SEQ ID NO 314
<211> LENGTH: 160
<212> TYPE: PRT
<213> ORGANISM: Artificial Sequence
<220> FEATURE:
<223> OTHER INFORMATION: Bet v 1 amino acid sequence from Uniprot:
      P15494

<400> SEQUENCE: 314

Met Gly Val Phe Asn Tyr Glu Thr Glu Thr Thr Ser Val Ile Pro Ala
1               5                   10                  15

Ala Arg Leu Phe Lys Ala Phe Ile Leu Asp Gly Asp Asn Leu Phe Pro
            20                  25                  30

Lys Val Ala Pro Gln Ala Ile Ser Ser Val Glu Asn Ile Glu Gly Asn
        35                  40                  45

Gly Gly Pro Gly Thr Ile Lys Lys Ile Ser Phe Pro Glu Gly Phe Pro
    50                  55                  60

Phe Lys Tyr Val Lys Asp Arg Val Asp Glu Val Asp His Thr Asn Phe
65                  70                  75                  80

Lys Tyr Asn Tyr Ser Val Ile Glu Gly Gly Pro Ile Gly Asp Thr Leu
                85                  90                  95

Glu Lys Ile Ser Asn Glu Ile Lys Ile Val Ala Thr Pro Asp Gly Gly
            100                 105                 110

Ser Ile Leu Lys Ile Ser Asn Lys Tyr His Thr Lys Gly Asp His Glu
        115                 120                 125

Val Lys Ala Glu Gln Val Lys Ala Ser Lys Glu Met Gly Glu Thr Leu
    130                 135                 140

Leu Arg Ala Val Glu Ser Tyr Leu Leu Ala His Ser Asp Ala Tyr Asn
145                 150                 155                 160

<210> SEQ ID NO 315
<211> LENGTH: 16
<212> TYPE: PRT
<213> ORGANISM: Artificial Sequence
<220> FEATURE:
<223> OTHER INFORMATION: AA 81-96 of Bet v1

<400> SEQUENCE: 315

Lys Tyr Asn Tyr Ser Val Ile Glu Gly Gly Pro Ile Gly Asp Thr Leu
1               5                   10                  15
```

<210> SEQ ID NO 316
<211> LENGTH: 446
<212> TYPE: PRT
<213> ORGANISM: Artificial Sequence
<220> FEATURE:
<223> OTHER INFORMATION: H4H17038P2 HC

<400> SEQUENCE: 316

```
Glu Val Gln Leu Val Glu Ser Gly Gly Asp Leu Val Gln Pro Gly Gly
1               5                   10                  15

Ser Leu Arg Leu Ser Cys Ala Ala Ser Gly Phe Thr Phe Ser Ser Tyr
            20                  25                  30

Glu Met Asn Trp Val Arg Gln Ala Pro Gly Lys Gly Leu Glu Trp Val
        35                  40                  45

Ser Phe Ile Ser Asp Ser Ser Asn Ile Tyr Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Thr Ser Leu Arg Ala Glu Asp Thr Ala Val Tyr Tyr Cys
                85                  90                  95

Ala Arg Glu Ala Ile Gly Ser Thr Ser Phe Asp Asn Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365
```

```
Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
                435                 440                 445
```

<210> SEQ ID NO 317
<211> LENGTH: 214
<212> TYPE: PRT
<213> ORGANISM: Artificial Sequence
<220> FEATURE:
<223> OTHER INFORMATION: H4H17038P2 LC

<400> SEQUENCE: 317

```
Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Ser
                20                  25                  30

Leu Ala Trp Tyr Gln Gln Lys Pro Gly Gln Ala Pro Arg Arg Leu Ile
            35                  40                  45

Tyr Ser Ala Ser Thr Arg Ala Thr Gly Ile Pro Ala Arg Phe Ser Gly
        50                  55                  60

Ser Gly Ser Gly Thr Glu Phe Thr Leu Thr Ile Ser Ser Leu Gln Ser
65                  70                  75                  80

Glu Asp Phe Ala Ile Tyr Tyr Cys His Gln Tyr Asn Asn Trp Pro Leu
                85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
    210
```

<210> SEQ ID NO 318
<211> LENGTH: 446
<212> TYPE: PRT
<213> ORGANISM: Artificial Sequence
<220> FEATURE:
<223> OTHER INFORMATION: H4H16987P HC

<400> SEQUENCE: 318

```
Glu Val Gln Leu Val Glu Ser Gly Gly Gly Leu Val Gln Pro Gly Gly
```

-continued

```
1               5                   10                  15
Ser Leu Arg Leu Ser Cys Ala Ala Ser Gly Phe Thr Val Ser Ser Asn
            20                  25                  30

Ser Met Ser Trp Val Arg Gln Ala Pro Gly Glu Gly Leu Glu Trp Val
            35                  40                  45

Ser Val Ile Phe Ser Gly Gly Ile Thr Tyr Tyr Ser Asp Ser Val Lys
            50                  55                  60

Gly Arg Phe Thr Ile Ser Arg His Asn Ser Lys Asn Thr Leu Tyr Leu
65                  70                  75                  80

Gln Met Asn Ser Leu Arg Thr Glu Asp Thr Ala Val Tyr Tyr Cys Ala
            85                  90                  95

Arg His Ser Asn Trp Asn Phe Asp Ala Phe Asp Ile Trp Gly Gln Gly
            100                 105                 110

Thr Met Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
            130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
            245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
            290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
            325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
            405                 410                 415

Gln Glu Gly Asn Val Phe Ser Cys Ser Val Met His Glu Ala Leu His
            420                 425                 430
```

```
Asn His Tyr Thr Gln Lys Ser Leu Ser Leu Ser Leu Gly Lys
        435                 440                 445

<210> SEQ ID NO 319
<211> LENGTH: 214
<212> TYPE: PRT
<213> ORGANISM: Artificial Sequence
<220> FEATURE:
<223> OTHER INFORMATION: H4H16987P LC

<400> SEQUENCE: 319

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Phe Asp Thr Tyr
            20                  25                  30

Leu Asn Trp Tyr Gln Gln Lys Pro Gly Lys Ala Pro Asn Leu Leu Ile
        35                  40                  45

Tyr Ala Thr Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Gly Thr Tyr Tyr Cys Gln Gln Ser Tyr Ser Ile Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 320
<211> LENGTH: 443
<212> TYPE: PRT
<213> ORGANISM: Artificial Sequence
<220> FEATURE:
<223> OTHER INFORMATION: H4H16992P HC

<400> SEQUENCE: 320

Gln Val Gln Leu Gln Glu Ser Gly Pro Gly Leu Val Lys Pro Ser Glu
1               5                   10                  15

Thr Leu Ser Leu Thr Cys Ser Val Ser Gly Gly Ser Ile Thr Asn Tyr
            20                  25                  30

Phe Trp Thr Trp Ile Arg Gln Ser Pro Gly Lys Gly Leu Glu Trp Ile
        35                  40                  45

Gly Tyr Ile Tyr Tyr Ser Gly Gly Thr Asn Tyr Asn Pro Ser Leu Lys
50                  55                  60

Ser Arg Val Thr Ile Ser Ile Asp Thr Ser Lys Asn Gln Phe Ser Leu
```

Asn Met Asn Ser Val Thr Ala Ala Asp Thr Ala Val Tyr Tyr Cys Ala
 65                  70                  75                  80

Gly Ser Tyr Tyr Tyr Gly Val Asp Val Trp Gly Gln Gly Thr Thr Val
             85                  90                  95

Thr Val Ser Ser Ala Ser Thr Lys Gly Pro Ser Val Phe Pro Leu Ala
        100                 105                 110

Pro Cys Ser Arg Ser Thr Ser Glu Ser Thr Ala Ala Leu Gly Cys Leu
    115                 120                 125

Val Lys Asp Tyr Phe Pro Glu Pro Val Thr Val Ser Trp Asn Ser Gly
130                 135                 140

Ala Leu Thr Ser Gly Val His Thr Phe Pro Ala Val Leu Gln Ser Ser
145                 150                 155                 160

Gly Leu Tyr Ser Leu Ser Ser Val Val Thr Val Pro Ser Ser Ser Leu
                165                 170                 175

Gly Thr Lys Thr Tyr Thr Cys Asn Val Asp His Lys Pro Ser Asn Thr
            180                 185                 190

Lys Val Asp Lys Arg Val Glu Ser Lys Tyr Gly Pro Pro Cys Pro Pro
        195                 200                 205

Cys Pro Ala Pro Glu Phe Leu Gly Gly Pro Ser Val Phe Leu Phe Pro
    210                 215                 220

Pro Lys Pro Lys Asp Thr Leu Met Ile Ser Arg Thr Pro Glu Val Thr
225                 230                 235                 240

Cys Val Val Val Asp Val Ser Gln Glu Asp Pro Glu Val Gln Phe Asn
                245                 250                 255

Trp Tyr Val Asp Gly Val Glu Val His Asn Ala Lys Thr Lys Pro Arg
            260                 265                 270

Glu Glu Gln Phe Asn Ser Thr Tyr Arg Val Val Ser Val Leu Thr Val
        275                 280                 285

Leu His Gln Asp Trp Leu Asn Gly Lys Glu Tyr Lys Cys Lys Val Ser
290                 295                 300

Asn Lys Gly Leu Pro Ser Ser Ile Glu Lys Thr Ile Ser Lys Ala Lys
305                 310                 315                 320

Gly Gln Pro Arg Glu Pro Gln Val Tyr Thr Leu Pro Pro Ser Gln Glu
                325                 330                 335

Glu Met Thr Lys Asn Gln Val Ser Leu Thr Cys Leu Val Lys Gly Phe
            340                 345                 350

Tyr Pro Ser Asp Ile Ala Val Glu Trp Glu Ser Asn Gly Gln Pro Glu
        355                 360                 365

Asn Asn Tyr Lys Thr Thr Pro Pro Val Leu Asp Ser Asp Gly Ser Phe
370                 375                 380

Phe Leu Tyr Ser Arg Leu Thr Val Asp Lys Ser Arg Trp Gln Glu Gly
385                 390                 395                 400

Asn Val Phe Ser Cys Ser Val Met His Glu Ala Leu His Asn His Tyr
                405                 410                 415

Thr Gln Lys Ser Leu Ser Leu Ser Leu Gly Lys
            420                 425                 430

<210> SEQ ID NO 321
<211> LENGTH: 214
<212> TYPE: PRT
<213> ORGANISM: Artificial Sequence
<220> FEATURE:
<223> OTHER INFORMATION: H4H16992P LC

<400> SEQUENCE: 321

```
Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Lys Ser Phe
            20                  25                  30

Leu Ala Trp Tyr Arg Gln Lys Pro Gly Gln Ala Pro Arg Leu Leu Ile
        35                  40                  45

Tyr Asp Ala Ser Asn Arg Pro Thr Gly Ile Pro Ala Arg Phe Ser Gly
    50                  55                  60

Ser Gly Ser Gly Thr Asp Phe Thr Leu Thr Ile Asn Ser Leu Glu Ser
65                  70                  75                  80

Glu Asp Phe Ala Val Tyr Phe Cys Gln Gln Arg Asn Asn Trp Pro Phe
                85                  90                  95

Thr Phe Gly Pro Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

```
<210> SEQ ID NO 322
<211> LENGTH: 447
<212> TYPE: PRT
<213> ORGANISM: Artificial Sequence
<220> FEATURE:
<223> OTHER INFORMATION: H4H17082P2 HC
```

<400> SEQUENCE: 322

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ile Ser Tyr
            20                  25                  30

Asn Ile Phe Trp Val Arg Gln Ala Thr Gly Gln Gly Leu Asp Trp Met
        35                  40                  45

Gly Trp Met Asn Pro Phe Arg Asn Asn Ala Gly Tyr Ala Gln Lys Phe
    50                  55                  60

Gln Gly Arg Val Thr Val Thr Trp Asp Thr Ser Ile Ser Thr Ala Tyr
65                  70                  75                  80

Met Glu Leu Ser Ser Leu Ser Ser Glu Asp Thr Ala Ile Tyr Tyr Cys
                85                  90                  95

Ala Arg Glu His Gly Ser Ser Trp Gly Phe Phe Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
```

```
              130                 135                 140
Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 323
<211> LENGTH: 215
<212> TYPE: PRT
<213> ORGANISM: Artificial Sequence
<220> FEATURE:
<223> OTHER INFORMATION: H4H17082P2 LC

<400> SEQUENCE: 323

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
```

-continued

```
            50                  55                  60
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                     85                  90                  95

Trp Thr Phe Gly Gln Gly Thr Lys Val Glu Ile Lys Arg Thr Val Ala
                100                 105                 110

Ala Pro Ser Val Phe Ile Phe Pro Pro Ser Asp Glu Gln Leu Lys Ser
            115                 120                 125

Gly Thr Ala Ser Val Val Cys Leu Leu Asn Asn Phe Tyr Pro Arg Glu
            130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
            195                 200                 205

Ser Phe Asn Arg Gly Glu Cys
210                 215
```